United States Patent
Friedland et al.

(10) Patent No.: US 11,001,844 B2
(45) Date of Patent: May 11, 2021

(54) CRISPR/CAS-RELATED METHODS AND COMPOSITIONS FOR TREATING HERPES SIMPLEX VIRUS

(71) Applicant: EDITAS MEDICINE, INC., Cambridge, MA (US)

(72) Inventors: Ari E. Friedland, Boston, MA (US); Penrose O'Donnell, Yarmouth, ME (US); David A. Bumcrot, Belmont, MA (US)

(73) Assignee: EDITAS MEDICINE, INC., Cambridge, MA (US)

( * ) Notice: Subject to any disclaimer, the term of this patent is extended or adjusted under 35 U.S.C. 154(b) by 0 days.

(21) Appl. No.: 15/966,897

(22) Filed: Apr. 30, 2018

(65) Prior Publication Data

US 2018/0251770 A1   Sep. 6, 2018

Related U.S. Application Data

(63) Continuation of application No. PCT/US2016/059502, filed on Oct. 28, 2016.

(60) Provisional application No. 62/249,159, filed on Oct. 30, 2015, provisional application No. 62/249,071, filed on Oct. 30, 2015.

(51) Int. Cl.
  *C12N 15/113*  (2010.01)
  *C12N 9/22*    (2006.01)
  *C12N 15/10*   (2006.01)

(52) U.S. Cl.
  CPC ............ *C12N 15/1133* (2013.01); *C12N 9/22* (2013.01); *C12N 15/102* (2013.01); *C12N 2310/10* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 8,999,641 B2 * | 4/2015 | Zhang ............... C12N 9/22 |
|---|---|---|
| | | 424/94.1 |
| 9,963,719 B1 * | 5/2018 | Friedland ........... C12N 9/22 |
| 10,006,054 B1 * | 6/2018 | Friedland ........... C12N 9/22 |
| 10,071,098 B2 * | 9/2018 | Clifford ......... A61K 31/4184 |

FOREIGN PATENT DOCUMENTS

| WO | WO 2015/070083 A  | 5/2015 |
|---|---|---|
| WO | WO 2015/126927 A2 | 8/2015 |
| WO | WO 2015/153789 A1 | 10/2015 |
| WO | WO 2015/153791 A1 | 10/2015 |
| WO | WO 2015/153889 A2 | 10/2015 |
| WO | WO 2016/115355 A1 | 7/2016 |

OTHER PUBLICATIONS

Kang et al (Virology, 2003, p. 233-244).*
Nishimasu (Cell, Aug. 2015, p. 1113-1126).*
International Search Report dated Mar. 22, 2017 in International Application No. PCT/US2016/059502.
Kleinstiver et al., "Engineered CRISPR-Cas9 nucleases with altered PAM specificities," Nature, 523(7561):481-485 (2015).
Nishiyama et al., "Function of Herpes Simplex Virus Gene Products," Virus 51(1):29-36 (2001) [with full English translation].

* cited by examiner

*Primary Examiner* — Agnieszka Boesen
(74) *Attorney, Agent, or Firm* — Baker Botts L.L.P.

(57) ABSTRACT

CRISPR/CAS-related systems, compositions and methods for editing RS1, RL2, and/or LAT genes in human cells are described, as are cells and compositions including cells edited according to the same.

26 Claims, 31 Drawing Sheets

Specification includes a Sequence Listing.

*Streptococcus thermophilus*
a) Structure (See, e.g., Karvelis et al. RNA Biology. 2013; 10 (5): 841-851)

```
                    Targeting      First Complementarity
                    Domain         Domain
                    ⌢⎯⎯⎯⎯⎯⎯⌢      ⌢⎯⎯⎯⎯⎯⎯⌢
5'-NNNNNNNNNNNNNNNNNNNNGUUUUAGAGCUGUGUUGUUUCG-3'    (SEQ ID NO: 45)
                                    ||||||||||||
                   CAACUCAUGCCUGAUUCGGAAUAAAAUU CGACACAACAAAGCGGG-5'  (SEQ ID NO: 46)
                   ⌣⎯⎯⎯⎯⌣           GAG        ⌣⎯⎯⎯⌣
                   Proximal              Second     5' Extension
                   Domain                Complementarity  Domain
                                         Domain
AGCCACGGUGGAAAAGUUC
|||||||
U   UCGGUGUUUU-3'
⌣⎯⎯⎯⌣
Tail
Domain
```

FIG. 1F

Alignment

S. pyogenes      5'-NNNNNNNNNNNNNNNNNNNNGUUUUAGAGCUAUGCUGUUUUG-3'   (SEQ ID NO: 39)
S. thermophilus  5'-NNNNNNNNNNNNNNNNNNNNGUUUUAGAGCUGUGUUGUUUCG-3'   (SEQ ID NO: 45)
                    *******************   *****  *

S. pyogenes      5'-GAACCAUUCAAAACAGCAUAGCAAGUUAAAAUAAGGC-UAGUCCGUUAUCAACUUGAAAAAGUGGCACCGAGUCGGUGCUUUUUUU-3' (SEQ ID NO: 47)
S. thermophilus  5'-------GGGCGAAACAACAACACAGGCGAGUUAAAAUAAGGCUUAGUCCGUACUCAACUUGAAAAGGUGGCACCGAUUCGGUGUUUUU---3' (SEQ ID NO: 46)
                           * ***   * *************** *****  *************** ***** **

FIG. 1G (SEQ ID NO: 42)

CLUSTAL format alignment by MAFFT (v7.058b)

```
SM      MKKPYSIGLDIGTNSVGWAVITDDYKVPAKKMKVLGNTDKSHIEKNLLGALLFDSGMTAED
SP      MDKKYSIGLDIGTNSVGWAVITDEYKVPSKKFKVLGNTDRHSIKKNLIGALLFDSGETAEA
ST      MTKPYSIGLDIGTNSVGWAVITDNYKVPSKKMKVLGNTSKKYIKNLLGVLLFDSGITAEG
LI      MKKPYTTGLDIGTNSVGWAVITDQYDLVKRKMKIAGDSEKKQIKGFWGVRLFDEGQTAAD
        *:****  ********** :    ::***:    ::*::  *:   *** *  **
Motif:  M-K-Y*IGLDIGTNSVGWAV-TD-Y-*-*K*K*-G*****-I*KN*-G--LFD-G-TA--

SM      RRLKRTARRRYTRRRNRILYLQEIFSEEMGKVDDSFFHRLEDSFLVTEDKRGERHPIFGN
SP      TRLKRTARRRYTRRKNRICYLQEIFSNEMAKVDDSFFHRLEESFLVEEDKKHERHPIFGN
ST      RRLKRTARRRYTRRRNRILYLQEIFSTEMATLDDAFFQRLDDSFLVPDDKRDSKYPIFGN
LI      RRMARTARRPIERRRNRISYLQGIFAEEMSKTDANFFCRLSDSFYVDMEKRNSRHPFFAT
        *: *****  *:*::*** :**  * :  *:  ..*  **  **.  :  .    *  
Motif:  -R*-RTARRR--RP*NRI-YLQ-IF*-EM---D--FF-RL--SF-V-**K*-*P*F--

SM      LEEEVKYHERFPTIYHLRQYLADNPEKVDLRLVYLALAHIIKFRGHFLIEGKFDTRNMDV
SP      IVDEVAYHEKYPTIYHLRKKLVDSTDKADLRLIYLALAHMIKFRGHFLIEGDLANPDMSDV
ST      LVEEKAYHDEFPTIYHLRKYLADSTKKADLRLVYLALAHMIKYRGHFLIEGEFNSKDMDI
LI      IEEEVEYHKNYPTIYHLREELVNSSEKADLRLVYLALAHIIKYRGNFLIEGALDTQNTSV
        : :*  *E--YH-**PTIYHLR*-L-*---K-DLRL*YLALAH*IK*RGNFLIEG-**-*
Motif:  *-*E--YH-**PTIYHLR*-L-*---K-DLRL*YLALAH*IK*RGNFLIEG-**--N--*
```

FIG. 2A

```
SM      QRLFQEFLAVYDNTFENSS------LQEQNVQVEEILTDKISKSAKKDRVLKLFPNEKSN
SP      DKLFIQLVQTYNQLFEENP------INASGVDAKAILSARLSKSRRLENLIAQLPGEKKN
ST      QKNFQDFLDTYNAIFESDL------SLENSKQLEEIVKDKISKLEKKDRILKLFPGEKNS
LI      DGIYKQFIQTYNQVFASGIEDGSLKKLEDNKDVAKILVEKVTRKEKLERILKLYPGEKSA
         :  : ::: .*:  *  ..         ..  :   *:   ::::   :  :.::    *.**.
Motif:  *--*-***--Y*--f----------------*---I*--****--*-*-**---P-EK--

SM      GRPAEFLKLIVGNQADFKKHPELEEKAPLQFSKDTYEEELEVLLAQIGDNYAELFLSAKK
SP      GLFGNLIALSLGLTPNFKSNFDLAEDAKLQLSKDTYDDDLDNLLAQIGDQYADLFLAAKN
ST      GIFSEFLKLIVGNQADFRKCFNLDEKASLHFSKESYDEDLETLLGYIGDDYSDVPLKAKK
LI      GNFAQFISLIVGSKGNFQKPFDLIEKSDIECAKDSYEEDLESLLALIGDEYAELFVAAKN
         * *.::;  *  :*     :*:.  *:*  *.:  :. :*::*:::*;  **. ***:*:::*;  **;
Motif:  G-F-***-L-*G---*F---*L-E-*-*---KY*L*-LL--IGD*Y***F*-AK*

SM      LYDSILLSGILTVTDVGTKAPLSASMIQRYNEHQMDLAQLKQFIRQKLSDKYNEVFSDVS
SP      LSDAILLSDILRVNTEITKAPLSASMIKRYDEHHQDLTLLKALVRQQLPEKYKEIFFDQS
ST      LYDAILLSGFLTVTDNETEAPLSSAMIKRYNEHKEDLALLKEYIRNISLKTYNEVFKDDT
LI      AYSAVVLSSIITVAETETNAKLSASMIERFDTHEEDLGELKAFIKLHLPKHYEEIFSNTE
         .:::**.::  *   *:*  **::**:*::  *.  **  **   ::    . *:*:*  :
Motif:  ---****LS-**-V----T*A-LS**MI*R**-H--DL--LK--**------Y*E*F-*--

SM      KDGYAGYIDGKTNQEAFYKYLKGLLNKIEGSGYFLDKIEREDFLRKQRTFDNGSIPHQIH
SP      KNGYAGYIDGGASQEEFYKFIKPILEKMDGTEELLVKLNREDLLRKQRTFDNGSIPHQIH
ST      KNGYAGYIDGKTNQEDFYVYLKKLLAEFEGADYFLEKIDREDFLRKQRTFDNGSIPYQIH
LI      KNGYAGYIDGKTKQADFYKYMKNTLENIEGADYPIAKIEKENFLRKQRTFDNGAIPHQLH
        *.********  :.*   **  **  ::*   *  :::*:   ::  *:::******** :**;*:*
Motif:  K-GYAGYIDG-*-Q--FY-K--L-*G*----K*E**LRKQRTFDNG*IP*Q*H
```

FIG. 2B

```
SM      LQEMRAIIRRQAEFYPFLADNQDRIEKLLTFRIPYYVGPLARGKSDFAWLSRKSADKITP
SP      LGELHAILRRQEDFYPFLKDNREKIEKILTFRIPYYVGPLARGNSRFAWMTRKSEETITP
ST      LQEMRAILDKQAKFYPFLAKNKERIEKILTFRIPYYVGPLARGNSDFAWSIRKRNEKITP
LI      LEELEAILHQQAKYYPFLKENYDKIKSLVTFRIPYFVGPLANGQSEFAWLTRKADGEIRP
         * *:;**; :*  .:****  .*  ::*:.::*******;*****.*:*  ***   **      * *
Motif:  L-E*-AI*-*Q--*YPFL--N-**I*-**TFRIPY*VGPLA-G*S-FAW--RK----I-P SM      WNFDEIVDKESSAEAFINRMTNYDLYLPNQKVLPKHSLLYEKFTVYNELTKVKYKTE-QG
SP      WNFEEVVDKGASAQSFIERMTNFDKNLPNEKVLPKHSLLYEYFTVYNELTKVKYVTEGMR
ST      WNFEDVIDKESSAEAFINRMTSFDLYLPEEKVLPKHSLLYETFNVYNELTKVRFIAESMR
LI      WNIEEKVDFGKSAVDFIEKMTNKDTYLPKENVLPKHSLCYQKYLVYNELTKVRYIND-QG
        **:;;  :*     **    **:;**. *    **;;;*******  *;  ;  ********;;   :
Motif:  WN***-*D---SA--FI**MT--D--LP***VLPKHSL-Y*-*-VYNELTKV**--*---

SM      KTAFFDANMKQEIFDGVPKVYRKVTKDKLMDFLEKEFDEFRIVDLTGLDKENKVFNASYG
SP      KPAFLSGEQKKAIVDLLFKTNRKVTVKQLKEDYFKKIECFDSVEISGVEDR---FNASLG
ST      DYQFLDSKQKKDIVRLYFKDKRKVTDKDIIEYL-HAIYGYDGIELKGIEKQ---FNSSLS
LI      KTSYFSGQEKEQIFNDLFKQKRKVKKKDLELFL-RNMSHVESPTIEGLEDS---FNSSYS
          .  ;;..; *; *. ** ***. ..;     ;;          ; *;;.       **;* .
Motif:  ---*--*-K*-I----FK--RKV----*------*-*--------*-G**------FN*S--

SM      TYHDLCKIL-DKDFLDNSKNEKILEDIVLTLTLFEDREMIRKRLENYSDLLTKEQVKKLE
SP      TYHDLLKIIKDKDFLDNEENEDILEDIVLTLTLFEDREMIEERLKTYAHLFDDKVMKQLK
ST      TYHDLLNIIINDKEFLDDSSNEAIIEEIIHTLTIFEDREMIKQRLSKFENIFDKSVLKKLS
LI      TYHDLLKVGIKQEILDNPVNTEMLENIVKILTVFEDKRMIKEQLQQFSDVLDGVVLKKLE
        ***** ;;  .;;;**;   *   ;;*;*;   **;***;.**.;;*.  ;  .;;     ;*;*.
Motif:  TYHDL-**----***LD*--N--**E*I*--LT*FED*-MI-**L--*--**----*K*L-
```

```
SM      GNSDK--LIPRKTKFYWDTKKYGGFDSPIVAYSILVIADIEKGKSKLLKTVKALVGVTIM
SP      RMSDK--LIARKKD---WDPKKYGGFDSPTVAYSVLVVAKVEKGKSKLLSVKELLGITIM
ST      PNSNENLVGAKEY---LDPKKYGGYAGISNSFTVLVKGTIEKGAKKKITMVLEFQGISIL
LI      GNSSK--LIPRKTN---WDPMKYGGLDSPMMAYAVVI--EYAKGKN-KLVFEKKIRVTIM
        **.:  *:   *    :  ****  .*     .     :   :      :: :**:
Motif:  --NS---L*--*--K------D--KYGG----*-*******---*---KG---K*-----*--*--*I*

SM      EKMTFERDPVAFLERKGYRNVQEENIIKLPKYSLEKLELENGRKLLAS------ARELQK
SP      ERSSFEKMPIDFLEAKGYKEVKKDLIIKLPKYSLFELENGRKRMLAS-------AGELQK
ST      DRINYRIDKLNFLLEKGYKDI--ELIIELPKYSLFELSDGSRRMLASILSTNNKRGEIHK
LI      ERKAFEKDEKAFLEEQGYRQP--KVLAKLPKYTLYECEEGRRMLAS--------AMEAQK
         : :::   **  : ****   .  :  :*****:: .:   :*:***        * :*
Motif:  **-------*--*--*--FL--*GY*---*--*LPKY*L**--*G--*R*LAS------E--*K SM      GNEIVLPMHLGTLLYHAKNIHKV-----DEPKHLDYVDKHKDEFKELLDVVSNFSKKYT
SP      GNELALPSKYVMFLYLASHYEKLKGSPEDMEQKQL-FVEQHKHYLDEIIEQISEFSKRVI
ST      GNQIFLSQKFVKLLYHAKRISNT-----INEMHRKYVENHKKEFEELFYYILEFNENYV
LI      GMQQVLPMHLVTLLHHAAWCEVS-----DGKSLDYIESNREMFAELLAHVSEFAKRYT
        *:  :::  :  ** :::::: :        . :*::*:: : *.*   ::
Motif:  GM*---L*--*--A---------*L*--*-------------E---*-------*F--*---

SM      LAEGNLEKIKELYAQMNGEDLKELASSFI------NLLTFTAIGAPATFKFFDKMIDR
SP      LADAMLDKVLSAYNKHRDKPIREQAENII------HLFTLTNLGAPAAFKYFDTTIDR
ST      GAKKNGKLLMNSAFQSWQMHSIDELCSSFIGPTGSERKGLFELTSRGSAADFEFLGVKIPR
LI      LAEAMLNKINQLFEQMKEGDIKATAQSFV------DLMAPNAMGAPASFKFFETTIER
         * : :.*: : :    : .  : ::.*:       * :  :. .*:::*::*  :
Motif:  --A--M------*----*----*----*--**---------L*--*--G**-A-F***--I-R
```

FIG. 2F

```
SM      KR-YTSTTEILMATLIHQSITGLYETRIDLNKLGGD    (SEQ ID NO:1)
SP      KR-YTSTKEVLDATLIHQSITGLYETRIDLSQLGGD    (SEQ ID NO:2)
ST      YRDYTPSSLLKDATLIHQSVTGLYETRIDLAKLGEG    (SEQ ID NO:4)
LI      KR-YNNLKELLNSTIYQSITGLYESRKRLD----D     (SEQ ID NO:5)
         *  .  :  ::  ::***:*******:*:  *

Motif:  -R-Y-----*-**T*I-QS*TGLYE*R--L------    (SEQ ID NO:14)
```

FIG. 2G

Alignment of the N terminal RuvC-like Domains disclosed in Chylinski et al.
(excluding sequence outliers).
(CLUSTAL format alignment by MAFFT (v7.058b))

```
1, 12   DIGTNSVGWAVT    (SEQ ID NO:120)
3, 20   DVGTNSVGWAVT    (SEQ ID NO:121)
15      DMGTNSVGWAVT    (SEQ ID NO:122)
4       DVGTSSVGWAVT    (SEQ ID NO:123)
7       DIGTASVGWAVT    (SEQ ID NO:52)
6       DVGTGSVGWAVT    (SEQ ID NO:53)
9       DIGTNSVGWAVV    (SEQ ID NO:54)
10      DIGTNSVGWAVI    (SEQ ID NO:55)
11      DIGTNSVGWAVL    (SEQ ID NO:56)
42      DLGTNSIGWAVL    (SEQ ID NO:57)
48      DLGTNSIGWAVV    (SEQ ID NO:58)
43      DLGTNSIGWAI-    (SEQ ID NO:59)
2       DLGTNSIGWALV    (SEQ ID NO:60)
14      DIGTNSVGWCVT    (SEQ ID NO:61)
5       DIGTNSVGYAVT    (SEQ ID NO:62)
16      DMGTGSLGWAVT    (SEQ ID NO:63)
8       DLGTSSVGWAAI    (SEQ ID NO:64)
22      DLGTGSVGWAVV    (SEQ ID NO:65)
23      DLGVGSVGWAIV    (SEQ ID NO:66)
24      DLGIASIGWAII    (SEQ ID NO:67)
25      DLGIASVGWAIV    (SEQ ID NO:68)
26      DLGVASVGWSIV    (SEQ ID NO:69)
28      DIGIASVGWAIL    (SEQ ID NO:70)
32      DLGISSVGMSVI    (SEQ ID NO:71)
33      DLGIASVGWSVI    (SEQ ID NO:72)
39      DWGISIGWAVI     (SEQ ID NO:73)
34      DLGVGSIGWAVI    (SEQ ID NO:74)
47      DLGVGSIGFAIV    (SEQ ID NO:75)
50      DTGTNSLGWAIV    (SEQ ID NO:76)
49      DLGTNSIGWCLL    (SEQ ID NO:77)
18      DIGTDSLGWAVF    (SEQ ID NO:78)
41      DIGSNSIGFAVV    (SEQ ID NO:79)
45      DLGVGSIGVAVA    (SEQ ID NO:80)
        DLGIASGWGVV
```

FIG. 3A

| | | |
|---|---|---|
| 21 | DLGIASVGWCLT | (SEQ ID NO:81) |
| 27 | DIGIGSVGVGIL | (SEQ ID NO:82) |
| 29 | DIGITSVGYGLI | (SEQ ID NO:83) |
| 30 | DIGITSVGFGII | (SEQ ID NO:84) |
| 31 | DVGITSTGYAVL | (SEQ ID NO:85) |
| 40 | DLGITSFGYAIL | (SEQ ID NO:86) |
| 17 | DIGNASVGWSAP | (SEQ ID NO:87) |
| 19 | DVGTNSCGWVAM | (SEQ ID NO:88) |
| 35 | DVGERSIGLAAV | (SEQ ID NO:89) |
| 36 | DVGLMSVGLAAV | (SEQ ID NO:90) |
| 37 | DVGLMSVGLAAI | (SEQ ID NO:91) |
| 38 | DVCTFSVGLAAI | (SEQ ID NO:92) |
| 13 | DICTGSVGYACM | (SEQ ID NO:92) |
| 44 | DLGTTSIGFAHI | (SEQ ID NO:94) |
| 46 | DLGTNSIGSSVR | (SEQ ID NO:95) |
| | * * * * | |

FIG. 3B

Alignment of the N terminal RuvC-like Domains disclosed in Chylinski et al.
(CLUSTAL format alignment by MAFFT (v7.058b))

```
1,12   D----IGTNSVGWAVT  (SEQ ID NO:120)
3,20   D----VGTNSVGWAVT  (SEQ ID NO:121)
15     D----MGTNSVGWAVT  (SEQ ID NO:122)
4      D----VGTSSVGWAVT  (SEQ ID NO:123)
7      D----IGTASVGWAVT  (SEQ ID NO:52)
6      D----VGTGSVGWAVT  (SEQ ID NO:53)
9      D----IGTNSVGWAVV  (SEQ ID NO:54)
10     D----IGTNSVGWAVI  (SEQ ID NO:55)
52     D----IGTNSVGWAVI  (SEQ ID NO:96)
11     D----IGTNSVGWAVL  (SEQ ID NO:56)
42     D----IGTNSVGWAVV  (SEQ ID NO:57)
48     D----LGTNSIGWAI-  (SEQ ID NO:58)
43     D----LGTNSIGWAIV  (SEQ ID NO:59)
2      D----IGTNSVGWCVI  (SEQ ID NO:60)
14     D----IGTNSVGIAVT  (SEQ ID NO:61)
5      D----MGTGSIGWAVT  (SEQ ID NO:62)
16     D----IGTSSVGWAAI  (SEQ ID NO:63)
8      D----LGTGSVGWAVV  (SEQ ID NO:64)
22     D----LGVGSVGWAIV  (SEQ ID NO:65)
23     D----LGIASIGWAII  (SEQ ID NO:66)
24     D----LGIASVGWAIV  (SEQ ID NO:67)
68     D----LGIASVGWAVV  (SEQ ID NO:97)
25     D----LGVASVGWSIV  (SEQ ID NO:68)
26     D----IGIASVGWAIL  (SEQ ID NO:69)
66     D----IGIASVGWAVL  (SEQ ID NO:98)
59     D----IGIASIGWAII  (SEQ ID NO:99)
61     D----IGIASVGWAII  (SEQ ID NO:100)
64     D----IGIASVGWAVI  (SEQ ID NO:101)
62     D----VGIASVGWAL-  (SEQ ID NO:102)
67     D----IGIASVGWAMV  (SEQ ID NO:103)
32     D----IGIASVGWSVI  (SEQ ID NO:71)
28     D----LGISSVGWSVI  (SEQ ID NO:70)
63     D----IGITSVGWAVI  (SEQ ID NO:104)
```

FIG. 4A

```
33   D-----VGIGSIGWAVI
57   D-----LGISSLGWAIV
39   D-----LGVGSIGFAIV
34   D-----IGYASIGWAVI
50   D-----LGTNSIGWCLL
54   D-----LGTNSIGWGLL
47   D-----TGTNSLGWAIV
49   D-----IGTDSLGWAVF
51   D-----LGSTSLGWAIP
58   D-----IGISSIGWAPS
21   D-----LGIASVGWCLT
45   D-----LGIASCGWGVV
18   D-----LGSNSIGFAVV
65   D-----IGTTSIGFSVI
29   D-----IGITSVGYGLI
30   D-----IGITSVGPGII
44   D-----LGTTSIGPAHI
27   D-----IGIGSVGVGIL
41   D-----LGVGSIGVAVA
31   D-----VGITSTGYAVL
40   D-----LGITSPGYAIL
53   D-----IGTSSIGWWLY
55   D-----LGSNSLGWFVT
56   D-----LGANSLGWFVV
17   D-----IGMASVGWNSAP
19   D-----VGTNSCGWVAM
35   D-----VGERSIGLAAV
36   D-----VGLNSVGLAAV
37   D-----VGLMSVGLAAI
38   D-----VGTFSVGLAAI
13   D-----IGTGSVGYACM
46   D-----LGTNSIGSSVR
60   DIGLRIGITSCGWSI-
69   D-----MGAKYTGVFYA
73   D-----LGGKNTGFFSF
74   D-----LGVKNTGVFSA
70   D-----LGAKFTGVALY
71   D-----LGGKFTGVCLS
72   D-----LGGTYTGTFIT
```

FIG. 4B

Alignment of the HNH-like Domains disclosed in Chylinski et al.
(CLUSTAL format alignment by MAFFT (v7.058b))

```
1   YDIDHIYPRS-LTKD------DSP-DMLVLCERTAN  (SEQ ID NO:196)
2   -DIDHIYPRSKVID------DSP-DMLVLVLKNEN  (SEQ ID NO:197)
3   -DRDHIYPQS-KIKD------DSI-DMLVLVNKTYN  (SEQ ID NO:198)
4   -DIDHIYPQS-KIKD------DSI-TNRVLVEKQIN  (SEQ ID NO:195)
6   -DIDHIYPQS-KIKD------DSI-SNRVLVCSSCN  (SEQ ID NO:124)
5   -DIDHIYPQS-KTMD------DSL-NNRVLVKDNYN  (SEQ ID NO:125)
7   -DQDHIYPKS-KIYD------DSL-ENRVLVKKNLN  (SEQ ID NO:126)
8   -QIDHIVPQS-LVKD------DSP-DMRVLVVPSEN  (SEQ ID NO:127)
9   -DIDHIIPQA-PIKD------NSI-DMRVLTSSKEN  (SEQ ID NO:128)
12  -DIDHIIPQA-FLKD------NSI-DMKVLVSSASN  (SEQ ID NO:129)
16  -DIDHIIPQA-YTKD------NSL-DMRVLVSNITN  (SEQ ID NO:130)
11  -DIDHIVPQS-FITD------NSI-DMLVLTSSAGN  (SEQ ID NO:131)
10  -DVDHIVPQS-FLKD------DSI-DMKVLTRSDKN  (SEQ ID NO:132)
14  -NIDHIYPOS-MVKD------DSL-DMKVLVQSEIN  (SEQ ID NO:133)
18  -DIDHILPQS-LIKD------DSL-DMRVLVNATIN  (SEQ ID NO:134)
19  -DIDHILPQS-PIKD------DSL-EMRVLVKKAVN  (SEQ ID NO:135)
13  -EVDHIIPRS-FIKD------DSI-DMKVLVIKKMN  (SEQ ID NO:136)
15  -EVDHIIPRS-YIKD------DSP-ENKVLVYREEN  (SEQ ID NO:137)
17  -DIDHIIPQA-VTQN------DSI-DMRVLVARAEN  (SEQ ID NO:138)
22  -EIDHIIPYS-ISPD------DSS-SNKLLVLABSN  (SEQ ID NO:139)
24  -EIDHIIPYS-LCPD------DSS-ANKVLVHKQSN  (SEQ ID NO:140)
32  -DIDHIIPYS-RSMD------DSY-SNKVLVLSGEN  (SEQ ID NO:141)
63  -DIDHIIPYS-KSMD------DSF-NNKVLCLABEN  (SEQ ID NO:142)
59  -DIDHIIPYS-RSMD------DSY-MNKVLVFTKQN  (SEQ ID NO:143)
65  -QIDHIYPYS-RSPD------DSY-MNKVLVLTDEN  (SEQ ID NO:144)
64  -EIDHIIPRS-RSPD------DSL-SNKILVLGSEN  (SEQ ID NO:145)
68  -EIDHIIPFS-RTMD------DSP-MNKVLVLABSN  (SEQ ID NO:146)
69  -EIDHALPFS-RTMD------DSP-MNKVLVLGSEN  (SEQ ID NO:147)
28  -EIDHIIPIS-ISLD------DSI-TNKVLVTHREN  (SEQ ID NO:148)
30  -EVDHIIPIS-ISLD------DSI-TNKVLVTHREN  (SEQ ID NO:149)
62  -QVDHALPYS-RSYD------DSK-NNKVLVLTHEN  (SEQ ID NO:150)
27  -EVDHILPLS-ITPD------DSL-ANKVLVVATAN  (SEQ ID NO:151)
26  -EIDHIIPRS-ISPD------DAR-SNKVLVYRSEN  (SEQ ID NO:152)
```

FIG. 5A

```
29  :EVDHILPRS-VSFD------NSY-HNKVLVKQSEN  (SEQ ID NO:153)
67  :DIDHILPYS-ITFD------DSP-RNKVLVTSQEN  (SEQ ID NO:154)
58  :EIDHILPRS-RSAD------DSP-ANKVLCLARAN  (SEQ ID NO:155)
51  :EIEHILPFS-LTLD------DSM-ANKTVCFRQAN  (SEQ ID NO:156)
55  :DIDHILPFS-VSLD------DSA-ANKVVCLREAN  (SEQ ID NO:157)
57  :DIDHILPFS-ISWD------DSA-ANKVVCMRYAN  (SEQ ID NO:158)
56  :DIDHILPVA-MTLD------DSP-ANKIIOMRYAN  (SEQ ID NO:159)
54  :DVDHILPYS-RTLD------DSP-PNRTLCLREAN  (SEQ ID NO:160)
52  :EIEHILPFS-RTLD------DSL-MNRTVAMRRAN  (SEQ ID NO:161)
31  :EVDHIIPYS-ISWD------DSY-TNKVLTSAKCN  (SEQ ID NO:162)
45  :QVDHILPWS-RPGD------DSY-LNKTLCTARSN  (SEQ ID NO:163)
53  :QVDHILPFS-KTLD------DSP-ANKVLAQHDAN  (SEQ ID NO:164)
60  :QIDHAPPLS-RSLD------DSQ-SNKVLCITSSN  (SEQ ID NO:165)
21  :DIDHIVPRS-ISPD------DSP-SNLIVNKLDN   (SEQ ID NO:166)
23  :EIEHIIPYS-MSYD------NSQ-ANKILTEKAEN  (SEQ ID NO:167)
25  :EIDHVIPYS-KSAD------DSW-FNKLLVKKSTN  (SEQ ID NO:168)
49  :EMDHILPYS-RSLD------NGW-HNRVLVHGKDN  (SEQ ID NO:169)
33  :EVDHIVPYS-LILD------NTI-MNKALVYAEEN  (SEQ ID NO:170)
42  :EIEHIVPQS-LYFD------DSP-SNKVICEAEVN  (SEQ ID NO:171)
43  :DIEHIVPQA-RLFD------DSP-SNKTLEARSVN  (SEQ ID NO:172)
44  :EIEHIVPKA-RVFD------DSP-SNKTLTFHRIN  (SEQ ID NO:173)
20  :DKDHIIPQS-MKKD------DSIMNLVLVNKNAN   (SEQ ID NO:174)
66  :EVEHIWPRS-RSPD------NSD-RNKTLCRKDVN  (SEQ ID NO:175)
61  :IVNHIIPIN-RSPD------DTY-HNRVLTLTETK  (SEQ ID NO:176)
46  :DMEHIIPKS-ISPD------NSD-QMLTLCESYYN  (SEQ ID NO:177)
47  :DIEHIIPRS-AGGD------STK-MNLUTLCSSRFN (SEQ ID NO:178)
48  :DIEHTIPRS-ISQD------NSQ-MNKTLCSLKFN  (SEQ ID NO:179)
50  :DIDHVIPLA-RGGR------DSL-DNMVLCQSDAN  (SEQ ID NO:180)
39  :DIEHIPPIA-ESED------NGR-MNLVISHSACN  (SEQ ID NO:181)
41  :DVDHIVPRD-DTAD------NSY-GNKVVAHRQCN  (SEQ ID NO:182)
40  :DIEHIVPQS-LGGL------STD-YNTIVTLKSVN  (SEQ ID NO:183)
35  :ELDHIVPRT-DCGS------NRH-ENLAITCGACN  (SEQ ID NO:184)
36  :EMDHIVPRKGVGST------NTR-TNFAAVCAECN  (SEQ ID NO:185)
37  :EMDHIVPRKGVGST------NTR-VNLAAACAACN  (SEQ ID NO:186)
38  :EMDHIVPRAGQGST------NTR-ENLVAVCHRCN  (SEQ ID NO:187)
70  :EIDHIIPRS-LIKDARGIVFMAE-PMLIYASSRGN  (SEQ ID NO:188)
71  :ELDHIIPRS-LTGRTKKTVPNSE-ANLIYCSSKGN  (SEQ ID NO:189)
73  :EIDHIIPRS-LTLKKSESIYNSE-VNLIFVSAQGN  (SEQ ID NO:190)
```

FIG. 5B

```
72  -EIDHIYPRS-LSKKHPGVIFNSE-VNLIYCSSQGN  (SEQ ID NO:191)
74  -EIDHILPRS-HTLKIYGTVPNPE-GNLIYVHQKCN  (SEQ ID NO:192)
75  -ELDHIIPRS-HKKY---GTLNDE-ANLICVTRGDN  (SEQ ID NO:193)
34  -BLEHIVPHS-PRQS-------NAL--SSLVLTWPGVN  (SEQ ID NO:194)
         :*        *              :
```

FIG. 5C

Alignment of the HNH-like Domains disclosed in Chylinski et al. (excluding sequence outliers). (CLUSTAL format alignment by MAFFT (v7.058b))

```
1   YDIDHIYPRS-LTKDDS-FDMLVLCERTAN   (SEQ ID NO:196)
2   -DIDHIYPRSKVIKDDS-FDMLVLVLKNEN   (SEQ ID NO:197)
3   -DRDHIYPQS-KIKDDS-IDMLVLVNKTTN   (SEQ ID NO:198)
4   -DIDHIYPRS-KIKDDS-ITNRVLVBKDIN   (SEQ ID NO:195)
6   -DIDHIYPQS-KIKDDS-ISNRVLVCSSCN   (SEQ ID NO:124)
5   -DIDHIYPQS-KTMDDS-LNMRVLVKKNTN   (SEQ ID NO:125)
7   -DQDHIYPKS-KIYDDS-LENRVLVKKQLN   (SEQ ID NO:126)
8   -QIDHIVPQS-LVKDDS-FDMRVLVVPSEN   (SEQ ID NO:127)
9   -DIDHIIPQA-FIKDNS-IDMRVLTSSKEN   (SEQ ID NO:128)
12  -DIDHIIPQA-FLKDNS-IDMKVLVSSASN   (SEQ ID NO:129)
16  -DIDHIIPQA-YTKDNS-LDMRVLVSNITN   (SEQ ID NO:130)
11  -DIDHIVPQS-FITDNS-IDMLVLTSSAGN   (SEQ ID NO:131)
10  -DVDHIVPQS-FLKDDS-IDMKVLTRSDKN   (SEQ ID NO:132)
14  -NIDHIYPQS-MVKDDS-LDMKVLVQSEIN   (SEQ ID NO:133)
18  -DIDHIVPQS-LIKDDS-LDMKVLVMATIN   (SEQ ID NO:134)
19  -DIDHILPQS-FIKDDS-LENRVLVMKAVN   (SEQ ID NO:135)
13  -EVDHIIPRS-FIKDDS-LDMKVLVIKKMN   (SEQ ID NO:136)
15  -EVDHIIPRS-YIKDDS-FEMKVLVYREEN   (SEQ ID NO:137)
17  -DIDHIIPQA-VTQNDS-IDMKVLVARAEN   (SEQ ID NO:138)
21  -DIDHIIPRS-ISFDDS-FSNLJVIVMKLDN  (SEQ ID NO:166)
22  -EIDHIIPYS-ISFDDS-SSMKLIVTLAESN  (SEQ ID NO:139)
24  -EIDHIIPYS-LCFDDS-SAMKVLVHKQSN   (SEQ ID NO:140)
28  -EIDHIIPIS-ISLDDS-INMKVLVLSKAN   (SEQ ID NO:148)
20  -EVDHIIPIS-ISLDDS-ITNKVLVTHREN   (SEQ ID NO:149)
27  -EVDHIIPLS-ITFDDS-LANKVLVYATAN   (SEQ ID NO:151)
26  -EIDHIIPRS-ISFDDA-RSMKVLVTRSEN   (SEQ ID NO:152)
29  -EVDHIIPRS-VSPDNS-YHMKVLVKQSEN   (SEQ ID NO:153)
31  -EVDHIIPYS-ISWDDS-YTNKVLTSAKCN   (SEQ ID NO:162)
32  -EIDHIIPYS-LILDNT-INMKALVYAEEN   (SEQ ID NO:141)
23  -EIEHIIPYS-MSYDNS-QANKILTEKAEN   (SEQ ID NO:167)
33  -EVDHIVPYS-LILDNT-INMKALVYAEEN   (SEQ ID NO:170)
25  -EIDHVIPYS-KSADDS-WFMKLLVKKSTN   (SEQ ID NO:168)
49  -EMDHIIPYS-RSLDNG-WHNRVLVHGKDN   (SEQ ID NO:169)
42  -EIEHVIPQS-LYFDDS-FSMKVICEAEVN   (SEQ ID NO:171)
43  -DIEHIIPQA-RLFDDS-PSMKTLEARSVN   (SEQ ID NO:172)
```

FIG. 6A

| | | |
|---|---|---|
| 44 | -EIEHIVPKA-RVFDDS-FSNKTLTFHRIN | (SEQ ID NO:173) |
| 20 | -DKDHIIPQS-MKKDDSIINNLVLVNKNAN | (SEQ ID NO:174) |
| 45 | -QVDHILPWS-RFGDDS-YLNKTLCTARSN | (SEQ ID NO:163) |
| 50 | -DIDHVIPLA-RGGRDS-LDNMVLCQSDAN | (SEQ ID NO:180) |
| 46 | -DMEHTIPKS-ISFDNS-DQNLTLCESYYN | (SEQ ID NO:177) |
| 47 | -DIEHTIPRS-AGGDST-KMNLTLCSSRFN | (SEQ ID NO:178) |
| 48 | -DIEHTIPRS-ISQDNS-QMNKTLCSLKFN | (SEQ ID NO:179) |
| 39 | -DIEHLFPIA-ESEDNG-RNNLVISHSACN | (SEQ ID NO:181) |
| 41 | -DVDHIFPRD-DTADNS-YGNKVVAHRQCN | (SEQ ID NO:182) |
| 40 | -DIEHIVPQS-LGGLST-DYNTIVTLKSVN | (SEQ ID NO:183) |
| 35 | -ELDHIVPRT-DGGSNR-HENLAITCGACN | (SEQ ID NO:184) |
| 36 | -EMDHIVPRKGVGSTNT-RTNFAAVCAECN | (SEQ ID NO:185) |
| 37 | -EMDHIVPRKGVGSTNT-RVNLAAACAACN | (SEQ ID NO:186) |
| 38 | -EMDHIVPRAGQGSTNT-RENLVAVCHRCN | (SEQ ID NO:187) |
| 34 | -ELEHIVPHS-FRQSNA-LSSLVLTWPGVN | (SEQ ID NO:194) |

FIG. 6B

CRISPR/CAS-RELATED METHODS AND COMPOSITIONS FOR TREATING HERPES SIMPLEX VIRUS

CROSS-REFERENCES TO RELATED APPLICATIONS

This application is a Continuation of International Patent Application No. PCT/US16/59502, filed Oct. 28, 2016, which claims priority to U.S. Provisional Application No. 62/249,071, filed Oct. 30, 2015 and U.S. Provisional Application No. 62/249,159, filed Oct. 30, 2015, the contents of each of which are hereby incorporated by reference in their entirety herein, and to each of which priority is claimed.

STATEMENT OF GOVERNMENT INTEREST

This invention was made with government support under Grant No. 1R43AI120302-01 awarded by the National Institutes of Health. The government has certain rights in the invention.

SEQUENCE LISTING

The present specification makes reference to a Sequence Listing (submitted electronically as a .txt file named "0841770175SL.txt" on Apr. 30, 2018). The 0841770175SL.txt file was generated on Apr. 30, 2018 and is 11,189,371 bytes in size. The entire contents of the Sequence Listing are hereby incorporated by reference.

FIELD OF THE INVENTION

The disclosure relates to CRISPR/CAS-related methods, compositions and genome editing systems for editing of a target nucleic acid sequence, e.g., editing a RS1, RL2, and/or LAT gene, and applications thereof in connection with herpes simplex virus (HSV).

BACKGROUND

Herpes simplex virus (HSV), e.g., herpes simplex virus type 1 (HSV-1) and herpes simplex virus type 2 (HSV-2), is a ubiquitous and highly contagious pathogen. HSV-1 generally causes intermittent, painful blistering of the mouth and mucous membranes. HSV-2 generally causes intermittent, painful blistering in the genital region. HSV can cause lifelong, recurring bouts of viral reactivity.

The majority of the population develops HSV-1 infection during childhood. By adulthood, up to 80% of the population in the U.S. is infected with HSV-1. New HSV-1 infections occur at a rate of 1.6 cases per 100 person years (Langenberg et al., 1999; New England Journal of Medicine 341:1432-1438). The most severe manifestations of HSV-1 infection include, e.g., keratitis, encephalitis, and meningitis.

More than 500 million people are infected with HSV-2 worldwide. Up to 23 million individuals are infected for the first time each year. In the U.S., approximately 1 in 5 adults is seropositive for HSV-2 infection (Xu et al., Abstract 739 in 42nd Annual Meeting of the Infectious Diseases Society of America; Sep. 30, 2004). The incidence of HSV-2 is increasing: since 1976, there has been a 30% increase in the presence of HSV-2 seropositivity in adults in the U.S. (Fleming et al., New England Journal of Medicine 1997; 337:1105-11). Infection with HSV-2 increases the risk of acquiring HIV infection, especially among patients with active lesions.

Infection with HSV-1 and/or HSV-2 is permanent. After initial infection with HSV-1 or HSV-2, the virus establishes latent infection that lasts for the lifetime of the host. Initial infection with HSV-1 generally causes painful blistering of the mucous membranes of the mouth, including the lips, mouth and nose. HSV-1 initial infection less commonly affects the anogenital region, causing painful blistering of the mucous membranes of the genital and anal region. Initial infection with HSV-2 generally causes painful blistering of the mucous membranes of the anogenital region. HSV-2 initial infection less commonly affects the mouth, causing painful blistering of the mucous membranes of the lips, mouth and nose.

After initial infection, HSV-1 and HSV-2 establish latent infection in all subjects. Following establishment of latent infection, reactivation of HSV-1 or HSV-2 can occur at any point during the lifetime of the subject. Reactivation of HSV-1 or HSV-2 is more likely to occur in the elderly and in immunocompromised individuals, including in those who have cancer, those who have HIV/AIDs and in those who have undergone solid organ or hematopoietic stem cell transplant.

HSV-1 and HSV-2 both cause ocular herpes. Historically, HSV-1 has been the causative agent in the majority of ocular herpes infections. However, HSV-2 related ocular infections have been increasing in incidence worldwide over the recent years.

Ocular infection with HSV-1 or HSV-2 can affect the epithelium of the eye, causing keratitis. Keratitis is the most common form of ocular herpes. HSV-related keratitis is the most common cause of infectious blindness in the developed world (Dawson et. al., Suvey of Ophthalmology 1976; 21(2): 121-135). Worldwide, there are approximately 1.5 million cases of HSV-related ophthalmologic disease and 40,000 cases of HSV-related blindness or severe monocular visual impairment annually (Krawczyk et. al., Public Library of Science One 2015; 10(1): e0116800. Farooq and Shukla 2012; Survey of Ophthalmology 57(5): 448-462). The incidence of ocular HSV infection appears to be increasing in the U.S. (Liesegang et al. 1989, Archives of Ophthalmology 107:1155-1159. Baratz et al. 2009, Investigations in Ophthalmologic Visual Science 50 e-abstract5044). There are 15.6 cases of epithelial keratitis per 100,000 person-years, or approximately 50,000 cases per year in the U.S. (Farooq and Shukla 2012; Survey of Ophthalmology 57(5): 448-462).

Ocular herpes may also affect the retina, causing retinitis. HSV-related retinitis occurs less frequently than HSV-related keratitis but carries a much greater risk of permanent visual damage. HSV-related retinitis most often affects adults and can cause acute retinal necrosis (ARN). ARN causes permanent visual damage in more than 50% of subjects (Roy et al., Ocular Immunology and Inflammation 2014; 22(3):170-174).

Newborns are a population at particular risk for developing severe HSV-1 and HSV-2 infections. The disease is transmitted from the mother to the fetus during childbirth. The chance of maternal-fetal transmission is highest in cases where the mother developed primary HSV-1 or HSV-2 infection during pregnancy. The incidence of neonatal herpes is approximately 4-30 per 100,000 births (Brown Z A, et al., 2003; Journal of the American Medical Association; 289(2): 203-209. Dinh T-H, et al., 2008; Sexually Transmitted Disease; 35(1): 19-21). Neonates may develop severe HSV-related keratitis, retinitis, encephalitis and/or meningitis. Neonatal ocular herpes can result in immediate, permanent vision loss. Ocular HSV puts neonates at risk for later developing ARN. There are no curative or preventative treatments for HSV-1 or HSV-2. Therapy is primarily given during acute infection. Primary HSV-1 or HSV-2 infections can be treated with antiviral therapy, including acyclovir, valacyclovir and famciclovir. These therapies may reduce viral shedding, decrease pain and improve healing time of lesions. Re-activated, latent infections may resolve without treatment (may be self-limiting) or may be treated with anti-viral therapy. Antiviral therapy may be given prophylactically in certain situations, including during childbirth in a mother with a recent HSV-1 or HSV-2 infection or reactivation.

Vaccines are in development for the prevention of HSV-1 and HSV-2 infections. However, in controlled clinical trials, vaccination efficacy has been limited. A recent vaccine for both HSV-1 and HSV-2 infections was only 35% effective in preventing HSV-1 infections (Belshe et al., 2012; New England Journal of Medicine 366(1): 34-43).

Despite advances in antiretroviral therapies, there remains a need for the treatment, prevention and/or reduction of HSV-1 and HSV-2 infections, particularly the treatment, prevention and/or reduction of HSV-1 and HSV-2 associated ocular infections, including keratitis and retinitis. A therapy that can cure, prevent, or treat HSV-1 and HSV-2 ocular infections would be superior to the current standard of care.

SUMMARY OF THE DISCLOSURE

Methods, genome editing systems, and compositions discussed herein provide for the treatment, prevention and/or reduction of herpes simplex virus (HSV) infections, e.g., ocular infections.

Methods, genome editing systems, and compositions discussed herein can be used to provide for treatment, prevention and/or reduction of herpes simplex virus ocular infections, including ocular infections caused by herpes simplex type 1 (HSV-1) and/or herpes simplex type 2 (HSV-2), or symptoms thereof, e.g., by altering (e.g., knocking out and/or knocking down) one or more of the HSV-1 or HSV-2 viral genes, e.g., by knocking out and/or knocking down one, two, or three of RS1, RL2, and/or LAT gene(s). RL2 comprises an open chromatin region, which is associated with the LAT gene and regulation of HSV-1 virus gene expression during latency, reactivation, and lytic infection (J. Gen. Virol. 2008 January; 89(Pt 1): 68-77).

Methods, genome editing systems, and compositions discussed herein provide for treatment, prevention and/or reduction of herpes simplex virus ocular infections, including ocular infections caused by HSV-1 and/or HSV-2, or its symptoms thereof, by knocking out the RS1, RL2, and/or LAT gene(s). Methods, genome editing systems, and compositions discussed herein provide for treatment, prevention and/or reduction of herpes simplex virus ocular infections, including ocular infections caused by HSV-1 and/or HSV-2, or its symptoms thereof, by knocking down the RS1, RL2, and/or LAT gene(s). Methods, genome editing systems, and compositions discussed herein provide for treatment, prevention and/or reduction of herpes simplex virus ocular infections, including ocular infections caused by HSV-1 and/or HSV-2, or its symptoms thereof, by concomitantly knocking out and knocking down the RS1, RL2, and/or LAT gene(s).

Methods, genome editing systems, and compositions discussed herein provide for treatment, prevention and/or reduction of herpes simplex virus (HSV) ocular infections, including ocular infections caused by HSV-1 and/or HSV-2, or its symptoms thereof, by alteration of one or more positions within the RS1, RL2, or LAT gene leading to its destruction and/or elimination from infected cells.

In one aspect, methods, genome editing systems, and compositions discussed herein may be used to alter, e.g., knock out or knock down expression of, one, two, or three of RS1, RL2, and/or LAT gene(s) to treat, prevent and/or reduce HSV-1 or HSV-2 infections by targeting the gene, e.g., the non-coding or coding regions of the gene.

In certain embodiments, the coding sequence, e.g., a coding region (also referred to as coding sequence herein), of one, two, or three of RS1, RL2, and/or LAT gene(s), is targeted for alteration and knock out and/or knock down of expression. In certain embodiments, the coding region is an early coding region, e.g., one, two, or three of RS1, RL2, and/or LAT gene(s). For example, and not by way of limitation, the methods, genome editing systems, and compositions discussed herein are used to alter one, two, or three of RS1, RL2, and/or LAT gene(s) to treat, prevent and/or reduce HSV-1 or HSV-2 infections by targeting a coding sequence, e.g., an intronic or exonic sequence, of one, two, or three of RS1, RL2, and/or LAT gene(s). In certain embodiments, the gene, e.g., the coding sequence of one, two, or three of RS1, RL2, and/or LAT gene(s), are targeted to knockout and/or knock down one, two, or three of RS1, RL2, and/or LAT gene(s), e.g., to eliminate expression of one, two, or three of RS1, RL2, and/or LAT gene(s); and/or to knockout one or more copies of one, two, or three of RS1, RL2, and/or LAT gene(s), e.g., by introduction of an alteration comprising a mutation (e.g., an insertion or deletion) in one, two, or three of RS1, RL2, and/or LAT gene(s). In certain embodiments, the methods, genome editing systems, and compositions provides an alteration that comprises an insertion or deletion in one, two, or three of RS1, RL2, and/or LAT gene(s).

In certain embodiments, an early coding sequence of one, two, or three of RS1, RL2, and/or LAT gene(s) is targeted to knockout or knockdown one, two, or three of RS1, RL2, and/or LAT gene(s). In certain embodiments, targeting affects one or more copies of the RS1, RL2, and/or LAT gene(s). In certain embodiments, a targeted knockout or targeted knockdown approach reduces or eliminates expression of one, two, or all functional RS1, RL2, and/or LAT gene product(s). In certain embodiments, the methods, genome editing systems, and compositions provide an alteration that comprises an insertion or deletion in one, two, or three of RS1, RL2, and/or LAT gene(s).

In another aspect, the methods, genome editing systems, and compositions the RS1, RL2, and/or LAT gene(s), e.g., a promoter, an enhancer, an intron, 5' UTR, 3'UTR, polyadenylation signal and/or an open chromatin region. In certain embodiments, the gene, e.g., the non-coding sequence of the RS1, RL2, and/or LAT gene(s), is targeted to knock out the gene, e.g., to eliminate expression of the gene, e.g., to knock out one or more copies of the RS1, RL2, and/or LAT gene(s), e.g., by induction of an alteration comprising a mutation (e.g., an insertion or deletion) in the RS1, RL2, and/or LAT gene(s). In certain embodiments, the methods, genome editing systems, and compositions provide an alteration that comprises an insertion or deletion in the RS1, RL2, and/or LAT gene(s).

In certain embodiments, altering (e.g., knocking out or knocking down) the RS1 gene refers to (1) reducing or eliminating RS1 gene expression, (2) interfering with the activity and/or function of the protein that is encoded by the RS1 gene, Transcriptional regulator ICP4, or (3) reducing or eliminating the intracellular, serum and/or intra-parenchymal levels of Transcriptional regulator ICP4 protein.

In certain embodiments, altering (e.g., knocking out or knocking down) the RL2 gene refers to (1) reducing or eliminating RL2 gene expression, (2) interfering with activity and/or function of ICP0 protein, which is encoded by the RL2 gene, and/or (3) reducing or eliminating the intracellular, serum and/or intra-parenchymal levels of ICP0 protein.

In certain embodiments, altering (e.g., knocking out or knocking down) the LAT gene refers to (1) reducing or eliminating LAT gene expression, (2) interfering with activity and/or function of the protein that is encoded by the LAT gene, and/or (3) reducing or eliminating the intracellular, serum and/or intra-parenchymal levels of the protein that is encoded by the LAT gene.

In certain embodiments, the methods, genome editing systems, and compositions of the present disclosure provide an alteration that comprises disrupting the RS1, RL2, and/or LAT gene(s) by the insertion or deletion of one or more nucleotides mediated by a Cas9 molecule (e.g., enzymatically active Cas9 (eaCas9), e.g., Cas9 nuclease or Cas9 nickase) or Cas9-fusion protein as described below. This type of alteration is also referred to as "knocking out" the RS1, RL2, and/or LAT gene(s). In certain embodiments, knocking out the RS1, RL2, and/or LAT gene(s) comprises knocking out one or more copies of the RS1, RL2, and/or LAT gene(s), e.g., by introduction of an alteration comprising a mutation (e.g., an insertion or deletion) in the RS1, RL2, and/or LAT gene(s). In certain embodiments, the alteration comprises an insertion or deletion in the RS1, RL2, and/or LAT gene(s). In certain embodiments, a targeted knockout approach is mediated by non-homologous end joining (NHEJ), e.g., using a CRISPR/Cas system comprising a Cas9 molecule (e.g., an eaCas9 molecule) or a Cas9-fusion protein. In certain embodiments, the Cas9 molecule or Cas9-fusion protein is a Cas9 variant, e.g., a *S. pyogenes* Cas9 variant or a *S. aureus* Cas9 variant. In certain embodiments, the *S. pyogenes* Cas9 variant is the EQR variant. In certain embodiments, the *S. pyogenes* Cas9 variant is the VRER variant. In certain embodiments, a targeted knockout approach reduces or eliminates expression of a functional RL2 gene product. In certain embodiments, a targeted knockout approach reduces or eliminates expression of a functional LAT gene product. In certain embodiments, a targeted knockout approach reduces or eliminates expression of a functional RS1 gene product.

In certain embodiments, the methods, genome editing systems, and compositions of the present disclosure provide an alteration of the expression of the RS1, RL2, and/or LAT gene(s) that does not comprise nucleotide insertion or deletion in the RS1, RL2, and/or LAT gene(s). This type of alteration is also referred to as "knocking down" the expression of the RS1, RL2, and/or LAT gene(s). In certain embodiments, this approach gives rise to a reduction, decrease, repression, or elimination of the expression of the RS1, RL2, and/or LAT gene(s). In certain embodiments, a targeted knockdown approach is mediated by a CRISPR/Cas system comprising a Cas9 molecule (e.g., an enzymatically inactive Cas9 (eiCas9) molecule) or a Cas9-fusion protein (e.g., an eiCas9 fusion protein (e.g., an eiCas9 fused to a transcription repressor domain or chromatin modifying protein)) to alter transcription (e.g., to block, reduce, or decrease transcription) of the RS1, RL2, and/or LAT gene(s). In certain embodiments, a non-coding region (e.g., an enhancer region, a promoter region, 5' UTR, 3'UTR, polyadenylation signal and/or open chromatin region) of the RS1, RL2, and/or LAT gene(s) is targeted to alter the expression of the RS1, RL2, and/or LAT gene(s). In certain embodiments, the open chromatin region of the RL2 gene is targeted to alter the expression of the RL2 gene. In certain embodiments, a transcriptional regulatory region, e.g., a promoter region (e.g., a promoter region that controls the transcription of the RS1, RL2, and/or LAT gene(s)) is targeted to alter (e.g., knockdown) the expression of the RS1, RL2, and/or LAT gene(s). In certain embodiments, one or more gRNA molecules comprise a targeting domain are configured to target an eiCas9 molecule or an eiCas9 fusion protein sufficiently close to the transcriptional regulatory region, e.g., a promoter region (e.g., a promoter region that controls the transcription of the RS1, RL2, and/or LAT gene(s)) to reduce, decrease or repress expression of the RS1, RL2, and/or LAT gene(s). In certain embodiments, the coding region of the RL2 gene is targeted to alter (e.g., knockdown) the expression of the RL2 gene. In certain embodiments, the coding region of the RS1 gene is targeted to alter (e.g., knocking down) the expression of the RS1 gene. In certain embodiments, the coding region of the LATgene is targeted to alter (e.g., knockdown) the expression of the LAT gene. In certain embodiments, the eiCas9 molecule is a Cas9 variant, e.g., a *S. pyogenes* Cas9 variant or a *S. aureus* Cas9 variant. In certain embodiments, the *S. pyogenes* Cas9 variant is the EQR variant. In certain embodiments, the *S. pyogenes* Cas9 variant is the VRER variant In certain embodiments, a targeted knockdown approach reduces or eliminates expression of a functional RL2 gene product. In certain embodiments, a targeted knockdown approach reduces or eliminates expression of a functional LAT gene product. In certain embodiments, a targeted knockdown approach reduces or eliminates expression of a functional RS1 gene product.

In certain embodiments, knocking down the RS1, RL2, and/or LAT gene(s) cures HSV infections. In certain embodiments, the knocking down the R RS1, RL2, and/or LAT gene(s) provide a functional cure of HSV infections. In certain embodiments, knocking down the RS1, RL2, and/or LAT gene(s) leads to a sustained virologic response to HSV infections.

In certain embodiments, a region of the RS1, RL2, and/or LAT gene(s) that is known to be integrated into the subject genome is targeted for knockdown. In certain embodiments, a region of the RS1, RL2, and/or LAT gene(s) that is known not to be integrated into the subject genome is targeted for knockout. In certain embodiments, the method comprises knocking out a region of the RS1, RL2, and/or LAT gene(s) that is not integrated into the subject genome.

Knockout, knockdown, and concomitant knockout and knockdown of the RS1, RL2, and/or LAT gene(s) can reduce HSV infectivity, replication, packaging and can therefore treat, prevent and/or reduce HSV infection. Knockout, knockdown, and concomitant knockout and knockdown of the expression of the RS1, RL2, and/or LAT gene(s) may cause any of the following, singly or in combination: decreased HSV DNA production, decreased viral infectivity, decreased packaging of viral particles, decreased viral shedding, and/or decreased production of viral proteins encoded by the RS1, RL2, and/or LAT gene(s), e.g., ICP0 and/or ICP4 proteins. In certain embodiments, the method comprises concomitant 1) knocking out and 2) knocking down of two distinct regions of the RS1, RL2, and/or LAT gene, e.g., 1) knocking down of a region of the RS1, RL2, or LAT gene that is integrated into the subject genome and 2) knocking out of a different region of the RS1, RL2, or LAT gene that is not integrated into the subject genome.

The presently disclosed subject matter provides a genome editing system comprising: a gRNA molecule comprising a targeting domain that is complementary with a target sequence of a Herpes simplex virus (HSV) viral gene selected from the group consisting of a RS1 gene, a RL2 gene, and a LAT gene; and a Cas9 molecule. In certain embodiments, the targeting domain is configured to form a double strand break or a single strand break within about 500 bp, about 450 bp, about 400 bp, about 350 bp, about 300 bp, about 250 bp, about 200 bp, about 150 bp, about 100 bp, about 50 bp, about 25 bp, or about 10 bp of an HSV target position, thereby altering said HSV viral gene. In certain embodiments, altering said HSV viral gene comprises knockout of said HSV viral gene, knockdown of said HSV viral gene, or concomitant knockout and knockdown of said HSV viral gene.

In certain embodiments, the targeting domain is configured to target a coding region or a non-coding region of the HSV viral gene, wherein the non-coding region comprises a promoter region, an enhancer region, an intron, the 3' UTR, the 5' UTR, or a polyadenylation signal region of said HSV viral gene; and said coding region comprises an early coding region of said HSV viral gene.

In certain embodiments, the targeting domain comprises a nucleotide sequence that is identical to, or differs by no more than 3 nucleotides from, a nucleotide sequence selected from SEQ ID NOS: 208 to 58749.

In certain embodiments, the Cas9 molecule is an S. pyogenes Cas9 molecule, said genome editing system knocks out the HSV-1 RS1 gene, and the targeting domain comprises a nucleotide sequence that is identical to, or differs by no more than 3 nucleotides from, a nucleotide sequence selected from the group consisting of: SEQ ID NOS: 208 to 2509.

In certain embodiments, the Cas9 molecule is an S. pyogenes Cas9 molecule, said genome editing system knocks out the HSV-2 RS1 gene, and said targeting domain comprises a nucleotide sequence that is identical to, or differs by no more than 3 nucleotides from, a nucleotide sequence selected from the group consisting of: SEQ ID NOS: 7098 to 9292.

In certain embodiments, the Cas9 molecule is an S. pyogenes Cas9 molecule, said genome editing system knocks out said HSV-1 RL2 gene, and said targeting domain comprises a nucleotide sequence that is identical to, or differs by no more than 3 nucleotides from, a nucleotide sequence selected from the group consisting of: SEQ ID NOS: 21324 to 22744.

In certain embodiments, the Cas9 molecule is an S. pyogenes Cas9 molecule, said genome editing system knocks out said HSV-2 RL2 gene, and said targeting domain comprises a nucleotide sequence that is identical to, or differs by no more than 3 nucleotides from, a nucleotide sequence selected from the group consisting of: SEQ ID NOS: 26613 to 28037.

In certain embodiments, the Cas9 molecule is an S. pyogenes Cas9 molecule, said genome editing system knocks out said HSV-1 LAT gene, and said targeting domain comprises a nucleotide sequence that is identical to, or differs by no more than 3 nucleotides from, a nucleotide sequence selected from the group consisting of: SEQ ID NOS: 31730 to 32746.

In certain embodiments, the Cas9 molecule is an S. pyogenes Cas9 molecule, said genome editing system knocks out said HSV-2 LAT gene, and said targeting domain comprises a nucleotide sequence that is identical to, or differs by no more than 3 nucleotides from, a nucleotide sequence selected from the group consisting of: SEQ ID NOS: 35617 to 36926.

In certain embodiments, the Cas9 molecule is an S. aureus Cas9 molecule, said genome editing system knocks out said HSV-1 RS1 gene, and said targeting domain comprises a nucleotide sequence that is identical to, or differs by no more than 3 nucleotides from, a nucleotide sequence selected from the group consisting of: SEQ ID NOS: 2510 to 7073.

In certain embodiments, the Cas9 molecule is an S. aureus Cas9 molecule, said genome editing system knocks out said HSV-2 RS1 gene, and said targeting domain comprises a nucleotide sequence that is identical to, or differs by no more than 3 nucleotides from, a nucleotide sequence selected from the group consisting of: SEQ ID NOS: 9293 to 13614.

In certain embodiments, the Cas9 molecule is an S. aureus Cas9 molecule, said genome editing system knocks out said HSV-1 RL2 gene, and said targeting domain comprises a nucleotide sequence that is identical to, or differs by no more than 3 nucleotides from, a nucleotide sequence selected from the group consisting of: SEQ ID NOS: 22745 to 26601.

In certain embodiments, the Cas9 molecule is an S. aureus Cas9 molecule, said genome editing system knocks out said HSV-2 RL2 gene, and said targeting domain comprises a nucleotide sequence that is identical to, or differs by no more than 3 nucleotides from, a nucleotide sequence selected from the group consisting of: SEQ ID NOS: 28038 to 31720.

In certain embodiments, the Cas9 molecule is an S. aureus Cas9 molecule, said genome editing system knocks out said HSV-1 LAT gene, and said targeting domain comprises a nucleotide sequence that is identical to, or differs by no more than 3 nucleotides from, a nucleotide sequence selected from the group consisting of: SEQ ID NOS: 32747 to 35600.

In certain embodiments, the Cas9 molecule is an S. aureus Cas9 molecule, said genome editing system knocks out said HSV-2 LAT gene, and said targeting domain comprises a nucleotide sequence that is identical to, or differs by no more than 3 nucleotides from, a nucleotide sequence selected from the group consisting of: SEQ ID NOS: 36927 to 40871.

In certain embodiments, the Cas9 molecule is an S. pyogenes Cas9 molecule, said genome editing system knocks down said HSV-1 RS1 gene, and said targeting domain comprises a nucleotide sequence that is identical to, or differs by no more than 3 nucleotides from, a nucleotide sequence selected from the group consisting of: SEQ ID NOS: 13637 to 14794.

In certain embodiments, the Cas9 molecule is an S. pyogenes Cas9 molecule, said genome editing system knocks down said HSV-2 RS1 gene, and said targeting domain comprises a nucleotide sequence that is identical to, or differs by no more than 3 nucleotides from, a nucleotide sequence selected from the group consisting of: SEQ ID NOS: 17753 to 18784.

In certain embodiments, the Cas9 molecule is an S. pyogenes Cas9 molecule, said genome editing system knocks down said HSV-1 RL2 gene, and said targeting domain comprises a nucleotide sequence that is identical to, or differs by no more than 3 nucleotides from, a nucleotide sequence selected from the group consisting of: SEQ ID NOS: 40886 to 42078.

In certain embodiments, the Cas9 molecule is an S. pyogenes Cas9 molecule, said genome editing system knocks down said HSV-2 RL2 gene, and said targeting domain comprises a nucleotide sequence that is identical to, or differs by no more than 3 nucleotides from, a nucleotide sequence selected from the group consisting of: SEQ ID NOS: 49498 to 50652.

In certain embodiments, the Cas9 molecule is an *S. pyogenes* Cas9 molecule, said genome editing system knocks down said HSV-1 LAT gene, and said targeting domain comprises a nucleotide sequence that is identical to, or differs by no more than 3 nucleotides from, a nucleotide sequence selected from the group consisting of: SEQ ID NOS: 45340 to 46479.

In certain embodiments, the Cas9 molecule is an *S. pyogenes* Cas9 molecule, said genome editing system knocks down said HSV-2 LAT gene, and said targeting domain comprises a nucleotide sequence that is identical to, or differs by no more than 3 nucleotides from, a nucleotide sequence selected from the group consisting of: SEQ ID NOS: 53858 to 55056.

In certain embodiments, the Cas9 molecule is an *S. aureus* Cas9 molecule, said genome editing system knocks down said HSV-1 RS1 gene, and said targeting domain comprises a nucleotide sequence that is identical to, or differs by no more than 3 nucleotides from, a nucleotide sequence selected from the group consisting of: SEQ ID NOS: 14795 to 17741.

In certain embodiments, the Cas9 molecule is an *S. aureus* Cas9 molecule, said genome editing system knocks down said HSV-2 RS1 gene, and said targeting domain comprises a nucleotide sequence that is identical to, or differs by no more than 3 nucleotides from, a nucleotide sequence selected from the group consisting of: SEQ ID NOS: 18785 to 21311.

In certain embodiments, the Cas9 molecule is an *S. aureus* Cas9 molecule, said genome editing system knocks down said HSV-1 RL2 gene, and said targeting domain comprises a nucleotide sequence that is identical to, or differs by no more than 3 nucleotides from, a nucleotide sequence selected from the group consisting of: SEQ ID NOS: 42079 to 45315.

In certain embodiments, the Cas9 molecule is an *S. aureus* Cas9 molecule, said genome editing system knocks down said HSV-2 RL2 gene, and said targeting domain comprises a nucleotide sequence that is identical to, or differs by no more than 3 nucleotides from, a nucleotide sequence selected from the group consisting of: SEQ ID NOS: 50653 to 53824.

In certain embodiments, the Cas9 molecule is an *S. aureus* Cas9 molecule, said genome editing system knocks down said HSV-1 LAT gene, and said targeting domain comprises a nucleotide sequence that is identical to, or differs by no more than 3 nucleotides from, a nucleotide sequence selected from the group consisting of: SEQ ID NOS: 46480 to 49479.

In certain embodiments, the Cas9 molecule is an *S. aureus* Cas9 molecule, said genome editing system knocks down said HSV-2 LAT gene, and said targeting domain comprises a nucleotide sequence that is identical to, or differs by no more than 3 nucleotides from, a nucleotide sequence selected from the group consisting of: SEQ ID NOS: 55057 to 58731.

In certain embodiments, the *S. pyogenes* Cas9 molecule recognizes a Protospacer Adjacent Motif (PAM) of NGG.

In certain embodiments, the *S. aureus* Cas9 molecule recognizes a PAM of either NNGRRT (SEQ ID NO: 204) or NNGRRV (SEQ ID NO: 205).

The presently disclosed subject matter provides a gRNA molecule, e.g., an isolated or non-naturally occurring gRNA molecule, comprising a targeting domain which is complementary to a target domain (also referred to as "target sequence") of a RS1, RL2, or LAT gene. The presently disclosed subject matter provides a composition comprising such gRNA molecule. Furthermore, the presently disclosed subject matter provides a vector comprising such gRNA molecule. In addition, the presently disclosed subject matter provides cells comprising a presently disclosed genome editing system, vector, or composition. In certain embodiments, the cell is selected from the group consisting of an epithelial cell, a neuronal cell, and an optic cell.

In certain embodiments, the targeting domain of the gRNA molecule is configured to provide a cleavage event, e.g., a double strand break or a single strand break, sufficiently close to an HSV RS1 target position, an HSV RL2 target position, or an HSV LAT target position to allow an alteration, e.g., an alteration associated with NHEJ, of an HSV RS1 target position, an HSV RL2 target position, or an HSV LAT target position. In certain embodiments, the targeting domain is configured such that a cleavage event, e.g., a double strand or single strand break, is positioned within 1, 2, 3, 4, 5, 10, 15, 20, 25, 30, 35, 40, 45, 50, 60, 70, 80, 90, 100, 150 or 200 nucleotides of an HSV RS1 target position, an HSV RL2 target position, or an HSV LAT target position. The break, e.g., a double strand or single strand break, can be positioned upstream or downstream of an HSV RS1 target position, an HSV RL2 target position, or an HSV LAT target position. In certain embodiments, the targeting domain of the gRNA molecule is configured to provide a cleavage event selected from a double strand break and a single strand break, within 500 (e.g., within 500, 400, 300, 250, 200, 150, 100, 80, 60, 40, 20, or 10) nucleotides of an HSV RS1 target position, an HSV RL2 target position, or an HSV LAT target position.

In certain embodiments, a second gRNA molecule comprising a second targeting domain is configured to provide a cleavage event, e.g., a double strand break or a single strand break, sufficiently close to an HSV RS1 target position, an HSV RL2 target position, or an HSV LAT target position, to allow alteration, e.g., alteration associated with NHEJ, of an HSV RS1 target position, an HSV RL2 target position, or an HSV LAT target position, either alone or in combination with the break positioned by the first gRNA molecule. In certain embodiments, the targeting domains of the first and second gRNA molecules are configured such that a cleavage event, e.g., a double strand or single strand break, is positioned, independently for each of the gRNA molecules, within 1, 2, 3, 4, 5, 10, 15, 20, 25, 30, 35, 40, 45, 50, 60, 70, 80, 90, 100, 150 or 200 nucleotides of the target position. In certain embodiments, the breaks, e.g., double strand or single strand breaks, are positioned on both sides of an HSV RS1 target position, an HSV RL2 target position, or an HSV LAT target position. In certain embodiments, the breaks, e.g., double strand or single strand breaks, are positioned on one side, e.g., upstream or downstream, of an HSV RS1 target position, an HSV RL2 target position, or an HSV LAT target position. In certain embodiments, the targeting domain of the first and/or second gRNA molecule is configured to provide a cleavage event selected from a double strand break and a single strand break, within 500 (e.g., within 500, 400, 300, 250, 200, 150, 100, 80, 60, 40, 20, or 10) nucleotides of an an HSV RS1 target position, an HSV RL2 target position, or an HSV LAT target position.

In certain embodiments, a single strand break is accompanied by an additional single strand break, positioned by a second gRNA molecule, as discussed below. For example, the targeting domains are configured such that a cleavage event, e.g., the two single strand breaks, are positioned within 1, 2, 3, 4, 5, 10, 15, 20, 25, 30, 35, 40, 45, 50, 60, 70, 80, 90, 100, 150 or 200 nucleotides of an HSV RS1 target position, an HSV RL2 target position, or an HSV LAT target position. In certain embodiments, the first and second gRNA molecules are configured such, that when guiding a Cas9 molecule or Cas9-fusion protein, e.g., a Cas9 nickase, a single strand break is accompanied by an additional single strand break, positioned by a second gRNA molecule, sufficiently close to one another to result in alteration of an HSV RS1 target position, an HSV RL2 target position, or an HSV LAT target position. In certain embodiments, the first and second gRNA molecules are configured such that a single strand break positioned by the second gRNA is within 10, 20, 30, 40, or 50 nucleotides of the break positioned by the first gRNA molecule, e.g., when the Cas9 molecule or Cas9-fusion protein is a nickase. In certain embodiments, the two gRNA molecules are configured to position cuts at the same position, or within a few nucleotides of one another, on different strands, e.g., essentially mimicking a double strand break.

In certain embodiments, a double strand break can be accompanied by an additional double strand break, positioned by a second gRNA molecule, as is discussed below. For example, the targeting domain of a first gRNA molecule is configured such that a double strand break is positioned upstream of an HSV RS1 target position, an HSV RL2 target position, or an HSV LAT target position, e.g., within 1, 2, 3, 4, 5, 10, 15, 20, 25, 30, 35, 40, 45, 50, 60, 70, 80, 90, 100, 150 or 200 nucleotides of the target position; and the targeting domain of a second gRNA molecule is configured such that a double strand break is positioned downstream of an HSV RS1 target position, an HSV RL2 target position, or an HSV LAT target position, e.g., within 1, 2, 3, 4, 5, 10, 15, 20, 25, 30, 35, 40, 45, 50, 60, 70, 80, 90, 100, 150 or 200 nucleotides of the target position.

In certain embodiments, a double strand break can be accompanied by two additional single strand breaks, positioned by a second gRNA molecule and a third gRNA molecule. For example, the targeting domain of a first gRNA molecule is configured such that a double strand break is positioned upstream of an HSV RS1 target position, an HSV RL2 target position, or an HSV LAT target position, e.g., within 1, 2, 3, 4, 5, 10, 15, 20, 25, 30, 35, 40, 45, 50, 60, 70, 80, 90, 100, 150 or 200 nucleotides of the target position; and the targeting domains of a second and third gRNA molecule are configured such that two single strand breaks are positioned downstream of an HSV RL2 target position or HSV LAT target position or HSV RS1 target position, e.g., within 1, 2, 3, 4, 5, 10, 15, 20, 25, 30, 35, 40, 45, 50, 60, 70, 80, 90, 100, 150 or 200 nucleotides of the target position.

In certain embodiments, the targeting domain of the first, second and third gRNA molecules are configured such that a cleavage event, e.g., a double strand or single strand break, is positioned, independently for each of the gRNA molecules.

In certain embodiments, a first and second single strand breaks can be accompanied by two additional single strand breaks positioned by a third gRNA molecule and a fourth gRNA molecule. For example, the targeting domain of a first and second gRNA molecule are configured such that two single strand breaks are positioned upstream of an HSV RS1 target position, an HSV RL2 target position, or an HSV LAT target position, e.g., within 1, 2, 3, 4, 5, 10, 15, 20, 25, 30, 35, 40, 45, 50, 60, 70, 80, 90, 100, 150 or 200 nucleotides of the target position; and the targeting domains of a third and fourth gRNA molecule are configured such that two single strand breaks are positioned downstream of an HSV RS1 target position, an HSV RL2 target position, or an HSV LAT target position, e.g., within 1, 2, 3, 4, 5, 10, 15, 20, 25, 30, 35, 40, 45, 50, 60, 70, 80, 90, 100, 150 or 200 nucleotides of the target position. In certain embodiments, the targeting domain of the first, second, third, and/or fourth gRNA molecule is configured to provide a cleavage event selected from a double strand break and a single strand break, within 500 (e.g., within 500, 400, 300, 250, 200, 150, 100, 80, 60, 40, 20, or 10) nucleotides of an HSV RS1 target position, an HSV RL2 target position, or an HSV LAT target position.

In certain embodiments, when multiple gRNAs are used to generate (1) two single stranded breaks in close proximity, (2) two double stranded breaks, e.g., flanking an HSV RS1 target position, an HSV RL2 target position, or an HSV LAT target position (e.g., to remove a piece of DNA, e.g., to create a deletion mutation) or to create more than one indel in the gene, e.g., in a coding region, e.g., an early coding region, (3) one double stranded break and two paired nicks flanking an HSV RS1 target position, an HSV RL2 target position, or an HSV LAT target position (e.g., to remove a piece of DNA, e.g., to insert a deletion) or (4) four single stranded breaks, two on each side of a position, that they are targeting the same HSV RL2 target position or HSV LAT target position or HSV RS1 target position. In certain embodiments, multiple gRNAs may be used to target more than one HSV RS1 target position, HSV RL2 target position, or HSV LAT target position.

In certain embodiments, the targeting domain of the first gRNA molecule and the targeting domain of the second gRNA molecules are complementary to opposite strands of the target nucleic acid molecule. In certain embodiments, the gRNA molecule and the second gRNA molecule are configured such that the PAMs are oriented outward.

In certain embodiments, the targeting domain of a gRNA molecule is configured to avoid unwanted target chromosome elements, including, but not limited to, repeat elements, e.g., Alu repeats, in the target domain. The gRNA molecule may be a first, second, third and/or fourth gRNA molecule, as described herein.

In certain embodiments, the targeting domain of a gRNA molecule is configured to position a cleavage event sufficiently far from a preselected nucleotide, e.g., the nucleotide of a coding region, such that the nucleotide is not altered. In certain embodiments, the targeting domain of a gRNA molecule is configured to position an intronic cleavage event sufficiently far from an intron/exon border, or naturally occurring splice signal, to avoid alteration of the exonic sequence or unwanted splicing events. The gRNA molecule may be a first, second, third and/or fourth gRNA molecule, as described herein.

In certain embodiments, the targeting domain of a gRNA molecule targeting an HSV1 RS1 target knockout position comprises a nucleotide sequence that is identical to, or differs by no more than 1, no more than 2, no more than 3, no more than 4, or no more than 5 nucleotides from, a nucleotide sequence selected from SEQ ID NOS: 208 to 2509 and 2510 to 7073.

In certain embodiments, the targeting domain of a gRNA molecule targeting an HSV2 RS1 target knockout position comprises a nucleotide sequence that is identical to, or differs by no more than 1, no more than 2, no more than 3, no more than 4, or no more than 5 nucleotides from, a nucleotide sequence selected from SEQ ID NOS: 7098 to 9292 and 9293 to 13614.

In certain embodiments, the targeting domain of a gRNA molecule targeting an HSV1 RL2 target knockout position comprises a nucleotide sequence that is identical to, or differs by no more than 1, no more than 2, no more than 3, no more than 4, or no more than 5 nucleotides from, a nucleotide sequence selected from SEQ ID NOS: 21324 to 22744 and 22745 to 26601.

In certain embodiments, the targeting domain of a gRNA molecule targeting an HSV2 RL2 target knockout position comprises a nucleotide sequence that is identical to, or differs by no more than 1, no more than 2, no more than 3, no more than 4, or no more than 5 nucleotides from, a nucleotide sequence selected from SEQ ID NOS: 26613 to 28037 and 28038 to 31720.

In certain embodiments, the targeting domain of a gRNA molecule targeting an HSV1 LAT target knockout position comprises a nucleotide sequence that is identical to, or differs by no more than 1, no more than 2, no more than 3, no more than 4, or no more than 5 nucleotides from, a nucleotide sequence selected from SEQ ID NOS: 31730 to 32746 and 32747 to 35600.

In certain embodiments, the targeting domain of a gRNA molecule targeting an HSV2 LAT target knockout position comprises a nucleotide sequence that is identical to, or differs by no more than 1, no more than 2, no more than 3, no more than 4, or no more than 5 nucleotides from, a nucleotide sequence selected from SEQ ID NOS: 35617 to 36926 and 36927 to 40871.

In certain embodiments, the targeting domain of a gRNA molecule targeting an HSV1 RS1 target knockdown position comprises a nucleotide sequence that is identical to, or differs by no more than 1, no more than 2, no more than 3, no more than 4, or no more than 5 nucleotides from, a nucleotide sequence selected from SEQ ID NOS: 13637 to 14794 and 14795 to 17741.

In certain embodiments, the targeting domain of a gRNA molecule targeting an HSV2 RS1 target knockdown position comprises a nucleotide sequence that is identical to, or differs by no more than 1, no more than 2, no more than 3, no more than 4, or no more than 5 nucleotides from, a nucleotide sequence selected from SEQ ID NOS: 17753 to 18784 and 18785 to 21311.

In certain embodiments, the targeting domain of a gRNA molecule targeting an HSV1 RL2 target knockdown position comprises a nucleotide sequence that is identical to, or differs by no more than 1, no more than 2, no more than 3, no more than 4, or no more than 5 nucleotides from, a nucleotide sequence selected from SEQ ID NOS: 40886 to 42078 and 42079 to 45315.

In certain embodiments, the targeting domain of a gRNA molecule targeting an HSV2 RL2 target knockdown position comprises a nucleotide sequence that is identical to, or differs by no more than 1, no more than 2, no more than 3, no more than 4, or no more than 5 nucleotides from, a nucleotide sequence selected from SEQ ID NOS: 49498 to 50652 and 50653 to 53824.

In certain embodiments, the targeting domain of a gRNA molecule targeting an HSV1 LAT target knockdown position comprises a nucleotide sequence that is identical to, or differs by no more than 1, no more than 2, no more than 3, no more than 4, or no more than 5 nucleotides from, a nucleotide sequence selected from SEQ ID NOS: 45340 to 46479 and 46480 to 49479.

In certain embodiments, the targeting domain of a gRNA molecule targeting an HSV2 LAT target knockdown position comprises a nucleotide sequence that is identical to, or differs by no more than 1, no more than 2, no more than 3, no more than 4, or no more than 5 nucleotides from, a nucleotide sequence selected from SEQ ID NOS: 53858 to 55056 and 55057 to 58731.

In certain embodiments, the gRNA molecule is a unimolecular or chimeric gRNA molecule.

In certain embodiments, the targeting domain of a presently disclosed gRNA molecule is 16, 17, 18, 19, 20, 21, 22, 23, 24, 25 or 26 nucleotides in length.

In certain embodiments, the gRNA molecule comprises from 5' to 3': a targeting domain (comprising a "core domain", and optionally a "secondary domain"); a first complementarity domain; a linking domain; a second complementarity domain; and a proximal domain. In certain embodiments, the gRNA molecule further comprises a tail domain. In certain embodiments, the proximal domain and tail domain are taken together as a single domain.

In certain embodiments, a gRNA molecule comprises a linking domain of no more than 25 nucleotides in length; a proximal and tail domain, that taken together, are at least 20, 30, 35, or 40 nucleotides in length; and a targeting domain equal to or greater than 16, 17, 18, 19, 20, 21, 22, 23, 24, 25 or 26 nucleotides in length.

A cleavage event, e.g., a double strand or single strand break, can be generated by a Cas9 molecule or Cas9-fusion protein. The Cas9 molecule or Cas9-fusion protein may be an enzymatically active Cas9 (eaCas9) molecule, e.g., an eaCas9 molecule that forms a double strand break in a target nucleic acid or an eaCas9 molecule forms a single strand break in a target nucleic acid (e.g., a nickase molecule). In certain embodiments, the eaCas9 molecule can be a Cas9 variant. For example, and not by way of limitation, the Cas9 variant can be a *S. pyogenes* Cas9 variant or a *S. aureus* Cas9 variant. In certain embodiments, the *S. pyogenes* Cas9 variant is the EQR variant. In certain embodiments, the *S. pyogenes* Cas9 variant is the VRER variant. In addition to Cas9 molecules or Cas9-fusion proteins, other nucleases, disclosed herein, can be used to generate a cleavage event.

In certain embodiments, the eaCas9 molecule or eaCas9-fusion protein catalyzes a double strand break.

In certain embodiments, the eaCas9 molecule or eaCas9-fusion protein comprises HNH-like domain cleavage activity but has no, or no significant, N-terminal RuvC-like domain cleavage activity. In this case, the eaCas9 molecule or eaCas9-fusion protein is an HNH-like domain nickase, e.g., the eaCas9 molecule or eaCas9-fusion protein comprises a mutation at D10, e.g., D10A. In certain embodiments, the eaCas9 molecule or eaCas9-fusion protein comprises N-terminal RuvC-like domain cleavage activity but has no, or no significant, HNH-like domain cleavage activity. In certain embodiments, the eaCas9 molecule or eaCas9-fusion protein is an N-terminal RuvC-like domain nickase, e.g., the eaCas9 molecule comprises a mutation at H840, e.g., H840A. In certain embodiments, the eaCas9 molecule or eaCas9-fusion protein is an N-terminal RuvC-like domain nickase, e.g., the eaCas9 molecule or eaCas9-fusion protein comprises a mutation at N863, e.g., N863A.

In certain embodiments, a single strand break is formed in the strand of the target nucleic acid to which the targeting domain of the gRNA molecule is complementary. In certain embodiments, a single strand break is formed in the strand of the target nucleic acid other than the strand to which the targeting domain of the gRNA molecule is complementary.

Furthermore, the presently disclosed subject matter provides a nucleic acid composition, e.g., an isolated or non-naturally occurring nucleic acid composition, e.g., DNA, that comprises (a) a first nucleotide sequence that encodes a presently disclosed gRNA molecule, e.g., a gRNA molecule comprising a targeting domain that is complementary with a target sequence of a RS1, RL2, or LAT gene, e.g., at an HSV RS1 target position, an HSV RL2 target position, or an HSV LAT target position.

In certain embodiments, the nucleic acid composition further comprises (b) a second nucleotide sequence that encodes a Cas9 molecule or Cas9-fusion protein as described herein. In certain embodiments, the Cas9 molecule is an eiCas9 molecule. In certain embodiments, the Cas9 molecule is an eaCas9 molecule. In certain embodiments, the Cas9 molecule, e.g., an eiCas9 molecule or an eaCas9 molecule, can be a Cas9 variant, e.g., an *S. pyogenes* Cas9 variant or an *S. aureus* Cas9 variant.

The Cas9 molecule or Cas9-fusion protein may be a nickase molecule, an enzymatically activating Cas9 (eaCas9) molecule or eaCas9-fusion protein, e.g., an eaCas9 molecule or eaCas9-fusion protein that forms a double strand break in a target nucleic acid and/or an eaCas9 molecule or eaCas9-fusion protein that forms a single strand break in a target nucleic acid. In certain embodiments, a single strand break is formed in the strand of the target nucleic acid to which the targeting domain of the gRNA molecule is complementary. In certain embodiments, a single strand break is formed in the strand of the target nucleic acid other than the strand to which to which the targeting domain of said gRNA molecule is complementary.

In certain embodiments, the nucleic acid composition further comprise (c)(i) a third nucleotide sequence that encodes a second gRNA molecule described herein having a targeting domain that is complementary to a second target sequence of the RS1, RL2, or LAT gene, and optionally, (c)(ii) a sequence that encodes a third gRNA molecule described herein having a targeting domain that is complementary to a third target sequence of the RS1, RL2, or LAT gene; and optionally, (c)(iii) a sequence that encodes a fourth gRNA molecule described herein having a targeting domain that is complementary to a fourth target sequence of the RS1, RL2, or LAT gene. In certain embodiments, (a) and (b) are present on the same nucleic acid molecule, e.g., the same vector, e.g., the same viral vector, e.g., the same adeno-associated virus (AAV) vector or Lentiviral (LV) vector. In certain embodiments, the nucleic acid molecule is an LV vector. In certain embodiments, the nucleic acid molecule is an AAV vector. Exemplary AAV vectors that may be used in any of the described compositions and methods include an AAV2 vector, a modified AAV2 vector, an AAV3 vector, a modified AAV3 vector, an AAV6 vector, a modified AAV6 vector, an AAV8 vector and an AAV9 vector. In certain embodiments, the Cas9 molecule is an eiCas9 molecule. In certain embodiments, the Cas9 molecule is an eaCas9 molecule. In certain embodiments, the Cas9 molecule, e.g., an eiCas9 molecule or an eaCas9 molecule, can be a Cas9 variant, e.g., a *S. pyogenes* Cas9 variant or a *S. aureus* Cas9 variant.

In certain embodiments, (a) is present on a first nucleic acid molecule, e.g. a first vector, e.g., a first viral vector, e.g., a first AAV vector or a first LV vector; and (b) is present on a second nucleic acid molecule, e.g., a second vector, e.g., a second vector, e.g., a second AAV vector or a second LV vector. The first and second nucleic acid molecules may be AAV vectors. In certain embodiments, the first and second nucleic acid molecules can be LV vectors.

In certain embodiments, (a) and (c)(i) are present on one nucleic acid molecule, e.g., one vector, e.g., one viral vector, e.g., one AAV vector or LV vector. In certain embodiments, the nucleic acid molecule is an AAV vector. In certain embodiments, the nucleic acid molecule is an LV vector. In certain embodiments, (a) and (c)(i) are on different vectors.

In certain embodiments, (a) is present on a first nucleic acid molecule, e.g. a first vector, e.g., a first viral vector, e.g., a first AAV vector or LV vector; and (c)(i) is present on a second nucleic acid molecule, e.g., a second vector, e.g., a second vector, e.g., a second AAV vector or second LV vector. In certain embodiments, the first and second nucleic acid molecules are AAV vectors. In certain embodiments, the first and second nucleic acid molecules are LV vectors.

In certain embodiments, each of (a), (b), and (c)(i) are present on one nucleic acid molecule, e.g., one vector, e.g., one viral vector, e.g., an AAV vector or LV vector. In certain embodiments, the nucleic acid molecule is an AAV vector. In certain embodiments, the nucleic acid molecule is an LV vector. In certain embodiments, one of (a), (b), and (c)(i) is encoded on a first nucleic acid molecule, e.g., a first vector, e.g., a first viral vector, e.g., a first AAV vector or LV vector; and a second and third of (a), (b), and (c)(i) is encoded on a second nucleic acid molecule, e.g., a second vector, e.g., a second vector, e.g., a second AAV vector or LV vector. The first and second nucleic acid molecule may be AAV vectors or LV vectors.

In certain embodiments, (a) is present on a first nucleic acid molecule, e.g., a first vector, e.g., a first viral vector, a first AAV vector or LV vector; and (b) and (c)(i) are present on a second nucleic acid molecule, e.g., a second vector, e.g., a second vector, e.g., a second AAV vector or LV vector. The first and second nucleic acid molecule may be AAV vectors or LV vectors.

In certain embodiments, (b) is present on a first nucleic acid molecule, e.g., a first vector, e.g., a first viral vector, e.g., a first AAV vector or LV vector; and (a) and (c)(i) are present on a second nucleic acid molecule, e.g., a second vector, e.g., a second vector, e.g., a second AAV vector or LV vector. The first and second nucleic acid molecule may be AAV vectors or LV vectors.

In certain embodiments, (c)(i) is present on a first nucleic acid molecule, e.g., a first vector, e.g., a first viral vector, e.g., a first AAV vector or LV vector; and (b) and (a) are present on a second nucleic acid molecule, e.g., a second vector, e.g., a second vector, e.g., a second AAV vector or LV vector. The first and second nucleic acid molecule may be AAV vectors. In certain embodiments, the first and second nucleic acid molecule may be LV vectors.

In certain embodiments, each of (a), (b) and (c)(i) are present on different nucleic acid molecules, e.g., different vectors, e.g., different viral vectors, e.g., different AAV vector or LV vector. For example, (a) may be on a first nucleic acid molecule, (b) on a second nucleic acid molecule, and (c)(i) on a third nucleic acid molecule. The first, second and third nucleic acid molecules may be AAV vectors. In certain embodiments, the first, second and third nucleic acid molecules may be LV vectors.

In certain embodiments, when a third and/or fourth gRNA molecule are present, each of (a), (b), (c)(i), (c)(ii) and (c)(iii) may be present on one nucleic acid molecule, e.g., one vector, e.g., one viral vector, e.g., an AAV vector or LV vector. In certain embodiments, the nucleic acid molecule is an AAV vector. In certain embodiments, the nucleic acid molecule is an LV vector. In certain embodiments, each of (a), (b), (c)(i), (c)(ii) and (c)(iii) may be present on the different nucleic acid molecules, e.g., different vectors, e.g., the different viral vectors, e.g., different AAV vectors or different LV vectors. In a further embodiment, each of (a), (b), (c)(i), (c)(ii) and (c)(iii) may be present on more than one nucleic acid molecule, but fewer than five nucleic acid molecules, e.g., AAV vectors or LV vectors.

In certain embodiments, the second gRNA molecule is configured to provide a cleavage event, e.g., a double strand break or a single strand break, sufficiently close to an HSV RS1 target position, an HSV RL2 target position, or an HSV LAT target position, to allow alteration, e.g., alteration associated with NHEJ, of an HSV RS1 target position, an HSV RL2 target position, or an HSV LAT target position, either alone or in combination with the break positioned by the first gRNA molecule.

In certain embodiments, the third gRNA molecule is configured to provide a cleavage event, e.g., a double strand break or a single strand break, sufficiently close to an HSV RS1 target position, an HSV RL2 target position, or an HSV LAT target position to allow alteration, e.g., alteration associated with NHEJ, of an HSV RS1 target position, an HSV RL2 target position, or an HSV LAT target position, either alone or in combination with the break positioned by the first and/or second gRNA molecule.

In certain embodiments, the fourth gRNA molecule is configured to provide a cleavage event, e.g., a double strand break or a single strand break, sufficiently close to an HSV RS1 target position, an HSV RL2 target position, or an HSV LAT target position to allow alteration, e.g., an alteration associated with NHEJ, of an HSV RS1 target position, an HSV RL2 target position, or an HSV LAT target position, either alone or in combination with the break positioned by the first gRNA molecule, the second gRNA molecule and/or the third gRNA molecule.

In certain embodiments, the second gRNA is selected to target the same HSV RS1 target position, HSV RL2 target position, or HSV LAT target position as the first gRNA molecule. In certain embodiments, the third gRNA molecule and the fourth gRNA molecule are selected to target the same HSV RS1 target position, HSV RL2 target position, or HSV LAT target position as the first and second gRNA molecules.

The targeting domain of the second, third and fourth gRNA molecules can be independently selected from the nucleotide sequences set forth in SEQ ID NOS: 208 to 58749. The second, third or fourth gRNA molecules can be a modular gRNA molecule or a chimeric gRNA molecules.

One or more nucleic acids present within a nucleic acid composition and/or a nucleic acid composition described herein may comprise a promoter operably linked to the nucleotide sequence that encodes the gRNA molecule of (a), e.g., a promoter described herein. The nucleic acid and/or a nucleic acid composition may further comprise a second promoter operably linked to the nucleotide sequence that encodes the second, third and/or fourth gRNA molecule of (c), e.g., a promoter described herein. The promoter and second promoter differ from one another. In certain embodiments, the promoter and second promoter are the same.

The nucleic acid compositions described herein may further comprise a promoter operably linked to the nucleotide sequence that encodes the Cas9 molecule or a Cas9-fusion protein of (b), e.g., a promoter described herein.

The presently disclosed subject matter further provides a composition comprising (a) a presently disclosed gRNA molecule, e.g., a gRNA molecule comprising a targeting domain that is complementary with a target sequence of a RS1, RL2, or LAT gene. In certain embodiments, the composition further comprises (b) a Cas9 molecule (e.g., an eaCas9 molecule or an eiCas9 molecule) or a Cas9-fusion protein, as described herein. In certain embodiments, the Cas9 molecule, e.g., eaCas9 molecule or eiCas9 molecule, can be a Cas9 variant. For example, and not by way of limitation, the Cas9 variant can be a *S. pyogenes* Cas9 variant or an *S. aureus* Cas9 variant. In certain embodiments, the *S. pyogenes* Cas9 variant is the EQR variant. In certain embodiments, the *S. pyogenes* Cas9 variant is the VRER variant. In certain embodiments, the composition further comprises (c) a second, third and/or fourth gRNA molecule, e.g., a second, third and/or fourth gRNA molecule, as described herein. In certain embodiments, the composition is a pharmaceutical composition. The compositions described herein, e.g., pharmaceutical compositions described herein, can be used in treating, preventing, and/or reducing HSV-1 or HSV-2 infections in a subject, e.g., in accordance with a method disclosed herein.

The presently disclosed subject matter further provides a method of altering a HSV viral gene selected from the group consisting of a RS1 gene, a RL2 gene, and a LAT gene e in a cell, comprising administering to said cell one of:

(i) a genome editing system comprising a gRNA molecule comprising a targeting domain that is complementary with a target sequence of said HSV viral gene, and at least a Cas9 molecule;

(ii) a vector comprising a polynucleotide encoding a gRNA molecule comprising a targeting domain that is complementary with a target sequence of said HSV viral gene, and a polynucleotide encoding a Cas9 molecule; or (iii) a composition comprising a gRNA molecule comprising a targeting domain that that is complementary with a target sequence of said HSV viral gene, and at least a Cas9 molecule.

In another aspect, disclosed herein is a method of altering a RS1, RL2 or LAT gene a cell, e.g., altering the structure, e.g., altering the sequence, of a target nucleic acid of a cell, comprising contacting said cell with: (a) a presently disclosed gRNA molecule; and (b) a Cas9 molecule (e.g., an eaCas9 molecule) or a Cas9-fusion protein, e.g., a Cas9 molecule as described herein; and optionally, (c) a second, third and/or fourth gRNA molecule that targets the RS1, RL2 or LAT gene, e.g., a second, third and/or fourth gRNA molecule, as described herein. In certain embodiments, the Cas9 molecule can be a Cas9 variant.

In certain embodiments, the method comprises contacting a cell from a subject suffering from or likely to develop HSV-1 and/or HSV-2. The cell may be from a subject that would benefit from having a mutation at an HSV RS1 target position, an HSV RL2 target position, or an HSV LAT target position.

In certain embodiments, the contacting step may be performed in vivo.

In certain embodiments, the method of altering a cell as described herein comprises acquiring knowledge of the sequence of an HSV RS1 target position, an HSV RL2 target position, or an HSV LAT target position in said cell, prior to the contacting step. Acquiring knowledge of the sequence of an HSV RS1 target position, an HSV RL2 target position, or an HSV LAT target position in the cell may be by sequencing one or more of the RS1, RL2 or LAT gene, or a portion of the RS1, RL2 or LAT gene.

In certain embodiments, the contacting step of the method comprises contacting the cell with a nucleic acid composition, e.g., a vector, e.g., an AAV vector or LV vector, that expresses at least one of (a), (b), and (c). In certain embodiments, the contacting step of the method comprises contacting the cell with a nucleic acid composition, e.g., a vector, e.g., an AAV vector or an LV vector, that expresses each of (a), (b), and (c). In certain embodiments, the contacting step of the method comprises delivering to the cell a Cas9 molecule or a Cas9-fusion protein of (b) and a nucleic acid composition which encodes a gRNA molecule of (a) and optionally, a second gRNA molecule (c)(i), and further optionally, a third gRNA molecule (c)(ii) and/or fourth gRNA molecule (c)(iii).

In certain embodiments, the contacting step comprises contacting the cell with a nucleic acid composition, e.g., a vector, e.g., an AAV vector or LV vector, that expresses at least one of (a), (b), (c) and (d). In certain embodiments, the contacting step of the method comprises contacting the cell with a nucleic acid composition, e.g., a vector, e.g., an AAV vector, that expresses each of (a), (b), and (c). In certain embodiments, the contacting step of the method comprises delivering to the cell a Cas9 molecule or a Cas9-fusion protein of (b), a nucleic acid composition which encodes a gRNA molecule of (a) and a template nucleic acid of (d), and optionally, a second gRNA molecule (c)(i), and further optionally, a third gRNA molecule (c)(iv) and/or fourth gRNA molecule (c)(iii).

In certain embodiments, the contacting step comprises contacting the cell with a nucleic acid composition, e.g., a vector, e.g., an AAV vector, e.g., an AAV2 vector, a modified AAV2 vector, an AAV3 vector, a modified AAV3 vector, an AAV6 vector, a modified AAV6 vector, an AAV8 vector or an AAV9 vector, as described herein. In certain embodiments, the vector is an LV vector.

In certain embodiments, contacting comprises delivering to the cell a Cas9 molecule or a Cas9-fusion protein of (b), as a protein or an mRNA, and a nucleic acid composition which encodes a gRNA molecule of (a) and optionally a second, third and/or fourth gRNA molecule of (c).

In certain embodiments, the contacting step comprises delivering to the cell a Cas9 molecule or Cas9-fusion protein of (b), as a protein or an mRNA, said gRNA molecule of (a), as an RNA, and optionally said second, third and/or fourth gRNA molecule of (c), as an RNA.

In certain embodiments, contacting comprises delivering to the cell a gRNA molecule of (a) as an RNA, optionally the second, third and/or fourth gRNA molecule of (c) as an RNA, and a nucleic acid composition that encodes the Cas9 molecule or a Cas9-fusion protein of (b).

The presently disclosed subject matter further provides a method of treating, preventing, and/or reducing a subject suffering from or likely to develop HSV-1 and/or HSV-2, e.g., by altering the structure, e.g., sequence, of a target nucleic acid of the subject, comprising contacting the subject (or a cell from the subject) with:

(a) a present disclosed gRNA molecule, e.g., a gRNA molecule that targets the RS1, RL2 or LAT gene;

(b) a Cas9 molecule (e.g., an eaCas9 molecule or an eiCas9 molecule) or Cas9-fusion protein, e.g., a Cas9 molecule disclosed herein; and optionally, (c)(i) a second gRNA molecule that targets the RS1, RL2 or LAT gene, e.g., a second gRNA molecule disclosed herein, and further optionally, (c)(ii) a third gRNA molecule, and still further optionally, (c)(iii) a fourth gRNA that targets the RL2 or LAT or RS1 gene, e.g., a third and fourth gRNA molecule disclosed herein.

In certain embodiments, the method comprises introducing a mutation at an HSV RS1 target position, an HSV RL2 target position, or an HSV LAT target position, e.g., by NHEJ.

In certain embodiments, a cell of the subject is contacted in vivo (e.g., by intravenous delivery) with (a), (b) and optionally (c)(i), further optionally (c)(ii), and still further optionally (c)(iii).

In certain embodiments, the contacting step comprises contacting the subject with a nucleic acid composition, e.g., a vector, e.g., an AAV vector or an LV vector, described herein, e.g., a nucleic acid composition that encodes at least one of (a), (b), and optionally (c)(i), further optionally (c)(ii), and still further optionally (c)(iii).

In certain embodiments, the contacting step comprises delivering to said subject said Cas9 molecule or Cas9-fusion protein of (b), as a protein or mRNA, and a nucleic acid composition which encodes (a), and optionally (c)(i), further optionally (c)(ii), and still further optionally (c)(iii).

In certain embodiments, the contacting step comprises delivering to the subject the Cas9 molecule or Cas9-fusion protein of (b), as a protein or mRNA, the gRNA molecule of (a), as an RNA, and optionally the second gRNA of (c)(i), further optionally (c)(ii), and still further optionally (c)(iii), as an RNA.

In certain embodiments, the contacting step comprises delivering to the subject the gRNA molecule of (a), as an RNA, optionally said second gRNA of (c)(i), further optionally (c)(ii), and still further optionally (c)(iii), as an RNA, a nucleic acid composition that encodes the Cas9 molecule or Cas9-fusion protein of (b).

When the method comprises (1) introducing a mutation at an HSV RS1 target position, an HSV RL2 target position, or an HSV LAT target position by NHEJ or (2) knocking down expression of one or more of the RS1, RL2 and/or LAT gene(s), e.g., by targeting the promoter region, a Cas9 molecule or Cas9-fusion protein of (b) and at least one gRNA molecule, e.g., a gRNA molecule of (a) are included in the contacting step.

The presently disclosed subject matter provides a reaction mixture comprising a gRNA molecule, a nucleic acid composition, or a composition described herein, and a cell, e.g., a cell from a subject having, or likely to develop HSV-1 and/or HSV-2, or a subject which would benefit from a mutation at an HSV RL2 target position or HSV LAT target position or HSV RS1 target position.

The presently disclosed subject matter provides a kit comprising, (a) a gRNA molecule described herein, or nucleic acid composition that encodes the gRNA molecule, and one or more of the following:

(b) a Cas9 molecule (e.g., an eaCas9 molecule or an eiCas9 molecule) or Cas9-fusion protein, e.g., a Cas9 molecule described herein, or a nucleic acid or mRNA that encodes the Cas9;

(c)(i) a second gRNA molecule, e.g., a second gRNA molecule described herein or a nucleic acid that encodes (c)(i);

(c)(ii) a third gRNA molecule, e.g., a third gRNA molecule described herein or a nucleic acid that encodes (c)(ii); or (c)(iii) a fourth gRNA molecule, e.g., a fourth gRNA molecule described herein or a nucleic acid that encodes (c)(iii). In certain embodiments, the Cas9 molecule can be a Cas9 variant. For example, and not by way of limitation, the Cas9 variant can be an S. pyogenes Cas9 variant or an S. aureus Cas9 variant. In certain embodiments, the S. pyogenes Cas9 variant is the EQR variant. In certain embodiments, the S. pyogenes Cas9 variant is the VRER variant.

In certain embodiments, the kit comprises nucleic acid, e.g., an AAV vector or LV vector, that encodes one or more of (a), (b), (c)(i), (c)(ii), and (c)(iii).

The presently disclosed subject matter provides a gRNA molecule, e.g., a gRNA molecule described herein, for use in treating, preventing, reducing, or delaying the onset or progression of HSV-1 and/or HSV-2 infection in a subject, e.g., in accordance with a method of treating, preventing, reducing, or delaying the onset or progression of HSV-1 and/or HSV-2 infection as described herein.

In certain embodiments, the gRNA molecule is used in combination with a Cas9 molecule (e.g., an eaCas9 molecule or an eiCas9 molecule) or Cas9-fusion protein, e.g., a Cas9 molecule described herein. For example, and not by way of limitation, the Cas9 molecule or Cas9-fusion protein is a Cas9 variant. For example, and not by way of limitation, the Cas9 variant can be a S. pyogenes Cas9 variant or a S. aureus Cas9 variant. In certain embodiments, the S. pyogenes Cas9 variant is the EQR variant. In certain embodiments, the S. pyogenes Cas9 variant is the VRER variant. Additionally or alternatively, in certain embodiments, the gRNA molecule is used in combination with a second, third and/or fourth gRNA molecule, e.g., a second, third and/or fourth gRNA molecule described herein.

The presently disclosed subject matter provides use of a gRNA molecule, e.g., a gRNA molecule described herein, in the manufacture of a medicament for treating, or delaying the onset or progression of HSV-1 and/or HSV-2 in a subject, e.g., in accordance with a method of treating, preventing, reducing, or delaying the onset or progression of HSV-1 and/or HSV-2 as described herein.

In certain embodiments, the medicament comprises a Cas9 molecule (e.g., an eaCas9 molecule or an eiCas9 molecule) or Cas9-fusion protein, e.g., a Cas9 molecule described herein. Additionally or alternatively, in certain embodiments, the medicament comprises a second, third and/or fourth gRNA molecule, e.g., a second, third and/or fourth gRNA molecule described herein. In certain embodiments, the Cas9 molecule can be a Cas9 variant. For example, and not by way of limitation, the Cas9 variant can be a S. pyogenes Cas9 variant or a S. aureus Cas9 variant. In certain embodiments, the S. pyogenes Cas9 variant is the EQR variant. In certain embodiments, the S. pyogenes Cas9 variant is the VRER variant.

The gRNA molecules, genome editing systems, methods, compositions, reaction mixtures and kits, as disclosed herein, can also include a governing gRNA molecule, e.g., a governing gRNA molecule disclosed herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Headings, including numeric and alphabetical headings and subheadings, are for organization and presentation and are not intended to be limiting.

Other features and advantages of the invention will be apparent from the detailed description, drawings, and from the claims.

BRIEF DESCRIPTION OF THE DRAWINGS

FIGS. 1A-1I are representations of several exemplary gRNAs. FIG. 1A depicts a modular gRNA molecule derived in part (or modeled on a sequence in part) from *Streptococcus pyogenes* (*S. pyogenes*) as a duplexed structure (SEQ ID NOs:39 and 40, respectively, in order of appearance); FIG. 1B depicts a unimolecular gRNA molecule derived in part from *S. pyogenes* as a duplexed structure (SEQ ID NO:41); FIG. 1C depicts a unimolecular gRNA molecule derived in part from *S. pyogenes* as a duplexed structure (SEQ ID NO:42); FIG. 1D depicts a unimolecular gRNA molecule derived in part from *S. pyogenes* as a duplexed structure (SEQ ID NO:43); FIG. 1E depicts a unimolecular gRNA molecule derived in part from *S. pyogenes* as a duplexed structure (SEQ ID NO:44); FIG. 1F depicts a modular gRNA molecule derived in part from *Streptococcus thermophilus* (*S. thermophilus*) as a duplexed structure (SEQ ID NOs:45 and 46, respectively, in order of appearance); and FIG. 1G depicts an alignment of modular gRNA molecules of *S. pyogenes* and *S. thermophilus* (SEQ ID NOs:39, 45, 47, and 46, respectively, in order of appearance). FIGS. 1H-1I depicts additional exemplary structures of unimolecular gRNA molecules. FIG. 1H shows an exemplary structure of a unimolecular gRNA molecule derived in part from *S. pyogenes* as a duplexed structure (SEQ ID NO:42). FIG. 1I shows an exemplary structure of a unimolecular gRNA molecule derived in part from *S. aureus* as a duplexed structure (SEQ ID NO:38).

Figure 2D:
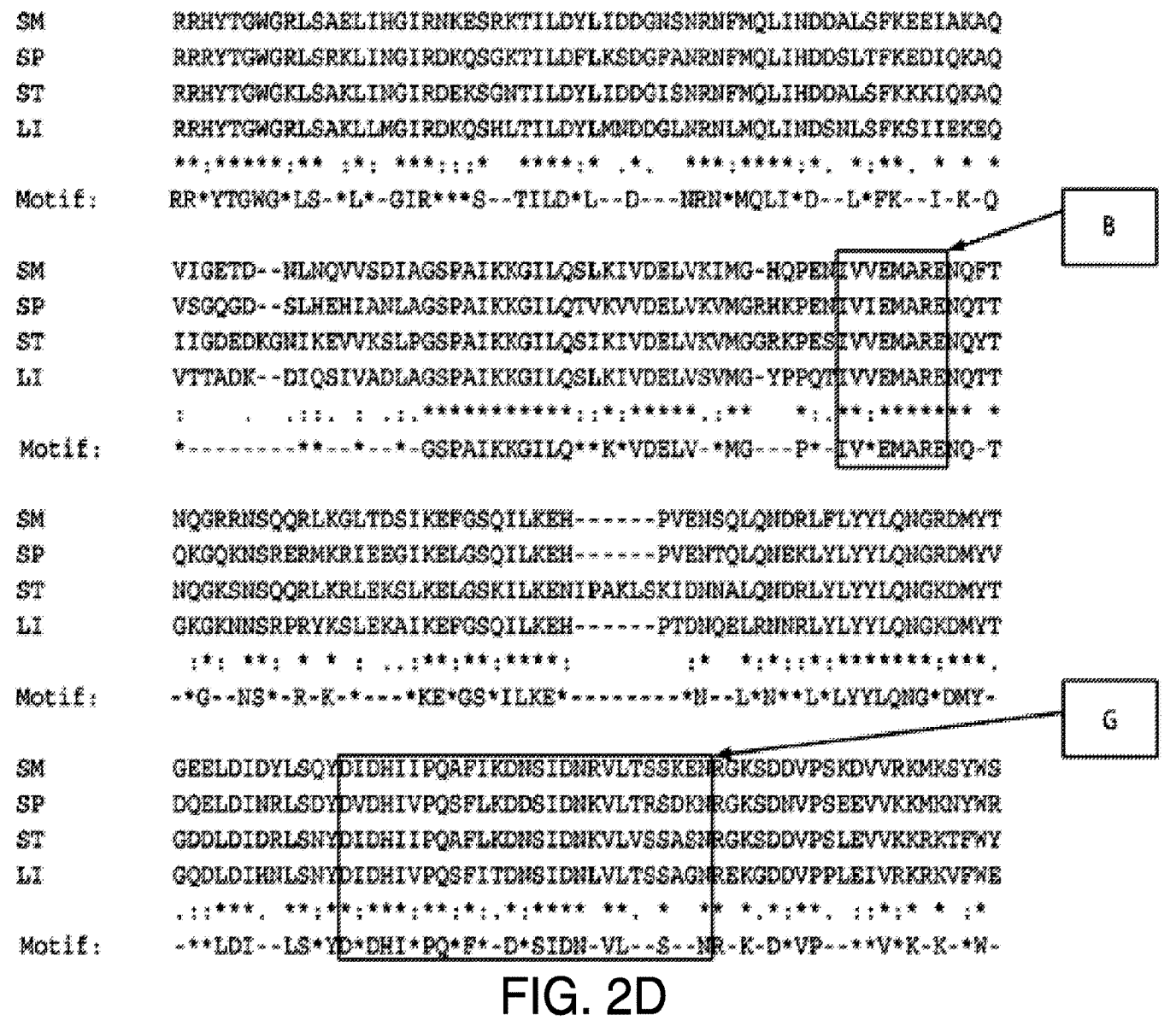
Figure 2E:
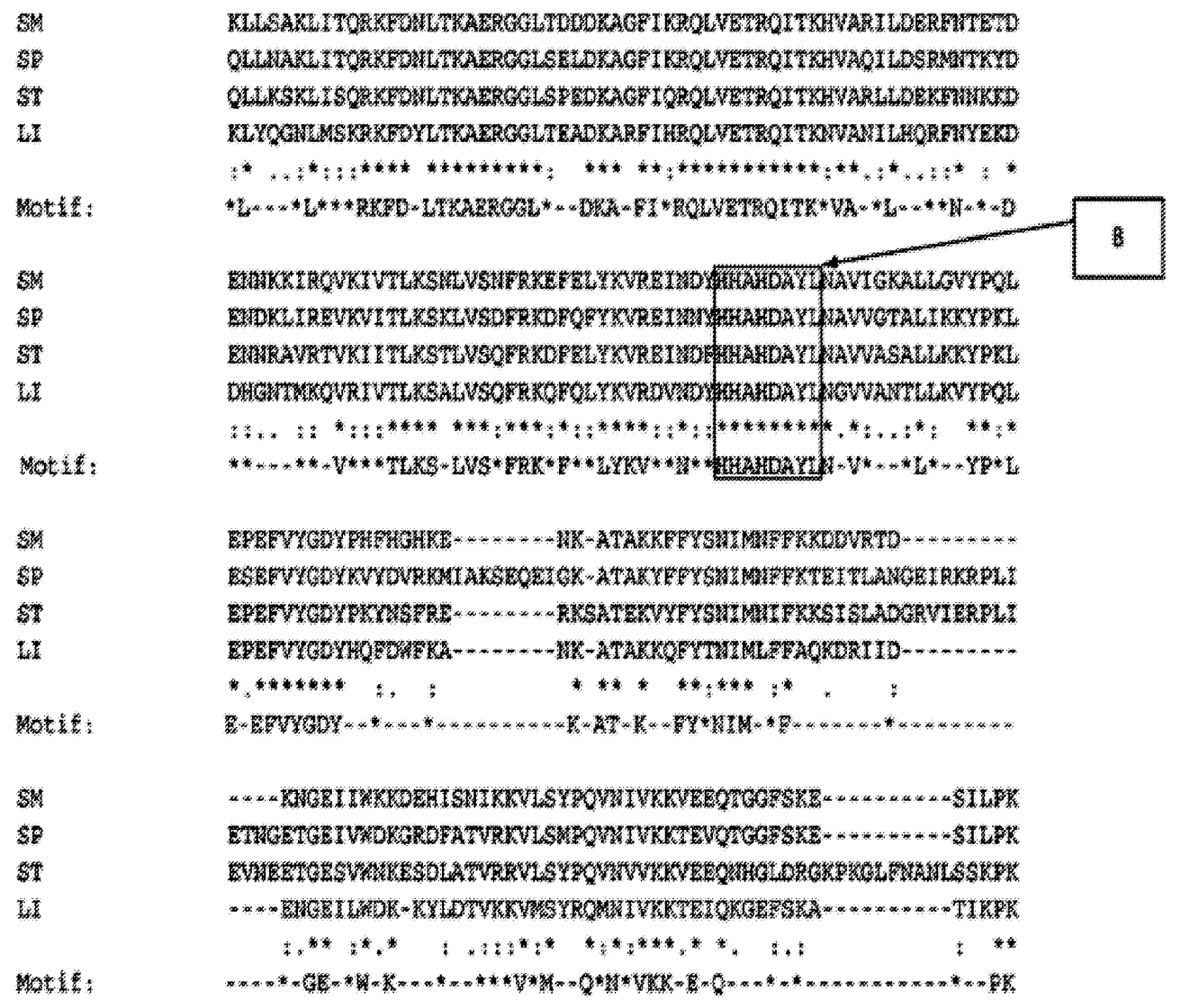

FIGS. 2A-2G depict an alignment of Cas9 sequences (Chylinski 2013). The N-terminal RuvC-like domain is boxed and indicated with a "Y." The other two RuvC-like domains are boxed and indicated with a "B." The HNH-like domain is boxed and indicated by a "G." Sm: *S. mutans* (SEQ ID NO:1); Sp: *S. pyogenes* (SEQ ID NO:2); St: *S. thermophilus* (SEQ ID NO:4); and Li: *L. innocua* (SEQ ID NO:5). "Motif" (SEQ ID NO:14) is a consensus sequence based on the four sequences. Residues conserved in all four sequences are indicated by single letter amino acid abbreviation; "*" indicates any amino acid found in the corresponding position of any of the four sequences; and "-" indicates absent.

FIGS. 3A-3B show an alignment of the N-terminal RuvC-like domain from the Cas9 molecules disclosed in Chylinski 2013 (SEQ ID NOs:52-95, 120-123). The last line of FIG. 3B identifies 4 highly conserved residues.

FIGS. 4A-4B show an alignment of the N-terminal RuvC-like domain from the Cas9 molecules disclosed in Chylinski 2013 with sequence outliers removed (SEQ ID NOs:52-123). The last line of FIG. 4B identifies 3 highly conserved residues.

FIGS. 5A-5C show an alignment of the HNH-like domain from the Cas9 molecules disclosed in Chylinski 2013 (SEQ ID NOs:124-198). The last line of FIG. 5C identifies conserved residues.

FIGS. 6A-6B show an alignment of the HNH-like domain from the Cas9 molecules disclosed in Chylinski 2013 with sequence outliers removed (SEQ ID NOs:124-141, 148, 149, 151-153, 162, 163, 166-174, 177-187, 194-198). The last line of FIG. 6B identifies 3 highly conserved residues.

FIG. 8A shows the organization of the Cas9 domains, including amino acid positions, in reference to the two lobes of Cas9 (recognition (REC) and nuclease (NUC) lobes). FIG. 8B shows the percent homology of each domain across 83 Cas9 orthologs.

Figure 1A:
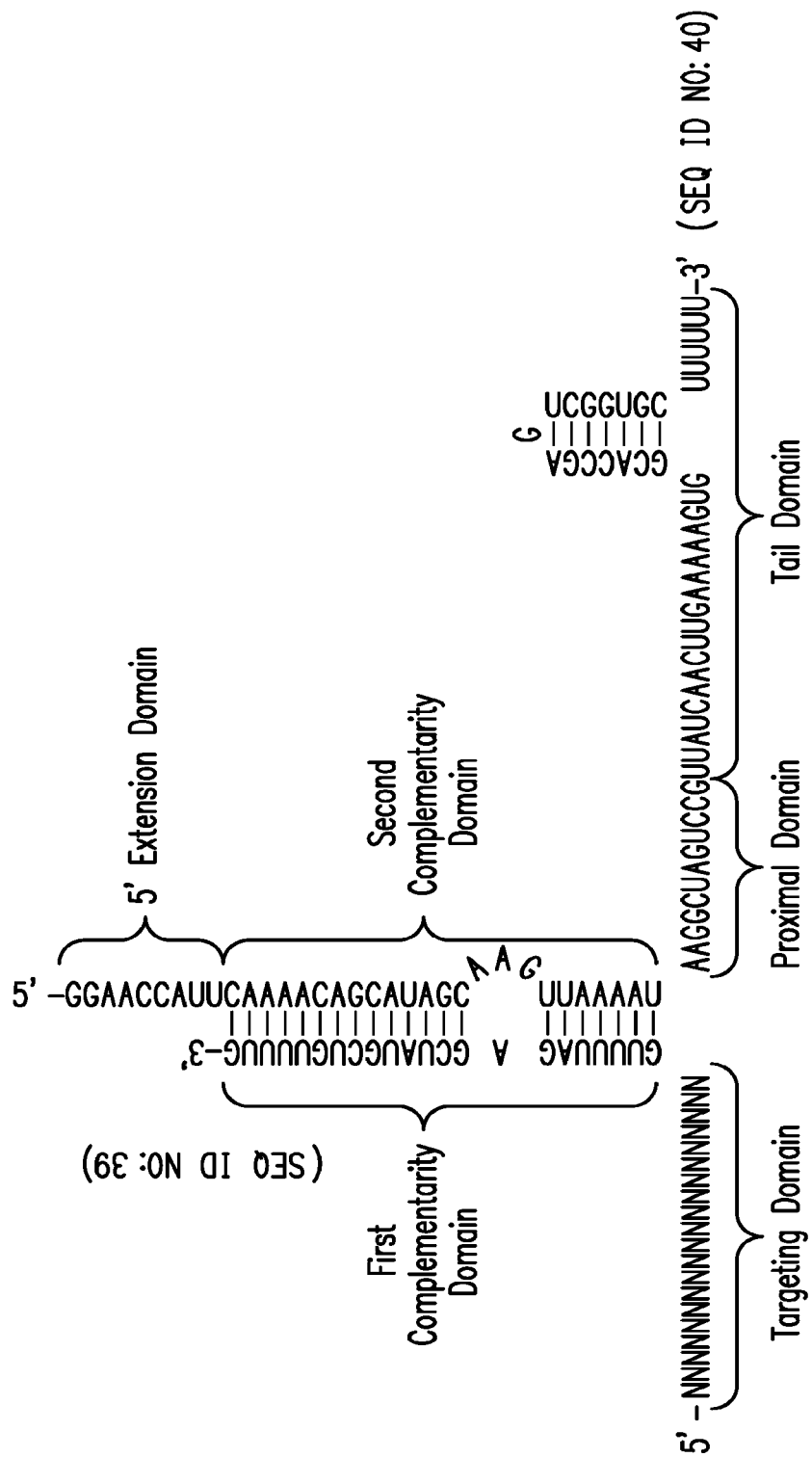
Figure 1B:
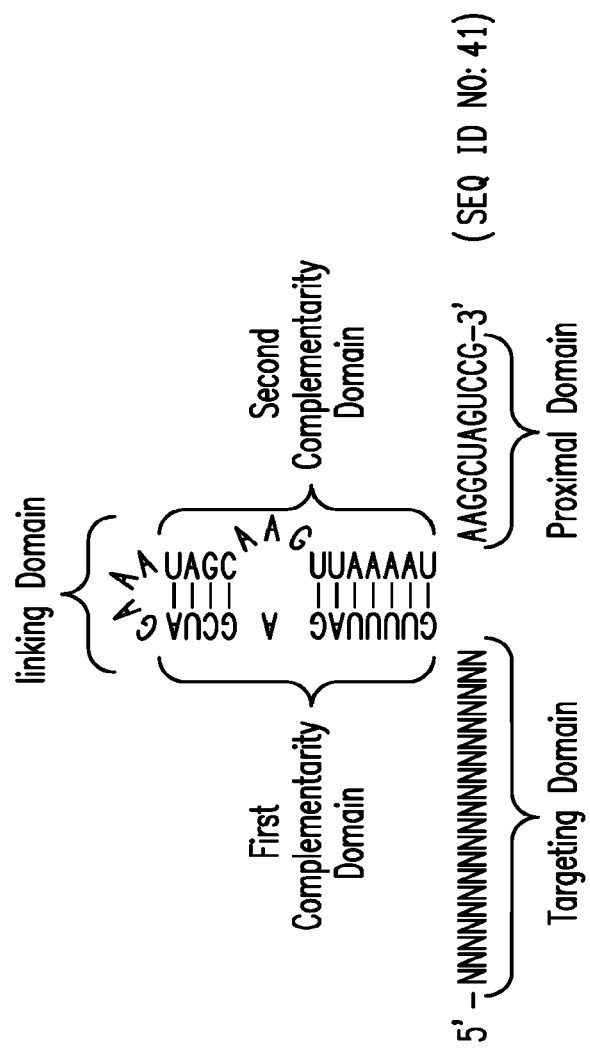
Figure 1C:
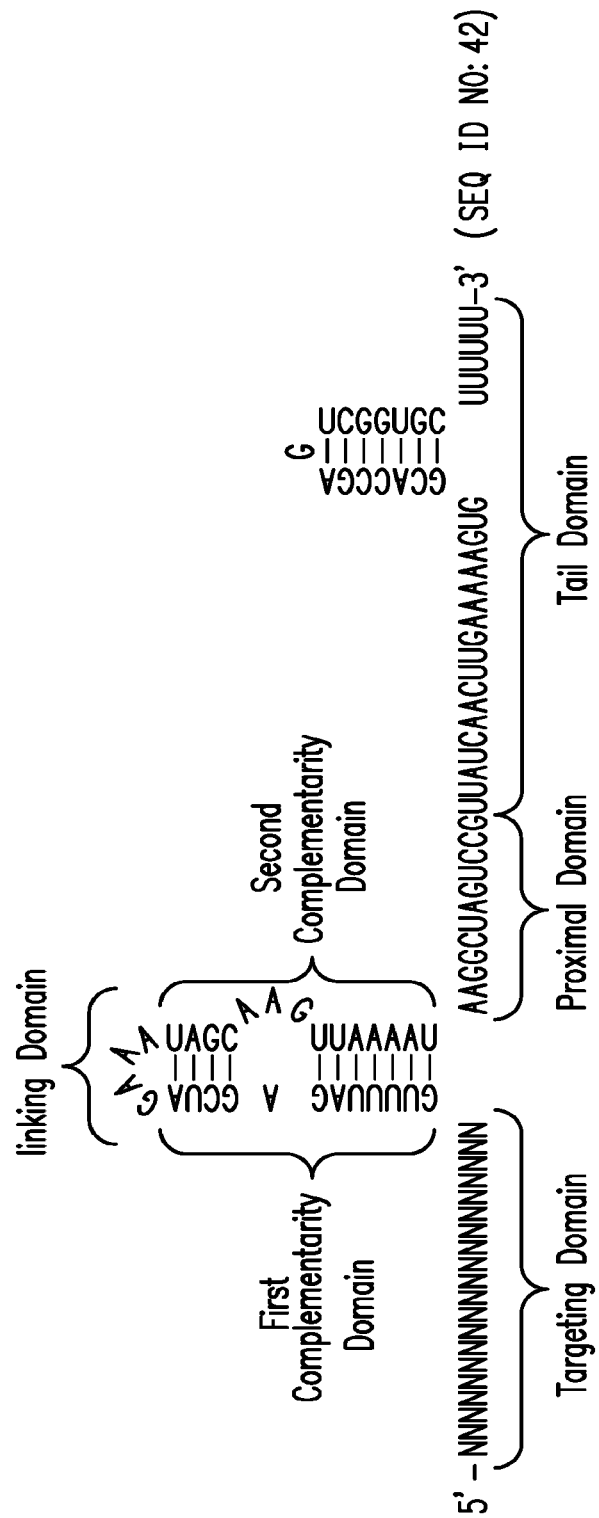
Figure 1D:
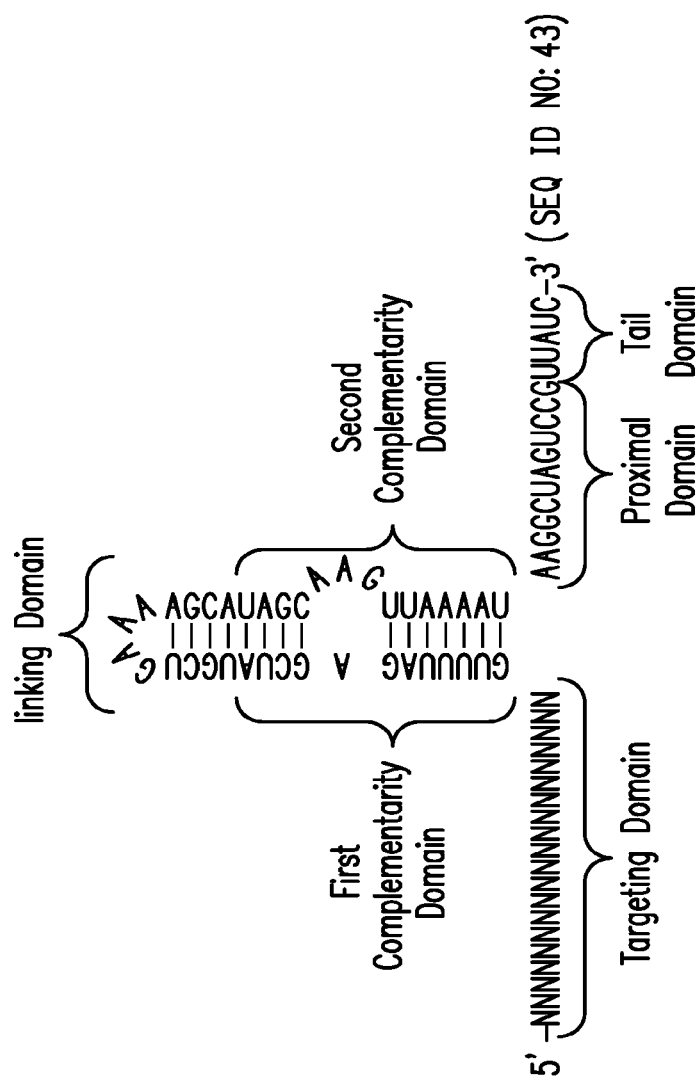
Figure 1E:
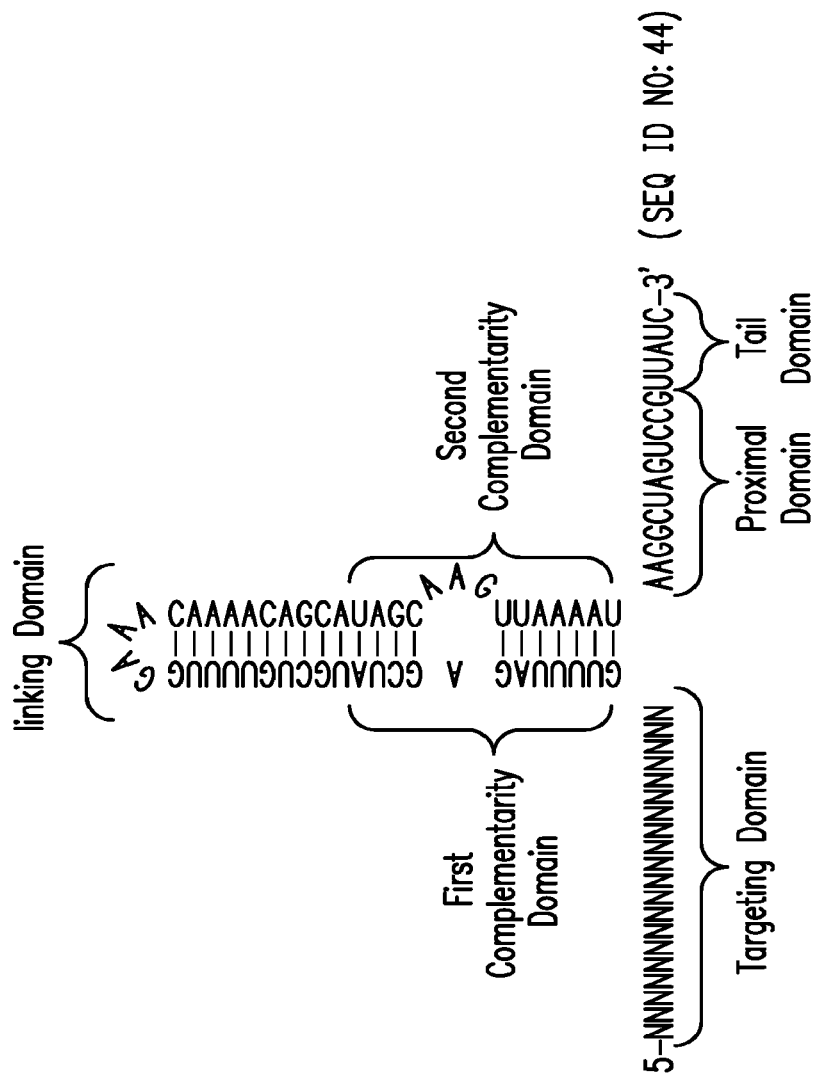

(see Example 3). (B) shows HSV1 target knockdown of RS1 listed in Table 19 (see Example 3).

DETAILED DESCRIPTION

For purposes of clarity of disclosure and not by way of limitation, the detailed description is divided into the following subsections:
1. Definitions
2. Herpes Simplex Virus
3. Methods to Treat, Prevent and/or Reduce HSV-related Ocular Infection;
4. Methods of Altering RS1, RL2, and/or LAT gene(s)
5. Guide RNA (gRNA) Molecules
6. Methods for Designing gRNAs
7. Cas9 Molecules
8. Functional Analysis of Candidate Molecules
9. Genome Editing Approaches
10. Target Cells
11. Delivery, Formulations and Routes of Administration
12. Modified Nucleosides, Nucleotides, and Nucleic Acids

1. Definitions

As used herein, the term "about" or "approximately" means within an acceptable error range for the particular value as determined by one of ordinary skill in the art, which can depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, a "genome editing system" refers to any system having RNA-guided DNA editing activity. Genome editing systems of the present disclosure include at least two components adapted from naturally occurring CRISPR systems: a guide RNA (gRNA) and an RNA-guided nuclease. These two components form a complex that is capable of associating with a specific nucleic acid sequence in a cell and editing the DNA in or around that nucleic acid sequence, for instance by making one or more of a single-strand break (an SSB or nick), a double-strand break (a DSB) and/or a point mutation.

Genome editing systems may comprise, in various embodiments, (a) one or more Cas9/gRNA complexes, and (b) separate Cas9 molecules and gRNAs that are capable of associating in a cell to form one or more Cas9/gRNA complexes. A genome editing system according to the present disclosure may be encoded by one or more nucleotides (e.g. RNA, DNA) comprising coding sequences for Cas9 and/or gRNAs that can associate to form a Cas9/gRNA complex, and the one or more nucleotides encoding the gene editing system may be carried by a vector as described herein.

In certain embodiments, the genome editing system targets a HSV viral gene selected from the group consisting of a RS1 gene, a RL2 gene and a LAT gene. A presently disclosed genome editing system can be used to alter (knock out or knock down) one or more HSV viral gene, e.g., a RS1 gene, a RL2 gene, and/or a LAT gene.

In certain embodiments, the genome editing system targets a RS1 gene. In certain embodiments, the RS1 gene is a human RS1 gene. In certain embodiments, the genome editing system targets a RL2 gene. In certain embodiments, the RL2 gene is a human RL2 gene. In certain embodiments, the genome editing system targets a LAT gene. In certain embodiments, the LAT gene is a human LAT gene. In certain embodiments, the genome editing system targets two or three of RS1, RL2 and LAT genes.

In certain embodiments, the genome editing system that targets a RS1 gene comprises a first gRNA molecule comprising a targeting domain complementary to a target domain (also referred to as "target sequence") in the RS1 gene, or a polynucleotide encoding thereof, and at least one Cas9 molecule or polynucleotide(s) encoding thereof. In certain embodiments, the genome editing system that targets a RS1 gene further comprises a second gRNA molecule comprising a targeting domain complementary to a second target domain in the RS1 gene, or a polynucleotide encoding thereof. The the genome editing system that targets a RS1 gene may further comprise a third and a fourth gRNA molecules that target the RS1 gene.

In certain embodiments, the genome editing system that targets a RL2 gene comprises a first gRNA molecule comprising a targeting domain complementary to a target domain in the RL2 gene, or a polynucleotide encoding thereof, and at least one Cas9 molecule or polynucleotide(s) encoding thereof. In certain embodiments, the genome editing system that targets a RL2 gene further comprises a second gRNA molecule comprising a targeting domain complementary to a second target domain in the RL2 gene, or a polynucleotide encoding thereof. The the genome editing system that targets a RL2 gene may further comprise a third and a fourth gRNA molecules that target the RL2 gene.

In certain embodiments, the genome editing system that targets a LAT gene comprises a first gRNA molecule comprising a targeting domain complementary to a target domain in the LAT gene, or a polynucleotide encoding thereof, and at least one Cas9 molecule or polynucleotide(s) encoding thereof. In certain embodiments, the genome editing system that targets a LAT gene further comprises a second gRNA molecule comprising a targeting domain complementary to a second target domain in the LAT gene, or a polynucleotide encoding thereof. The the genome editing system that targets a LAT gene may further comprise a third and a fourth gRNA molecules that target the LAT gene.

In certain embodiments, the genome editing system is implemented in a cell or in an in vitro or in vivo contact. In certain embodiments, the genome editing system is used in a medicament, e.g., a medicament for modifying one or more target genes (e.g., RS1, RL2 and/or LAT genes), or a medicament for treating, preventing, and/or reducing HSV infection (HSV-1 or HSV-2 infection). In certain embodiments, the genome editing system is used in therapy.

"Target gene" as used herein, refers to any nucleotide sequence encoding a known or putative gene product. In certain embodiments, the target gene is a HSV viral gene. As used herein, a "HSV viral gene" refers to a (HSV-1 or HSV-2) RS1 gene, a (HSV-1 or HSV-2) RL2 gene, or a (HSV-1 or HSV-2) LAT gene.

"HSV1 RS1 target knockout position," as used herein, refers to a position in the RS1 gene of HSV1, which if altered by NHEJ-mediated alteration, results in reduction or elimination of expression of a functional RS1 gene product. In certain embodiments, the position is in the coding region (e.g., an early coding region) of the RS1 gene. In certain embodiments, the position is in the non-coding region of the RS1 gene.

"HSV2 RS1 target knockout position," as used herein, refers to a position in the RS1 gene of HSV2, which if altered by NHEJ-mediated alteration, results in reduction or elimination of expression of a functional RS1 gene product. In certain embodiments, the position is in the coding region (e.g., an early coding region) of the RS1 gene. In certain embodiments, the position is in the non-coding region of the RS1 gene.

"HSV RS1 target knockout position," as used herein, refers to a position in the RS1 gene of HSV (e.g., HSV-1 or HSV-2), which if altered by NHEJ-mediated alteration, results in reduction or elimination of expression of a functional RS1 gene product. In certain embodiments, the position is in the coding region (e.g., an early coding region) of the RS1 gene. In certain embodiments, the position is in the non-coding region of the RS1 gene.

"HSV1 RS1 target knockdown position", as used herein, refers to a position in the RS1 gene of HSV1, which if targeted by an eiCas9 or an eiCas9-fusion protein described herein, results in reduction or elimination of expression of functional RS1 gene product. In certain embodiments, transcription is reduced or eliminated. In certain embodiments, the position is in the promoter region of the RS1 gene (e.g., a position in the promoter region of the RS1 gene is targeted by an eiCas9 or an eiCas9-fusion protein).

"HSV2 RS1 target knockdown position", as used herein, refers to a position in the RS1 gene of HSV2, which if targeted by an eiCas9 or an eiCas9-fusion protein described herein, results in reduction or elimination of expression of functional RS1 gene product. In certain embodiments, transcription is reduced or eliminated. In certain embodiments, the position is in the promoter region of the RS1 gene (e.g., a position in the promoter region of the RS1 gene is targeted by an eiCas9 or an eiCas9-fusion protein).

"HSV RS1 target knockdown position", as used herein, refers to a position in the RS1 gene of HSV (e.g., HSV-1 or HSV-2), which if targeted by an eiCas9 or an eiCas9-fusion protein described herein, results in reduction or elimination of expression of functional RS1 gene product. In certain embodiments, transcription is reduced or eliminated. In certain embodiments, the position is in the promoter region of the RS1 gene (e.g., a position in the promoter region of the RS1 gene is targeted by an eiCas9 or an eiCas9-fusion protein).

"HSV RS1 target position", as used herein, includes HSV RS1 target knockdown position and/or HSV RS1 target knockout position.

"HSV1 RL2 target knockout position," as used herein, refers to a position in the RL2 gene of HSV1, which if altered by NHEJ-mediated alteration, results in reduction or elimination of expression of a functional RL2 gene product. In certain embodiments, the position is in the coding region (e.g., an early coding region) of the RL2 gene. In certain embodiments, the position is in the non-coding region of the RL2 gene.

"HSV2 RL2 target knockout position," as used herein, refers to a position in the RL2 gene of HSV2, which if altered by NHEJ-mediated alteration, results in reduction or elimination of expression of a functional RL2 gene product. In certain embodiments, the position is in the coding region (e.g., an early coding region) of the RL2 gene. In certain embodiments, the position is in the non-coding region of the RL2 gene.

"HSV RL2 target knockout position", as used herein, refers to a position in the RL2 gene of HSV (e.g., HSV-1 or HSV-2), which if altered by NHEJ-mediated alteration, results in reduction or elimination of expression of a functional RL2 gene product. In certain embodiments, the position is in the coding region (e.g., an early coding region) of the RL2 gene. In certain embodiments, the position is in the non-coding region of the RL2 gene.

"HSV1 RL2 target knockdown position", as used herein, refers to a position in the RL2 gene of HSV1, which if targeted by an eiCas9 or an eiCas9-fusion protein described herein, results in reduction or elimination of expression of functional RL2 gene product. In certain embodiments, transcription is reduced or eliminated. In certain embodiments, the position is in the promoter region of the RL2 gene (e.g., a position in the promoter region of the RL2 gene is targeted by an eiCas9 or an eiCas9-fusion protein).

"HSV2 RL2 target knockdown position", as used herein, refers to a position in the RL2 gene of HSV2, which if targeted by an eiCas9 or an eiCas9-fusion protein described herein, results in reduction or elimination of expression of functional RL2 gene product. In certain embodiments, transcription is reduced or eliminated. In certain embodiments, the position is in the promoter region of the RL2 gene (e.g., a position in the promoter region of the RL2 gene is targeted by an eiCas9 or an eiCas9-fusion protein).

"HSV RL2 target knockdown position", as used herein, refers to a position in the RL2 gene of HSV (e.g., HSV-1 or HSV-2), which if targeted by an eiCas9 or an eiCas9-fusion protein described herein, results in reduction or elimination of expression of functional RL2 gene product. In certain embodiments, transcription is reduced or eliminated. In certain embodiments, the position is in the promoter region of the RL2 gene (e.g., a position in the promoter region of the RL2 gene is targeted by an eiCas9 or an eiCas9-fusion protein).

"HSV RL2 target position", as used herein, refers to an HSV RL2 target knockout position and/or an HSV RL2 target knockdown position.

"HSV1 LAT target knockout position," as used herein, refers to a position in the LAT gene of HSV1, which if altered by NHEJ-mediated alteration, results in reduction or elimination of expression of a functional LAT gene product. In certain embodiments, the position is in the coding region (e.g., an early coding region) of the LAT gene. In certain embodiments, the position is in the non-coding region of the LAT gene.

"HSV2 LAT target knockout position," as used herein, refers to a position in the LAT gene of HSV2, which if altered by NHEJ-mediated alteration, results in reduction or elimination of expression of a functional LAT gene product. In certain embodiments, the position is in the coding region (e.g., an early coding region) of the LAT gene. In certain embodiments, the position is in the non-coding region of the LAT gene.

"HSV LAT target knockout position", as used herein, refers to a position in the LAT gene of HSV (e.g., HSV-1 or HSV-2), which if altered by NHEJ-mediated alteration, results in reduction or elimination of expression of a functional LAT gene product. In certain embodiments, the position is in the LAT gene coding region, e.g., an early coding region. In certain embodiments, the position is in the non-coding region of the LAT gene.

"HSV1 LAT target knockdown position", as used herein, refers to a position in the LAT gene of HSV1, which if targeted by an eiCas9 or an eiCas9-fusion protein described herein, results in reduction or elimination of expression of functional LAT gene product. In certain embodiments, transcription is reduced or eliminated. In certain embodiments, the position is in the promoter region of the LAT gene (e.g., a position in the promoter region of the LAT gene is targeted by an eiCas9 or an eiCas9-fusion protein).

"HSV2 LAT target knockdown position", as used herein, refers to a position in the LAT gene of HSV2, which if targeted by an eiCas9 or an eiCas9-fusion protein described herein, results in reduction or elimination of expression of functional LAT gene product. In certain embodiments, transcription is reduced or eliminated. In certain embodiments, the position is in the promoter region of the LAT gene (e.g., a position in the promoter region of the LAT gene is targeted by an eiCas9 or an eiCas9-fusion protein).

"HSV LAT target knockdown position", as used herein, refers to a position in the RL2 gene of HSV (e.g., HSV-1 or HSV-2), which if targeted by an eiCas9 or an eiCas9-fusion protein described herein, results in reduction or elimination of expression of functional LAT gene product. In certain embodiments, transcription is reduced or eliminated. In certain embodiments, the position is in the promoter region of the LAT gene (e.g., a position in the promoter region of the LAT gene is targeted by an eiCas9 or an eiCas9-fusion protein).

"HSV LAT target position", as used herein, refers to an HSV LAT target knockout position and/or an HSV LAT target knockdown position.

"Domain", as used herein, is used to describe segments of a protein or nucleic acid. Unless otherwise indicated, a domain is not required to have any specific functional property.

Calculations of homology or sequence identity between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frame shift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

"Governing gRNA molecule", as used herein, refers to a gRNA molecule that comprises a targeting domain that is complementary to a target domain on a nucleic acid that comprises a sequence that encodes a component of the CRISPR/Cas system that is introduced into a cell or subject. A governing gRNA does not target an endogenous cell or subject sequence. In certain embodiments, a governing gRNA molecule comprises a targeting domain that is complementary with a target sequence on: (a) a nucleic acid that encodes a Cas9 molecule; (b) a nucleic acid that encodes a gRNA which comprises a targeting domain that targets the RS1, RL2, or LAT gene (a target gene gRNA); or on more than one nucleic acid that encodes a CRISPR/Cas component, e.g., both (a) and (b). In certain embodiments, a nucleic acid molecule that encodes a CRISPR/Cas component, e.g., that encodes a Cas9 molecule or a target gene gRNA, comprises more than one target domain that is complementary with a governing gRNA targeting domain. In certain embodiments, a governing gRNA molecule complexes with a Cas9 molecule and results in Cas9 mediated inactivation of the targeted nucleic acid, e.g., by cleavage or by binding to the nucleic acid, and results in cessation or reduction of the production of a CRISPR/Cas system component. In certain embodiments, the Cas9 molecule forms two complexes: a complex comprising a Cas9 molecule with a target gene gRNA, which complex can alter the RS1, RL2, or LAT gene; and a complex comprising a Cas9 molecule with a governing gRNA molecule, which complex can act to prevent further production of a CRISPR/Cas system component, e.g., a Cas9 molecule or a target gene gRNA molecule. In certain embodiments, a governing gRNA molecule/Cas9 molecule complex binds to or promotes cleavage of a control region sequence, e.g., a promoter, operably linked to a sequence that encodes a Cas9 molecule, a sequence that encodes a transcribed region, an exon, or an intron, for the Cas9 molecule. In certain embodiments, a governing gRNA molecule/Cas9 molecule complex binds to or promotes cleavage of a control region sequence, e.g., a promoter, operably linked to a gRNA molecule, or a sequence that encodes the gRNA molecule. In certain embodiments, the governing gRNA, e.g., a Cas9-targeting governing gRNA molecule, or a target gene gRNA-targeting governing gRNA molecule, limits the effect of the Cas9 molecule/target gene gRNA molecule complex-mediated gene targeting. In certain embodiments, a governing gRNA places temporal, level of expression, or other limits, on activity of the Cas9 molecule/target gene gRNA molecule complex. In certain embodiments, a governing gRNA reduces off-target or other unwanted activity. In certain embodiments, a governing gRNA molecule inhibits, e.g., entirely or substantially entirely inhibits, the production of a component of the Cas9 system and thereby limits, or governs, its activity.

"Modulator", as used herein, refers to an entity, e.g., a drug that can alter the activity (e.g., enzymatic activity, transcriptional activity, or translational activity), amount, distribution, or structure of a subject molecule or genetic sequence. In certain embodiments, modulation comprises cleavage, e.g., breaking of a covalent or non-covalent bond, or the forming of a covalent or non-covalent bond, e.g., the attachment of a moiety, to the subject molecule. In certain embodiments, a modulator alters the, three dimensional, secondary, tertiary, or quaternary structure, of a subject molecule. A modulator can increase, decrease, initiate, or eliminate a subject activity.

"Large molecule", as used herein, refers to a molecule having a molecular weight of at least 2, 3, 5, 10, 20, 30, 40, 50, 60, 70, 80, 90, or 100 kD. Large molecules include proteins, polypeptides, nucleic acids, biologics, and carbohydrates.

"Polypeptide", as used herein, refers to a polymer of amino acids having less than 100 amino acid residues. In certain embodiments, it has less than 50, 20, or 10 amino acid residues.

A "Cas9 molecule" or "Cas9 polypeptide" as used herein refers to a molecule or polypeptide, respectively, that can interact with a gRNA molecule and, in concert with the gRNA molecule, localize to a site comprising a target domain (also referred to as "target sequence") and, in certain embodiments, a PAM sequence. Cas9 molecules and Cas9 polypeptides include both naturally occurring Cas9 molecules and Cas9 polypeptides and engineered, altered, or modified Cas9 molecules or Cas9 polypeptides that differ, e.g., by at least one amino acid residue, from a reference sequence, e.g., the most similar naturally occurring Cas9 molecule.

In certain embodiments, the Cas9 molecule is a wild-type S. pyogenes Cas9, which recognizes a NGG PAM sequence. In certain embodiments, the Cas9 molecule is an S. pyogenes Cas9 EQR variant, which recognizes a NGAG PAM sequence, A NGCG PAM sequence, a NGGG PAM sequence, a NGTG PAM sequence, a NGAA PAM sequence, a NGAT PAM sequence or a NGAC PAM sequence. In certain embodiments, the Cas9 molecule is an S. pyogenes Cas9 VRER variant, which recognizes a NGCG PAM sequence, a NGCA PAM sequence, a NGCT PAM sequence, or a NGCC PAM sequence. In certain embodiments, the Cas9 molecule is a wild-type S. aureus Cas9, which recognizes a NNGRRT PAM sequence, or a NNGRRV PAM sequence.

A "reference molecule" as used herein refers to a molecule to which a modified or candidate molecule is compared. For example, a reference Cas9 molecule refers to a Cas9 molecule to which a modified or candidate Cas9 molecule is compared. Likewise, a reference gRNA refers to a gRNA molecule to which a modified or candidate gRNA molecule is compared. The modified or candidate molecule may be compared to the reference molecule on the basis of sequence (e.g., the modified or candidate molecule may have X % sequence identity or homology with the reference molecule) or activity (e.g., the modified or candidate molecule may have X % of the activity of the reference molecule). For example, where the reference molecule is a Cas9 molecule, a modified or candidate molecule may be characterized as having no more than 10% of the nuclease activity of the reference Cas9 molecule. Examples of reference Cas9 molecules include naturally occurring unmodified Cas9 molecules, e.g., a naturally occurring Cas9 molecule from S. pyogenes, S. aureus, or N. meningitidis. In certain embodiments, the reference Cas9 molecule is the naturally occurring Cas9 molecule having the closest sequence identity or homology with the modified or candidate Cas9 molecule to which it is being compared. In certain embodiments, the reference Cas9 molecule is a parental molecule having a naturally occurring or known sequence on which a mutation has been made to arrive at the modified or candidate Cas9 molecule.

"Replacement", or "replaced", as used herein with reference to a modification of a molecule does not require a process limitation but merely indicates that the replacement entity is present.

"Small molecule", as used herein, refers to a compound having a molecular weight less than about 2 kD, e.g., less than about 2 kD, less than about 1.5 kD, less than about 1 kD, or less than about 0.75 kD.

"Subject", as used herein, may mean either a human or non-human animal. The term includes, but is not limited to, mammals (e.g., humans, other primates, pigs, rodents (e.g., mice and rats or hamsters), rabbits, guinea pigs, cows, horses, cats, dogs, sheep, and goats). In certain embodiments, the subject is a human. In other embodiments, the subject is poultry.

"Treat", "treating" and "treatment", as used herein, mean the treatment of a disease in a mammal, e.g., in a human, including (a) inhibiting the disease, i.e., arresting or preventing its development or progression; (b) relieving the disease, i.e., causing regression of the disease state; (c) relieving one or more symptoms of the disease; and (d) curing the disease.

"Prevent," "preventing," and "prevention" as used herein means the prevention of a disease in a mammal, e.g., in a human, including (a) avoiding or precluding the disease; (b) affecting the predisposition toward the disease; (c) preventing or delaying the onset of at least one symptom of the disease.

"X" as used herein in the context of an amino acid sequence, refers to any amino acid (e.g., any of the twenty natural amino acids) unless otherwise specified.

2. Herpes Simplex Virus

Herpes simplex viruses (HSVs) are categorized into at least two types: herpes simplex virus type 1 (HSV-1) and herpes simplex virus type 2 (HSV-2). HSV-1 and HSV-2 are also known as human herpesvirus 1 (HHV-1) and human herpesvirus (HHV-2), respectively.

The structure of herpes viruses includes a relatively large double-stranded, linear DNA genome encased within an icosahedral protein cage (capsid), which is wrapped in a lipid bilayer called (envelope). The envelope is joined to the capsid by means of a tegument. This complete particle is known as the virion (Mettenleiter et al. (2006) Curr. Opin. Microbiol. 9 (4): 423-429). HSV-1 and HSV-2 each contain at least 74 genes (or open reading frames, ORFs), or even as many as 84 unique protein coding genes by 94 putative ORFs, within their genomes (McGeoch et al. (2006) Virus Res. 117 (1): 90-104; Rajcáni et al. (2004) Virus Genes 28 (3): 293-310). These genes encode a variety of proteins involved in forming the capsid, tegument and envelope of the virus, as well as controlling the replication and infectivity of the virus.

The genomes of HSV-1 and HSV-2 are complex and contain two unique regions, i.e., the long unique region (UL) and the short unique region (US), each containing multiple viral genes. Immediate early genes encode, e.g., proteins that regulate the expression of early and late viral genes. Early genes encode, e.g., enzymes involved in DNA replication and the production of certain envelope glycoproteins. Late genes encode, e.g., proteins that form the virion particle. Transcription of HSV genes is catalyzed by RNA polymerase II of the infected host (McGeoch et al. (2006) Virus Res. 117 (1): 90-104).

Entry of HSV into the host cell involves interactions of several glycoproteins (e.g., glycoprotein B (gB), glycoprotein C (gC), glycoprogein D (gD), glycoprotein H (gH), and glycoprotein L (gL)) on the surface of the enveloped virus, with receptors (e.g., herpesvirus entry mediator (HVEM), nectin-1, or 3-O sulfated heparan sulfate) on the surface of the host cell. The envelope, when bound to specific receptors on the cell surface, will fuse with the host cell membrane and create a pore, through which the virus enters the host cell. The virus can also be endocytosed after binding to the receptors, and the fusion could occur at the endosome. After the viral capsid enters the cellular cytoplasm, it is transported to the cell nucleus. Once attached to the nucleus at a nuclear entry pore, the capsid ejects its DNA contents via the capsid portal. Following infection of a cell, a cascade of herpes virus proteins, e.g., immediate-early, early, and late, are produced.

HSVs may persist in a quiescent but persistent form known as latent infection. During latent infection of a cell, HSVs express Latency Associated Transcript (LAT) RNA. LAT can regulate the host cell genome and interfere with natural cell death mechanisms. By maintaining the host cells, LAT expression preserves a reservoir of the virus, which allows subsequent, usually symptomatic, periodic recurrences or "outbreaks" characteristic of non-latency. Whether or not recurrences are symptomatic, viral shedding occurs to produce further infections. Herpes virus DNA contains a gene that encodes ICP4, which is a transactivator of genes associated with lytic infection (Pinnoji et al. (2007) Virol. J. 4: 56). The human neuronal protein Neuronal Restrictive Silencing Factor (NRSF) or human Repressor Element Silencing Transcription Factor (REST) can bind to the elements surrounding the ICP4 gene and lead to histone deacetylation, which prevents initiation of transcription from this gene, thereby preventing transcription of other viral genes involved in the lytic cycle (Pinnoji et al. (2007) Virol. J. 4: 56; Bedadala et al. (2007) Cell Res. 17 (6): 546-555). The inhibition of ICP4 protein synthesis can be reversed by viral protein ICP0, which dissociates NRSF from the ICP4 gene and thus prevents silencing of the viral DNA (Roizman et al. (2005) Cell Cycle 4 (8): 1019-21).

2.1 HSV-Infections

The herpes simplex viruses enter the host via infection of epithelial cells within the skin and mucous membranes. Most commonly, HSV-1 enters the host via infection of epithelial cells of the oropharynx, including the epithelium of the mouth, lips and nose. Most commonly, HSV-2 enters the host via infection of epithelial cells of the anogenital region, including the epithelium of the genitals and anus. However, HSV-1 can primarily infect the anogenital region and HSV-2 can primarily infect the oropharynx.

HSV-1 causes intermittent sores of the mouth and mucous membranes. It is a ubiquitous and highly contagious pathogen. Initial infection with HSV-1 generally causes painful blistering of the mucous membranes of the lips and mouth.

HSV-2 is a sexually transmitted virus. It is most commonly known as genital herpes. Initial infection with HSV-2 generally causes painful blistering in the genital region. The disease causes lifelong, recurring bouts of viral reactivity. It is highly contagious and increases the risk of acquiring HIV infection, especially among patients with active lesions.

HSV-1 and HSV-2 infections persist for the lifetime of the host. During primary infection, the virus most often infects cells of the oropharynx and ano-genital region, causing painful vesicles in the affected region. Re-activation of HSV infections most often occurs in the oropharynx or ano-genital region. However, re-activation infections of the eye and central nervous system are the most severe and damaging HSV manifestations, as they can lead to blindness and permanent neurologic disability, respectively. Primary and re-activation infections can cause permanent neurologic sequelae and blindness. HSV-2 also increases a subject's risk of developing HIV. There is a considerable need for methods to treat, prevent and/or reduce HSV-1 and/or HSV-2 infections.

The herpes simplex virus produces immediate early genes within the epithelial cells, which encode enzymes and binding proteins necessary for viral synthesis. After primary infection, the virus travels up sensory nerve axons via retrograde transport to the sensory dorsal root ganglion (DRG). HSV-1 mainly travels to the trigeminal DRG, but can travel to other sensory ganglia depending upon the site of primary infection. HSV-2 mainly travels to the sensory DRG located within the sacrum, but can travel to other sensory ganglia depending upon the site of primary infection. Within the DRG, the virus establishes a latent infection. The latent infection persists for the lifetime of the host. Within the DRG cell, the virus uncoats, viral DNA is transported into the nucleus, and key viral RNAs associated with latency are transcribed (including the LAT RNAs).

During the primary infection, subjects generally experience painful blistering in the oral or ano-genital region that lasts 4-15 days. The sores most commonly involve the lips, gums and nasal mucous membranes in HSV-1 primary infections. Less commonly, HSV-1 primary infections may involve the ano-genital region. HSV-2 primary infections most commonly involve the ano-genital region, including the vagina, labia, cervix, penis, scrotum, anus and skin around the thighs. Less commonly, HSV-2 primary infections involve the oropharynx. Rarely, HSV-1 and HSV-2 primary infections may involve the eyes, central nervous system, the fingers and fingernail beds (herpetic whitlow). HSV-1 infection is transmitted primarily through saliva and/or sexual activity. HSV-2 infection is transmitted primarily through sexual activity but may also be transmitted through saliva. The blisters of an HSV infection may break, releasing clear fluid that is highly infectious. Primary infection is often accompanied by a flu-like illness, including fever, chills and muscle aches.

Host immune defense is very important to combating HSV infection. CD4+ T-cells and CD8+ cells are responsible for recognizing and clearing the pathogen. Subjects with impaired T-cell responses, including those with HIV, those receiving immunosuppressants following organ transplants, and neonates with developing immune systems, are subject to the most severe manifestations of HSV-1 and HSV-2 infections.

Reactivations of latent infections are generally less severe and may be of shorter duration. Reactivation of HSV-1 infection most often affects the oral region, but can also affect other areas, including the ano-genital region, the eye, the central nervous system (CNS), the fingernails, and the pharynx. Reactivation of HSV-2 infection most often affects the ano-genital region, but can also affect other areas, including the oral region, the eye, the central nervous system (CNS), the fingernails, and the pharynx. Reactivation of either HSV-1 or HSV-2 infection can cause ophthalmologic disease, including keratitis (epithelial keratitis, stromal keratitis and disciform keratitis). Generally, ophthalmologic manifestations of HSV-1 and HSV-2 include pain, tearing, redness of the eyes and sensitivity to light. Most HSV-related ocular infections resolve without permanent visual damage. However, ocular herpes infections may rarely cause scarring, secondary infection with bacterial pathogens and rarely, blindness. Reactivation of either HSV-1 or HSV-2 infection can also cause retinitis. HSV-associated retinitis is rare but severe and carries a high risk of permanent blindness.

Newborns are a population at particular risk for developing severe HSV-1 and HSV-2 infections. The disease is transmitted from the mother to the fetus during childbirth. The chance of maternal-fetal transmission is highest in cases where the mother developed primary HSV infection during pregnancy. The incidence of neonatal herpes is approximately 4-30 per 100,000 births. Neonates may develop severe HSV-1 or HSV-2 encephalitis and/or meningitis. In spite of prompt treatment with antiviral therapy, the rate of permanent neurologic sequelae in newborns infected with HSV-1 or HSV-2 is significant. In a study of infants with HSV-encephalitis or meningitis treated with high dose antiviral therapy, there was found to be a 4% mortality rate and 69% of survivors had permanent neurologic sequelae (Kimberlin et al., Pediatrics. 2001; 108: 230-238).

Primary HSV-1 and HSV-2 infections may be treated with antiviral therapy, including acyclovir, valacyclovir and famciclovir. These therapies have been demonstrated to reduce viral shedding, decrease pain and improve healing time of lesions. Re-activation of latent infections may resolve without treatment (it may be self-limiting) or may be treated with anti-viral therapy. Therapy is primarily given during acute infection. There are no curative or preventative treatments. Therapy may be given prophylactically in certain situations, including during childbirth in a mother with a recent HSV-1 or HSV-2 infection or reactivation.

There is no effective therapy that prevents HSV-1 or HSV-2 infection. The use of antiviral therapy during active infection and the use of condoms decrease transmission rates by approximately 50%.

Human immunodeficiency virus-1 (HIV-1) acquisition rates are dramatically increased in subjects who are seropositive for HSV-2. The risk of infection with HIV-1 is 3-fold higher in subjects with HSV-2. Antivirals have no impact on reducing risk of HIV acquisition.

2.2 HSV-Related Ocular Disease

HSV infections, e.g., HSV-1 and/or HSV-2 infections of the eye, either primary or reactivation infections, are called HSV-related ocular disease. HSV-related ocular disease most commonly causes infection of the anterior chamber of the eye, known as keratitis, stromal keratitis and/or disciform keratitis. HSV-related ocular disease may, more rarely, cause infection of the posterior chamber of the eye, known as retinitis. HSV-1 keratitis is acutely painful and unpleasant. It may, in rare instances, cause scarring, secondary infection with bacterial pathogens and rarely, blindness. HSV-related retinitis is a rare manifestation of HSV-related ocular disease but carries a much higher risk of permanent visual damage.

Reactivation infections occur in the eye via anterograde transport of the virus into the eye from the trigeminal ganglion, along the ophthalmic branch of the trigeminal nerve (the fifth cranial nerve) and into the eye. Re-activation of the virus may also occur from within the cornea. Latency within the trigeminal ganglion is established via one of two mechanisms. First, HSV-1 or HSV-2 can travel via retrograde transport along the trigeminal nerve from the eye (after an eye infection) into the trigeminal ganglion. Alternatively, it can spread to the trigeminal ganglion via hematogenous spread following infection of the oral mucosa, genital region, or other extraocular site. After establishing latent infection of the trigeminal ganglion, at any time, particularly in the event of an immunocompromised host, the virus can re-establish infection by traveling anterograde along the trigeminal nerve and into the eye.

When ocular herpes affects the posterior chamber of the eye, it causes retinitis. In adults, HSV-1 is responsible for the majority of cases of HSV-retinitis (Pepose et al., Ocular Infection and Immunity 1996; Mosby 1155-1168). In neonates and children, HSV-2 is responsible for the majority of cases of HSV-retinitis (Pepose et al., Ocular Infection and Immunity 1996; Mosby 1155-1168). HSV-related retinitis can lead to acute retinal necrosis (ARN), which will destroy the retina within 2 weeks without treatment (Banerjee and Rouse, Human Herpesviruses 2007; Cambridge University Press, Chapter 35). Even with treatment, the risk of permanent visual damage following ARN is higher than 50% (Roy et al., Ocular Immunology and Inflammation 2014; 22(3): 170-174).

Keratitis is the most common form of ocular herpes. HSV keratitis can manifest as dentritic keratitis, stromal keratitis, blepharatis and conjunctivitis. HSV-1 is responsible for the majority of HSV-associated keratitis, accounting for 58% of cases (Dawson et. al., Suvey of Ophthalmology 1976; 21(2): 121-135). HSV-2 accounts for the remainder of HSV-associated keratitis cases, or approximately 42% of cases. In the U.S., there are approximately 48,000 cases of recurrent or primary HSV-related keratitis infections annually (Liesegang et. al., 1989; 107(8): 1155-1159). Of all cases of HSV-related keratitis, approximately 1.5-3% of subjects experience severe, permanent visual impairment (Wilhelmus et. al., Archives of Ophthalmology 1981; 99(9): 1578-82). The risk to a subject of permanent visual damage due to HSV-related ocular disease increases with increasing numbers of ocular related HSV-reactivations.

Overall, stromal keratitis represents approximately 15% of keratitis cases and is associated with the highest risk of permanent visual damage from keratitis. Stromal keratitis results in scarring and irregular astimagtism. Previous ocular HSV infection increases the risk for developing stromal infection, which means that subjects who have had a prior ocular HSV infection have an increased risk for permanent visual damage on reactivation. In children, stromal keratitis represents up to 60% of all keratitis cases. Therefore, children are particularly at risk for permanent visual damage from HSV-associated keratitis. A retrospective study in the U.S. from 1950-1982 found that there are approximately 2.6 new or recurrent stromal keratitis cases per 100,000 person years, or approximately 8,000 cases of stromal keratitis annually (Liesegang et. al., 1989; 107(8): 1155-1159). A more recent study in France in 2002 estimated the incidence of new or recurrent stromal keratitis cases to be 9.6 per 100,000 (Labetoulle et al., Ophthalmology 2005; 112(5): 888-895). The incidence of HSV-associated keratitis may be increasing in the developed world (Farooq and Shukla 2012; Survey of Ophthalmology 57(5): 448-462).

The genome editing systems, compositions and methods described herein can be used for the treatment, prevention and/or reduction of HSV-1 and/or HSV-2 ocular infections, including but not limited to HSV-1 stromal keratitis, HSV-1 dentritic keratitis, HSV-1 blepharatis, HSV-1 conjunctivitis, HSV-1 retinitis, HSV-2 stromal keratitis, HSV-2 dentritic keratitis, HSV-2 blepharatis, HSV-2 conjunctivitis, and HSV-2 retinitis.

3. Methods to Treat, Prevent and/or Reduce HSV-Related Ocular Infection

Disclosed herein are the approaches to treat, prevent, and/or reduce HSV-related ocular infections, using the methods, genome editing systems, and compositions described herein. HSV-related ocular infection may be caused by an HSV-1 and/or HSV-2 infection. For example, and not by way of limitation. The methods, genome editing systems, and compositions disclosed herein can be used to treat, prevent, and/or reduce HSV-1 infection, HSV-2 infection, or both HSV-1 and HSV-2 infections.

The RS1, RL2, and LAT genes of HSV-1 and HSV-2 are associated with viral infection, proliferation and assembly, as well as maintenance of latency and re-activation of the virus from latency. Knockout or knockdown of any of these genes singly or in combination can reduce HSV-1 and/or HSV-2 infections. As the HSV-1 or HSV-2 virus establishes latency in discrete, localized regions within the body, it is highly amenable to local delivery that delivers a disabling treatment in the region of latency. Targeting knock-out to a discrete region or regions, (e.g., the trigeminal dorsal root ganglion, the cornea, the cervical dorsal root ganglia, or the sacral dorsal root ganglia) can reduce or eliminate latent infection by disabling the HSV-1 and/or HSV-2 virus.

Described herein are the approaches to treat, prevent and/or reduce HSV-1 and/or HSV-2 infections by knocking out or knocking down viral genes. Methods described herein include the knockout or knockdown of the following HSV-1 and/or HSV-2 encoded genes: RL2, LAT and RS1, or any combination thereof (e.g., any single gene, e.g., RL2, e.g., LAT, e.g., RS1, or any two genes, e.g., RL2 and LAT, e.g., RL2 and RS1, e.g., RS1 and LAT, or three three genes). When there are two alterations events (e.g., knocking down or knocking out the expression of the RS1, RL2, and/or LAT gene), the two alteration events may occur sequentially or simultaneously. In certain embodiments, the knockout of the RS1, RL2, and/or LAT gene occurs prior to knockdown of the RS1, RL2, and/or LAT gene gene. In certain embodiments, the knockout of the RS1, RL2, and/or LAT gene is concurrent with knockdown of the RS1, RL2, and/or LAT gene. In certain embodiments, the knockout of the RS1, RL2, and/or LAT gene is subsequent to the knockdown of the RS1, RL2, and/or LAT gene. In certain embodiments, the effect of the alterations is synergistic.

RL2 encodes the gene ICP0, a 775 amino acid protein that is a transactivator of gene expression. The RL2 gene is one of five immediate early genes expressed by herpes viruses. ICP0 is involved in activating the expression of delayed early and late genes (Lees-Miller et al. 1996, Journal of Virology 70(11): 7471-7477). ICP0 is thought to be involved in neurovirulence. In cell culture, ICP0 has been found to be required for reactivation from latency (Leib et al. 1989, Journal of Virology 63:759-768). Deletion mutants not expressing RL2 have been shown to be unable to replicate in vitro (Sacks and Schaffer 1987, Journal of Virology 61(3):829-839). In certain embodiments, knock out of RL2 can disable the ability of HSV-1 and/or HSV-2 to reactivate from latency. In certain embodiments, knock out or knockdown of RL2 can disable the ability of HSV-1 and/or HSV-2 to replicate. In certain embodiments, knockout or knockdown of RL2 can disable the ability of HSV-1 and/or HSV-2 to infect and/or establish latent infections in neural tissue.

LAT encodes the only gene expressed by herpes viruses during the latency period. The latency period is the time in which the virus establishes a quiescent infection in host tissue, often in neural tissue, including the trigeminal ganglion or the sacral ganglia. LAT is thought to be involved in the reactivation of herpes virus infections, allowing the virus to re-infect epithelial and other tissue. In certain embodiments, knockout or knockdown of LAT can disable HSV-1 and/or HSV-2 gene latency and/or reactivation, disrupting the ability of HSV-1 and/or HSV-2 to sustain a latent infection and/or reactivate following latent infection. In certain embodiments, knockout or knockdown of LAT expression eliminates latent infection by HSV-1 and/or HSV-2. In certain embodiments, knockout or knockdown of LAT expression shortens the duration of, treats, and/or cures HSV-1 and/or HSV-2 infections.

RS1 plays an important role in the expression of the immediate early genes by HSV-1 and HSV-2. RS1 is one of five immediate early genes expressed by herpes viruses and is a major transcriptional regulator. RS1 encodes the viral protein ICP4. ICP4 is important for controlling the overall expression of both early and late genes produced by HSV-1 and HSV-2. The RS1 gene is similar in HSV-1 and HSV-2.

In certain embodiments, knockout or knockdown of the RS1, RL2, and/or LAT gene disables HSV-1 and/or HSV-2 gene expression, or reduces one or more of viral replication, assembly, maturation, packaging, or infection. In certain embodiments, knockout of RS1, RL2, and/or LAT gene expression shortens the duration of HSV-1 and/or HSV-2 infections. In certain embodiments, knockout or knockdown of RS1, RL2, and/or LAT gene expression treats or cures HSV-1 and/or HSV-2 infections.

In certain embodiments, reducing the duration, number and/or frequency of ocular related HSV-reactivations can decrease the risk of permanent visual damage in subjects infected with HSV-1 and/or HSV-2.

In certain embodiments, knocking out and/or knocking down RS1, RL2, and/or LAT gene, individually or in combination can make HSV-1 and/or HSV-2 more susceptible to antiviral therapy. Mutations in important genes can render HSV-1, HSV-2 and other viruses more susceptible to treatment with antivirals (Zhou et al., Journal of Virology 2014; 88(19): 11121-11129). Knocking-out or knocking down of the RL2 and LAT and/or RS1 genes, individually or in combination may be combined with an antiviral therapy to treat, prevent and/or reduce HSV-1 and/or HSV-2 infection. The compositions and methods described herein can be used in combination with another antiviral therapy, e.g., another anti-HSV-1 therapy or anti-HSV-2 therapy described herein, to treat, prevent and/or reduce HSV-1 or HSV-2 infection.

In one approach, one, two, or three of the RS1, RL2, and LAT genes is targeted as a targeted knockout or knockdown, e.g., to inhibit one or more viral functions, including, e.g., viral gene regulation, viral gene transcription, viral genome replication, expression of viral latency genes and viral capsid formation. In certain embodiments, said approach comprises knocking out one HSV-1 and/or HSV-2 gene (e.g., RS1, RL2, or LAT gene gene). In certain embodiments, said approach comprises knocking down one HSV-1 and/or HSV-2 gene (e.g., RS1, RL2, or LAT gene). In certain embodiments, said approach comprises knocking out two HSV-1 and/or HSV-2 genes, e.g., both RL2 and LAT genes, e.g., both RL2 and RS1 genes, e.g., both RS1 and LAT genes. In certain embodiments, said approach comprises knocking down two HSV-1 and/or HSV-2 genes, e.g., both RL2 and LAT genes, e.g., both RL2 and RS1 genes, e.g., both RS1 and LAT genes. In certain embodiments, said approach comprises knocking out three HSV-1 and/or HSV-2 genes, e.g., all three RL2, LAT and RS1 genes. In certain embodiments, said approach comprises knocking down three HSV-1 and/or HSV-2 genes, e.g., all three RS1, RL2, and LAT genes.

In certain embodiments, inhibiting one or more viral functions, e.g., viral gene regulation, viral gene transcription, viral genome replication and viral capsid formation, decreases the duration of primary or recurrent infection and/or decreases shedding of viral particles. Subjects may also experience shorter duration(s) of illness, decreased risk of transmission to sexual partners, decreased risk of transmission to the fetus in the case of pregnancy and/or the potential for full clearance of HSV-1 and/or HSV-2 (cure).

Knockout or knockdown of one or more copies (e.g., 1, 2, 3, 4, 5, 6, 7, 8, 9, 10, 20, 30, 40 50, 100, 200, 300, 400, 500, 600, 700, 800, 900, 1000 or more copies) of one or more target gene(s) (e.g., the RS1, RL2, or LAT gene) may be performed prior to disease onset or after disease onset, preferably early in the disease course.

In certain embodiments, the method comprises initiating treatment of a subject prior to disease onset.

In certain embodiments, the method comprises initiating treatment of a subject after disease onset.

In certain embodiments, the method comprises initiating treatment of a subject after disease onset, e.g., 1, 2, 3, 4, 5, 6, 7, 8, 9, 10, 12, 16, 24, 36, 48 or more months after onset of an HSV-1 and/or HSV-2 infection. In certain embodiments, the method comprises initiating treatment of a subject after disease onset, e.g., 1, 2, 3, 4, 5, 10, 15, 20, 25, 40, 50 or 60 years after onset of an HSV-1 and/or HSV-2 infection.

In certain embodiments, the method comprises initiating treatment of a subject in an advanced stage of disease, e.g., during acute or latent periods. In certain embodiments, the method comprises initiating treatment of a subject in severe, acute stages of the disease affecting the central nervous system, eyes, oropharynx, genital region, and/or other regions.

Overall, initiation of treatment for subjects at all stages of disease is expected to improve healing, decrease duration of disease and be of benefit to subjects.

In certain embodiments, the method comprises initiating treatment of a subject prior to disease progression. In certain embodiments, the method comprises initiating treatment of a subject in an early stage of disease, e.g., when a subject has been exposed to HSV-1 and/or HSV-2 or is thought to have been exposed to HSV-1 and/or HSV-2.

In certain embodiments, the method comprises initiating treatment of a subject prior to disease progression. In certain embodiments, the method comprises initiating treatment of a subject in an early stage of disease, e.g., when a subject has tested positive for HSV-1 and/or HSV-2 infections but has no signs or symptoms.

In certain embodiments, the method comprises initiating treatment at the appearance of one or more of the following findings consistent or associated with an HSV-1 and/or HSV-2 infection: fever, headache, body aches, ano-genital blistering, oral ulceration, encephalitis, or keratitis.

In certain embodiments, the method comprises initiating treatment of a subject at the appearance of painful blistering in or around the mouth, e.g., oral or oropharynx, e.g., in an infant, child, adult or young adult.

In certain embodiments, the method comprises initiating treatment of a subject at the appearance of painful blistering in the ano-genital region, geneital ulcers, and/or a flu-like symptom, e.g., in an infant, child, adult or young adult.

In certain embodiments, the method comprises initiating treatment of a subject suspected of having HSV-1 and/or HSV-2 meningitis and/or HSV-1 and/or HSV-2 encephalitis.

In certain embodiments, the method comprises initiating treatment at the appearance of one or more of the following symptoms consistent or associated with HSV-1 and/or HSV-2 meningitis and/or encephalitis: fever, headache, vomiting, photophobia, seizure, decline in level of consciousness, lethargy, or drowsiness.

In certain embodiments, the method comprises initiating treatment at the appearance of any of the following signs consistent or associated with HSV-1 and/or HSV meningitis and/or encephalitis: positive CSF culture for HSV-1 and/or HSV-2, elevated WBC in CSF, neck stiffness/positive Brudzinski's sign. In certain embodiments, the method comprises initiating treatment in a patient with signs consistent with HSV-1 and/or HSV-2 encephalitis and/or meningitis on EEG, CSF exam, MRI, PCR of CSF specimen, and/or PCR of brain biopsy specimen.

In certain embodiments, the method comprises initiating treatment at the appearance of any of the following symptoms consistent or associated with optic HSV-1 and/or HSV-2: pain, photophobia, blurred vision, tearing, redness/injection, loss of vision, floaters, or flashes.

In certain embodiments, the method comprises initiating treatment at the appearance of any of the following findings on ophthalmologic exam consistent or associated with optic HSV-1 and/or HSV-2, also known as HSV-1 and/or HSV-2 keratitis: small, raised clear vesicles on corneal epithelium; irregular corneal surface, punctate epithelial erosions; dense stromal infiltrate; ulceration; necrosis; focal, multifocal, or diffuse cellular infiltrates; immune rings; neovascularization; or ghost vessels at any level of the cornea.

In certain embodiments, the method comprises initiating treatment at the appearance of any of the following findings on ophthalmologic exam consistent or associated with HSV-1 and/or HSV-2 retinitis or acute retinal necrosis: reduced visual acuity; uveitis; vitritis; scleral injection; inflammation of the anterior and/or vitreous chamber/s; vitreous haze; optic nerve edema; peripheral retinal whitening; retinal tear; retinal detachment; retinal necrosis; evidence of occlusive vasculopathy with arterial involvement, including arterioloar sheathing and arteriolar attenuation.

In certain embodiments, the method comprises initiating treatment at the appearance of symptoms and/or signs consistent or associated with either an HSV-1 or an HSV-2 infection of the eye, oropharynx, ano-genital region or central nervous system. In certain embodiments, initiating treatment for an HSV-1 and/or HSV-2 infection in a case of suspected HSV-1 or HSV-2 infection early in the disease course is beneficial.

In certain embodiments, the method comprises initiating treatment in utero. In certain embodiments, the subject is at high risk of maternal-to-fetal transmission.

In certain embodiments, the method comprises initiating treatment during pregnancy in case of mother who has an active HSV-1 and/or HSV-2 infection or has recent primary HSV-1 and/or HSV-2 infection.

In certain embodiments, the method comprises initiating treatment prior to organ transplantation or immediately following organ transplantation.

In certain embodiments, the method comprises initiating treatment in case of suspected exposure to HSV-1 and/or HSV-2.

In certain embodiments, the method comprises initiating treatment prophylactically, in case of suspected HSV-encephalitis or meningitis.

In certain embodiments, it is considered that both HIV positive subjects and post-transplant subjects may experience severe HSV-1 and/or HSV-2 activation or reactivation, including HSV-encephalitis and meningitis, due to immunodeficiency. Neonates are also at risk for severe HSV-encephalitis due to maternal-fetal transmission during childbirth. Inhibiting one or more viral functions, e.g., viral gene regulation, viral gene transcription, viral genome replication, and viral capsid formation, may provide superior protection to said populations at risk for severe HSV-1 and/or HSV-2 infections. Subjects may experience lower rates of HSV-1 and/or HSV-2 encephalitis and/or lower rates of severe neurologic sequelae following HSV-1 and/or HSV-2 encephalitis, which will profoundly improve quality of life.

In certain embodiments, the method comprises initiating treatment of a subject who suffers from or is at risk of developing severe manifestations of HSV-1 and/or HSV-2 infections, e.g., a neonates, a subjects with HIV, a subject who is undergoing an immunosuppressant therapy, e.g., following organ transplantation, a subject who has cancer, a subject who is undergoing chemotherapy, a subject who is undergoing chemotherapy, a subject who is undergoing radiation therapy, a subject who will undergo radiation therapy.

In certain embodiments, both HIV positive subjects and post-transplant subjects may experience severe HSV-1 and/or HSV-2 activation or reactivation, including HSV-encephalitis and meningitis, due to immunodeficiency. Neonates are also at risk for severe HSV-encephalitis due to maternal-fetal transmission during childbirth. Inhibiting essential viral functions, e.g., viral gene regulation, viral gene transcription, expression of viral latency genes, viral genome replication and viral capsid formation, may provide superior protection to said populations at risk for severe HSV-1 and/or HSV-2 infections. Subjects may experience lower rates of HSV-1 and/or HSV-2 encephalitis and/or lower rates of severe neurologic sequelae following HSV-1 and/or HSV-2 encephalitis, which will profoundly improve quality of life.

In certain embodiments, the method comprises initiating treatment of a subject who has tested positive for HSV-1 and/or HSV-2.

In certain embodiments, the method comprises initiating treatment in a subject who has tested positive for HSV-1 and/or HSV-2 infection. HSV-1 and/or HSV-2 infections can be tested, e.g., using viral culture, direct fluorescent antibody study, skin biopsy, PCR, blood serologic test, CSF serologic test, CSF PCR, or brain biopsy. In certain embodiments, the method comprises initiating treatment in a subject who has tested positive for HSV-2 infection via diagnostic vitrectomy, endoretinal biopsy, or PCR of aqueous fluid, PCR of vitreous sample.

In certain embodiments, the method comprises initiating treatment in a subject exposed to HSV-1 and/or HSV-2 and at high risk for severe sequelae from HSV infection.

In certain embodiments, a cell is manipulated by editing (e.g., introducing a mutation in) one or more target genes, e.g., the RS1, RL2, or LAT gene. In certain embodiments, the expression of one or more target genes (e.g., one or more RS1, RL2, or LAT gene described herein) is modulated, e.g., in vivo.

In certain embodiments, the method comprises delivery of gRNA molecule by an adeno-associated virus (AAV). In certain embodiments, the method comprises delivery of gRNA molecule by a lentivirus (LV). In certain embodiments, the method comprises delivery of gRNA molecule by a nanoparticle.

In certain embodiments, the method further comprising administering to the subject a second antiviral therapy or therapeutic agent, e.g., an anti-HSV-1 or anti-HSV-2 therapy or therapeutic agent described herein. The composition and the other therapy or therapeutic agent can be administered in any order. For example, the compositions described herein can be administered concurrently with, prior to, or subsequent to, one or more additional therapies or therapeutic agents. In certain embodiments, the effect of the two or more therapies or therapeutic agents is synergistic. Exemplary anti-HSV-1 and anti-HSV-2 therapies and therapeutic agents include, but are not limited to, acyclovir, valacyclovir, famciclovir, penciclovir, or a vaccine.

4. Methods of Altering RS1, RL2, and/or LAT Gene(s)

As disclosed herein, the RS1, RL2, and/or LAT gene can be altered by the genome editing systems, compositions and methods as described herein.

Methods, genome editing systems, and compositions discussed herein, provide for altering (e.g., knocking out or knocking down) an HSV RS1 target position, an HSV RL2 target position, or an HSV LAT target position.

As disclosed herein, an HSV RS1 target position, an HSV RL2 target position, or an HSV LAT target position, can be altered, alone or in combination, by gene editing, e.g., using CRISPR-Cas9 mediated methods, genome editing systems, and composition described herein. Altering (e.g., knocking out or knocking down) an HSV RS1 target position, an HSV RL2 target position, or an HSV LAT target position can be achieved, e.g., by:

(1) knocking out the RS1, RL2, or LAT gene:
 (a) insertion or deletion (e.g., NHEJ-mediated insertion or deletion) of one or more nucleotides in close proximity to or within the early coding region of the RS1, RL2, or LAT gene; or
 (b) deletion (e.g., NHEJ-mediated deletion) of a genomic sequence or multiple genomic sequences including at least a portion of the RS1, RL2, or LAT gene; or
(2) knocking down the RS1, RL2, or LAT gene mediated by an eiCas9 molecule or an eiCas9-fusion protein by targeting a non-coding region, e.g., a promoter region, of the RS1, RL2, or LAT gene.

All approaches give rise to altering (e.g., knocking out or knocking down) the RS1, RL2, and/or LAT gene(s). Exemplary mechanisms that can be associated with an alteration of one or both of the RS1, RL2, and/or LAT gene(s) include, but are not limited to, non-homologous end joining (e.g., classical or alternative), microhomology-mediated end joining (MMEJ), homology-directed repair (e.g., endogenous donor template mediated), SDSA (synthesis dependent strand annealing), single strand annealing or single strand invasion.

In certain embodiments, the methods, genome editing systems, and composition described herein introduce one or more breaks near the early coding region of the RS1, RL2, and/or LAT gene(s). In certain embodiments, methods, genome editing systems, and compositions described herein introduce two or more breaks to flank at least a portion of the RS1, RL2, and/or LAT gene(s). The two or more breaks remove (e.g., delete) a genomic sequence including at least a portion of the RS1, RL2, and/or LAT gene(s). In certain embodiments, methods described herein comprise knocking down the RS1, RL2, and/or LAT gene(s) mediated by eiCas9 molecule or an eiCas9-fusion protein by targeting the promoter region of HSV RL2 and/or HSV LAT and/or RS1 target knockdown position(s). All methods described herein result in altering (e.g., knocking out or knocking down) the RS1, RL2, and/or LAT gene(s).

4.1 Knocking Out the RS1, RL2, or LAT Gene by Introducing an Indel or a Deletion in the RS1, RL2, or LAT Gene In certain embodiments, the method comprises introducing an insertion or deletion of one or more nucleotides in close proximity to an HSV RS1 target knockout position, an HSV RL2 target knockout position, or an HSV LAT target knockout position (e.g., the early coding region) of the RS1, RL2, and/or LAT gene(s). As described herein, in certain embodiments, the method comprises the introduction of one or more breaks (e.g., single strand breaks or double strand breaks) sufficiently close to (e.g., either 5' or 3' to) the early coding region of an HSV RL2 target knockout position, or an HSV LAT target knockout position, such that the break-induced indel could be reasonably expected to span an HSV RL2 target knockout position, or an HSV LAT target knockout position (e.g., the early coding region). NHEJ-mediated repair of the break(s) allows for the NHEJ-mediated introduction of an indel in close proximity to or within the early coding region of an HSV RL2 target knockout position, or an HSV LAT target knockout position.

In certain embodiments, the method comprises introducing a deletion of a genomic sequence comprising at least a portion of the RS1, RL2, and/or LAT gene. As described herein, in an embodiment, the method comprises the introduction of two double stand breaks—one 5' and the other 3' to (i.e., flanking) the RL2, LAT or RS1 target position. In an embodiment, two gRNAs, e.g., unimolecular (or chimeric) or modular gRNA molecules, are configured to position the two double strand breaks on opposite sides of the RL2, LAT or RS1 target knockout position in the RS1, RL2, and/or LAT gene.

In certain embodiments, a single strand break is introduced (e.g., positioned by one gRNA molecule) at or in close proximity to an HSV RS1 target position, an HSV RL2 target position, or an HSV LAT target position. In certain embodiments, a single gRNA molecule (e.g., with a Cas9 nickase) is used to create a single strand break at or in close proximity to an HSV RS1 target position, an HSV RL2 target position, or an HSV LAT target position, e.g., the gRNA molecule is configured such that the single strand break is positioned either upstream (e.g., within 200 bp upstream) or downstream (e.g., within 200 bp downstream) of an HSV RS1 target position, an HSV RL2 target position, or an HSV LAT target position. In certain embodiments, the break is positioned to avoid unwanted target chromosome elements, such as repeat elements, e.g., an Alu repeat.

In certain embodiments, a double strand break is introduced (e.g., positioned by one gRNA molecule) at or in close proximity to an HSV RS1 target position, an HSV RL2 target position, or an HSV LAT target position. In certain embodiments, a single gRNA molecule (e.g., with a Cas9 nuclease other than a Cas9 nickase) is used to create a double strand break at or in close proximity to an HSV RS1 target position, an HSV RL2 target position, or an HSV LAT target position, e.g., the gRNA molecule is configured such that the double strand break is positioned either upstream (e.g., within 200 bp upstream) or downstream of (e.g., within 200 bp downstream) of an HSV RS1 target position, an HSV RL2 target position, or an HSV LAT target position. In certain embodiments, the break is positioned to avoid unwanted target chromosome elements, such as repeat elements, e.g., an Alu repeat.

In certain embodiments, two single strand breaks are introduced (e.g., positioned by two gRNA molecules) at or in close proximity to an HSV RS1 target position, an HSV RL2 target position, or an HSV LAT target position. In certain embodiments, two gRNA molecules (e.g., with one or two Cas9 nickases) are used to create two single strand breaks at or in close proximity to an HSV RS1 target position, an HSV RL2 target position, or an HSV LAT target position, e.g., the gRNAs molecules are configured such that both of the single strand breaks are positioned upstream (e.g., within 200 bp upstream) or downstream (e.g., within 200 bp downstream) of an HSV RS1 target position, an HSV RL2 target position, or an HSV LAT target position. In certain embodiments, two gRNA molecules (e.g., with two Cas9 nickases) are used to create two single strand breaks at or in close proximity to an HSV RS1 target position, an HSV RL2 target position, or an HSV LAT target position, e.g., the gRNAs molecules are configured such that one single strand break is positioned upstream (e.g., within 200 bp upstream) and a second single strand break is positioned downstream (e.g., within 200 bp downstream) of an HSV RS1 target position, an HSV RL2 target position, or an HSV LAT target position. In certain embodiments, the breaks are positioned to avoid unwanted target chromosome elements, such as repeat elements, e.g., an Alu repeat.

In certain embodiments, two double strand breaks are introduced (e.g., positioned by two gRNA molecules) at or in close proximity to an HSV RS1 target position, an HSV RL2 target position, or an HSV LAT target position. In certain embodiments, two gRNA molecules (e.g., with one or two Cas9 nucleases that are not Cas9 nickases) are used to create two double strand breaks to flank an HSV RS1 target position, an HSV RL2 target position, or an HSV LAT target position, e.g., the gRNA molecules are configured such that one double strand break is positioned upstream (e.g., within 200 bp upstream) and a second double strand break is positioned downstream (e.g., within 200 bp downstream) of an HSV RS1 target position, an HSV RL2 target position, or an HSV LAT target position. In certain embodiments, the breaks are positioned to avoid unwanted target chromosome elements, such as repeat elements, e.g., an Alu repeat.

In certain embodiments, one double strand break and two single strand breaks are introduced (e.g., positioned by three gRNA molecules) at or in close proximity to an HSV RS1 target position, an HSV RL2 target position, or an HSV LAT target position. In certain embodiments, three gRNA molecules (e.g., with a Cas9 nuclease other than a Cas9 nickase and one or two Cas9 nickases) to create one double strand break and two single strand breaks to flank an HSV RS1 target position, an HSV RL2 target position, or an HSV LAT target position, e.g., the gRNA molecules are configured such that the double strand break is positioned upstream or downstream of (e.g., within 200 bp upstream or downstream) oft an HSV RS1 target position, an HSV RL2 target position, or an HSV LAT target position, and the two single strand breaks are positioned at the opposite site, e.g., downstream or upstream (within 200 bp downstream or upstream), of an HSV RS1 target position, an HSV RL2 target position, or an HSV LAT target position. In certain embodiments, the breaks are positioned to avoid unwanted target chromosome elements, such as repeat elements, e.g., an Alu repeat.

In certain embodiments, four single strand breaks are introduced (e.g., positioned by four gRNA molecules) at or in close proximity to an HSV RS1 target position, an HSV RL2 target position, or an HSV LAT target position. In certain embodiments, four gRNA molecule (e.g., with one or more Cas9 nickases are used to create four single strand breaks to flank an HSV RS1 target position, an HSV RL2 target position, or an HSV LAT target position, e.g., the gRNA molecules are configured such that a first and second single strand breaks are positioned upstream (e.g., within 200 bp upstream) of an HSV RS1 target position, an HSV RL2 target position, or an HSV LAT target position, and a third and a fourth single stranded breaks are positioned downstream (e.g., within 200 bp downstream) of an HSV RS1 target position, an HSV RL2 target position, or an HSV LAT target position. In certain embodiments, the breaks are positioned to avoid unwanted target chromosome elements, such as repeat elements, e.g., an Alu repeat.

In certain embodiments, two or more (e.g., three or four) gRNA molecules are used with one Cas9 molecule or Cas9-fusion protein. In certain embodiments, when two or more (e.g., three or four) gRNAs are used with two or more Cas9 molecules, at least one Cas9 molecule is from a different species than the other Cas9 molecule(s). For example, when two gRNA molecules are used with two Cas9 molecules, one Cas9 molecule can be from one species and the other Cas9 molecule can be from a different species. Both Cas9 species are used to generate a single or double-strand break, as desired.

4.2. Knocking Out the One or More of the RS1, RL2, and/or LAT Gene(s) by Deleting (e.g., NHEJ-Mediated Deletion) a Genomic Sequence or Multiple Genomic Sequences Comprising at Least a Portion of the RS1, RL2, and/or LAT Gene(s)

In certain embodiments, the method comprises deleting (e.g., NHEJ-mediated deletion) a genomic sequence including at least a portion of the RS1, RL2, and/or LAT gene(s) or multiple genomic sequences including at least a portion of the RS1, RL2, and/or LAT gene(s). In certain embodiments, the method comprises the introduction of two double stand breaks—one 5' and the other 3' to (i.e., flanking) an HSV RS1 target knockout position, an HSV RL2 target knockout position or an HSV LAT target knockout position. In certain embodiments, two gRNAs, e.g., unimolecular (or chimeric) or modular gRNA molecules, are configured to position the two double strand breaks on opposite sides of the HSV RL2 target knockout position in the RL2 gene. In certain embodiments, two gRNAs, e.g., unimolecular (or chimeric) or modular gRNA molecules, are configured to position the two double strand breaks on opposite sides of the HSV LAT target knockout position in the LAT gene. In certain embodiments, two gRNAs, e.g., unimolecular (or chimeric) or modular gRNA molecules, are configured to position the two double strand breaks on opposite sides of the HSV RS1 target knockout position in the RS1 gene.

4.3. Knocking Down One or More of the RS1, RL2, and/or LAT Gene(s) Mediated by an Enzymatically Inactive Cas9 (eiCas9) Molecule or an eiCas9 Fusion Protein A targeted knockdown approach reduces or eliminates expression of functional RS1, RL2, and/or LAT gene product(s). As described herein, in certain embodiments, a targeted knockdown is mediated by targeting an enzymatically inactive Cas9 (eiCas9) molecule or an eiCas9-fusion protein (e.g., a eiCas9 fused to a transcription repressor domain or chromatin modifying protein) to one, two, or three of the RS1, RL2, and/or LAT gene(s).

Methods and compositions discussed herein may be used to alter the expression of one or more of the RS1, RL2, and/or LAT gene(s) to treat or prevent HSV-1 or HSV-2 infection by targeting a transcriptional regulatory region, e.g., a promoter region (e.g., a promoter region that controls the transcription of one or more of the RS1, RL2, and LAT genes). In certain embodiments, the promoter region is targeted to knock down expression of one or more of the RS1, RL2, and/or LAT genes. A targeted knockdown approach reduces or eliminates expression of functional RS1, RL2, and/or LAT gene product(s).

In certain embodiments, one or more eiCas9s may be used to block binding of one or more endogenous transcription factors. In certain embodiments, an eiCas9 can be fused to a chromatin modifying protein. Altering chromatin status can result in decreased expression of the target gene. One or more eiCas9s fused to one or more chromatin modifying proteins may be used to alter chromatin status.

In certain embodiments, eiCas9 mediated reduction in the expression of one or more of the RS1, RL2, and/or LAT gene(s) causes the reduction and/or cessation of transcription of RS1, RL2, and/or LAT RNA. In certain embodiments, eiCas9 mediated reduction in the expression of one or more of the RS1, RL2, and/or LAT gene(s) leads to reduction and/or cessation of translation of HSV-1 or HSV-2 proteins encoded by the RS1, RL2, and/or LAT gene(s), e.g., ICP0 protein and/or LAT protein and/or transcriptional regulator ICP4 protein. In certain embodiments, eiCas9 mediated reduction in the expression of one or more of the RS1, RL2, and/or LAT genes gives rise to any of the following, singly or in combination: decreased HSV DNA production, decreased HSV shedding, decreased HSV replication, decreased viral infectivity, decreased packaging of viral particles, decreased production of viral proteins, e.g., ICP0 proteins, e.g., transcriptional regulator ICP4 protein.

In certain embodiments, knockdown of one or more of the RS1, RL2, and/or LAT gene(s) cures HSV-1 or HSV-2 infection. In certain embodiments, knock down of one or more of the RS1, RL2, and/or LAT gene(s) leads to a functional cure of HSV-1 or HSV-2 infection. In certain embodiments, knock down of one or more of the RS1, RL2, and/or LAT gene(s) leads to a sustained virologic response to HSV-1 or HSV-2 infection. A targeted knockdown approach during an acute episode may decrease viral shedding, replication, which leads to decreased inflammation, which can decease damage to eyes. In certain embodiments, the eiCas9 molecule can be a Cas9 variant, as disclosed herein. For example, and not by way of limitation, the Cas9 variant can be a *S. pyogenes* Cas9 variant or a *S. aureus* Cas9 variant. In certain embodiments, the *S. pyogenes* Cas9 variant is the EQR variant. In certain embodiments, the *S. pyogenes* Cas9 variant is the VRER variant.

5. Guide RNA (gRNA) Molecules

Figure 7:
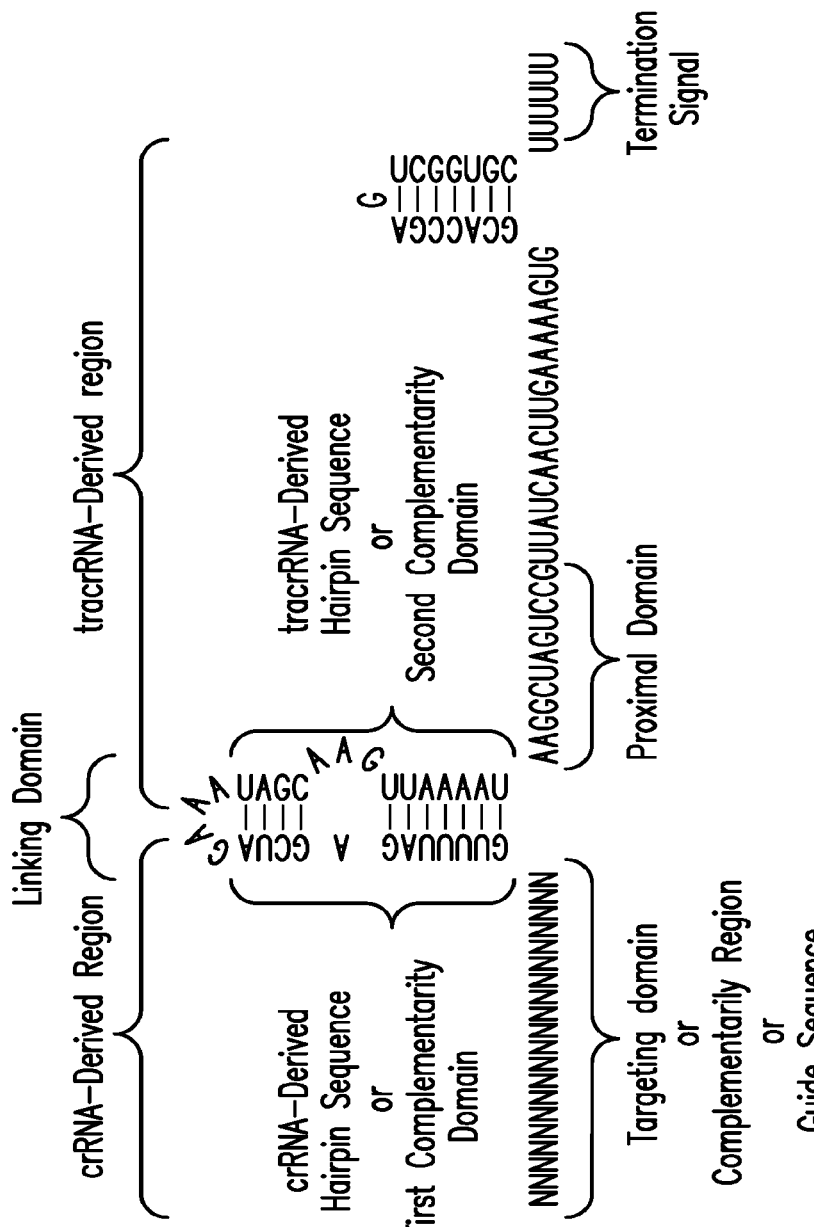
FIG. 7 illustrates gRNA domain nomenclature using an exemplary gRNA sequence (SEQ ID NO:42).

A gRNA molecule, as that term is used herein, refers to a nucleic acid that promotes the specific targeting or homing of a gRNA molecule/Cas9 molecule complex to a target nucleic acid. gRNA molecules can be unimolecular (having a single RNA molecule) (e.g., chimeric), or modular (comprising more than one, and typically two, separate RNA molecules). The gRNA molecules provided herein comprise a targeting domain comprising, consisting of, or consisting essentially of a nucleic acid sequence fully or partially complementary to a target domain (also referred to as "target sequence"). In certain embodiments, the gRNA molecule further comprises one or more additional domains, including for example a first complementarity domain, a linking domain, a second complementarity domain, a proximal domain, a tail domain, and a 5' extension domain. Each of these domains is discussed in detail below. In certain embodiments, one or more of the domains in the gRNA molecule comprises a nucleotide sequence identical to or sharing sequence homology with a naturally occurring sequence, e.g., from *S. pyogenes, S. aureus*, or *S. thermophilus*. In certain embodiments, one or more of the domains in the gRNA molecule comprises a nucleotide sequence identical to or sharing sequence homology with a naturally occurring sequence, e.g., from *S. pyogenes* or *S. aureus*, Several exemplary gRNA structures are provided in FIGS. 1A-1I. With regard to the three-dimensional form, or intra- or inter-strand interactions of an active form of a gRNA, regions of high complementarity are sometimes shown as duplexes in FIGS. 1A-1I and other depictions provided herein. FIG. 7 illustrates gRNA domain nomenclature using the gRNA sequence of SEQ ID NO:42, which contains one hairpin loop in the tracrRNA-derived region. In certain embodiments, a gRNA may contain more than one (e.g., two, three, or more) hairpin loops in this region (see, e.g., FIGS. 1H-1I).

In certain embodiments, a unimolecular, or chimeric, gRNA comprises, preferably from 5' to 3':

a targeting domain complementary to a target domain in a RL2, LAT, or a RS1 gene, e.g., a targeting domain comprising a nucleotide sequence selected from SEQ ID NOs: 208 to 58749;

a first complementarity domain;

a linking domain;

a second complementarity domain (which is complementary to the first complementarity domain);

a proximal domain; and optionally, a tail domain.

In certain embodiments, a modular gRNA comprises:
a first strand comprising, preferably from 5' to 3':
a targeting domain complementary to a target domain in a RL2, LAT, or RS1 gene, e.g., a targeting domain comprising a nucleotide sequence selected from SEQ ID NOs: 208 to 58749; and
a first complementarity domain; and
a second strand, comprising, preferably from 5' to 3':
optionally, a 5' extension domain;
a second complementarity domain;
a proximal domain; and
optionally, a tail domain.

5.1 Targeting Domain

The targeting domain (sometimes referred to alternatively as the guide sequence) comprises, consists of, or consists essentially of a nucleic acid sequence that is complementary or partially complementary to a target nucleic acid sequence in a RL2, LAT, or RS1 gene. The nucleic acid sequence in a RL2, LAT, or RS1 gene to which all or a portion of the targeting domain is complementary or partially complementary is referred to herein as the target domain.

Methods for selecting targeting domains are known in the art (see, e.g., Fu 2014; Sternberg 2014). Examples of suitable targeting domains for use in the methods, compositions, and kits described herein comprise nucleotide sequences set forth in SEQ ID NOs: 208 to 58749.

The strand of the target nucleic acid comprising the target domain is referred to herein as the complementary strand because it is complementary to the targeting domain sequence. Since the targeting domain is part of a gRNA molecule, it comprises the base uracil (U) rather than thymine (T); conversely, any DNA molecule encoding the gRNA molecule can comprise thymine rather than uracil. In a targeting domain/target domain pair, the uracil bases in the targeting domain will pair with the adenine bases in the target domain. In certain embodiments, the degree of complementarity between the targeting domain and target domain is sufficient to allow targeting of a Cas9 molecule to the target nucleic acid.

In certain embodiments, the targeting domain comprises a core domain and an optional secondary domain. In certain of these embodiments, the core domain is located 3' to the secondary domain, and in certain of these embodiments the core domain is located at or near the 3' end of the targeting domain. In certain of these embodiments, the core domain consists of or consists essentially of about 8 to about 13 nucleotides at the 3' end of the targeting domain. In certain embodiments, only the core domain is complementary or partially complementary to the corresponding portion of the target domain, and in certain of these embodiments the core domain is fully complementary to the corresponding portion of the target domain. In certain embodiments, the secondary domain is also complementary or partially complementary to a portion of the target domain. In certain embodiments, the core domain is complementary or partially complementary to a core domain target in the target domain, while the secondary domain is complementary or partially complementary to a secondary domain target in the target domain. In certain embodiments, the core domain and secondary domain have the same degree of complementarity with their respective corresponding portions of the target domain. In certain embodiments, the degree of complementarity between the core domain and its target and the degree of complementarity between the secondary domain and its target may differ. In certain of these embodiments, the core domain may have a higher degree of complementarity for its target than the secondary domain, whereas in other embodiments the secondary domain may have a higher degree of complementarity than the core domain.

In certain embodiments, the targeting domain and/or the core domain within the targeting domain is 3 to 100, 5 to 100, 10 to 100, or 20 to 100 nucleotides in length, and in certain of these embodiments the targeting domain or core domain is 3 to 15, 3 to 20, 5 to 20, 10 to 20, 15 to 20, 5 to 50, 10 to 50, or 20 to 50 nucleotides in length. In certain embodiments, the targeting domain and/or the core domain within the targeting domain is 6, 7, 8, 9, 10, 11, 12, 13, 14, 15, 16, 17, 18, 19, 20, 21, 22, 23, 24, 25, or 26 nucleotides in length. In certain embodiments, the targeting domain and/or the core domain within the targeting domain is 6+/−2, 7+/−2, 8+/−2, 9+/−2, 10+/−2, 10+/−4, 10+/−5, 11+/−2, 12+/−2, 13+/−2, 14+/−2, 15+/−2, or 16+−2, 20+/−5, 30+/−5, 40+/−5, 50+/−5, 60+/−5, 70+/−5, 80+/−5, 90+/−5, or 100+/−5 nucleotides in length.

In certain embodiments wherein the targeting domain includes a core domain, the core domain is 3 to 20 nucleotides in length, and in certain of these embodiments the core domain 5 to 15 or 8 to 13 nucleotides in length. In certain embodiments wherein the targeting domain includes a secondary domain, the secondary domain is 0, 1, 2, 3, 4, 5, 6, 7, 8, 9, 10, 11, 12, 13, 14 or 15 nucleotides in length. In certain embodiments wherein the targeting domain comprises a core domain that is 8 to 13 nucleotides in length, the targeting domain is 26, 25, 24, 23, 22, 21, 20, 19, 18, 17, or 16 nucleotides in length, and the secondary domain is 13 to 18, 12 to 17, 11 to 16, 10 to 15, 9 to 14, 8 to 13, 7 to 12, 6 to 11, 5 to 10, 4 to 9, or 3 to 8 nucleotides in length, respectively.

In certain embodiments, the targeting domain is fully complementary to the target domain. Likewise, where the targeting domain comprises a core domain and/or a secondary domain, in certain embodiments one or both of the core domain and the secondary domain are fully complementary to the corresponding portions of the target domain. In certain embodiments, the targeting domain is partially complementary to the target domain, and in certain of these embodiments where the targeting domain comprises a core domain and/or a secondary domain, one or both of the core domain and the secondary domain are partially complementary to the corresponding portions of the target domain. In certain of these embodiments, the nucleic acid sequence of the targeting domain, or the core domain or targeting domain within the targeting domain, is at least about 80%, about 85%, about 90%, or about 95% complementary to the target domain or to the corresponding portion of the target domain. In certain embodiments, the targeting domain and/or the core or secondary domains within the targeting domain include one or more nucleotides that are not complementary with the target domain or a portion thereof, and in certain of these embodiments the targeting domain and/or the core or secondary domains within the targeting domain include 1, 2, 3, 4, 5, 6, 7, or 8 nucleotides that are not complementary with the target domain. In certain embodiments, the core domain includes 1, 2, 3, 4, or 5 nucleotides that are not complementary with the corresponding portion of the target domain. In certain embodiments wherein the targeting domain includes one or more nucleotides that are not complementary with the target domain, one or more of said non-complementary nucleotides are located within five nucleotides of the 5' or 3' end of the targeting domain. In certain of these embodiments, the targeting domain includes 1, 2, 3, 4, or 5 nucleotides within five nucleotides of its 5' end, 3' end, or both its 5' and 3' ends that are not complementary to the target domain. In certain embodiments wherein the targeting domain includes two or more nucleotides that are not complementary to the target domain, two or more of said non-complementary nucleotides are adjacent to one another, and in certain of these embodiments the two or more consecutive non-complementary nucleotides are located within five nucleotides of the 5' or 3' end of the targeting domain. In certain embodiments, the two or more consecutive non-complementary nucleotides are both located more than five nucleotides from the 5' and 3' ends of the targeting domain.

In certain embodiments, the targeting domain, core domain, and/or secondary domain do not comprise any modifications. In certain embodiments, the targeting domain, core domain, and/or secondary domain, or one or more nucleotides therein, have a modification, including but not limited to the modifications set forth below. In certain embodiments, one or more nucleotides of the targeting domain, core domain, and/or secondary domain may comprise a 2' modification (e.g., a modification at the 2' position on ribose), e.g., a 2-acetylation, e.g., a 2' methylation. In certain embodiments, the backbone of the targeting domain can be modified with a phosphorothioate. In certain embodiments, modifications to one or more nucleotides of the targeting domain, core domain, and/or secondary domain render the targeting domain and/or the gRNA comprising the targeting domain less susceptible to degradation or more bio-compatible, e.g., less immunogenic. In certain embodiments, the targeting domain and/or the core or secondary domains include 1, 2, 3, 4, 5, 6, 7, or 8 or more modifications, and in certain of these embodiments the targeting domain and/or core or secondary domains include 1, 2, 3, or 4 modifications within five nucleotides of their respective 5' ends and/or 1, 2, 3, or 4 modifications within five nucleotides of their respective 3' ends. In certain embodiments, the targeting domain and/or the core or secondary domains comprise modifications at two or more consecutive nucleotides.

In certain embodiments wherein the targeting domain includes core and secondary domains, the core and secondary domains contain the same number of modifications. In certain of these embodiments, both domains are free of modifications. In other embodiments, the core domain includes more modifications than the secondary domain, or vice versa.

In certain embodiments, modifications to one or more nucleotides in the targeting domain, including in the core or secondary domains, are selected to not interfere with targeting efficacy, which can be evaluated by testing a candidate modification using a system as set forth below. gRNAs having a candidate targeting domain having a selected length, sequence, degree of complementarity, or degree of modification can be evaluated using a system as set forth below. The candidate targeting domain can be placed, either alone or with one or more other candidate changes in a gRNA molecule/Cas9 molecule system known to be functional with a selected target, and evaluated.

In certain embodiments, all of the modified nucleotides are complementary to and capable of hybridizing to corresponding nucleotides present in the target domain. In certain embodiments, 1, 2, 3, 4, 5, 6, 7 or 8 or more modified nucleotides are not complementary to or capable of hybridizing to corresponding nucleotides present in the target domain.

5.2 First and Second Complementarity Domains

The first and second complementarity (sometimes referred to alternatively as the crRNA-derived hairpin sequence and tracrRNA-derived hairpin sequences, respectively) domains are fully or partially complementary to one another. In certain embodiments, the degree of complementarity is sufficient for the two domains to form a duplexed region under at least some physiological conditions. In certain embodiments, the degree of complementarity between the first and second complementarity domains, together with other properties of the gRNA, is sufficient to allow targeting of a Cas9 molecule to a target nucleic acid. Examples of first and second complementary domains are set forth in FIGS. 1A-1G.

In certain embodiments (see, e.g., FIGS. 1A-1B) the first and/or second complementarity domain includes one or more nucleotides that lack complementarity with the corresponding complementarity domain. In certain embodiments, the first and/or second complementarity domain includes 1, 2, 3, 4, 5, or 6 nucleotides that do not complement with the corresponding complementarity domain. For example, the second complementarity domain may contain 1, 2, 3, 4, 5, or 6 nucleotides that do not pair with corresponding nucleotides in the first complementarity domain. In certain embodiments, the nucleotides on the first or second complementarity domain that do not complement with the corresponding complementarity domain loop out from the duplex formed between the first and second complementarity domains. In certain of these embodiments, the unpaired loop-out is located on the second complementarity domain, and in certain of these embodiments the unpaired region begins 1, 2, 3, 4, 5, or 6 nucleotides from the 5' end of the second complementarity domain.

In certain embodiments, the first complementarity domain is 5 to 30, 5 to 25, 7 to 25, 5 to 24, 5 to 23, 7 to 22, 5 to 22, 5 to 21, 5 to 20, 7 to 18, 7 to 15, 9 to 16, or 10 to 14 nucleotides in length, and in certain of these embodiments the first complementarity domain is 5, 6, 7, 8, 9, 10, 11, 12, 13, 14, 15, 16, 17, 18, 19, 20, 21, 22, 23, 24, or 25 nucleotides in length. In certain embodiments, the second complementarity domain is 5 to 27, 7 to 27, 7 to 25, 5 to 24, 5 to 23, 5 to 22, 5 to 21, 7 to 20, 5 to 20, 7 to 18, 7 to 17, 9 to 16, or 10 to 14 nucleotides in length, and in certain of these embodiments the second complementarity domain is 5, 6, 7, 8, 9, 10, 11, 12, 13, 14, 15, 16, 17, 18, 19, 20, 21, 22, 23, 24, 25, or 26 nucleotides in length. In certain embodiments, the first and second complementarity domains are each independently 6+/−2, 7+/−2, 8+/−2, 9+/−2, 10+/−2, 11+/−2, 12+/−2, 13+/−2, 14+/−2, 15+/−2, 16+/−2, 17+/−2, 18+/−2, 19+/−2, or 20+/−2, 21+/−2, 22+/−2, 23+/−2, or 24+/−2 nucleotides in length. In certain embodiments, the second complementarity domain is longer than the first complementarity domain, e.g., 2, 3, 4, 5, or 6 nucleotides longer.

In certain embodiments, the first and/or second complementarity domains each independently comprise three subdomains, which, in the 5' to 3' direction are: a 5' subdomain, a central subdomain, and a 3' subdomain. In certain embodiments, the 5' subdomain and 3' subdomain of the first complementarity domain are fully or partially complementary to the 3' subdomain and 5' subdomain, respectively, of the second complementarity domain.

In certain embodiments, the 5' subdomain of the first complementarity domain is 4 to 9 nucleotides in length, and in certain of these embodiments the 5' domain is 4, 5, 6, 7, 8, or 9 nucleotides in length. In certain embodiments, the 5' subdomain of the second complementarity domain is 3 to 25, 4 to 22, 4 to 18, or 4 to 10 nucleotides in length, and in certain of these embodiments the 5' domain is 3, 4, 5, 6, 7, 8, 9, 10, 11, 12, 13, 14, 15, 16, 17, 18, 19, 20, 21, 22, 23, 24, or 25 nucleotides in length. In certain embodiments, the central subdomain of the first complementarity domain is 1, 2, or 3 nucleotides in length. In certain embodiments, the central subdomain of the second complementarity domain is 1, 2, 3, 4, or 5 nucleotides in length. In certain embodiments, the 3' subdomain of the first complementarity domain is 3 to 25, 4 to 22, 4 to 18, or 4 to 10 nucleotides in length, and in certain of these embodiments the 3' subdomain is 3, 4, 5, 6, 7, 8, 9, 10, 11, 12, 13, 14, 15, 16, 17, 18, 19, 20, 21, 22, 23, 24, or 25 nucleotides in length. In certain embodiments, the 3' subdomain of the second complementarity domain is 4 to 9, e.g., 4, 5, 6, 7, 8 or 9 nucleotides in length.

The first and/or second complementarity domains can share homology with, or be derived from, naturally occurring or reference first and/or second complementarity domain. In certain of these embodiments, the first and/or second complementarity domains have at least about 50%, about 60%, about 70%, about 80%, about 85%, about 90%, or about 95% homology with, or differ by no more than 1, 2, 3, 4, 5, or 6 nucleotides from, the naturally occurring or reference first and/or second complementarity domain. In certain of these embodiments, the first and/or second complementarity domains may have at least about 50%, about 60%, about 70%, about 80%, about 85%, about 90%, or about 95% homology with homology with a first and/or second complementarity domain from *S. pyogenes* or *S. aureus*.

In certain embodiments, the first and/or second complementarity domains do not comprise any modifications. In other embodiments, the first and/or second complementarity domains or one or more nucleotides therein have a modification, including but not limited to a modification set forth below. In certain embodiments, one or more nucleotides of the first and/or second complementarity domain may comprise a 2' modification (e.g., a modification at the 2' position on ribose), e.g., a 2-acetylation, e.g., a 2' methylation. In certain embodiments, the backbone of the targeting domain can be modified with a phosphorothioate. In certain embodiments, modifications to one or more nucleotides of the first and/or second complementarity domain render the first and/or second complementarity domain and/or the gRNA comprising the first and/or second complementarity less susceptible to degradation or more bio-compatible, e.g., less immunogenic. In certain embodiments, the first and/or second complementarity domains each independently include 1, 2, 3, 4, 5, 6, 7, or 8 or more modifications, and in certain of these embodiments the first and/or second complementarity domains each independently include 1, 2, 3, or 4 modifications within five nucleotides of their respective 5' ends, 3' ends, or both their 5' and 3' ends. In certain embodiments, the first and/or second complementarity domains each independently contain no modifications within five nucleotides of their respective 5' ends, 3' ends, or both their 5' and 3' ends. In certain embodiments, one or both of the first and second complementarity domains comprise modifications at two or more consecutive nucleotides.

In certain embodiments, modifications to one or more nucleotides in the first and/or second complementarity domains are selected to not interfere with targeting efficacy, which can be evaluated by testing a candidate modification in a system as set forth below. gRNAs having a candidate first or second complementarity domain having a selected length, sequence, degree of complementarity, or degree of modification can be evaluated in a system as set forth below. The candidate complementarity domain can be placed, either alone or with one or more other candidate changes in a gRNA molecule/Cas9 molecule system known to be functional with a selected target, and evaluated.

In certain embodiments, the duplexed region formed by the first and second complementarity domains is, for example, 6, 7, 8, 9, 10, 11, 12, 13, 14, 15, 16, 17, 18, 19, 20, 21, or 22 bp in length, excluding any looped out or unpaired nucleotides.

In certain embodiments, the first and second complementarity domains, when duplexed, comprise 11 paired nucleotides (see, for e.g., gRNA of SEQ ID NO:48). In certain embodiments, the first and second complementarity domains, when duplexed, comprise 15 paired nucleotides (see, e.g., gRNA of SEQ ID NO:50). In certain embodiments, the first and second complementarity domains, when duplexed, comprise 16 paired nucleotides (see, e.g., gRNA of SEQ ID NO:51). In certain embodiments, the first and second complementarity domains, when duplexed, comprise 21 paired nucleotides (see, e.g., gRNA of SEQ ID NO:29).

In certain embodiments, one or more nucleotides are exchanged between the first and second complementarity domains to remove poly-U tracts. For example, nucleotides 23 and 48 or nucleotides 26 and 45 of the gRNA of SEQ ID NO:48 may be exchanged to generate the gRNA of SEQ ID NOs:49 or 31, respectively. Similarly, nucleotides 23 and 39 of the gRNA of SEQ ID NO:29 may be exchanged with nucleotides 50 and 68 to generate the gRNA of SEQ ID NO:30.

5.3 Linking Domain

The linking domain is disposed between and serves to link the first and second complementarity domains in a unimolecular or chimeric gRNA. FIGS. 1B-1E provide examples of linking domains. In certain embodiments, part of the linking domain is from a crRNA-derived region, and another part is from a tracrRNA-derived region.

In certain embodiments, the linking domain links the first and second complementarity domains covalently. In certain of these embodiments, the linking domain consists of or comprises a covalent bond. In other embodiments, the linking domain links the first and second complementarity domains non-covalently. In certain embodiments, the linking domain is ten or fewer nucleotides in length, e.g., 1, 2, 3, 4, 5, 6, 7, 8, 9, or 10 nucleotides. In other embodiments, the linking domain is greater than 10 nucleotides in length, e.g., 11, 12, 13, 14, 15, 16, 17, 18, 19, 20, 21, 22, 23, 24, or 25 or more nucleotides. In certain embodiments, the linking domain is 2 to 50, 2 to 40, 2 to 30, 2 to 20, 2 to 10, 2 to 5, 10 to 100, 10 to 90, 10 to 80, 10 to 70, 10 to 60, 10 to 50, 10 to 40, 10 to 30, 10 to 20, 10 to 15, 20 to 100, 20 to 90, 20 to 80, 20 to 70, 20 to 60, 20 to 50, 20 to 40, 20 to 30, or 20 to 25 nucleotides in length. In certain embodiments, the linking domain is 10+/−5, 20+/−5, 20+/−10, 30+/−5, 30+/−10, 40+/−5, 40+/−10, 50+/−5, 50+/−10, 60+/−5, 60+/−10, 70+/−5, 70+/−10, 80+/−5, 80+/−10, 90+/−5, 90+/−10, 100+/−5, or 100+/−10 nucleotides in length.

In certain embodiments, the linking domain shares homology with, or is derived from, a naturally occurring sequence, e.g., the sequence of a tracrRNA that is 5' to the second complementarity domain. In certain embodiments, the linking domain has at least about 50%, about 60%, about 70%, about 80%, about 90%, or about 95% homology with or differs by no more than 1, 2, 3, 4, 5, or 6 nucleotides from a linking domain disclosed herein, e.g., the linking domains of FIGS. 1B-1E.

In certain embodiments, the linking domain does not comprise any modifications. In other embodiments, the linking domain or one or more nucleotides therein have a modification, including but not limited to the modifications set forth below. In certain embodiments, one or more nucleotides of the linking domain may comprise a 2' modification (e.g., a modification at the 2' position on ribose), e.g., a 2-acetylation, e.g., a 2' methylation. In certain embodiments, the backbone of the linking domain can be modified with a phosphorothioate. In certain embodiments, modifications to one or more nucleotides of the linking domain render the linking domain and/or the gRNA comprising the linking domain less susceptible to degradation or more bio-compatible, e.g., less immunogenic. In certain embodiments, the linking domain includes 1, 2, 3, 4, 5, 6, 7, or 8 or more modifications, and in certain of these embodiments the linking domain includes 1, 2, 3, or 4 modifications within five nucleotides of its 5' and/or 3' end. In certain embodiments, the linking domain comprises modifications at two or more consecutive nucleotides.

In certain embodiments, modifications to one or more nucleotides in the linking domain are selected to not interfere with targeting efficacy, which can be evaluated by testing a candidate modification in a system as set forth below. gRNAs having a candidate linking domain having a selected length, sequence, degree of complementarity, or degree of modification can be evaluated in a system as set forth below. The candidate linking domain can be placed, either alone or with one or more other candidate changes in a gRNA molecule/Cas9 molecule system known to be functional with a selected target, and evaluated.

In certain embodiments, the linking domain comprises a duplexed region, typically adjacent to or within 1, 2, or 3 nucleotides of the 3' end of the first complementarity domain and/or the 5' end of the second complementarity domain. In certain of these embodiments, the duplexed region of the linking region is 10+/−5, 15+/−5, 20+/−5, 20+/−10, or 30+/−5 bp in length. In certain embodiments, the duplexed region of the linking domain is 1, 2, 3, 4, 5, 6, 7, 8, 9, 10, 11, 12, 13, 14, or 15 bp in length. In certain embodiments, the sequences forming the duplexed region of the linking domain are fully complementarity. In other embodiments, one or both of the sequences forming the duplexed region contain one or more nucleotides (e.g., 1, 2, 3, 4, 5, 6, 7, or 8 nucleotides) that are not complementary with the other duplex sequence.

5.4 5' Extension Domain

In certain embodiments, a modular gRNA as disclosed herein comprises a 5' extension domain, i.e., one or more additional nucleotides 5' to the second complementarity domain (see, e.g., FIG. 1A). In certain embodiments, the 5' extension domain is 2 to 10 or more, 2 to 9, 2 to 8, 2 to 7, 2 to 6, 2 to 5, or 2 to 4 nucleotides in length, and in certain of these embodiments the 5' extension domain is 2, 3, 4, 5, 6, 7, 8, 9, or 10 or more nucleotides in length.

In certain embodiments, the 5' extension domain nucleotides do not comprise modifications, e.g., modifications of the type provided below. However, in certain embodiments, the 5' extension domain comprises one or more modifications, e.g., modifications that it render it less susceptible to degradation or more bio-compatible, e.g., less immunogenic. By way of example, the backbone of the 5' extension domain can be modified with a phosphorothioate, or other modification(s) as set forth below. In certain embodiments, a nucleotide of the 5' extension domain can comprise a 2' modification (e.g., a modification at the 2' position on ribose), e.g., a 2-acetylation, e.g., a 2' methylation, or other modification(s) as set forth below.

In certain embodiments, the 5' extension domain can comprise as many as 1, 2, 3, 4, 5, 6, 7, or 8 modifications. In certain embodiments, the 5' extension domain comprises as many as 1, 2, 3, or 4 modifications within 5 nucleotides of its 5' end, e.g., in a modular gRNA molecule. In certain embodiments, the 5' extension domain comprises as many as 1, 2, 3, or 4 modifications within 5 nucleotides of its 3' end, e.g., in a modular gRNA molecule.

In certain embodiments, the 5' extension domain comprises modifications at two consecutive nucleotides, e.g., two consecutive nucleotides that are within 5 nucleotides of the 5' end of the 5' extension domain, within 5 nucleotides of the 3' end of the 5' extension domain, or more than 5 nucleotides away from one or both ends of the 5' extension domain. In certain embodiments, no two consecutive nucleotides are modified within 5 nucleotides of the 5' end of the 5' extension domain, within 5 nucleotides of the 3' end of the 5' extension domain, or within a region that is more than 5 nucleotides away from one or both ends of the 5' extension domain. In certain embodiments, no nucleotide is modified within 5 nucleotides of the 5' end of the 5' extension domain, within 5 nucleotides of the 3' end of the 5' extension domain, or within a region that is more than 5 nucleotides away from one or both ends of the 5' extension domain.

Modifications in the 5' extension domain can be selected so as to not interfere with gRNA molecule efficacy, which can be evaluated by testing a candidate modification in a system as set forth below. gRNAs having a candidate 5' extension domain having a selected length, sequence, degree of complementarity, or degree of modification, can be evaluated in a system as set forth below. The candidate 5' extension domain can be placed, either alone, or with one or more other candidate changes in a gRNA molecule/Cas9 molecule system known to be functional with a selected target and evaluated.

In certain embodiments, the 5' extension domain has at least about 60%, about 70%, about 80%, about 85%, about 90%, or about 95% homology with, or differs by no more than 1, 2, 3, 4, 5, or 6 nucleotides from, a reference 5' extension domain, e.g., a naturally occurring, e.g., an *S. pyogenes*, *S. aureus*, or *S. thermophilus*, 5' extension domain, or a 5' extension domain described herein, e.g., from FIGS. 1A-1G.

5.5 Proximal Domain

FIGS. 1A-1G provide examples of proximal domains.

In certain embodiments, the proximal domain is 5 to 20 or more nucleotides in length, e.g., 5, 6, 7, 8, 9, 10, 11, 12, 13, 14, 15, 16, 17, 18, 19, 20, 21, 22, 23, 24, 25, or 26 nucleotides in length. In certain of these embodiments, the proximal domain is 6+/−2, 7+/−2, 8+/−2, 9+/−2, 10+/−2, 11+/−2, 12+/−2, 13+/−2, 14+/−2, 14+/−2, 16+/−2, 17+/−2, 18+/−2, 19+/−2, or 20+/−2 nucleotides in length. In certain embodiments, the proximal domain is 5 to 20, 7, to 18, 9 to 16, or 10 to 14 nucleotides in length.

In certain embodiments, the proximal domain can share homology with or be derived from a naturally occurring proximal domain. In certain of these embodiments, the proximal domain has at least about 50%, about 60%, about 70%, about 80%, about 85%, about 90%, or about 95% homology with or differs by no more than 1, 2, 3, 4, 5, or 6 nucleotides from a proximal domain disclosed herein, e.g., an *S. pyogenes*, *S. aureus*, or *S. thermophilus* proximal domain, including those set forth in FIGS. 1A-1G.

In certain embodiments, the proximal domain does not comprise any modifications. In other embodiments, the proximal domain or one or more nucleotides therein have a modification, including but not limited to the modifications set forth in herein. In certain embodiments, one or more nucleotides of the proximal domain may comprise a 2' modification (e.g., a modification at the 2' position on ribose), e.g., a 2-acetylation, e.g., a 2' methylation. In certain embodiments, the backbone of the proximal domain can be modified with a phosphorothioate. In certain embodiments, modifications to one or more nucleotides of the proximal domain render the proximal domain and/or the gRNA comprising the proximal domain less susceptible to degradation or more bio-compatible, e.g., less immunogenic. In certain embodiments, the proximal domain includes 1, 2, 3, 4, 5, 6, 7, or 8 or more modifications, and in certain of these embodiments the proximal domain includes 1, 2, 3, or 4 modifications within five nucleotides of its 5' and/or 3' end. In certain embodiments, the proximal domain comprises modifications at two or more consecutive nucleotides.

In certain embodiments, modifications to one or more nucleotides in the proximal domain are selected to not interfere with targeting efficacy, which can be evaluated by testing a candidate modification in a system as set forth below. gRNAs having a candidate proximal domain having a selected length, sequence, degree of complementarity, or degree of modification can be evaluated in a system as set forth below. The candidate proximal domain can be placed, either alone or with one or more other candidate changes in a gRNA molecule/Cas9 molecule system known to be functional with a selected target, and evaluated.

5.6 Tail Domain

A broad spectrum of tail domains are suitable for use in the gRNA molecules disclosed herein. FIGS. 1A and 1C-1G provide examples of such tail domains.

In certain embodiments, the tail domain is absent. In other embodiments, the tail domain is 1 to 100 or more nucleotides in length, e.g., 1, 2, 3, 4, 5, 6, 7, 8, 9, 10, 20, 30, 40, 50, 60, 70, 80, 90, or 100 nucleotides in length. In certain embodiments, the tail domain is 1 to 5, 1 to 10, 1 to 15, 1 to 20, 1 to 50, 10 to 100, 20 to 100, 10 to 90, 20 to 90, 10 to 80, 20 to 80, 10 to 70, 20 to 70, 10 to 60, 20 to 60, 10 to 50, 20 to 50, 10 to 40, 20 to 40, 10 to 30, 20 to 30, 20 to 25, 10 to 20, or 10 to 15 nucleotides in length. In certain embodiments, the tail domain is 5+/−5, 10+/−5, 20+/−10, 20+/−5, 25+/−10, 30+/−10, 30+/−5, 40+/−10, 40+/−5, 50+/−10, 50+/−5, 60+/−10, 60+/−5, 70+/−10, 70+/−5, 80+/−10, 80+/−5, 90+/−10, 90+/−5, 100+/−10, or 100+/−5 nucleotides in length, In certain embodiments, the tail domain can share homology with or be derived from a naturally occurring tail domain or the 5' end of a naturally occurring tail domain. In certain of these embodiments, the proximal domain has at least about 50%, about 60%, about 70%, about 80%, about 85%, about 90%, or about 95% homology with or differs by no more than 1, 2, 3, 4, 5, or 6 nucleotides from a naturally occurring tail domain disclosed herein, e.g., an *S. pyogenes*, *S. aureus*, or *S. thermophilus* tail domain, including those set forth in FIGS. 1A and 1C-1G.

In certain embodiments, the tail domain includes sequences that are complementary to each other and which, under at least some physiological conditions, form a duplexed region. In certain of these embodiments, the tail domain comprises a tail duplex domain which can form a tail duplexed region. In certain embodiments, the tail duplexed region is 3, 4, 5, 6, 7, 8, 9, 10, 11, or 12 bp in length. In certain embodiments, the tail domain comprises a single stranded domain 3' to the tail duplex domain that does not form a duplex. In certain of these embodiments, the single stranded domain is 3 to 10 nucleotides in length, e.g., 3, 4, 5, 6, 7, 8, 9, 10, or 4 to 6 nucleotides in length.

In certain embodiments, the tail domain does not comprise any modifications. In other embodiments, the tail domain or one or more nucleotides therein have a modification, including but not limited to the modifications set forth herein. In certain embodiments, one or more nucleotides of the tail domain may comprise a 2' modification (e.g., a modification at the 2' position on ribose), e.g., a 2-acetylation, e.g., a 2' methylation. In certain embodiments, the backbone of the tail domain can be modified with a phosphorothioate. In certain embodiments, modifications to one or more nucleotides of the tail domain render the tail domain and/or the gRNA comprising the tail domain less susceptible to degradation or more bio-compatible, e.g., less immunogenic. In certain embodiments, the tail domain includes 1, 2, 3, 4, 5, 6, 7, or 8 or more modifications, and in certain of these embodiments the tail domain includes 1, 2, 3, or 4 modifications within five nucleotides of its 5' and/or 3' end. In certain embodiments, the tail domain comprises modifications at two or more consecutive nucleotides.

In certain embodiments, modifications to one or more nucleotides in the tail domain are selected to not interfere with targeting efficacy, which can be evaluated by testing a candidate modification as set forth below. gRNAs having a candidate tail domain having a selected length, sequence, degree of complementarity, or degree of modification can be evaluated using a system as set forth below. The candidate tail domain can be placed, either alone or with one or more other candidate changes in a gRNA molecule/Cas9 molecule system known to be functional with a selected target, and evaluated.

In certain embodiments, the tail domain includes nucleotides at the 3' end that are related to the method of in vitro or in vivo transcription. When a T7 promoter is used for in vitro transcription of the gRNA, these nucleotides may be any nucleotides present before the 3' end of the DNA template. In certain embodiments, the gRNA molecule includes a 3' polyA tail that is prepared by in vitro transcription from a DNA template. In certain embodiments, the 5' nucleotide of the targeting domain of the gRNA molecule is a guanine nucleotide, the DNA template comprises a T7 promoter sequence located immediately upstream of the sequence that corresponds to the targeting domain, and the 3' nucleotide of the T7 promoter sequence is not a guanine nucleotide. In certain embodiments, the 5' nucleotide of the targeting domain of the gRNA molecule is not a guanine nucleotide, the DNA template comprises a T7 promoter sequence located immediately upstream of the sequence that corresponds to the targeting domain, and the 3' nucleotide of the T7 promoter sequence is a guanine nucleotide which is downstream of a nucleotide other than a guanine nucleotide.

When a U6 promoter is used for in vivo transcription, these nucleotides may be the sequence UUUUUU. When an H1 promoter is used for transcription, these nucleotides may be the sequence UUUU. When alternate pol-III promoters are used, these nucleotides may be various numbers of uracil bases depending on, e.g., the termination signal of the pol-III promoter, or they may include alternate bases.

In certain embodiments, the proximal and tail domain taken together comprise, consist of, or consist essentially of the sequence set forth in SEQ ID NOs:32, 33, 34, 35, 36, or 37.

5.7 Exemplary Unimolecular/Chimeric gRNAs

In certain embodiments, a gRNA as disclosed herein has the structure: 5' [targeting domain]-[first complementarity domain]-[linking domain]-[second complementarity domain]-[proximal domain]-[tail domain]-3', wherein:

the targeting domain comprises a core domain and optionally a secondary domain, and is 10 to 50 nucleotides in length;

the first complementarity domain is 5 to 25 nucleotides in length and, in certain embodiments has at least about 50%, about 60%, about 70%, about 80%, about 85%, about 90%, or about 95% homology with a reference first complementarity domain disclosed herein;

the linking domain is 1 to 5 nucleotides in length;

the second complementarity domain is 5 to 27 nucleotides in length and, in certain embodiments has at least about 50%, about 60%, about 70%, about 80%, about 85%, about 90%, or about 95% homology with a reference second complementarity domain disclosed herein; the proximal domain is 5 to 20 nucleotides in length and, in certain embodiments has at least about 50%, about 60%, about 70%, about 80%, about 85%, about 90%, or about 95% homology with a reference proximal domain disclosed herein; and the tail domain is absent or a nucleotide sequence is 1 to 50 nucleotides in length and, in certain embodiments has at least about 50%, about 60%, about 70%, about 80%, about 85%, about 90%, or about 95% homology with a reference tail domain disclosed herein.

In certain embodiments, a unimolecular gRNA as disclosed herein comprises, preferably from 5' to 3':

a targeting domain, e.g., comprising 10-50 nucleotides;
a first complementarity domain, e.g., comprising 15, 16, 17, 18, 19, 20, 21, 22, 23, 24, 25, or 26 nucleotides;
a linking domain;
a second complementarity domain;
a proximal domain; and
a tail domain,
wherein, (a) the proximal and tail domain, when taken together, comprise at least 15, 18, 20, 25, 30, 31, 35, 40, 45, 49, 50, or 53 nucleotides;

(b) there are at least 15, 18, 20, 25, 30, 31, 35, 40, 45, 49, 50, or 53 nucleotides 3' to the last nucleotide of the second complementarity domain; or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the sequence from (a), (b), and/or (c) has at least about 50%, about 60%, about 70%, about 75%, about 60%, about 70%, about 80%, about 85%, about 90%, about 95%, or about 99% homology with the corresponding sequence of a naturally occurring gRNA, or with a gRNA described herein.

In certain embodiments, the proximal and tail domain, when taken together, comprise at least 15, 18, 20, 25, 30, 31, 35, 40, 45, 49, 50, or 53 nucleotides.

In certain embodiments, there are at least 15, 18, 20, 25, 30, 31, 35, 40, 45, 49, 50, or 53 nucleotides 3' to the last nucleotide of the second complementarity domain.

In certain embodiments, there are at least 16, 19, 21, 26, 31, 32, 36, 41, 46, 50, 51, or 54 nucleotides 3' to the last nucleotide of the second complementarity domain that are complementary to the corresponding nucleotides of the first complementarity domain.

In certain embodiments, the targeting domain consists of, consists essentially of, or comprises 16, 17, 18, 19, 20, 21, 22, 23, 24, 25, or 26 nucleotides (e.g., 16, 17, 18, 19, 20, 21, 22, 23, 24, 25, or 26 consecutive nucleotides) complementary or partially complementary to the target domain or a portion thereof, e.g., the targeting domain is 16, 17, 18, 19, 20, 21, 22, 23, 24, 25, or 26 nucleotides in length. In certain of these embodiments, the targeting domain is complementary to the target domain over the entire length of the targeting domain, the entire length of the target domain, or both.

In certain embodiments, a unimolecular or chimeric gRNA molecule disclosed herein (comprising a targeting domain, a first complementary domain, a linking domain, a second complementary domain, a proximal domain and, optionally, a tail domain) comprises the amino acid sequence set forth in SEQ ID NO:42, wherein the targeting domain is listed as 20 N's (residues 1-20) but may range in length from 16 to 26 nucleotides, and wherein the final six residues (residues 97-102) represent a termination signal for the U6 promoter buy may be absent or fewer in number. In certain embodiments, the unimolecular, or chimeric, gRNA molecule is a *S. pyogenes* gRNA molecule.

In certain embodiments, a unimolecular or chimeric gRNA molecule disclosed herein (comprising a targeting domain, a first complementary domain, a linking domain, a second complementary domain, a proximal domain and, optionally, a tail domain) comprises the amino acid sequence set forth in SEQ ID NO:38, wherein the targeting domain is listed as 20 Ns (residues 1-20) but may range in length from 16 to 26 nucleotides, and wherein the final six residues (residues 97-102) represent a termination signal for the U6 promoter but may be absent or fewer in number. In certain embodiments, the unimolecular or chimeric gRNA molecule is an *S. aureus* gRNA molecule.

Figure 1H:
Figure 1I:
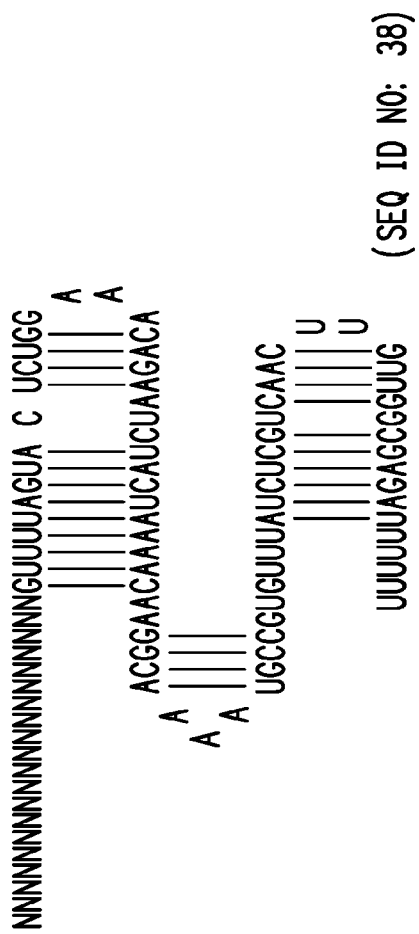

The sequences and structures of exemplary chimeric gRNAs are also shown in FIGS. 1H-1I.

5.8 Exemplary Modular gRNAs

In certain embodiments, a modular gRNA disclosed herein comprises:

a first strand comprising, preferably from 5' to 3';
a targeting domain, e.g., comprising 15, 16, 17, 18, 19, 20, 21, 22, 23, 24, 25, or 26 nucleotides;
a first complementarity domain; and
a second strand, comprising, preferably from 5' to 3':
optionally a 5' extension domain;
a second complementarity domain;
a proximal domain; and
a tail domain, wherein:

(a) the proximal and tail domain, when taken together, comprise at least 15, 18, 20, 25, 30, 31, 35, 40, 45, 49, 50, or 53 nucleotides;

(b) there are at least 15, 18, 20, 25, 30, 31, 35, 40, 45, 49, 50, or 53 nucleotides 3' to the last nucleotide of the second complementarity domain; or (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the sequence from (a), (b), or (c), has at least about 50%, about 60%, about 70%, about 80%, about 85%, about 90%, about 95%, or about 99% homology with the corresponding sequence of a naturally occurring gRNA, or with a gRNA described herein. In certain embodiments, the proximal and tail domain, when taken together, comprise at least 15, 18, 20, 25, 30, 31, 35, 40, 45, 49, 50, or 53 nucleotides.

In certain embodiments, there are at least 15, 18, 20, 25, 30, 31, 35, 40, 45, 49, 50, or 53 nucleotides 3' to the last nucleotide of the second complementarity domain.

In certain embodiments, there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 16, 17, 18, 19, 20, 21, 22, 23, 24, 25, or 26 nucleotides (e.g., 16, 17, 18, 19, 20, 21, 22, 23, 24, 25, or 26 consecutive nucleotides) having complementarity with the target domain, e.g., the targeting domain is 16, 17, 18, 19, 20, 21, 22, 23, 24, 25, or 26 nucleotides in length.

In certain embodiments, the targeting domain consists of, consists essentially of, or comprises 16, 17, 18, 19, 20, 21, 22, 23, 24, 25, or 26 nucleotides (e.g., 16, 17, 18, 19, 20, 21, 22, 23, 24, 25, or 26 consecutive nucleotides) complementary to the target domain or a portion thereof. In certain of these embodiments, the targeting domain is complementary to the target domain over the entire length of the targeting domain, the entire length of the target domain, or both.

In certain embodiments, the targeting domain comprises, has, or consists of, 16 nucleotides (e.g., 16 consecutive nucleotides) having complementarity with the target domain, e.g., the targeting domain is 16 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 16 nucleotides (e.g., 16 consecutive nucleotides) having complementarity with the target domain, e.g., the targeting domain is 16 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 16 nucleotides (e.g., 16 consecutive nucleotides) having complementarity with the target domain, e.g., the targeting domain is 16 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain has, or consists of, 17 nucleotides (e.g., 17 consecutive nucleotides) having complementarity with the target domain, e.g., the targeting domain is 17 nucleotides in length; and the proximal and tail domain, when taken together, comprise at least 15, 18, 20, 25, 30, 31, 35, 40, 45, 49, 50, or 53 nucleotides.

In certain embodiments, the targeting domain has, or consists of, 17 nucleotides (e.g., 17 consecutive nucleotides) having complementarity with the target domain, e.g., the targeting domain is 17 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain has, or consists of, 17 nucleotides (e.g., 17 consecutive nucleotides) having complementarity with the target domain, e.g., the targeting domain is 17 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain has, or consists of, 18 nucleotides (e.g., 18 consecutive nucleotides) having complementarity with the target domain, e.g., the targeting domain is 18 nucleotides in length; and the proximal and tail domain, when taken together, comprise at least 15, 18, 20, 25, 30, 31, 35, 40, 45, 49, 50, or 53 nucleotides.

In certain embodiments, the targeting domain has, or consists of, 18 nucleotides (e.g., 18 consecutive nucleotides) having complementarity with the target domain, e.g., the targeting domain is 18 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain has, or consists of, 18 nucleotides (e.g., 18 consecutive nucleotides) having complementarity with the target domain, e.g., the targeting domain is 18 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 19 nucleotides (e.g., 19 consecutive nucleotides) having complementarity with the target domain, e.g., the targeting domain is 19 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 19 nucleotides (e.g., 19 consecutive nucleotides) having complementarity with the target domain, e.g., the targeting domain is 19 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 19 nucleotides (e.g., 19 consecutive nucleotides) having complementarity with the target domain, e.g., the targeting domain is 19 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 20 nucleotides (e.g., 20 consecutive nucleotides) having complementarity with the target domain, e.g., the targeting domain is 20 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 20 nucleotides (e.g., 20 consecutive nucleotides) having complementarity with the target domain, e.g., the targeting domain is 20 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 20 nucleotides (e.g., 20 consecutive nucleotides) having complementarity with the target domain, e.g., the targeting domain is 20 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 21 nucleotides (e.g., 21 consecutive nucleotides) having complementarity with the target domain, e.g., the targeting domain is 21 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 21 nucleotides (e.g., 21 consecutive nucleotides) having complementarity with the target domain, e.g., the targeting domain is 21 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 21 nucleotides (e.g., 21 consecutive nucleotides) having complementarity with the target domain, e.g., the targeting domain is 21 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 22 nucleotides (e.g., 22 consecutive nucleotides) having complementarity with the target domain, e.g., the targeting domain is 22 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 22 nucleotides (e.g., 22 consecutive nucleotides) having complementarity with the target domain, e.g., the targeting domain is 22 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 22 nucleotides (e.g., 22 consecutive nucleotides) having complementarity with the target domain, e.g., the targeting domain is 22 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 23 nucleotides (e.g., 23 consecutive nucleotides) having complementarity with the target domain, e.g., the targeting domain is 23 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 23 nucleotides (e.g., 23 consecutive nucleotides) having complementarity with the target domain, e.g., the targeting domain is 23 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 23 nucleotides (e.g., 23 consecutive nucleotides) having complementarity with the target domain, e.g., the targeting domain is 23 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 24 nucleotides (e.g., 24 consecutive nucleotides) having complementarity with the target domain, e.g., the targeting domain is 24 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 24 nucleotides (e.g., 24 consecutive nucleotides) having complementarity with the target domain, e.g., the targeting domain is 24 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 24 nucleotides (e.g., 24 consecutive nucleotides) having complementarity with the target domain, e.g., the targeting domain is 24 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 25 nucleotides (e.g., 25 consecutive nucleotides) having complementarity with the target domain, e.g., the targeting domain is 25 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 25 nucleotides (e.g., 25 consecutive nucleotides) having complementarity with the target domain, e.g., the targeting domain is 25 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 25 nucleotides (e.g., 25 consecutive nucleotides) having complementarity with the target domain, e.g., the targeting domain is 25 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In certain embodiments, the targeting domain comprises, has, or consists of, 26 nucleotides (e.g., 26 consecutive nucleotides) having complementarity with the target domain, e.g., the targeting domain is 26 nucleotides in length; and the proximal and tail domain, when taken together, comprise at least 15, 18, 20, 25, 30, 31, 35, 40, 45, 49, 50, or 53 nucleotides.

In certain embodiments, the targeting domain comprises, has, or consists of, 26 nucleotides (e.g., 26 consecutive nucleotides) having complementarity with the target domain, e.g., the targeting domain is 26 nucleotides in length; and there are at least 15, 18, 20, 25, 30, 31, 35, 40, 45, 49, 50, or 53 nucleotides 3' to the last nucleotide of the second complementarity domain.

In certain embodiments, the targeting domain comprises, has, or consists of, 26 nucleotides (e.g., 26 consecutive nucleotides) having complementarity with the target domain, e.g., the targeting domain is 26 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

5.9 gRNA Delivery

In certain embodiments of the methods provided herein, the methods comprise delivery of one or more (e.g., two, three, or four) gRNA molecules as described herein. In certain of these embodiments, the gRNA molecules are delivered by intravenous injection, intramuscular injection, subcutaneous injection, or inhalation. In certain embodiments, the gRNA molecules are delivered with a Cas9 molecule in a genome editing system.

6. Methods for Designing gRNAs

Methods for selecting, designing, and validating targeting domains for use in the gRNAs described herein are provided. Exemplary targeting domains for incorporation into gRNAs are also provided herein.

Methods for selection and validation of target sequences as well as off-target analyses have been described previously (see, e.g., Mali 2013; Hsu 2013; Fu 2014; Heigwer 2014; Bae 2014; Xiao 2014). For example, a software tool can be used to optimize the choice of potential targeting domains corresponding to a user's target sequence, e.g., to minimize total off-target activity across the genome. Off-target activity may be other than cleavage. For each possible targeting domain choice using *S. pyogenes* Cas9, the tool can identify all off-target sequences (preceding either NAG or NGG PAMs) across the genome that contain up to certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible targeting domain is then ranked according to its total predicted off-target cleavage; the top-ranked targeting domains represent those that are likely to have the greatest on-target cleavage and the least off-target cleavage. Other functions, e.g., automated reagent design for CRISPR construction, primer design for the on-target Surveyor assay, and primer design for high-throughput detection and quantification of off-target cleavage via next-gen sequencing, can also be included in the tool. Candidate targeting domains and gRNAs comprising those targeting domains can be functionally evaluated using methods known in the art and/or as set forth herein.

As a non-limiting example, targeting domains for use in gRNAs for use with *S. pyogenes*, *S. aureus*, and *N. meningitidis* Cas9s were identified using a DNA sequence searching algorithm. 17-mer and 20-mer targeting domains were designed for *S. pyogenes* and *N. meningitidis* targets, while 18-mer, 19-mer, 20-mer, 21-mer, 22-mer, 23-mer, and 24-mer targeting domains were designed for *S. aureus* targets. gRNA design was carried out using custom gRNA design software based on the public tool cas-offinder (Bae 2014). This software scores guides after calculating their genome-wide off-target propensity. Typically matches ranging from perfect matches to 7 mismatches are considered for guides ranging in length from 17 to 24. Once the off-target sites are computationally determined, an aggregate score is calculated for each guide and summarized in a tabular output using a web-interface. In addition to identifying potential target sites adjacent to PAM sequences, the software also identifies all PAM adjacent sequences that differ by 1, 2, 3, or more than 3 nucleotides from the selected target sites. Genomic DNA sequences for each gene were obtained from the UCSC Genome browser and sequences were screened for repeat elements using the publically available RepeatMasker program. RepeatMasker searches input DNA sequences for repeated elements and regions of low complexity. The output is a detailed annotation of the repeats present in a given query sequence.

Following identification, targeting domain were ranked into tiers based on their distance to the target site, their orthogonality, and presence of a 5' G (based on identification of close matches in the human genome containing a relevant PAM, e.g., an NGG PAM for a wild-type *S. pyogenes* Cas9 molecule; an NNGRRT (SEQ ID NO:204) or NNGRRV (SEQ ID NO:205) PAM for a wild-type *S. aureus* Cas9 molecule, or a NNNNGATT or NNNNGCTT PAM for a wild-type *N. meningitidis* Cas9 molecule; a PAM selected from the group consisting of NGAG, NGCG, NGGG, NGTG, NGAA, NGAT and NGAC for a *S. pyogenes* Cas9 EQR variant; or a PAM selected from the group consisting of NGCG, NGCA, NGCT, and NGCC for a *S. pyogenes* Cas9 VRER variant). Orthogonality refers to the number of sequences in the human genome that contain a minimum number of mismatches to the target sequence. A "high level of orthogonality" or "good orthogonality" may, for example, refer to 20-mer targeting domain that have no identical sequences in the human genome besides the intended target, nor any sequences that contain one or two mismatches in the target sequence. Targeting domains with good orthogonality are selected to minimize off-target DNA cleavage.

Targeting domains were identified for both single-gRNA nuclease cleavage and for a dual-gRNA paired "nickase" strategy. Criteria for selecting targeting domains and the determination of which targeting domains can be used for the dual-gRNA paired "nickase" strategy is based on two considerations:

(1) Targeting domain pairs should be oriented on the DNA such that PAMs are facing out and cutting with the D10A Cas9 nickase can result in 5' overhangs; and (2) An assumption that cleaving with dual nickase pairs will result in deletion of the entire intervening sequence at a reasonable frequency. However, cleaving with dual nickase pairs can also result in indel mutations at the site of only one of the gRNAs. Candidate pair members can be tested for how efficiently they remove the entire sequence versus causing indel mutations at the target site of one targeting domain.

6.1 Targeting Domains for Use in Knocking Out the HSV-1 RS1 Gene

Targeting domains for use in gRNAs for knocking out the HSV-1 RS1 gene in conjunction with the methods disclosed herein were identified and ranked into 5 tiers for *S. pyogenes*, 7 tiers for *S. aureus*, and 5 tiers for *N. meningitidis*.

For *S. pyogenes*, and *N. meningitidis*, the targeting domain for tier 1 gRNA molecules were selected based on (1) distance to a target site (e.g., start codon), e.g., within 500 bp (e.g., downstream) of the target site (e.g., start codon), (2) a high level of orthogonality and (3) the presence of 5'G. The targeting domain for tier 2 gRNA molecules were selected based on (1) distance to a target site (e.g., start codon), e.g., within 500 bp (e.g., downstream) of the target site (e.g., start codon) and (2) a high level of orthogonality. The targeting domain for tier 3 gRNA molecules were selected based on (1) distance to a target site (e.g., start codon), e.g., within 500 bp (e.g., downstream) of the target site (e.g., start codon) and (2) the presence of 5'G. The targeting domain for tier 4 gRNA molecules were selected based on distance to a target site (e.g., start codon), e.g., within 500 bp (e.g., downstream) of the target site (e.g., start codon). The targeting domain for tier 5 gRNA molecules were selected based on distance to the target site (e.g., start codon), e.g., within reminder of the coding sequence, e.g., downstream of the first 500 bp of coding sequence (e.g., anywhere from +500 (relative to the start codon) to the stop codon).

For *S. aureus*, the targeting domain for tier 1 gRNA molecules were selected based on (1) distance to a target site (e.g., start codon), e.g., within 500 bp (e.g., downstream) of the target site (e.g., start codon), (2) a high level of orthogonality, (3) the presence of 5'G and (4) wherein the PAM is NNGRRT (SEQ ID NO: 204). The targeting domain for tier 2 gRNA molecules were selected based on (1) distance to a target site (e.g., start codon), e.g., within 500 bp (e.g., downstream) of the target site (e.g., start codon), (2) a high level of orthogonality, and (3) wherein the PAM is NNGRRT. The targeting domain for tier 3 gRNA molecules were selected based on (1) distance to a target site (e.g., start codon), e.g., within 500 bp (e.g., downstream) of the target site (e.g., start codon) and (2) wherein the PAM is NNGRRT. The targeting domain for tier 4 gRNA molecules were selected based on (1) distance to a target site (e.g., start codon), e.g., within 500 bp (e.g., downstream) of the target site (e.g., start codon) and (2) wherein the PAM is NNGRRV. The targeting domain for tier 5 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon), (2) the presence of 5'G and (3) wherein the PAM is NNGRRT. The targeting domain for tier 6 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon) and (2) wherein the PAM is NNGRRT. The targeting domain for tier 7 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon) and (2) wherein the PAM is NNGRRV. Note that tiers are non-inclusive (each gRNA is listed only once for the strategy). In certain instances, no gRNA was identified based on the criteria of the particular tier. Note that tiers are non-inclusive (each targeting domain is listed only once for the strategy). In certain instances, no targeting domain was identified based on the criteria of the particular tier. The identified targeting domains are summarized below in Table 1.

TABLE 1

Nucleotide sequences of S. pyogenes, S. aureus, and N. meningitidis targeting domains for knocking out the HSV-1 RS1 gene

| | S. pyogenes | S. aureus | N. meningitidis |
|---|---|---|---|
| Tier 1 | SEQ ID NOS: 208 to 254 | SEQ ID NOS: 2510 to 2531 | SEQ ID NO: 7074 |
| Tier 2 | SEQ ID NOS: 255 to 333 | SEQ ID NOS: 2532 to 2563 | SEQ ID NO: 7075 |
| Tier 3 | SEQ ID NOS: 334 to 425 | SEQ ID NOS: 2564 to 2586 | Not applicable |
| Tier 4 | SEQ ID NOS: 426 to 516 | SEQ ID NOS: 2587 to 3244 | Not applicable |
| Tier 5 | SEQ ID NOS: 517 to 2509 | SEQ ID NOS: 3245 to 3368 | SEQ ID NOS: 7076 to 7097 |
| Tier 6 | Not applicable | SEQ ID NOS: 3369 to 3545 | Not applicable |
| Tier 7 | Not applicable | SEQ ID NOS: 3546 to 7073 | Not applicable |

6.2 Targeting Domains for Use in Knocking Out the HSV-2 RS1 Gene

Targeting domains for use in gRNAs for knocking out the HSV-2 RS1 gene in conjunction with the methods disclosed herein were identified and ranked into 5 tiers for *S. pyogenes*, 7 tiers for *S. aureus*, and 5 tiers for *N. meningitidis*.

For *S. pyogenes*, and *N. meningitidis*, the targeting domain for tier 1 gRNA molecules were selected based on (1) distance to a target site (e.g., start codon), e.g., within 500 bp (e.g., downstream) of the target site (e.g., start codon), (2) a high level of orthogonality and (3) the presence of 5'G. The targeting domain for tier 2 gRNA molecules were selected based on (1) distance to a target site (e.g., start codon), e.g., within 500 bp (e.g., downstream) of the target site (e.g., start codon) and (2) a high level of orthogonality. The targeting domain for tier 3 gRNA molecules were selected based on (1) distance to a target site (e.g., start codon), e.g., within 500 bp (e.g., downstream) of the target site (e.g., start codon) and (2) the presence of 5'G. The targeting domain for tier 4 gRNA molecules were selected based on distance to a target site (e.g., start codon), e.g., within 500 bp (e.g., downstream) of the target site (e.g., start codon). The targeting domain for tier 5 gRNA molecules were selected based on distance to the target site (e.g., start codon), e.g., within reminder of the coding sequence, e.g., downstream of the first 500 bp of coding sequence (e.g., anywhere from +500 (relative to the start codon) to the stop codon).

For *S. aureus*, the targeting domain for tier 1 gRNA molecules were selected based on (1) distance to a target site (e.g., start codon), e.g., within 500 bp (e.g., downstream) of the target site (e.g., start codon), (2) a high level of orthogonality, (3) the presence of 5'G and (4) wherein the PAM is NNGRRT. The targeting domain for tier 2 gRNA molecules were selected based on (1) distance to a target site (e.g., start codon), e.g., within 500 bp (e.g., downstream) of the target site (e.g., start codon), (2) a high level of orthogonality, and (3) wherein the PAM is NNGRRT. The targeting domain for tier 3 gRNA molecules were selected based on (1) distance to a target site (e.g., start codon), e.g., within 500 bp (e.g., downstream) of the target site (e.g., start codon) and (2) wherein the PAM is NNGRRT. The targeting domain for tier 4 gRNA molecules were selected based on (1) distance to a target site (e.g., start codon), e.g., within 500 bp (e.g., downstream) of the target site (e.g., start codon) and (2) PAM is NNGRRV. The targeting domain for tier 5 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon), (2) the presence of 5'G and (3) wherein the PAM is NNGRRT. The targeting domain for tier 6 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon) and (2) wherein the PAM is NNGRRT. The targeting domain for tier 7 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon) and (2) wherein the PAM is NNGRRV. Note that tiers are non-inclusive (each gRNA is listed only once for the strategy). In certain instances, no gRNA was identified based on the criteria of the particular tier.

Note that tiers are non-inclusive (each targeting domain is listed only once for the strategy). In certain instances, no targeting domain was identified based on the criteria of the particular tier. The identified targeting domains are summarized below in Table 2.

TABLE 2

Nucleotide sequences of *S. pyogenes*, *S. aureus*, and *N. meningitidis* targeting domains for knocking out the HSV-2 RS1 gene

|  | S. pyogenes | S. aureus | N. meningitidis |
|---|---|---|---|
| Tier 1 | SEQ ID NOS: 7098 to 7148 | SEQ ID NOS: 9293 to 9314 | SEQ ID NO: 13615 |
| Tier 2 | SEQ ID NOS: 7149 to 7236 | SEQ ID NOS: 9315 to 9342 | SEQ ID NOS: 13616 to 13618 |
| Tier 3 | SEQ ID NOS: 7237 to 7286 | SEQ ID NOS: 9343 to 9355 | Not applicable |
| Tier 4 | SEQ ID NOS: 7287 to 7341 | SEQ ID NOS: 9356 to 9911 | Not applicable |
| Tier 5 | SEQ ID NOS: 7342 to 9292 | SEQ ID NOS: 9912 to 10034 | SEQ ID NOS: 13619 to 13636 |
| Tier 6 | Not applicable | SEQ ID NOS: 10035 to 10191 | Not applicable |
| Tier 7 | Not applicable | SEQ ID NOS: 10192 to 13614 | Not applicable |

6.3 Targeting Domains for Use in Knocking Out the HSV-1 RL2 Gene

Targeting domains for use in gRNAs for knocking out the HSV-1 RL2 gene in conjunction with the methods disclosed herein were identified and ranked into 5 tiers for *S. pyogenes*, 7 tiers for *S. aureus*, and 5 tiers for *N. meningitidis*.

For *S. pyogenes*, and *N. meningitidis*, the targeting domain for tier 1 gRNA molecules were selected based on (1) distance to a target site (e.g., start codon), e.g., within 500 bp (e.g., downstream) of the target site (e.g., start codon), (2) a high level of orthogonality and (3) the presence of 5'G. The targeting domain for tier 2 gRNA molecules were selected based on (1) distance to a target site (e.g., start codon), e.g., within 500 bp (e.g., downstream) of the target site (e.g., start codon) and (2) a high level of orthogonality. The targeting domain for tier 3 gRNA molecules were selected based on (1) distance to a target site (e.g., start codon), e.g., within 500 bp (e.g., downstream) of the target site (e.g., start codon) and (2) the presence of 5'G. The targeting domain for tier 4 gRNA molecules were selected based on distance to a target site (e.g., start codon), e.g., within 500 bp (e.g., downstream) of the target site (e.g., start codon). The targeting domain for tier 5 gRNA molecules were selected based on distance to the target site (e.g., start codon), e.g., within reminder of the coding sequence, e.g., downstream of the first 500 bp of coding sequence (e.g., anywhere from +500 (relative to the start codon) to the stop codon).

For *S. aureus*, the targeting domain for tier 1 gRNA molecules were selected based on (1) distance to a target site (e.g., start codon), e.g., within 500 bp (e.g., downstream) of the target site (e.g., start codon), (2) a high level of orthogonality, (3) the presence of 5'G and (4) wherein the PAM is NNGRRT. The targeting domain for tier 2 gRNA molecules were selected based on (1) distance to a target site (e.g., start codon), e.g., within 500 bp (e.g., downstream) of the target site (e.g., start codon), (2) a high level of orthogonality, and (3) wherein the PAM is NNGRRT. The targeting domain for tier 3 gRNA molecules were selected based on (1) distance to a target site (e.g., start codon), e.g., within 500 bp (e.g., downstream) of the target site (e.g., start codon) and (2) wherein the PAM is NNGRRT. The targeting domain for tier 4 gRNA molecules were selected based on (1) distance to a target site (e.g., start codon), e.g., within 500 bp (e.g., downstream) of the target site (e.g., start codon) and (2) wherein the PAM is NNGRRV. The targeting domain for tier 5 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon), (2) the presence of 5'G and (3) wherein the PAM is NNGRRT. The targeting domain for tier 6 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon) and (2) wherein the PAM is NNGRRT. The targeting domain for tier 7 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon) and (2) wherein the PAM is NNGRRV. Note that tiers are non-inclusive (each gRNA is listed only once for the strategy). In certain instances, no gRNA was identified based on the criteria of the particular tier.

Note that tiers are non-inclusive (each targeting domain is listed only once for the strategy). In certain instances, no targeting domain was identified based on the criteria of the particular tier. The identified targeting domains are summarized below in Table 3.

TABLE 3

Nucleotide sequences of *S. pyogenes*, *S. aureus*, and *N. meningitidis* targeting domains for knocking out the HSV-1 RL2 gene

|  | S. pyogenes | S. aureus | N. meningitidis |
|---|---|---|---|
| Tier 1 | SEQ ID NOS: 21324 to 21368 | SEQ ID NOS: 22745 to 22755 | SEQ ID NO: 26602 |
| Tier 2 | SEQ ID NOS: 21369 to 21441 | SEQ ID NOS: 22756 to 22769 | SEQ ID NO: 26603 |
| Tier 3 | SEQ ID NOS: 21442 to 21505 | SEQ ID NOS: 22770 to 22800 | Not applicable |
| Tier 4 | SEQ ID NOS: 21506 to 21567 | SEQ ID NOS: 22801 to 23486 | SEQ ID NO: 26604 |
| Tier 5 | SEQ ID NOS: 21568 to 22744 | SEQ ID NOS: 23487 to 23587 | SEQ ID NOS: 26605 to 26612 |
| Tier 6 | Not applicable | SEQ ID NOS: 23588 to 23745 | Not applicable |
| Tier 7 | Not applicable | SEQ ID NOS: 23746 to 26601 | Not applicable |

6.4 Targeting Domains for Use in Knocking Out the HSV-2 RL2 Gene

Targeting domains for use in gRNAs for knocking out the HSV-2 RL2 gene in conjunction with the methods disclosed herein were identified and ranked into 5 tiers for *S. pyogenes*, 7 tiers for *S. aureus*, and 5 tiers for *N. meningitidis*.

For *S. pyogenes*, and *N. meningitidis*, the targeting domain for tier 1 gRNA molecules were selected based on (1) distance to a target site (e.g., start codon), e.g., within 500 bp (e.g., downstream) of the target site (e.g., start codon), (2) a high level of orthogonality and (3) the presence of 5'G. The targeting domain for tier 2 gRNA molecules were selected based on (1) distance to a target site (e.g., start codon), e.g., within 500 bp (e.g., downstream) of the target site (e.g., start codon) and (2) a high level of orthogonality. The targeting domain for tier 3 gRNA molecules were selected based on (1) distance to a target site (e.g., start codon), e.g., within 500 bp (e.g., downstream) of the target site (e.g., start codon) and (2) the presence of 5'G. The targeting domain for tier 4 gRNA molecules were selected based on distance to a target site (e.g., start codon), e.g., within 500 bp (e.g., downstream) of the target site (e.g., start codon). The targeting domain for tier 5 gRNA molecules were selected based on distance to the target site (e.g., start codon), e.g., within reminder of the coding sequence, e.g., downstream of the first 500 bp of coding sequence (e.g., anywhere from +500 (relative to the start codon) to the stop codon).

For *S. aureus*, the targeting domain for tier 1 gRNA molecules were selected based on (1) distance to a target site (e.g., start codon), e.g., within 500 bp (e.g., downstream) of the target site (e.g., start codon), (2) a high level of orthogonality, (3) the presence of 5'G and (4) wherein the PAM is NNGRRT. The targeting domain for tier 2 gRNA molecules were selected based on (1) distance to a target site (e.g., start codon), e.g., within 500 bp (e.g., downstream) of the target site (e.g., start codon), (2) a high level of orthogonality, and (3) wherein the PAM is NNGRRT. The targeting domain for tier 3 gRNA molecules were selected based on (1) distance to a target site (e.g., start codon), e.g., within 500 bp (e.g., downstream) of the target site (e.g., start codon) and (2) wherein the PAM is NNGRRT. The targeting domain for tier 4 gRNA molecules were selected based on (1) distance to a target site (e.g., start codon), e.g., within 500 bp (e.g., downstream) of the target site (e.g., start codon) and (2) wherein the PAM is NNGRRV. The targeting domain for tier 5 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon), (2) the presence of 5'G and (3) wherein the PAM is NNGRRT. The targeting domain for tier 6 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon) and (2) wherein the PAM is NNGRRT. The targeting domain for tier 7 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon) and (2) wherein the PAM is NNGRRV. Note that tiers are non-inclusive (each gRNA is listed only once for the strategy). In certain instances, no gRNA was identified based on the criteria of the particular tier.

Note that tiers are non-inclusive (each targeting domain is listed only once for the strategy). In certain instances, no targeting domain was identified based on the criteria of the particular tier. The identified targeting domains are summarized below in Table 4.

TABLE 4

Nucleotide sequences of *S. pyogenes*, *S. aureus*, and *N. meningitidis* targeting domains for knocking out the HSV-2 RL2 gene

| | S. pyogenes | S. aureus | N. meningitidis |
|---|---|---|---|
| Tier 1 | SEQ ID NOS: 26613 to 26638 | SEQ ID NOS: 28038 to 28056 | SEQ ID NOS: 31721 to 31722 |
| Tier 2 | SEQ ID NOS: 26639 to 26670 | SEQ ID NOS: 28057 to 28107 | SEQ ID NOS: 31723 to 31726 |
| Tier 3 | SEQ ID NOS: 26671 to 26743 | SEQ ID NOS: 28108 to 28138 | Not applicable |
| Tier 4 | SEQ ID NOS: 26744 to 26863 | SEQ ID NOS: 28139 to 28740 | SEQ ID NO: 31727 |
| Tier 5 | SEQ ID NOS: 26864 to 28037 | SEQ ID NOS: 28741 to 28846 | SEQ ID NOS: 31728 to 31729 |
| Tier 6 | Not applicable | SEQ ID NOS: 28847 to 28999 | Not applicable |
| Tier 7 | Not applicable | SEQ ID NOS: 29000 to 31720 | Not applicable |

6.5 Targeting Domains for Use in Knocking Out the HSV-1 LAT Intron

Targeting domains for use in gRNAs for knocking out the HSV-1 LAT Intron in conjunction with the methods disclosed herein were identified and ranked into 5 tiers for *S. pyogenes*, 7 tiers for *S. aureus*, and 5 tiers for *N. meningitidis*.

For *S. pyogenes*, and *N. meningitidis*, the targeting domain for tier 1 gRNA molecules were selected based on (1) distance to a target site, e.g., within the first 500 bp of the LAT intron, (2) a high level of orthogonality and (3) the presence of 5'G. The targeting domain for tier 2 gRNA molecules were selected based on (1) distance to a target site, e.g., within the first 500 bp of the LAT intron and (2) a high level of orthogonality. The targeting domain for tier 3 gRNA molecules were selected based on (1) distance to a target site, e.g., within the first 500 bp of the LAT intron and (2) the presence of 5'G. The targeting domain for tier 4 gRNA molecules were selected based on distance to a target site, e.g., within the first 500 bp of the LAT intron. The targeting domain for tier 5 gRNA molecules were selected based on distance to the target site, e.g., within the reminder of the LAT intron, e.g., downstream of the first 500 bp of LAT intron.

For *S. aureus*, the targeting domain for tier 1 gRNA molecules were selected based on (1) distance to a target site, e.g., within the first 500 bp of the LAT intron, (2) a high level of orthogonality, (3) the presence of 5'G and (4) wherein the PAM is NNGRRT. The targeting domain for tier 2 gRNA molecules were selected based on (1) distance to a target site, e.g., within the first 500 bp of the LAT intron, (2) a high level of orthogonality, and (3) wherein the PAM is NNGRRT. The targeting domain for tier 3 gRNA molecules were selected based on (1) distance to a target site, e.g., within the first 500 bp of the LAT intron and (2) wherein the PAM is NNGRRT. The targeting domain for tier 4 gRNA molecules were selected based on (1) distance to a target site, e.g., within the first 500 bp of the LAT intron and (2) wherein the PAM is NNGRRV. The targeting domain for tier 5 gRNA molecules were selected based on (1) distance to the target site, e.g., within the reminder of the LAT intron, e.g., downstream of the first 500 bp of LAT intron, (2) the presence of 5'G and (3) wherein the PAM is NNGRRT. The targeting domain for tier 6 gRNA molecules were selected based on (1) distance to the target site, e.g., within the reminder of the LAT intron, e.g., downstream of the first 500 bp of LAT intron and (2) wherein the PAM is NNGRRT. The targeting domain for tier 7 gRNA molecules were selected based on (1) distance to the target site, e.g., within the reminder of the LAT intron, e.g., downstream of the first 500 bp of LAT intron and (2) wherein the PAM is NNGRRV. Note that tiers are non-inclusive (each gRNA is listed only once for the strategy). In certain instances, no gRNA was identified based on the criteria of the particular tier.

Note that tiers are non-inclusive (each targeting domain is listed only once for the strategy). In certain instances, no targeting domain was identified based on the criteria of the particular tier. The identified targeting domains are summarized below in Table 5.

TABLE 5

Nucleotide sequences of *S. pyogenes*, *S. aureus*, and *N. meningitidis* targeting domains for knocking out the HSV-1 LAT intron

| | S. pyogenes | S. aureus | N. meningitidis |
|---|---|---|---|
| Tier 1 | SEQ ID NOS: 31730 to 31762 | SEQ ID NOS: 32747 to 32782 | SEQ ID NO: 35601 |
| Tier 2 | SEQ ID NOS: 31763 to 31809 | SEQ ID NOS: 32783 to 32841 | SEQ ID NOS: 35602 to 35603 |
| Tier 3 | SEQ ID NOS: 31810 to 31897 | SEQ ID NOS: 32842 to 32893 | Not applicable |
| Tier 4 | SEQ ID NOS: 31898 to 32025 | SEQ ID NOS: 32894 to 33621 | SEQ ID NO: 35604 |
| Tier 5 | SEQ ID NOS: 32026 to 32746 | SEQ ID NOS: 33622 to 33716 | SEQ ID NOS: 35605 to 35616 |
| Tier 6 | Not applicable | SEQ ID NOS: 33717 to 33932 | Not applicable |
| Tier 7 | Not applicable | SEQ ID NOS: 33933 to 35600 | Not applicable |

6.6 Targeting Domains for Use in Knocking Out the HSV-2 LAT Intron

Targeting domains for use in gRNAs for knocking out the HSV-2 LAT Intron gene in conjunction with the methods disclosed herein were identified and ranked into 5 tiers for *S. pyogenes*, 7 tiers for *S. aureus*, and 5 tiers for *N. meningitidis*.

For *S. pyogenes*, and *N. meningitidis*, the targeting domain for tier 1 gRNA molecules were selected based on (1) distance to a target site, e.g., within the first 500 bp of the LAT intron, (2) a high level of orthogonality and (3) the presence of 5'G. The targeting domain for tier 2 gRNA molecules were selected based on (1) distance to a target site, e.g., within the first 500 bp of the LAT intron and (2) a high level of orthogonality. The targeting domain for tier 3 gRNA molecules were selected based on (1) distance to a target site, e.g., within the first 500 bp of the LAT intron and (2) the presence of 5'G. The targeting domain for tier 4 gRNA molecules were selected based on distance to a target site, e.g., within the first 500 bp of the LAT intron. The targeting domain for tier 5 gRNA molecules were selected based on distance to the target site, e.g., within the reminder of the LAT intron, e.g., downstream of the first 500 bp of the LAT intron.

For *S. aureus*, the targeting domain for tier 1 gRNA molecules were selected based on (1) distance to a target site, e.g., within the first 500 bp of the LAT intron, (2) a high level of orthogonality, (3) the presence of 5'G and (4) wherein the PAM is NNGRRT. The targeting domain for tier 2 gRNA molecules were selected based on (1) distance to a target site, e.g., within the first 500 bp of the LAT intron, (2) a high level of orthogonality, and (3) wherein the PAM is NNGRRT. The targeting domain for tier 3 gRNA molecules were selected based on (1) distance to a target site, e.g., within the first 500 bp of the LAT intron and (2) wherein the PAM is NNGRRT. The targeting domain for tier 4 gRNA molecules were selected based on (1) distance to a target site, e.g., within the first 500 bp of the LAT intron and (2) wherein the PAM is NNGRRV. The targeting domain for tier 5 gRNA molecules were selected based on (1) distance to the target site, e.g., within the reminder of the LAT intron, e.g., downstream of the first 500 bp of LAT intron, (2) the presence of 5'G and (3) wherein the PAM is NNGRRT. The targeting domain for tier 6 gRNA molecules were selected based on (1) distance to the target site, e.g., within the reminder of the LAT intron, e.g., downstream of the first 500 bp of LAT intron and (2) wherein the PAM is NNGRRT. The targeting domain for tier 7 gRNA molecules were selected based on (1) distance to the target site, e.g., within the reminder of the LAT intron, e.g., downstream of the first 500 bp of LAT intron and (2) wherein the PAM is NNGRRV.

Note that tiers are non-inclusive (each gRNA is listed only once for the strategy). In certain instances, no gRNA was identified based on the criteria of the particular tier.

Note that tiers are non-inclusive (each targeting domain is listed only once for the strategy). In certain instances, no targeting domain was identified based on the criteria of the particular tier. The identified targeting domains are summarized below in Table 6

TABLE 6

Nucleotide sequences of *S. pyogenes*, *S. aureus*, and *N. meningitidis* targeting domains for knocking out the HSV-2 LAT intron

| | S. pyogenes | S. aureus | N. meningitidis |
|---|---|---|---|
| Tier 1 | SEQ ID NOS: 35617 to 35640 | SEQ ID NOS: 36927 to 36941 | SEQ ID NOS: 40872 to 40873 |
| Tier 2 | SEQ ID NOS: 35641 to 35704 | SEQ ID NOS: 36942 to 36980 | Not applicable |
| Tier 3 | SEQ ID NOS: 35705 to 35795 | SEQ ID NOS: 36981 to 37038 | Not applicable |
| Tier 4 | SEQ ID NOS: 35796 to 35911 | SEQ ID NOS: 37039 to 37860 | Not applicable |
| Tier 5 | SEQ ID NOS: 35912 to 36926 | SEQ ID NOS: 37861 to 37960 | SEQ ID NOS: 40874 to 40885 |
| Tier 6 | Not applicable | SEQ ID NOS: 37961 to 38098 | Not applicable |
| Tier 7 | Not applicable | SEQ ID NOS: 38099 to 40871 | Not applicable |

6.7 Targeting Domains for Use in Knocking Down the HSV-1 RS1 Gene

Targeting domains for use in gRNAs for knocking down HSV-1 RS1 gene in conjunction with the methods disclosed herein were identified and ranked into 5 tiers for *S. pyogenes*, 7 tiers for *S. aureus*, and 5 tiers for *N. meningitidis*.

For *S. pyogenes*, and *N. meningitidis*, the targeting domain for tier 1 gRNA molecules were selected based on (1) distance to a target site e.g., within 500 bp (e.g., upstream or downstream) of a transcription start site (TSS), (2) a high level of orthogonality and (3) the presence of 5'G. The targeting domain for tier 2 gRNA molecules were selected based on (1) distance to a target site e.g., within 500 bp (e.g., upstream or downstream) of a transcription start site (TSS) and (2) a high level of orthogonality. The targeting domain for tier 3 gRNA molecules were selected based on (1) distance to a target site e.g., within 500 bp (e.g., upstream or downstream) of a transcription start site (TSS) and (2) the presence of 5'G. The targeting domain for tier 4 gRNA molecules were selected based on distance to a target site e.g., within 500 bp (e.g., upstream or downstream) of a transcription start site (TSS). The targeting domain for tier 5 gRNA molecules were selected based on distance to the target site, e.g., within the additional 500 bp (e.g., upstream or downstream) of a transcription start site (TSS), e.g., extending to 1 kb upstream and downstream of a TSS.

For *S. aureus*, the targeting domain for tier 1 gRNA molecules were selected based on (1) distance to a target site e.g., within 500 bp (e.g., upstream or downstream) of a transcription start site (TSS), (2) a high level of orthogonality, (3) the presence of 5'G and (4) wherein the PAM is NNGRRT. The targeting domain for tier 2 gRNA molecules were selected based on (1) distance to a target site e.g., within 500 bp (e.g., upstream or downstream) of a transcription start site (TSS), (2) a high level of orthogonality, and (3) wherein the PAM is NNGRRT. The targeting domain for tier 3 gRNA molecules were selected based on (1) distance to a target site e.g., within 500 bp (e.g., upstream or downstream) of a transcription start site (TSS) and (2) wherein the PAM is NNGRRT. The targeting domain for tier 4 gRNA molecules were selected based on (1) distance to a target site e.g., within 500 bp (e.g., upstream or downstream) of a transcription start site (TSS) and (2) wherein the PAM is NNGRRV. The targeting domain for tier 5 gRNA molecules were selected based on (1) distance to the target site, e.g., within the additional 500 bp (e.g., upstream or downstream) of a transcription start site (TSS), e.g., extending to 1 kb upstream and downstream of a TSS, (2) the presence of 5'G and (3) wherein the PAM is NNGRRT. The targeting domain for tier 6 gRNA molecules were selected based on (1) distance to the target site, e.g., within the additional 500 bp (e.g., upstream or downstream) of a transcription start site (TSS), e.g., extending to 1 kb upstream and downstream of a TSS and (2) PAM is NNGRRT. The targeting domain for tier 7 gRNA molecules were selected based on (1) distance to the target site, e.g., within the additional 500 bp (e.g., upstream or downstream) of a transcription start site (TSS), e.g., extending to 1 kb upstream and downstream of a TSS and (2) PAM is NNGRRV. Note that tiers are non-inclusive (each gRNA is listed only once for the strategy). In certain instances, no gRNA was identified based on the criteria of the particular tier.

Note that tiers are non-inclusive (each targeting domain is listed only once for the strategy). In certain instances, no targeting domain was identified based on the criteria of the particular tier. The identified targeting domains are summarized below in Table 7.

TABLE 7

Nucleotide sequences of S. pyogenes, S. aureus, and N. meningitidis targeting domains for knocking down the HSV-1 RS1 gene

|  | S. pyogenes | S. aureus | N. meningitidis |
| --- | --- | --- | --- |
| Tier 1 | SEQ ID NOS: 13637 to 13743 | SEQ ID NOS: 14795 to 14841 | SEQ ID NOS: 17742 to 17743 |
| Tier 2 | SEQ ID NOS: 13744 to 13957 | SEQ ID NOS: 14842 to 14938 | SEQ ID NOS: 17744 to 17748 |
| Tier 3 | SEQ ID NOS: 13958 to 14099 | SEQ ID NOS: 14939 to 14965 | Not applicable |
| Tier 4 | SEQ ID NOS: 14100 to 14274 | SEQ ID NOS: 14966 to 16394 | Not applicable |
| Tier 5 | SEQ ID NOS: 14275 to 14794 | SEQ ID NOS: 16395 to 16458 | SEQ ID NOS: 17749 to 17752 |
| Tier 6 | Not applicable | SEQ ID NOS: 16459 to 16548 | Not applicable |
| Tier 7 | Not applicable | SEQ ID NOS: 16549 to 17741 | Not applicable |

6.8 Targeting Domains for Use in Knocking Down the HSV-2 RS1 Gene

Targeting domains for use in gRNAs for knocking down HSV-2 RS1 gene in conjunction with the methods disclosed herein were identified and ranked into 5 tiers for S. pyogenes, 7 tiers for S. aureus, and 5 tiers for N. meningitidis.

For S. pyogenes, and N. meningitidis, the targeting domain for tier 1 gRNA molecules were selected based on (1) distance to a target site, e.g., within 500 bp (e.g., upstream or downstream) of a start codon, (2) a high level of orthogonality and (3) the presence of 5'G. The targeting domain for tier 2 gRNA molecules were selected based on (1) distance to a target site, e.g., within 500 bp (e.g., upstream or downstream) of a start codon and (2) a high level of orthogonality. The targeting domain for tier 3 gRNA molecules were selected based on (1) distance to a target site, e.g., within 500 bp (e.g., upstream or downstream) of a start codon and (2) the presence of 5'G. The targeting domain for tier 4 gRNA molecules were selected based on distance to a target site, e.g., within 500 bp (e.g., upstream or downstream) of a start codon. The targeting domain for tier 5 gRNA molecules were selected based on distance to the target site, e.g., within the additional 500 bp (e.g., upstream or downstream) of a start codon, e.g., extending to 1 kb upstream and downstream of a start codon.

For S. aureus, the targeting domain for tier 1 gRNA molecules were selected based on (1) distance to a target site, e.g., within 500 bp (e.g., upstream or downstream) of a start codon, (2) a high level of orthogonality, (3) the presence of 5'G and (4) wherein the PAM is NNGRRT. The targeting domain for tier 2 gRNA molecules were selected based on (1) distance to a target site, e.g., within 500 bp (e.g., upstream or downstream) of a start codon, (2) a high level of orthogonality, and (3) wherein the PAM is NNGRRT. The targeting domain for tier 3 gRNA molecules were selected based on (1) distance to a target site, e.g., within 500 bp (e.g., upstream or downstream) of a start codon and (2) wherein the PAM is NNGRRT. The targeting domain for tier 4 gRNA molecules were selected based on (1) distance to a target site, e.g., within 500 bp (e.g., upstream or downstream) of a start codon and (2) wherein the PAM is NNGRRV. The targeting domain for tier 5 gRNA molecules were selected based on (1) distance to the target site, e.g., within the additional 500 bp (e.g., upstream or downstream) of a start codon, e.g., extending to 1 kb upstream and downstream of a start codon, (2) the presence of 5'G and (3) wherein the PAM is NNGRRT. The targeting domain for tier 6 gRNA molecules were selected based on (1) distance to the target site, e.g., within the additional 500 bp (e.g., upstream or downstream) of a start codon, e.g., extending to 1 kb upstream and downstream of a start codon and (2) wherein the PAM is NNGRRT. The targeting domain for tier 7 gRNA molecules were selected based on (1) distance to the target site, e.g., within the additional 500 bp (e.g., upstream or downstream) of a start codon, e.g., extending to 1 kb upstream and downstream of a start codon and (2) wherein the PAM is NNGRRV. Note that tiers are non-inclusive (each gRNA is listed only once for the strategy). In certain instances, no gRNA was identified based on the criteria of the particular tier.

Note that tiers are non-inclusive (each targeting domain is listed only once for the strategy). In certain instances, no targeting domain was identified based on the criteria of the particular tier. The identified targeting domains are summarized below in Table 8.

TABLE 8

Nucleotide sequences of S. pyogenes, S. aureus, and N. meningitidis targeting domains for knocking down the HSV-2 RS1 gene

|  | S. pyogenes | S. aureus | N. meningitidis |
| --- | --- | --- | --- |
| Tier 1 | SEQ ID NOS: 17753 to 17850 | SEQ ID NOS: 18785 to 18816 | SEQ ID NO: 21312 |
| Tier 2 | SEQ ID NOS: 17851 to 18016 | SEQ ID NOS: 18817 to 18868 | SEQ ID NOS: 21313 to 21319 |
| Tier 3 | SEQ ID NOS: 18017 to 18102 | SEQ ID NOS: 18869 to 18889 | Not applicable |
| Tier 4 | SEQ ID NOS: 18103 to 18257 | SEQ ID NOS: 18890 to 20108 | Not applicable |
| Tier 5 | SEQ ID NOS: 18258 to 18784 | SEQ ID NOS: 20109 to 20151 | SEQ ID NOS: 21320 to 21323 |
| Tier 6 | Not applicable | SEQ ID NOS: 20152 to 20213 | Not applicable |

TABLE 8-continued

Nucleotide sequences of S. pyogenes, S. aureus, and N. meningitidis targeting domains for knocking down the HSV-2 RS1 gene

| | S. pyogenes | S. aureus | N. meningitidis |
|---|---|---|---|
| Tier 7 | Not applicable | SEQ ID NOS: 20214 to 21311 | Not applicable |

6.9 Targeting Domains for Use in Knocking Down the HSV-1 RL2 Gene

Targeting domains for use in gRNAs for knocking down HSV-1 RL2 gene in conjunction with the methods disclosed herein were identified and ranked into 5 tiers for S. pyogenes, 7 tiers for S. aureus, and 5 tiers for N. meningitidis.

For S. pyogenes, and N. meningitidis, the targeting domain for tier 1 gRNA molecules were selected based on (1) distance to a target site e.g., within 500 bp (e.g., upstream or downstream) of a transcription start site (TSS), (2) a high level of orthogonality and (3) the presence of 5'G. The targeting domain for tier 2 gRNA molecules were selected based on (1) distance to a target site e.g., within 500 bp (e.g., upstream or downstream) of a transcription start site (TSS) and (2) a high level of orthogonality. The targeting domain for tier 3 gRNA molecules were selected based on (1) distance to a target site e.g., within 500 bp (e.g., upstream or downstream) of a transcription start site (TSS) and (2) the presence of 5'G. The targeting domain for tier 4 gRNA molecules were selected based on distance to a target site e.g., within 500 bp (e.g., upstream or downstream) of a transcription start site (TSS). The targeting domain for tier 5 gRNA molecules were selected based on distance to the target site, e.g., within the additional 500 bp (e.g., upstream or downstream) of a transcription start site (TSS), e.g., extending to 1 kb upstream and downstream of a TSS.

For S. aureus, the targeting domain for tier 1 gRNA molecules were selected based on (1) distance to a target site e.g., within 500 bp (e.g., upstream or downstream) of a transcription start site (TSS), (2) a high level of orthogonality, (3) the presence of 5'G and (4) wherein the PAM is NNGRRT. The targeting domain for tier 2 gRNA molecules were selected based on (1) distance to a target site e.g., within 500 bp (e.g., upstream or downstream) of a transcription start site (TSS), (2) a high level of orthogonality, and (3) wherein the PAM is NNGRRT. The targeting domain for tier 3 gRNA molecules were selected based on (1) distance to a target site e.g., within 500 bp (e.g., upstream or downstream) of a transcription start site (TSS) and (2) wherein the PAM is NNGRRT. The targeting domain for tier 4 gRNA molecules were selected based on (1) distance to a target site e.g., within 500 bp (e.g., upstream or downstream) of a transcription start site (TSS) and (2) wherein the PAM is NNGRRV. The targeting domain for tier 5 gRNA molecules were selected based on (1) distance to the target site, e.g., within the additional 500 bp (e.g., upstream or downstream) of a transcription start site (TSS), e.g., extending to 1 kb upstream and downstream of a TSS, (2) the presence of 5'G and (3) wherein the PAM is NNGRRT. The targeting domain for tier 6 gRNA molecules were selected based on (1) distance to the target site, e.g., within the additional 500 bp (e.g., upstream or downstream) of a transcription start site (TSS), e.g., extending to 1 kb upstream and downstream of a TSS and (2) wherein the PAM is NNGRRT. The targeting domain for tier 7 gRNA molecules were selected based on (1) distance to the target site, e.g., within the additional 500 bp (e.g., upstream or downstream) of a transcription start site (TSS), e.g., extending to 1 kb upstream and downstream of a TSS and (2) wherein the PAM is NNGRRV. Note that tiers are non-inclusive (each gRNA is listed only once for the strategy). In certain instances, no gRNA was identified based on the criteria of the particular tier.

Note that tiers are non-inclusive (each targeting domain is listed only once for the strategy). In certain instances, no targeting domain was identified based on the criteria of the particular tier. The identified targeting domains are summarized below in Table 9.

TABLE 9

Nucleotide sequences of S. pyogenes, S. aureus, and N. meningitidis targeting domains for knocking down the HSV-1 RL2 gene

| | S. pyogenes | S. aureus | N. meningitidis |
|---|---|---|---|
| Tier 1 | SEQ ID NOS: 40886 to 40976 | SEQ ID NOS: 42079 to 42149 | SEQ ID NOS: 45316 to 45319 |
| Tier 2 | SEQ ID NOS: 40977 to 41180 | SEQ ID NOS: 42150 to 42299 | SEQ ID NOS: 45320 to 45327 |
| Tier 3 | SEQ ID NOS: 41181 to 41305 | SEQ ID NOS: 42300 to 42323 | Not applicable |
| Tier 4 | SEQ ID NOS: 41306 to 41493 | SEQ ID NOS: 42324 to 43715 | Not applicable |
| Tier 5 | SEQ ID NOS: 41494 to 42078 | SEQ ID NOS: 43716 to 43784 | SEQ ID NOS: 45328 to 45339 |
| Tier 6 | Not applicable | SEQ ID NOS: 43785 to 43921 | Not applicable |
| Tier 7 | Not applicable | SEQ ID NOS: 43922 to 45315 | Not applicable |

6.10 Targeting Domains for Use in Knocking Down the HSV-2 RL2 Gene

Targeting domains for use in gRNAs for knocking down HSV-2 RL2 gene in conjunction with the methods disclosed herein were identified and ranked into 5 tiers for S. pyogenes, 7 tiers for S. aureus, and 5 tiers for N. meningitidis. For S. pyogenes, and N. meningitidis, the targeting domain for tier 1 gRNA molecules were selected based on (1) distance to a target site, e.g., within 500 bp (e.g., upstream or downstream) of a start codon, (2) a high level of orthogonality and (3) the presence of 5'G. The targeting domain for tier 2 gRNA molecules were selected based on (1) distance to a target site, e.g., within 500 bp (e.g., upstream or downstream) of a start codon and (2) a high level of orthogonality. The targeting domain for tier 3 gRNA molecules were selected based on (1) distance to a target site, e.g., within 500 bp (e.g., upstream or downstream) of a start codon and (2) the presence of 5'G. The targeting domain for tier 4 gRNA molecules were selected based on distance to a target site, e.g., within 500 bp (e.g., upstream or downstream) of a start codon. The targeting domain for tier 5 gRNA molecules were selected based on distance to the target site, e.g., within the additional 500 bp (e.g., upstream or downstream) of a start codon, e.g., extending to 1 kb upstream and downstream of a start codon.

For S. aureus, the targeting domain for tier 1 gRNA molecules were selected based on (1) distance to a target site, e.g., within 500 bp (e.g., upstream or downstream) of a start codon, (2) a high level of orthogonality, (3) the presence of 5'G and (4) wherein the PAM is NNGRRT. The targeting domain for tier 2 gRNA molecules were selected based on (1) distance to a target site, e.g., within 500 bp (e.g., upstream or downstream) of a start codon, (2) a high level of orthogonality, and (3) wherein the PAM is NNGRRT. The targeting domain for tier 3 gRNA molecules were selected based on (1) distance to a target site, e.g., within 500 bp (e.g., upstream or downstream) of a start codon and (2) wherein the PAM is NNGRRT. The targeting domain for tier 4 gRNA molecules were selected based on (1) distance to a target site, e.g., within 500 bp (e.g., upstream or downstream) of a start codon and (2) wherein the PAM is NNGRRV. The targeting domain for tier 5 gRNA molecules were selected based on (1) distance to the target site, e.g., within the additional 500 bp (e.g., upstream or downstream) of a start codon, e.g., extending to 1 kb upstream and downstream of a start codon, (2) the presence of 5'G and (3) wherein the PAM is NNGRRT. The targeting domain for tier 6 gRNA molecules were selected based on (1) distance to the target site, e.g., within the additional 500 bp (e.g., upstream or downstream) of a start codon, e.g., extending to 1 kb upstream and downstream of a start codon and (2) wherein the PAM is NNGRRT. The targeting domain for tier 7 gRNA molecules were selected based on (1) distance to the target site, e.g., within the additional 500 bp (e.g., upstream or downstream) of a start codon, e.g., extending to 1 kb upstream and downstream of a start codon and (2) wherein the PAM is NNGRRV. Note that tiers are non-inclusive (each gRNA is listed only once for the strategy). In certain instances, no gRNA was identified based on the criteria of the particular tier.

Note that tiers are non-inclusive (each targeting domain is listed only once for the strategy). In certain instances, no targeting domain was identified based on the criteria of the particular tier. The identified targeting domains are summarized below in Table 10.

TABLE 10

Nucleotide sequences of S. pyogenes, S. aureus, and N. meningitidis targeting domains for knocking down the HSV-2 RL2 gene

|  | S. pyogenes | S. aureus | N. meningitidis |
| --- | --- | --- | --- |
| Tier 1 | SEQ ID NOS: 49498 to 49587 | SEQ ID NOS: 50653 to 50725 | SEQ ID NOS: 53825 to 53834 |
| Tier 2 | SEQ ID NOS: 49588 to 49738 | SEQ ID NOS: 50726 to 50857 | SEQ ID NOS: 53835 to 53843 |
| Tier 3 | SEQ ID NOS: 49739 to 49899 | SEQ ID NOS: 50858 to 50911 | Not applicable |
| Tier 4 | SEQ ID NOS: 49900 to 50151 | SEQ ID NOS: 50912 to 52535 | Not applicable |
| Tier 5 | SEQ ID NOS: 50152 to 50652 | SEQ ID NOS: 52536 to 52587 | SEQ ID NOS: 53844 to 53857 |
| Tier 6 | Not applicable | SEQ ID NOS: 52588 to 52696 | Not applicable |
| Tier 7 | Not applicable | SEQ ID NOS: 52697 to 53824 | Not applicable |

6.11 Targeting Domains for Use in Knocking Down the HSV-1 LAT Gene

Targeting domains for use in gRNAs for knocking down HSV-1 LAT gene in conjunction with the methods disclosed herein were identified and ranked into 5 tiers for *S. pyogenes,* 7 tiers for *S. aureus,* and 5 tiers for *N. meningitidis.*

For *S. pyogenes,* and *N. meningitidis,* the targeting domain for tier 1 gRNA molecules were selected based on (1) distance to a target site, e.g., within 500 bp (e.g., upstream or downstream) of a transcription start site (TSS), (2) a high level of orthogonality and (3) the presence of 5'G. The targeting domain for tier 2 gRNA molecules were selected based on (1) distance to a target site, e.g., within 500 bp (e.g., upstream or downstream) of a transcription start site (TSS) and (2) a high level of orthogonality. The targeting domain for tier 3 gRNA molecules were selected based on (1) distance to a target site, e.g., within 500 bp (e.g., upstream or downstream) of a transcription start site (TSS) and (2) the presence of 5'G. The targeting domain for tier 4 gRNA molecules were selected based on distance to a target site, e.g., within 500 bp (e.g., upstream or downstream) of a transcription start site (TSS). The targeting domain for tier 5 gRNA molecules were selected based on distance to the target site, e.g., within the additional 500 bp (e.g., upstream or downstream) of a transcription start site (TSS), e.g., extending to 1 kb upstream and downstream of a TSS.

For *S. aureus,* the targeting domain for tier 1 gRNA molecules were selected based on (1) distance to a target site, e.g., within 500 bp (e.g., upstream or downstream) of a transcription start site (TSS), (2) a high level of orthogonality, (3) the presence of 5'G and (4) wherein the PAM is NNGRRT. The targeting domain for tier 2 gRNA molecules were selected based on (1) distance to a target site, e.g., within 500 bp (e.g., upstream or downstream) of a transcription start site (TSS), (2) a high level of orthogonality, and (3) wherein the PAM is NNGRRT. The targeting domain for tier 3 gRNA molecules were selected based on (1) distance to a target site, e.g., within 500 bp (e.g., upstream or downstream) of a transcription start site (TSS) and (2) wherein the PAM is NNGRRT. The targeting domain for tier 4 gRNA molecules were selected based on (1) distance to a target site, e.g., within 500 bp (e.g., upstream or downstream) of a transcription start site (TSS) and (2) wherein the PAM is NNGRRV. The targeting domain for tier 5 gRNA molecules were selected based on (1) distance to the target site, e.g., within the additional 500 bp (e.g., upstream or downstream) of a transcription start site (TSS), e.g., extending to 1 kb upstream and downstream of a TSS, (2) the presence of 5'G and (3) wherein the PAM is NNGRRT. The targeting domain for tier 6 gRNA molecules were selected based on (1) distance to the target site, e.g., within the additional 500 bp (e.g., upstream or downstream) of a transcription start site (TSS), e.g., extending to 1 kb upstream and downstream of a TSS and (2) wherein the PAM is NNGRRT. The targeting domain for tier 7 gRNA molecules were selected based on (1) distance to the target site, e.g., within the additional 500 bp (e.g., upstream or downstream) of a transcription start site (TSS), e.g., extending to 1 kb upstream and downstream of a TSS and (2) wherein the PAM is NNGRRV. Note that tiers are non-inclusive (each gRNA is listed only once for the strategy). In certain instances, no gRNA was identified based on the criteria of the particular tier.

Note that tiers are non-inclusive (each targeting domain is listed only once for the strategy). In certain instances, no targeting domain was identified based on the criteria of the particular tier. The identified targeting domains are summarized below in Table 11.

TABLE 11

Nucleotide sequences of S. pyogenes, S. aureus, and N. meningitidis targeting domains for knocking down the HSV-1 LAT gene

|  | S. pyogenes | S. aureus | N. meningitidis |
| --- | --- | --- | --- |
| Tier 1 | SEQ ID NOS: 45340 to 45427 | SEQ ID NOS: 46480 to 46533 | Not applicable |
| Tier 2 | SEQ ID NOS: 45428 to 45589 | SEQ ID NOS: 46534 to 46619 | SEQ ID NOS: 49480 to 49488 |
| Tier 3 | SEQ ID NOS: 45590 to 45707 | SEQ ID NOS: 46620 to 46664 | Not applicable |
| Tier 4 | SEQ ID NOS: 45708 to 45897 | SEQ ID NOS: 46665 to 47789 | SEQ ID NO: 49489 |
| Tier 5 | SEQ ID NOS: 45898 to 46479 | SEQ ID NOS: 47790 to 47887 | SEQ ID NOS: 49490 to 49497 |
| Tier 6 | Not applicable | SEQ ID NOS: 47888 to 48041 | Not applicable |
| Tier 7 | Not applicable | SEQ ID NOS: 48042 to 49479 | Not applicable |

6.12 Targeting Domains for Use in Knocking Down the HSV-2 LAT Gene

Targeting domains for use in gRNAs for knocking down HSV-2 LAT gene in conjunction with the methods disclosed herein were identified and ranked into 5 tiers for *S. pyogenes*, 7 tiers for *S. aureus*, and 5 tiers for *N. meningitidis*.

For *S. pyogenes*, and *N. meningitidis*, the targeting domain for tier 1 gRNA molecules were selected based on (1) distance to a target site, e.g., within 500 bp (e.g., upstream or downstream) of a transcription start site (TSS), (2) a high level of orthogonality and (3) the presence of 5'G. The targeting domain for tier 2 gRNA molecules were selected based on (1) distance to a target site, e.g., within 500 bp (e.g., upstream or downstream) of a transcription start site (TSS) and (2) a high level of orthogonality. The targeting domain for tier 3 gRNA molecules were selected based on (1) distance to a target site, e.g., within 500 bp (e.g., upstream or downstream) of a transcription start site (TSS) and (2) the presence of 5'G. The targeting domain for tier 4 gRNA molecules were selected based on distance to a target site, e.g., within 500 bp (e.g., upstream or downstream) of a transcription start site (TSS). The targeting domain for tier 5 gRNA molecules were selected based on distance to the target site, e.g., within the additional 500 bp (e.g., upstream or downstream) of a transcription start site (TSS), e.g., extending to 1 kb upstream and downstream of a TSS.

For *S. aureus*, the targeting domain for tier 1 gRNA molecules were selected based on (1) distance to a target site, e.g., within 500 bp (e.g., upstream or downstream) of a transcription start site (TSS), (2) a high level of orthogonality, (3) the presence of 5'G and (4) wherein the PAM is NNGRRT. The targeting domain for tier 2 gRNA molecules were selected based on (1) distance to a target site, e.g., within 500 bp (e.g., upstream or downstream) of a transcription start site (TSS), (2) a high level of orthogonality, and (3) wherein the PAM is NNGRRT. The targeting domain for tier 3 gRNA molecules were selected based on (1) distance to a target site, e.g., within 500 bp (e.g., upstream or downstream) of a transcription start site (TSS) and (2) wherein the PAM is NNGRRT. The targeting domain for tier 4 gRNA molecules were selected based on (1) distance to a target site, e.g., within 500 bp (e.g., upstream or downstream) of a transcription start site (TSS) and (2) wherein the PAM is NNGRRV. The targeting domain for tier 5 gRNA molecules were selected based on (1) distance to the target site, e.g., within the additional 500 bp (e.g., upstream or downstream) of a transcription start site (TSS), e.g., extending to 1 kb upstream and downstream of a TSS, (2) the presence of 5'G and (3) wherein the PAM is NNGRRT. The targeting domain for tier 6 gRNA molecules were selected based on (1) distance to the target site, e.g., within the additional 500 bp (e.g., upstream or downstream) of a transcription start site (TSS), e.g., extending to 1 kb upstream and downstream of a TSS and (2) wherein the PAM is NNGRRT. The targeting domain for tier 7 gRNA molecules were selected based on (1) distance to the target site, e.g., within the additional 500 bp (e.g., upstream or downstream) of a transcription start site (TSS), e.g., extending to 1 kb upstream and downstream of a TSS and (2) wherein the PAM is NNGRRV. Note that tiers are non-inclusive (each gRNA is listed only once for the strategy). In certain instances, no gRNA was identified based on the criteria of the particular tier.

Note that tiers are non-inclusive (each targeting domain is listed only once for the strategy). In certain instances, no targeting domain was identified based on the criteria of the particular tier. The identified targeting domains are summarized below in Table 12.

TABLE 12

Nucleotide sequences of *S. pyogenes*, *S. aureus*, and *N. meningitidis* targeting domains for knocking down the HSV-2 LAT gene

| | S. pyogenes | S. aureus | N. meningitidis |
|---|---|---|---|
| Tier 1 | SEQ ID NOS: 53858 to 53916 | SEQ ID NOS: 55057 to 55080 | SEQ ID NOS: 58732 to 58736 |
| Tier 2 | SEQ ID NOS: 53917 to 54030 | SEQ ID NOS: 55081 to 55119 | SEQ ID NOS: 58737 to 58743 |
| Tier 3 | SEQ ID NOS: 54031 to 54240 | SEQ ID NOS: 55120 to 55140 | Not applicable |
| Tier 4 | SEQ ID NOS: 54241 to 54468 | SEQ ID NOS: 55141 to 56792 | Not applicable |
| Tier 5 | SEQ ID NOS: 54469 to 55056 | SEQ ID NOS: 56793 to 56865 | SEQ ID NOS: 58744 to 58749 |
| Tier 6 | Not applicable | SEQ ID NOS: 56866 to 56970 | Not applicable |
| Tier 7 | Not applicable | SEQ ID NOS: 56971 to 58731 | Not applicable |

One or more of the gRNA molecules described herein, e.g., those comprising the targeting domains described in Tables 1-12 can be used with at least one Cas9 molecule (e.g., a *S. pyogenes* Cas9 molecule and/or a *S. aureus* Cas9 molecule) to form a single or a double stranded cleavage, e.g., with a Cas9 nickase molecule to generate a single strand break, or with a Cas9 nuclease molecule to generate a double strand break.

In certain embodiments, when a single gRNA molecule is used to target a Cas9 nickase to create a single strand break in close proximity to a RS1, RL2, or LAT target position, e.g., the gRNA is used to target either upstream of (e.g., within 500 bp upstream), or downstream of (e.g., within 500 bp downstream) of the RS1, RL2, or LAT target position.

In certain embodiments, when a single gRNA molecule is used to target a Cas9 nuclease to create a double strand break to in close proximity to the RL2, LAT, or RS1 target position, e.g., the gRNA is used to target either upstream of (e.g., within 500 bp upstream), or downstream of (e.g., within 500 bp downstream) of the RS1, RL2, or LAT target position.

In certain embodiments, two or more (e.g., three or four) gRNA molecules are used with one Cas9 molecule or Cas9-fusion protein. In certain embodiments, when two or more (e.g., three or four) gRNAs are used with two or more Cas9 molecules or Cas9-fusion proteins, at least one Cas9 molecule is from a different species than the other Cas9 molecule(s). When two gRNAs designed for use to target two Cas9 molecules, one Cas9 can be one species, the second Cas9 can be from a different species. Both Cas9 species are used to generate a single or double-strand break, as desired.

Any upstream gRNA described in Tables 1-12 may be paired with any downstream gRNA described in Tables 1-12. When an upstream gRNA designed for use with one species of Cas9 is paired with a downstream gRNA designed for use from a different species of Cas9, both Cas9 species are used to generate a single or double-strand break, as desired.

7. Cas9 Molecules

Cas9 molecules of a variety of species can be used in the methods and compositions described herein. While the *S. pyogenes*, *S. aureus* and *Neisseria meningitidis* Cas9 molecules are the subject of much of the disclosure herein, Cas9 molecules, derived from, or based on the Cas9 proteins of other species listed herein can be used as well. These include, for example, Cas9 molecules from *Acidovorax avenae, Actinobacillus pleuropneumonias, Actinobacillus succinogenes, Actinobacillus suis, Actinomyces* sp., *cycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus Puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, gamma proteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae.*

7.1 Cas9 Domains

Crystal structures have been determined for two different naturally occurring bacterial Cas9 molecules (Jinek 2014) and for *S. pyogenes* Cas9 with a guide RNA (e.g., a synthetic fusion of crRNA and tracrRNA) (Nishimasu 2014; Anders 2014).

Figure 8A:
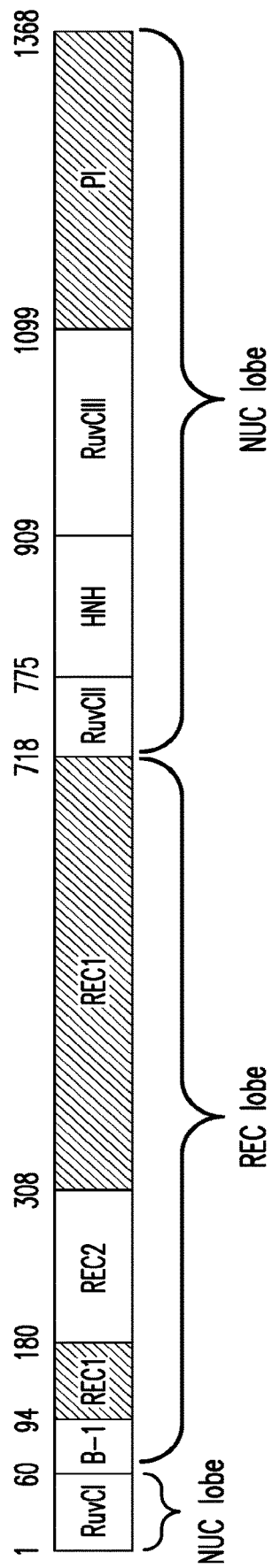
FIGS. 8A and 8B provide schematic representations of the domain organization of *S. pyogenes* Cas9.
Figure 8B:
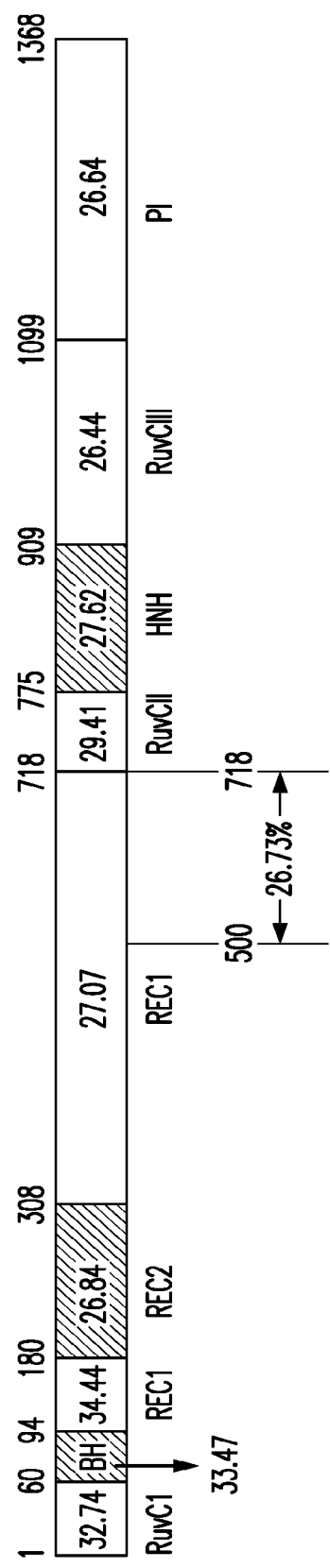

A naturally occurring Cas9 molecule comprises two lobes: a recognition (REC) lobe and a nuclease (NUC) lobe; each of which further comprise domains described herein. FIGS. 8A-8B provide a schematic of the organization of important Cas9 domains in the primary structure. The domain nomenclature and the numbering of the amino acid residues encompassed by each domain used throughout this disclosure is as described previously (Nishimasu 2014). The numbering of the amino acid residues is with reference to Cas9 from *S. pyogenes.*

The REC lobe comprises the arginine-rich bridge helix (BH), the REC1 domain, and the REC2 domain. The REC lobe does not share structural similarity with other known proteins, indicating that it is a Cas9-specific functional domain. The BH domain is a long a helix and arginine rich region and comprises amino acids 60-93 of the sequence of *S. pyogenes* Cas9. The REC1 domain is important for recognition of the repeat:anti-repeat duplex, e.g., of a gRNA or a tracrRNA, and is therefore critical for Cas9 activity by recognizing the target sequence. The REC1 domain comprises two REC1 motifs at amino acids 94 to 179 and 308 to 717 of the sequence of *S. pyogenes* Cas9. These two REC1 domains, though separated by the REC2 domain in the linear primary structure, assemble in the tertiary structure to form the REC1 domain. The REC2 domain, or parts thereof, may also play a role in the recognition of the repeat:anti-repeat duplex. The REC2 domain comprises amino acids 180-307 of the sequence of *S. pyogenes* Cas9.

The NUC lobe comprises the RuvC domain, the HNH domain, and the PAM-interacting (PI) domain. The RuvC domain shares structural similarity to retroviral integrase superfamily members and cleaves a single strand, e.g., the non-complementary strand of the target nucleic acid molecule. The RuvC domain is assembled from the three split RuvC motifs (RuvC I, RuvCII, and RuvCIII, which are often commonly referred to in the art as RuvCI domain, or N-terminal RuvC domain, RuvCII domain, and RuvCIII domain) at amino acids 1-59, 718-769, and 909-1098, respectively, of the sequence of *S. pyogenes* Cas9. Similar to the REC1 domain, the three RuvC motifs are linearly separated by other domains in the primary structure, however in the tertiary structure, the three RuvC motifs assemble and form the RuvC domain. The HNH domain shares structural similarity with HNH endonucleases and cleaves a single strand, e.g., the complementary strand of the target nucleic acid molecule. The HNH domain lies between the RuvC II-III motifs and comprises amino acids 775-908 of the sequence of *S. pyogenes* Cas9. The PI domain interacts with the PAM of the target nucleic acid molecule, and comprises amino acids 1099-1368 of the sequence of *S. pyogenes* Cas9.

7.1.1 RuvC-Like Domain and HNH-Like Domain

In certain embodiments, a Cas9 molecule or Cas9 polypeptide comprises an HNH-like domain and a RuvC-like domain, and in certain of these embodiments cleavage activity is dependent on the RuvC-like domain and the HNH-like domain. A Cas9 molecule or Cas9 polypeptide can comprise one or more of a RuvC-like domain and an HNH-like domain. In certain embodiments, a Cas9 molecule or Cas9 polypeptide comprises a RuvC-like domain, e.g., a RuvC-like domain described below, and/or an HNH-like domain, e.g., an HNH-like domain described below. RuvC-like domains In certain embodiments, a RuvC-like domain cleaves a single strand, e.g., the non-complementary strand of the target nucleic acid molecule. The Cas9 molecule or Cas9 polypeptide can include more than one RuvC-like domain (e.g., one, two, three or more RuvC-like domains). In certain embodiments, a RuvC-like domain is at least 5, 6, 7, 8 amino acids in length but not more than 20, 19, 18, 17, 16 or 15 amino acids in length. In certain embodiments, the Cas9 molecule or Cas9 polypeptide comprises an N-terminal RuvC-like domain of about 10 to 20 amino acids, e.g., about 15 amino acids in length.

7.1.2 N-Terminal RuvC-Like Domains

Some naturally occurring Cas9 molecules comprise more than one RuvC-like domain with cleavage being dependent on the N-terminal RuvC-like domain. Accordingly, a Cas9 molecule or Cas9 polypeptide can comprise an N-terminal RuvC-like domain. Exemplary N-terminal RuvC-like domains are described below.

In certain embodiments, a Cas9 molecule or Cas9 polypeptide comprises an N-terminal RuvC-like domain comprising an amino acid sequence of Formula I:

$$D\text{-}X_1\text{-}G\text{-}X_2\text{-}X_3\text{-}X_4\text{-}X_5\text{-}G\text{-}X_6\text{-}X_7\text{-}X_8\text{-}X_9 \quad \text{(SEQ ID NO:20)},$$

wherein, $X_1$ is selected from I, V, M, L, and T (e.g., selected from I, V, and L);

$X_2$ is selected from T, I, V, S, N, Y, E, and L (e.g., selected from T, V, and I);

$X_3$ is selected from N, S, G, A, D, T, R, M, and F (e.g., A or N);

$X_4$ is selected from S, Y, N, and F (e.g., S);

$X_5$ is selected from V, I, L, C, T, and F (e.g., selected from V, I and L);

$X_6$ is selected from W, F, V, Y, S, and L (e.g., W);

$X_7$ is selected from A, S, C, V, and G (e.g., selected from A and S);

$X_8$ is selected from V, I, L, A, M, and H (e.g., selected from V, I, M and L); and $X_9$ is selected from any amino acid or is absent (e.g., selected from T, V, I, L, A, F, S, A, Y, M, and R, or, e.g., selected from T, V, I, L, and A).

In certain embodiments, the N-terminal RuvC-like domain differs from a sequence of SEQ ID NO:20 by as many as 1 but no more than 2, 3, 4, or 5 residues.

In certain embodiments, the N-terminal RuvC-like domain is cleavage competent. In other embodiments, the N-terminal RuvC-like domain is cleavage incompetent.

In certain embodiments, a Cas9 molecule or Cas9 polypeptide comprises an N-terminal RuvC-like domain comprising an amino acid sequence of Formula II:

$$D-X_1-G-X_2-X_3-S-X_5-G-X_6-X_7-X_8-X_9, \quad \text{(SEQ ID NO:21)},$$

wherein $X_1$ is selected from I, V, M, L, and T (e.g., selected from I, V, and L);

$X_2$ is selected from T, I, V, S, N, Y, E, and L (e.g., selected from T, V, and I);

$X_3$ is selected from N, S, G, A, D, T, R, M and F (e.g., A or N);

$X_5$ is selected from V, I, L, C, T, and F (e.g., selected from V, I and L);

$X_6$ is selected from W, F, V, Y, S, and L (e.g., W);

$X_7$ is selected from A, S, C, V, and G (e.g., selected from A and S);

$X_8$ is selected from V, I, L, A, M, and H (e.g., selected from V, I, M and L); and $X_9$ is selected from any amino acid or is absent (e.g., selected from T, V, I, L, A, F, S, A, Y, M, and R or selected from e.g., T, V, I, L, and A).

In certain embodiments, the N-terminal RuvC-like domain differs from a sequence of SEQ ID NO:21 by as many as 1 but not more than 2, 3, 4, or 5 residues.

In certain embodiments, the N-terminal RuvC-like domain comprises an amino acid sequence of Formula III:

$$D-I-G-X_2-X_3-S-V-G-W-A-X_8-X_9 \quad \text{(SEQ ID NO:22)},$$

wherein $X_2$ is selected from T, I, V, S, N, Y, E, and L (e.g., selected from T, V, and I);

$X_3$ is selected from N, S, G, A, D, T, R, M, and F (e.g., A or N);

$X_8$ is selected from V, I, L, A, M, and H (e.g., selected from V, I, M and L); and $X_9$ is selected from any amino acid or is absent (e.g., selected from T, V, I, L, A, F, S, A, Y, M, and R or selected from e.g., T, V, I, L, and A).

In certain embodiments, the N-terminal RuvC-like domain differs from a sequence of SEQ ID NO:22 by as many as 1 but not more than, 2, 3, 4, or 5 residues.

In certain embodiments, the N-terminal RuvC-like domain comprises an amino acid sequence of Formula IV:

$$D-I-G-T-N-S-V-G-W-A-V-X \quad \text{(SEQ ID NO:23)},$$

wherein

X is a non-polar alkyl amino acid or a hydroxyl amino acid, e.g., X is selected from V, I, L, and T (e.g., the Cas9 molecule can comprise an N-terminal RuvC-like domain shown in FIGS. 2A-2G (depicted as Y)).

In certain embodiments, the N-terminal RuvC-like domain differs from a sequence of SEQ ID NO:23 by as many as 1 but not more than, 2, 3, 4, or 5 residues.

In certain embodiments, the N-terminal RuvC-like domain differs from a sequence of an N-terminal RuvC like domain disclosed herein, e.g., in FIGS. 3A-3B, as many as 1 but no more than 2, 3, 4, or 5 residues. In certain embodiments, 1, 2, 3 or all of the highly conserved residues identified in FIGS. 3A-3B are present.

In certain embodiments, the N-terminal RuvC-like domain differs from a sequence of an N-terminal RuvC-like domain disclosed herein, e.g., in FIGS. 4A-4B, as many as 1 but no more than 2, 3, 4, or 5 residues. In certain embodiments, 1, 2, or all of the highly conserved residues identified in FIGS. 4A-4B are present.

7.1.3 Additional RuvC-Like Domains

In addition to the N-terminal RuvC-like domain, the Cas9 molecule or Cas9 polypeptide can comprise one or more additional RuvC-like domains. In certain embodiments, the Cas9 molecule or Cas9 polypeptide comprises two additional RuvC-like domains. In certain embodiments, the additional RuvC-like domain is at least 5 amino acids in length and, e.g., less than 15 amino acids in length, e.g., 5 to 10 amino acids in length, e.g., 8 amino acids in length.

An additional RuvC-like domain can comprise an amino acid sequence of Formula V:

$$I-X_1-X_2-E-X_3-A-R-E \quad \text{(SEQ ID NO:15)}$$

wherein, $X_1$ is V or H;

$X_2$ is I, L or V (e.g., I or V); and $X_3$ is M or T.

In certain embodiments, the additional RuvC-like domain comprises an amino acid sequence of Formula VI:

$$I-V-X_2-E-M-A-R-E \quad \text{(SEQ ID NO:16)},$$

wherein $X_2$ is I, L or V (e.g., I or V) (e.g., the Cas9 molecule or Cas9 polypeptide can comprise an additional RuvC-like domain shown in FIG. 2A-2G (depicted as B)).

An additional RuvC-like domain can comprise an amino acid sequence of Formula VII:

$$H-H-A-X_1-D-A-X_2-X_3 \quad \text{(SEQ ID NO:17)},$$

wherein $X_1$ is H or L;

$X_2$ is R or V; and $X_3$ is E or V.

In certain embodiments, the additional RuvC-like domain comprises the amino acid sequence: H-H-A-H-D-A-Y-L (SEQ ID NO:18).

In certain embodiments, the additional RuvC-like domain differs from a sequence of SEQ ID NOs:15-18 by as many as 1 but not more than 2, 3, 4, or 5 residues.

In certain embodiments, the sequence flanking the N-terminal RuvC-like domain has the amino acid sequence of Formula VIII:

$$K-X_1'-Y-X_2'-X_3'-X_4'-Z-T-D-X_9'-Y \quad \text{(SEQ ID NO: 19)},$$

wherein $X_1'$ is selected from K and P;

$X_2'$ is selected from V, L, I, and F (e.g., V, I and L);

$X_3'$ is selected from G, A and S (e.g., G);

$X_4'$ is selected from L, I, V, and F (e.g., L);

$X_9'$ is selected from D, E, N, and Q; and

Z is an N-terminal RuvC-like domain, e.g., as described above, e.g., having 5 to 20 amino acids.

7.1.4 HNH-Like Domains

In certain embodiments, an HNH-like domain cleaves a single stranded complementary domain, e.g., a complementary strand of a double stranded nucleic acid molecule. In certain embodiments, an HNH-like domain is at least 15, 20, or 25 amino acids in length but not more than 40, 35, or 30 amino acids in length, e.g., 20 to 35 amino acids in length, e.g., 25 to 30 amino acids in length. Exemplary HNH-like domains are described below.

In certain embodiments, a Cas9 molecule or Cas9 polypeptide comprises an HNH-like domain having an amino acid sequence of Formula IX:

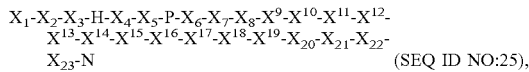
(SEQ ID NO:25), wherein
$X_1$ is selected from D, E, Q and N (e.g., D and E);
$X^2$ is selected from L, I, R, Q, V, M, and K;
$X_3$ is selected from D and E;
$X_4$ is selected from I, V, T, A, and L (e.g., A, I and V);
$X_5$ is selected from V, Y, I, L, F, and W (e.g., V, I and L);
$X_6$ is selected from Q, H, R, K, Y, I, L, F, and W;
$X_7$ is selected from S, A, D, T, and K (e.g., S and A);
$X_8$ is selected from F, L, V, K, Y, M, I, R, A, E, D, and Q (e.g., F);
$X_9$ is selected from L, R, T, I, V, S, C, Y, K, F, and G;
$X_{10}$ is selected from K, Q, Y, T, F, L, W, M, A, E, G, and S;
$X_{11}$ is selected from D, S, N, R, L, and T (e.g., D);
$X_{12}$ is selected from D, N and S;
$X_{13}$ is selected from S, A, T, G, and R (e.g., S);
$X_{14}$ is selected from I, L, F, S, R, Y, Q, W, D, K, and H (e.g., I, L and F);
$X_{15}$ is selected from D, S, I, N, E, A, H, F, L, Q, M, G, Y, and V;
$X_{16}$ is selected from K, L, R, M, T, and F (e.g., L, R and K);
$X_{17}$ is selected from V, L, I, A and T;
$X_{18}$ is selected from L, I, V, and A (e.g., L and I);
$X_{19}$ is selected from T, V, C, E, S, and A (e.g., T and V);
$X_{20}$ is selected from R, F, T, W, E, L, N, C, K, V, S, Q, I, Y, H, and A;
$X_{21}$ is selected from S, P, R, K, N, A, H, Q, G, and L;
$X_{22}$ is selected from D, G, T, N, S, K, A, I, E, L, Q, R, and Y; and
$X_{23}$ is selected from K, V, A, E, Y, I, C, L, S, T, G, K, M, D, and F.

In certain embodiments, a HNH-like domain differs from a sequence of SEQ ID NO:25 by at least one but not more than, 2, 3, 4, or 5 residues.

In certain embodiments, the HNH-like domain is cleavage competent. In certain embodiments, the HNH-like domain is cleavage incompetent.

In certain embodiments, a Cas9 molecule or Cas9 polypeptide comprises an HNH-like domain comprising an amino acid sequence of Formula X:

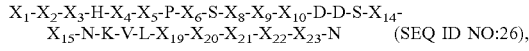
(SEQ ID NO:26), wherein
$X_1$ is selected from D and E;
$X_2$ is selected from L, I, R, Q, V, M, and K;
$X_3$ is selected from D and E;
$X_4$ is selected from I, V, T, A, and L (e.g., A, I and V);
$X_5$ is selected from V, Y, I, L, F, and W (e.g., V, I and L);
$X_6$ is selected from Q, H, R, K, Y, I, L, F, and W;
$X_8$ is selected from F, L, V, K, Y, M, I, R, A, E, D, and Q (e.g., F);
$X_9$ is selected from L, R, T, I, V, S, C, Y, K, F, and G;
$X_{10}$ is selected from K, Q, Y, T, F, L, W, M, A, E, G, and S;
$X_{14}$ is selected from I, L, F, S, R, Y, Q, W, D, K, and H (e.g., I, L and F);
$X_{15}$ is selected from D, S, I, N, E, A, H, F, L, Q, M, G, Y, and V;
$X_{19}$ is selected from T, V, C, E, S, and A (e.g., T and V);
$X_{20}$ is selected from R, F, T, W, E, L, N, C, K, V, S, Q, I, Y, H, and A;
$X_{21}$ is selected from S, P, R, K, N, A, H, Q, G, and L;
$X_{22}$ is selected from D, G, T, N, S, K, A, I, E, L, Q, R, and Y; and
$X_{23}$ is selected from K, V, A, E, Y, I, C, L, S, T, G, K, M, D, and F.

In certain embodiment, the HNH-like domain differs from a sequence of SEQ ID NO:26 by 1, 2, 3, 4, or 5 residues.

In certain embodiments, a Cas9 molecule or Cas9 polypeptide comprises an HNH-like domain comprising an amino acid sequence of Formula XI:

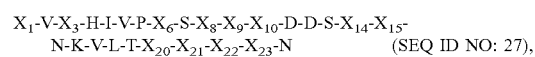
(SEQ ID NO: 27), wherein
$X_1$ is selected from D and E;
$X_3$ is selected from D and E;
$X_6$ is selected from Q, H, R, K, Y, I, L, and W;
$X_8$ is selected from F, L, V, K, Y, M, I, R, A, E, D, and Q (e.g., F);
$X_9$ is selected from L, R, T, I, V, S, C, Y, K, F, and G;
$X_{10}$ is selected from K, Q, Y, T, F, L, W, M, A, E, G, and S;
$X_{14}$ is selected from I, L, F, S, R, Y, Q, W, D, K, and H (e.g., I, L and F);
$X_{15}$ is selected from D, S, I, N, E, A, H, F, L, Q, M, G, Y, and V;
$X_{20}$ is selected from R, F, T, W, E, L, N, C, K, V, S, Q, I, Y, H, and A;
$X_{21}$ is selected from S, P, R, K, N, A, H, Q, G, and L;
$X_{22}$ is selected from D, G, T, N, S, K, A, I, E, L, Q, R, and Y; and
$X_{23}$ is selected from K, V, A, E, Y, I, C, L, S, T, G, K, M, D, and F.

In certain embodiments, the HNH-like domain differs from a sequence of SEQ ID NO:27 by 1, 2, 3, 4, or 5 residues.

In certain embodiments, a Cas9 molecule or Cas9 polypeptide comprises an HNH-like domain having an amino acid sequence of Formula XII:

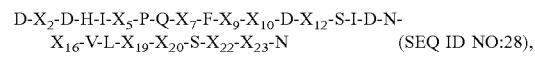
(SEQ ID NO:28), wherein
$X_2$ is selected from I and V;
$X_5$ is selected from I and V;
$X_7$ is selected from A and S;
$X_9$ is selected from I and L;
$X_{10}$ is selected from K and T;
$X_{12}$ is selected from D and N;
$X_{16}$ is selected from R, K, and L;
$X_{19}$ is selected from T and V;
$X_{20}$ is selected from S, and R;
$X_{22}$ is selected from K, D, and A; and
$X_{23}$ is selected from E, K, G, and N (e.g., the Cas9 molecule or Cas9 polypeptide can comprise an HNH-like domain as described herein).

In certain embodiments, the HNH-like domain differs from a sequence of SEQ ID NO:28 by as many as 1 but no more than 2, 3, 4, or 5 residues.

In certain embodiments, a Cas9 molecule or Cas9 polypeptide comprises the amino acid sequence of Formula XIII:

L-Y-Y-L-Q-N-G-$X_1'$-D-M-Y-$X_2'$-D-M-Y-$X_2'$-$X_3'$-$X_4'$-$X_5'$-L-D-I-$X_6'$-$X_7'$-L-S-$X_8'$-Y-Z-N-R-$X_9'$-K-$X_{10}'$-D-$X_{11}'$-Y-P  (SEQ ID NO:24), wherein
$X_1'$ is selected from K and R;
$X_2'$ is selected from V and T;
$X_3'$ is selected from G and D;
$X_4'$ is selected from E, Q and D;
$X_5'$ is selected from E and D;
$X_6'$ is selected from D, N, and H;
$X_7'$ is selected from Y, R, and N;
$X_8'$ is selected from Q, D, and N;
$X_9'$ is selected from G and E;
$X_{10}'$ is selected from S and G;
$X_{11}'$ is selected from D and N; and
Z is an HNH-like domain, e.g., as described above.

In certain embodiments, the Cas9 molecule or Cas9 polypeptide comprises an amino acid sequence that differs from a sequence of SEQ ID NO:24 by as many as 1 but not more than 2, 3, 4, or 5 residues.

In certain embodiments, the HNH-like domain differs from a sequence of an HNH-like domain disclosed herein, e.g., in FIGS. 5A-5C, by as many as 1 but not more than 2, 3, 4, or 5 residues. In certain embodiments, 1 or both of the highly conserved residues identified in FIGS. 5A-5C are present.

In certain embodiments, the HNH-like domain differs from a sequence of an HNH-like domain disclosed herein, e.g., in FIGS. 6A-6B, by as many as 1 but not more than 2, 3, 4, or 5 residues. In certain embodiments, 1, 2, or all 3 of the highly conserved residues identified in FIGS. 6A-6B are present.

7.2 Cas9 Activities

In certain embodiments, the Cas9 molecule or Cas9 polypeptide is capable of cleaving a target nucleic acid molecule. Typically wild-type Cas9 molecules cleave both strands of a target nucleic acid molecule. Cas9 molecules and Cas9 polypeptides can be engineered to alter nuclease cleavage (or other properties), e.g., to provide a Cas9 molecule or Cas9 polypeptide which is a nickase, or which lacks the ability to cleave target nucleic acid. A Cas9 molecule or Cas9 polypeptide that is capable of cleaving a target nucleic acid molecule is referred to herein as an eaCas9 (an enzymatically active Cas9) molecule or eaCas9 polypeptide.

In certain embodiments, an eaCas9 molecule or eaCas9 polypeptide comprises one or more of the following enzymatic activities:

a nickase activity, i.e., the ability to cleave a single strand, e.g., the non-complementary strand or the complementary strand, of a nucleic acid molecule;

a double stranded nuclease activity, i.e., the ability to cleave both strands of a double stranded nucleic acid and create a double stranded break, which in certain embodiments is the presence of two nickase activities;

an endonuclease activity;

an exonuclease activity; and a helicase activity, i.e., the ability to unwind the helical structure of a double stranded nucleic acid.

In certain embodiments, an enzymatically active Cas9 ("eaCas9") molecule or eaCas9 polypeptide cleaves both DNA strands and results in a double stranded break. In certain embodiments, an eaCas9 molecule or eaCas9 polypeptide cleaves only one strand, e.g., the strand to which the gRNA hybridizes to, or the strand complementary to the strand the gRNA hybridizes with. In certain embodiments, an eaCas9 molecule or eaCas9 polypeptide comprises cleavage activity associated with an HNH domain. In certain embodiments, an eaCas9 molecule or eaCas9 polypeptide comprises cleavage activity associated with a RuvC domain. In certain embodiments, an eaCas9 molecule or eaCas9 polypeptide comprises cleavage activity associated with an HNH domain and cleavage activity associated with a RuvC domain. In certain embodiments, an eaCas9 molecule or eaCas9 polypeptide comprises an active, or cleavage competent, HNH domain and an inactive, or cleavage incompetent, RuvC domain. In certain embodiments, an eaCas9 molecule or eaCas9 polypeptide comprises an inactive, or cleavage incompetent, HNH domain and an active, or cleavage competent, RuvC domain.

In certain embodiments, the Cas9 molecules or Cas9 polypeptides have the ability to interact with a gRNA molecule, and in conjunction with the gRNA molecule localize to a core target domain, but are incapable of cleaving the target nucleic acid, or incapable of cleaving at efficient rates. Cas9 molecules having no, or no substantial, cleavage activity are referred to herein as an enzymatically inactive Cas9 ("eiCas9") molecule or eiCas9 polypeptide. For example, an eiCas9 molecule or eiCas9 polypeptide can lack cleavage activity or have substantially less, e.g., less than 20, 10, 5, 1 or 0.1% of the cleavage activity of a reference Cas9 molecule or eiCas9 polypeptide, as measured by an assay described herein.

7.3 Targeting and PAMs

A Cas9 molecule or Cas9 polypeptide can interact with a gRNA molecule and, in concert with the gRNA molecule, localizes to a site which comprises a target domain, and in certain embodiments, a PAM sequence. In certain embodiments, the Cas9 molecules or Cas9 polypeptides of the present disclosure (e.g., an eaCas9 or eiCas9) can be targeted using the gRNAs disclosed in WO 2015/089465, which is incorporated by reference herein in its entirety. In certain embodiments, the Cas9 molecule or Cas9 polypeptide targeted using the gRNAs disclosed in WO 2015/089465 is an *S. pyogenes* Cas9. In certain embodiments, the Cas9 molecule or Cas9 polypeptide targeted using the gRNAs disclosed in WO 2015/089465 is an *S. aureus* Cas9.

In certain embodiments, the ability of an eaCas9 molecule or eaCas9 polypeptide to interact with and cleave a target nucleic acid is PAM sequence dependent. A PAM sequence is a sequence in the target nucleic acid. In certain embodiments, cleavage of the target nucleic acid occurs upstream from the PAM sequence. eaCas9 molecules from different bacterial species can recognize different sequence motifs (e.g., PAM sequences). In certain embodiments, an eaCas9 molecule of *S. pyogenes* recognizes the sequence motif NGG and directs cleavage of a target nucleic acid sequence 1 to 10, e.g., 3 to 5, bp upstream from that sequence (see, e.g., *Mali* 2013).

In certain embodiments, the Cas9 molecule is an *S. pyogenes* Cas9 EQR variant or an *S. pyogenes* Cas9 VRER variant.

In certain embodiments, the *S. pyogenes* Cas9 EQR variant recognizes a PAM sequence of NGAG, NGCG, NGGG, NGTG, NGAA, NGAT or NGAC and directs cleavage of a target nucleic acid sequence at 1 to 10, e.g., 3 to 5, base pairs upstream from that sequence. In certain embodiments, the *S. pyogenes* Cas9 EQR variant recognizes a PAM sequence of NGAG and directs cleavage of a target nucleic acid sequence at 1 to 10, e.g., 3 to 5, base pairs upstream from that sequence. See Kleinstiver et al., *NATURE* 2015; 523(7561):481-5.

In certain embodiments, the *S. pyogenes* Cas9 VRER variant recognizes a PAM sequence of NGCG, NGCA, NGCT PAM, or NGCC and directs cleavage of a target nucleic acid sequence at 1 to 10, e.g., 3 to 5, base pairs upstream from that sequence. In certain embodiments, the *S. pyogenes* Cas9 VRER variant recognizes the sequence motif of NGCG and directs cleavage of a target nucleic acid sequence 1 to 10, e.g., 3 to 5, base pairs upstream from that sequence. See Kleinstiver Kleinstiver et al., *NATURE* 2015; 523(7561):481-5.

In certain embodiments, the *S. thermophilus* Cas9 molecule recognizes a PAM sequence of NGGNG (SEQ ID NO:199) and/or NNAGAAW (W=A or T) (SEQ ID NO:200) and directs cleavage of a target nucleic acid sequence 1 to 10, e.g., 3 to 5, bp upstream from these sequences (see, e.g., Horvath 2010; Deveau 2008).

In certain embodiments, *S. mutans* Cas9 molecule recognizes a PAM sequence of NGG and/or NAAR (R=A or G) (SEQ ID NO:201) and directs cleavage of a target nucleic acid sequence 1 to 10, e.g., 3 to 5 bp, upstream from this sequence (see, e.g., Deveau 2008).

In certain embodiments, an *S. aureus* Cas9 molecule recognizes a PAM sequence of NNGRR (R=A or G) (SEQ ID NO:202) and directs cleavage of a target nucleic acid sequence 1 to 10, e.g., 3 to 5, bp upstream from that sequence.

In certain embodiments, an *S. aureus* recognizes a PAM sequence of NNGRRN (R=A or G) (SEQ ID NO:203) and directs cleavage of a target nucleic acid sequence 1 to 10, e.g., 3 to 5, bp upstream from that sequence. In certain embodiments, an *S. aureus* Cas9 molecule recognizes a PAM sequence of NNGRRT (R=A or G) (SEQ ID NO:204) and directs cleavage of a target nucleic acid sequence 1 to 10, e.g., 3 to 5, bp upstream from that sequence. In certain embodiments, an *S. aureus* Cas9 molecule recognizes a PAM sequence of NNGRRV (R=A or G) (SEQ ID NO:205) and directs cleavage of a target nucleic acid sequence 1 to 10, e.g., 3 to 5, bp upstream from that sequence.

In certain embodiments, an *Neisseria meningitidis* Cas9 molecule recognizes a PAM sequence of NNNNGATT or NNNGCTT and directs cleavage of a target nucleic acid sequence 1 to 10, e.g., 3 to 5, base pairs upstream from that sequence. See, e.g., Hou et al., PNAS Early Edition 2013, 1-6.

The ability of a Cas9 molecule to recognize a PAM sequence can be determined, e.g., using a transformation assay as described previously (Jinek 2012). In the aforementioned embodiments, N can be any nucleotide residue, e.g., any of A, G, C, or T.

As is discussed herein, Cas9 molecules can be engineered to alter the PAM specificity of the Cas9 molecule.

Exemplary naturally occurring Cas9 molecules have been described previously (see, e.g., Chylinski 2013). Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 11 bacterial family, a cluster 12 bacterial family, a cluster 13 bacterial family, a cluster 14 bacterial family, a cluster 15 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

Exemplary naturally occurring Cas9 molecules include a Cas9 molecule of a cluster 1 bacterial family. Examples include a Cas9 molecule of: *S. aureus, S. pyogenes* (e.g., strain SF370, MGAS10270, MGAS10750, MGAS2096, MGAS315, MGAS5005, MGAS6180, MGAS9429, NZ131 and SSI-1), *S. thermophilus* (e.g., strain LIVID-9), *S. pseudoporcinus* (e.g., strain SPIN 20026), *S. mutans* (e.g., strain UA159, NN2025), *S. macacae* (e.g., strain NCTC11558), *S. gallolyticus* (e.g., strain UCN34, ATCC BAA-2069), *S. equines* (e.g., strain ATCC 9812, MGCS 124), *S. dysdalactiae* (e.g., strain GGS 124), *S. bovis* (e.g., strain ATCC 700338), *S. anginosus* (e.g., strain F0211), *S. agalactiae* (e.g., strain NEM316, A909), *Listeria monocytogenes* (e.g., strain F6854), *Listeria innocua* (*L. innocua*, e.g., strain Clip11262), *Enterococcus italicus* (e.g., strain DSM 15952), or *Enterococcus faecium* (e.g., strain 1,231,408).

Additional exemplary Cas9 molecules are a Cas9 molecule of *Neisseria meningitidis* (Hou et al., PNAS Early Edition 2013, 1-6) and an *S. aureus* cas9 molecule.

In certain embodiments, a Cas9 molecule or Cas9 polypeptide comprises an amino acid sequence:

having about 60%, about 65%, about 70%, about 75%, about 80%, about 85%, about 90%, about 95%, about 96%, about 97%, about 98% or about 99% homology with;

differs at no more than, about 2%, about 5%, about 10%, about 15%, about 20%, about 30%, or about 40% of the amino acid residues when compared with;

differs by at least 1, 2, 5, 10 or 20 amino acids, but by no more than 100, 80, 70, 60, 50, 40 or 30 amino acids from; or identical to any Cas9 molecule sequence described herein, or to a naturally occurring Cas9 molecule sequence, e.g., a Cas9 molecule from a species listed herein (e.g., SEQ ID NOs:1, 2, 4-6, or 12) or described in Chylinski 2013. In certain embodiments, the Cas9 molecule or Cas9 polypeptide comprises one or more of the following activities: a nickase activity; a double stranded cleavage activity (e.g., an endonuclease and/or exonuclease activity); a helicase activity; or the ability, together with a gRNA molecule, to localize to a target nucleic acid.

In certain embodiments, a Cas9 molecule or Cas9 polypeptide comprises any of the amino acid sequence of the consensus sequence of FIGS. 2A-2G, wherein "*" indicates any amino acid found in the corresponding position in the amino acid sequence of a Cas9 molecule of *S. pyogenes, S. thermophilus, S. mutans*, or *L. innocua*, and "-" indicates absent. In certain embodiments, a Cas9 molecule or Cas9 polypeptide differs from the sequence of the consensus sequence disclosed in FIGS. 2A-2G by at least 1, but no more than 2, 3, 4, 5, 6, 7, 8, 9, or 10 amino acid residues. In certain embodiments, a Cas9 molecule or Cas9 polypeptide comprises the amino acid sequence of SEQ ID NO:2. In other embodiments, a Cas9 molecule or Cas9 polypeptide differs from the sequence of SEQ ID NO:2 by at least 1, but no more than 2, 3, 4, 5, 6, 7, 8, 9, or 10 amino acid residues.

A comparison of the sequence of a number of Cas9 molecules indicate that certain regions are conserved. These are identified below as:

region 1 (residues 1 to 180, or in the case of region 1'residues 120 to 180)
region 2 (residues 360 to 480);
region 3 (residues 660 to 720);
region 4 (residues 817 to 900); and
region 5 (residues 900 to 960).

In certain embodiments, a Cas9 molecule or Cas9 polypeptide comprises regions 1-5, together with sufficient additional Cas9 molecule sequence to provide a biologically active molecule, e.g., a Cas9 molecule having at least one activity described herein. In certain embodiments, each of regions 1-5, independently, have about 50%, about 60%, about 70%, about 80%, about 85%, about 90%, about 95%, about 96%, about 97%, about 98% or about 99% homology with the corresponding residues of a Cas9 molecule or Cas9 polypeptide described herein, e.g., a sequence from FIGS. 2A-2G.

In certain embodiments, a Cas9 molecule or Cas9 polypeptide comprises an amino acid sequence referred to as region 1:

having about 50%, about 60%, about 70%, about 80%, about 85%, about 90%, about 95%, about 96%, about 97%, about 98% or about 99% homology with amino acids 1-180 (the numbering is according to the motif sequence in FIG. 2; 52% of residues in the four Cas9 sequences in FIGS. 2A-2G are conserved) of the amino acid sequence of Cas9 of *S. pyogenes*;

differs by at least 1, 2, 5, 10 or 20 amino acids but by no more than 90, 80, 70, 60, 50, 40 or 30 amino acids from amino acids 1-180 of the amino acid sequence of Cas9 of *S. pyogenes, S. thermophilus, S. mutans*, or *Listeria innocua*; or is identical to amino acids 1-180 of the amino acid sequence of Cas9 of *S. pyogenes, S. thermophilus, S. mutans*, or *L. innocua*.

In certain embodiments, a Cas9 molecule or Cas9 polypeptide comprises an amino acid sequence referred to as region 1':

having about 55%, about 60%, about 65%, about 70%, about 75%, about 80%, about 85%, about 90%, about 95%, about 96%, about 97%, about 98% or about 99% homology with amino acids 120-180 (55% of residues in the four Cas9 sequences in FIG. 2 are conserved) of the amino acid sequence of Cas9 of *S. pyogenes, S. thermophilus, S. mutans* or *L. innocua;* differs by at least 1, 2, or 5 amino acids but by no more than 35, 30, 25, 20 or 10 amino acids from amino acids 120-180 of the amino acid sequence of Cas9 of *S. pyogenes, S. thermophilus, S. mutans*, or *L. innocua*; or is identical to amino acids 120-180 of the amino acid sequence of Cas9 of *S. pyogenes, S. thermophilus, S. mutans*, or *L. innocua*.

In certain embodiments, a Cas9 molecule or Cas9 polypeptide comprises an amino acid sequence referred to as region 2:

having about 50%, about 55%, about 60%, about 65%, about 70%, about 75%, about 80%, about 85%, about 90%, about 95%, about 96%, about 97%, about 98% or about 99% homology with amino acids 360-480 (52% of residues in the four Cas9 sequences in FIG. 2 are conserved) of the amino acid sequence of Cas9 of *S. pyogenes, S. thermophilus, S. mutans*, or *L. innocua;* differs by at least 1, 2, or 5 amino acids but by no more than 35, 30, 25, 20 or 10 amino acids from amino acids 360-480 of the amino acid sequence of Cas9 of *S. pyogenes, S. thermophilus, S. mutans*, or *L. innocua*; or is identical to amino acids 360-480 of the amino acid sequence of Cas9 of *S. pyogenes, S. thermophilus, S. mutans*, or *L. innocua*.

In certain embodiments, a Cas9 molecule or Cas9 polypeptide comprises an amino acid sequence referred to as region 3:

having about 55%, about 60%, about 65%, about 70%, about 75%, about 80%, about 85%, about 90%, about 95%, about 96%, about 97%, about 98%, or about 99% homology with amino acids 660-720 (56% of residues in the four Cas9 sequences in FIG. 2 are conserved) of the amino acid sequence of Cas9 of *S. pyogenes, S. thermophilus, S. mutans* or *L. innocua;* differs by at least 1, 2, or 5 amino acids but by no more than 35, 30, 25, 20 or 10 amino acids from amino acids 660-720 of the amino acid sequence of Cas9 of *S. pyogenes, S. thermophilus, S. mutans* or *L. innocua*; or is identical to amino acids 660-720 of the amino acid sequence of Cas9 of *S. pyogenes, S. thermophilus, S. mutans* or *L. innocua*.

In certain embodiments, a Cas9 molecule or Cas9 polypeptide comprises an amino acid sequence referred to as region 4:

having about 50%, about 55%, about 60%, about 65%, about 70%, about 75%, about 80%, about 85%, about 90%, about 95%, about 96%, about 97%, about 98%, or about 99% homology with amino acids 817-900 (55% of residues in the four Cas9 sequences in FIGS. 2A-2G are conserved) of the amino acid sequence of Cas9 of *S. pyogenes, S. thermophilus, S. mutans*, or *L. innocua;* differs by at least 1, 2, or 5 amino acids but by no more than 35, 30, 25, 20 or 10 amino acids from amino acids 817-900 of the amino acid sequence of Cas9 of *S. pyogenes, S. thermophilus, S. mutans*, or *L. innocua*; or is identical to amino acids 817-900 of the amino acid sequence of Cas9 of *S. pyogenes, S. thermophilus, S. mutans*, or *L. innocua*.

In certain embodiments, a Cas9 molecule or Cas9 polypeptide comprises an amino acid sequence referred to as region 5:

having about 50%, about 55%, about 60%, about 65%, about 70%, about 75%, about 80%, about 85%, about 90%, about 95%, about 96%, about 97%, about 98%, or about 99% homology with amino acids 900-960 (60% of residues in the four Cas9 sequences in FIGS. 2A-2G are conserved)

of the amino acid sequence of Cas9 of *S. pyogenes, S. thermophilus, S. mutans*, or *L. innocua*;

differs by at least 1, 2, or 5 amino acids but by no more than 35, 30, 25, 20 or 10 amino acids from amino acids 900-960 of the amino acid sequence of Cas9 of *S. pyogenes, S. thermophilus, S. mutans*, or *L. innocua*; or is identical to amino acids 900-960 of the amino acid sequence of Cas9 of *S. pyogenes, S. thermophilus, S. mutans*, or *L. innocua*.

7.4 Engineered or Altered Cas9

Cas9 molecules and Cas9 polypeptides described herein can possess any of a number of properties, including nuclease activity (e.g., endonuclease and/or exonuclease activity); helicase activity; the ability to associate functionally with a gRNA molecule; and the ability to target (or localize to) a site on a nucleic acid (e.g., PAM recognition and specificity). In certain embodiments, a Cas9 molecule or Cas9 polypeptide can include all or a subset of these properties. In certain embodiments, a Cas9 molecule or Cas9 polypeptide has the ability to interact with a gRNA molecule and, in concert with the gRNA molecule, localize to a site in a nucleic acid. Other activities, e.g., PAM specificity, cleavage activity, or helicase activity can vary more widely in Cas9 molecules and Cas9 polypeptides.

Cas9 molecules include engineered Cas9 molecules and engineered Cas9 polypeptides (engineered, as used in this context, means merely that the Cas9 molecule or Cas9 polypeptide differs from a reference sequences, and implies no process or origin limitation). An engineered Cas9 molecule or Cas9 polypeptide can comprise altered enzymatic properties, e.g., altered nuclease activity, (as compared with a naturally occurring or other reference Cas9 molecule) or altered helicase activity. As discussed herein, an engineered Cas9 molecule or Cas9 polypeptide can have nickase activity (as opposed to double strand nuclease activity). In certain embodiments, an engineered Cas9 molecule or Cas9 polypeptide can have an alteration that alters its size, e.g., a deletion of amino acid sequence that reduces its size, e.g., without significant effect on one or more, or any Cas9 activity. In certain embodiments, an engineered Cas9 molecule or Cas9 polypeptide can comprise an alteration that affects PAM recognition. In certain embodiments, an engineered Cas9 molecule is altered to recognize a PAM sequence other than that recognized by the endogenous wild-type PI domain. In certain embodiments, a Cas9 molecule or Cas9 polypeptide can differ in sequence from a naturally occurring Cas9 molecule but not have significant alteration in one or more Cas9 activities.

Cas9 molecules or Cas9 polypeptides with desired properties can be made in a number of ways, e.g., by alteration of a parental, e.g., naturally occurring, Cas9 molecules or Cas9 polypeptides, to provide an altered Cas9 molecule or Cas9 polypeptide having a desired property. For example, one or more mutations or differences relative to a parental Cas9 molecule, e.g., a naturally occurring or engineered Cas9 molecule, can be introduced. Such mutations and differences comprise: substitutions (e.g., conservative substitutions or substitutions of non-essential amino acids); insertions; or deletions. In certain embodiments, a Cas9 molecule or Cas9 polypeptide can comprises one or more mutations or differences, e.g., at least 1, 2, 3, 4, 5, 10, 15, 20, 30, 40 or 50 mutations but less than 200, 100, or 80 mutations relative to a reference, e.g., a parental, Cas9 molecule.

In certain embodiments, a mutation or mutations do not have a substantial effect on a Cas9 activity, e.g. a Cas9 activity described herein. In certain embodiments, a mutation or mutations have a substantial effect on a Cas9 activity, e.g. a Cas9 activity described herein.

7.5 Modified-Cleavage Cas9

In certain embodiments, a Cas9 molecule or Cas9 polypeptide comprises a cleavage property that differs from naturally occurring Cas9 molecules, e.g., that differs from the naturally occurring Cas9 molecule having the closest homology. For example, a Cas9 molecule or Cas9 polypeptide can differ from naturally occurring Cas9 molecules, e.g., a Cas9 molecule of *S. pyogenes*, as follows: its ability to modulate, e.g., decreased or increased, cleavage of a double stranded nucleic acid (endonuclease and/or exonuclease activity), e.g., as compared to a naturally occurring Cas9 molecule (e.g., a Cas9 molecule of *S. pyogenes*); its ability to modulate, e.g., decreased or increased, cleavage of a single strand of a nucleic acid, e.g., a non-complementary strand of a nucleic acid molecule or a complementary strand of a nucleic acid molecule (nickase activity), e.g., as compared to a naturally occurring Cas9 molecule (e.g., a Cas9 molecule of *S. pyogenes*); or the ability to cleave a nucleic acid molecule, e.g., a double stranded or single stranded nucleic acid molecule, can be eliminated.

In certain embodiments, an eaCas9 molecule or eaCas9 polypeptide comprises one or more of the following activities: cleavage activity associated with an N-terminal RuvC-like domain; cleavage activity associated with an HNH-like domain; cleavage activity associated with an HNH-like domain and cleavage activity associated with an N-terminal RuvC-like domain.

In certain embodiments, an eaCas9 molecule or eaCas9 polypeptide comprises an active, or cleavage competent, HNH-like domain (e.g., an HNH-like domain described herein, e.g., SEQ ID NOs:24-28) and an inactive, or cleavage incompetent, N-terminal RuvC-like domain. An exemplary inactive, or cleavage incompetent N-terminal RuvC-like domain can have a mutation of an aspartic acid in an N-terminal RuvC-like domain, e.g., an aspartic acid at position 9 of the consensus sequence disclosed in FIG. 2A-2G or an aspartic acid at position 10 of SEQ ID NO:2, e.g., can be substituted with an alanine. In certain embodiments, the eaCas9 molecule or eaCas9 polypeptide differs from wild-type in the N-terminal RuvC-like domain and does not cleave the target nucleic acid, or cleaves with significantly less efficiency, e.g., less than about 20%, about 10%, about 5%, about 1% or about 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of *S. pyogenes, S. aureus*, or *S. thermophilus*. In certain embodiments, the reference Cas9 molecule is the naturally occurring Cas9 molecule having the closest sequence identity or homology.

In certain embodiments, an eaCas9 molecule or eaCas9 polypeptide comprises an inactive, or cleavage incompetent, HNH domain and an active, or cleavage competent, N-terminal RuvC-like domain (e.g., a RuvC-like domain described herein, e.g., SEQ ID NOs:15-23). Exemplary inactive, or cleavage incompetent HNH-like domains can have a mutation at one or more of: a histidine in an HNH-like domain, e.g., a histidine shown at position 856 of the consensus sequence disclosed in FIGS. 2A-2G, e.g., can be substituted with an alanine; and one or more asparagines in an HNH-like domain, e.g., an asparagine shown at position 870 of the consensus sequence disclosed in FIGS. 2A-2G and/or at position 879 of the consensus sequence disclosed in FIGS. 2A-2G, e.g., can be substituted with an alanine. In certain embodiments, the eaCas9 differs from wild-type in the HNH-like domain and does not cleave the target nucleic acid, or cleaves with significantly less efficiency, e.g., less than about 20%, about 10%, about 5%, about 1% or about 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of *S. pyogenes, S. aureus*, or *S. thermophilus*. In certain embodiments, the reference Cas9 molecule is the naturally occurring Cas9 molecule having the closest sequence identity or homology.

In certain embodiments, exemplary Cas9 activities comprise one or more of PAM specificity, cleavage activity, and helicase activity. A mutation(s) can be present, e.g., in: one or more RuvC domains, e.g., an N-terminal RuvC domain; an HNH domain; a region outside the RuvC domains and the HNH domain. In certain embodiments, a mutation(s) is present in a RuvC domain. In certain embodiments, a mutation(s) is present in an HNH domain. In certain embodiments, mutations are present in both a RuvC domain and an HNH domain.

Exemplary mutations that may be made in the RuvC domain with reference to the *S. pyogenes* Cas9 sequence include: D10A, E762A, and/or D986A. Exemplary mutations that may be made in the HNH domain with reference to the *S. pyogenes* Cas9 sequence include: H840A, N854A, and/or N863A. Exemplary mutations that may be made in the RuvC domain with reference to the *S. aureus* Cas9 sequence include: D10A (see, e.g., SEQ ID NO:10). Exemplary mutations that may be made in the HNH domain with reference to the *S. aureus* Cas9 sequence include: N580A (see, e.g., SEQ ID NO:11).

Whether or not a particular sequence, e.g., a substitution, may affect one or more activity, such as targeting activity, cleavage activity, etc., can be evaluated or predicted, e.g., by evaluating whether the mutation is conservative. In certain embodiments, a "non-essential" amino acid residue, as used in the context of a Cas9 molecule, is a residue that can be altered from the wild-type sequence of a Cas9 molecule, e.g., a naturally occurring Cas9 molecule, e.g., an eaCas9 molecule, without abolishing or more preferably, without substantially altering a Cas9 activity (e.g., cleavage activity), whereas changing an "essential" amino acid residue results in a substantial loss of activity (e.g., cleavage activity).

In certain embodiments, a Cas9 molecule or Cas9 polypeptide comprises a cleavage property that differs from naturally occurring Cas9 molecules, e.g., that differs from the naturally occurring Cas9 molecule having the closest homology. For example, a Cas9 molecule can differ from naturally occurring Cas9 molecules, e.g., a Cas9 molecule of *S aureus* or *S. pyogenes*, as follows: its ability to modulate, e.g., decreased or increased, cleavage of a double stranded break (endonuclease and/or exonuclease activity), e.g., as compared to a naturally occurring Cas9 molecule (e.g., a Cas9 molecule of *S aureus* or *S. pyogenes*); its ability to modulate, e.g., decreased or increased, cleavage of a single strand of a nucleic acid, e.g., a non-complimentary strand of a nucleic acid molecule or a complementary strand of a nucleic acid molecule (nickase activity), e.g., as compared to a naturally occurring Cas9 molecule (e.g., a Cas9 molecule of *S aureus* or *S. pyogenes*); or the ability to cleave a nucleic acid molecule, e.g., a double stranded or single stranded nucleic acid molecule, can be eliminated. In certain embodiments, the nickase is *S. aureus* Cas9-derived nickase comprising the sequence of SEQ ID NO:10 (D10A) or SEQ ID NO:11 (N580A) (Friedland 2015).

In certain embodiments, the altered Cas9 molecule is an eaCas9 molecule comprising one or more of the following activities: cleavage activity associated with a RuvC domain; cleavage activity associated with an HNH domain; cleavage activity associated with an HNH domain and cleavage activity associated with a RuvC domain.

In certain embodiments, the altered Cas9 molecule or Cas9 polypeptide comprises a sequence in which:

the sequence corresponding to the fixed sequence of the consensus sequence disclosed in FIGS. 2A-2G differs at no more than about 1%, about 2%, about 3%, about 4%, about 5%, about 10%, about 15%, or about 20% of the fixed residues in the consensus sequence disclosed in FIGS. 2A-2G; and the sequence corresponding to the residues identified by "*" in the consensus sequence disclosed in FIGS. 2A-2G differs at no more than about 1%, about 2%, about 3%, about 4%, about 5%, about 10%, about 15%, about 20%, about 25%, about 30%, about 35%, or about 40% of the "*" residues from the corresponding sequence of naturally occurring Cas9 molecule, e.g., an *S. pyogenes, S. thermophilus, S. mutans*, or *L. innocua* Cas9 molecule.

In certain embodiments, the altered Cas9 molecule or Cas9 polypeptide is an eaCas9 molecule or eaCas9 polypeptide comprising the amino acid sequence of *S. pyogenes* Cas9 disclosed in FIGS. 2A-2G with one or more amino acids that differ from the sequence of *S. pyogenes* (e.g., substitutions) at one or more residues (e.g., 2, 3, 5, 10, 15, 20, 30, 50, 70, 80, 90, 100, or 200 amino acid residues) represented by an "*" in the consensus sequence disclosed in FIGS. 2A-2G.

In certain embodiments, the altered Cas9 molecule or Cas9 polypeptide is an eaCas9 molecule or eaCas9 polypeptide comprising the amino acid sequence of *S. thermophilus* Cas9 disclosed in FIGS. 2A-2G with one or more amino acids that differ from the sequence of *S. thermophilus* (e.g., substitutions) at one or more residues (e.g., 2, 3, 5, 10, 15, 20, 30, 50, 70, 80, 90, 100, or 200 amino acid residues) represented by an "*" in the consensus sequence disclosed in FIGS. 2A-2G.

In certain embodiments, the altered Cas9 molecule or Cas9 polypeptide is an eaCas9 molecule or eaCas9 polypeptide comprising the amino acid sequence of *S. mutans* Cas9 disclosed in FIGS. 2A-2G with one or more amino acids that differ from the sequence of *S. mutans* (e.g., substitutions) at one or more residues (e.g., 2, 3, 5, 10, 15, 20, 30, 50, 70, 80, 90, 100, or 200 amino acid residues) represented by an "*" in the consensus sequence disclosed in FIGS. 2A-2G.

In certain embodiments, the altered Cas9 molecule or Cas9 polypeptide is an eaCas9 molecule or eaCas9 polypeptide comprising the amino acid sequence of *L. innocua* Cas9 disclosed in FIGS. 2A-2G with one or more amino acids that differ from the sequence of *L. innocua* (e.g., substitutions) at one or more residues (e.g., 2, 3, 5, 10, 15, 20, 30, 50, 70, 80, 90, 100, or 200 amino acid residues) represented by an "*" in the consensus sequence disclosed in FIGS. 2A-2G.

In certain embodiments, the altered Cas9 molecule or Cas9 polypeptide, e.g., an eaCas9 molecule or eaCas9 polypeptide, can be a fusion, e.g., of two of more different Cas9 molecules, e.g., of two or more naturally occurring Cas9 molecules of different species. For example, a fragment of a naturally occurring Cas9 molecule of one species can be fused to a fragment of a Cas9 molecule of a second species. As an example, a fragment of a Cas9 molecule of *S. pyogenes* comprising an N-terminal RuvC-like domain can be fused to a fragment of Cas9 molecule of a species other than *S. pyogenes* (e.g., *S. thermophilus*) comprising an HNH-like domain.

7.6 Cas9 with Altered or No PAM Recognition

Naturally occurring Cas9 molecules can recognize specific PAM sequences, for example the PAM recognition sequences described above for, e.g., *S. pyogenes, S. thermophilus, S. mutans*, and *S. aureus*.

In certain embodiments, a Cas9 molecule or Cas9 polypeptide has the same PAM specificities as a naturally occurring Cas9 molecule. In certain embodiments, a Cas9 molecule or Cas9 polypeptide has a PAM specificity not associated with a naturally occurring Cas9 molecule, or a PAM specificity not associated with the naturally occurring Cas9 molecule to which it has the closest sequence homology. For example, a naturally occurring Cas9 molecule can be altered, e.g., to alter PAM recognition, e.g., to alter the PAM sequence that the Cas9 molecule or Cas9 polypeptide recognizes in order to decrease off-target sites and/or improve specificity; or eliminate a PAM recognition requirement. In certain embodiments, a Cas9 molecule or Cas9 polypeptide can be altered, e.g., to increase length of PAM recognition sequence and/or improve Cas9 specificity to high level of identity (e.g., about 98%, about 99% or about 100% match between gRNA and a PAM sequence), e.g., to decrease off-target sites and/or increase specificity. In certain embodiments, the length of the PAM recognition sequence is at least 4, 5, 6, 7, 8, 9, 10 or 15 amino acids in length. In certain embodiments, the Cas9 specificity requires at least about 90%, about 95%, about 96%, about 97%, about 98%, or about 99% homology between the gRNA and the PAM sequence. Cas9 molecules or Cas9 polypeptides that recognize different PAM sequences and/or have reduced off-target activity can be generated using directed evolution. Exemplary methods and systems that can be used for directed evolution of Cas9 molecules are described (see, e.g., Esvelt 2011). Candidate Cas9 molecules can be evaluated, e.g., by methods described below.

7.7 Size-Optimized Cas9

Engineered Cas9 molecules and engineered Cas9 polypeptides described herein include a Cas9 molecule or Cas9 polypeptide comprising a deletion that reduces the size of the molecule while still retaining desired Cas9 properties, e.g., essentially native conformation, Cas9 nuclease activity, and/or target nucleic acid molecule recognition. Provided herein are Cas9 molecules or Cas9 polypeptides comprising one or more deletions and optionally one or more linkers, wherein a linker is disposed between the amino acid residues that flank the deletion. Methods for identifying suitable deletions in a reference Cas9 molecule, methods for generating Cas9 molecules with a deletion and a linker, and methods for using such Cas9 molecules will be apparent to one of ordinary skill in the art upon review of this document.

A Cas9 molecule, e.g., an *S. aureus* or *S. pyogenes* Cas9 molecule, having a deletion is smaller, e.g., has reduced number of amino acids, than the corresponding naturally-occurring Cas9 molecule. The smaller size of the Cas9 molecules allows increased flexibility for delivery methods, and thereby increases utility for genome editing. A Cas9 molecule can comprise one or more deletions that do not substantially affect or decrease the activity of the resultant Cas9 molecules described herein. Activities that are retained in the Cas9 molecules comprising a deletion as described herein include one or more of the following:

a nickase activity, i.e., the ability to cleave a single strand, e.g., the non-complementary strand or the complementary strand, of a nucleic acid molecule; a double stranded nuclease activity, i.e., the ability to cleave both strands of a double stranded nucleic acid and create a double stranded break, which in certain embodiments is the presence of two nickase activities;

an endonuclease activity;

an exonuclease activity;

a helicase activity, i.e., the ability to unwind the helical structure of a double stranded nucleic acid;

and recognition activity of a nucleic acid molecule, e.g., a target nucleic acid or a gRNA.

Activity of the Cas9 molecules described herein can be assessed using the activity assays described herein or in the art.

7.8 Identifying Regions Suitable for Deletion

Suitable regions of Cas9 molecules for deletion can be identified by a variety of methods. Naturally-occurring orthologous Cas9 molecules from various bacterial species can be modeled onto the crystal structure of *S. pyogenes* Cas9 (Nishimasu 2014) to examine the level of conservation across the selected Cas9 orthologs with respect to the three-dimensional conformation of the protein. Less conserved or unconserved regions that are spatially located distant from regions involved in Cas9 activity, e.g., interface with the target nucleic acid molecule and/or gRNA, represent regions or domains are candidates for deletion without substantially affecting or decreasing Cas9 activity.

7.9 Nucleic Acids Encoding Cas9 Molecules

Nucleic acids encoding the Cas9 molecules or Cas9 polypeptides, e.g., an eaCas9 molecule or eaCas9 polypeptides are provided herein. Exemplary nucleic acids encoding Cas9 molecules or Cas9 polypeptides have been described previously (see, e.g., Cong 2013; Wang 2013; *Mali* 2013; Jinek 2012).

In certain embodiments, a nucleic acid encoding a Cas9 molecule or Cas9 polypeptide can be a synthetic nucleic acid sequence. For example, the synthetic nucleic acid molecule can be chemically modified, e.g., as described herein. In certain embodiments, the Cas9 mRNA has one or more (e.g., all of the following properties: it is capped, polyadenylated, substituted with 5-methylcytidine and/or pseudouridine.

Additionally or alternatively, the synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein.

Additionally or alternatively, a nucleic acid encoding a Cas9 molecule or Cas9 polypeptide may comprise a nuclear localization sequence (NLS). Nuclear localization sequences are known in the art.

An exemplary codon optimized nucleic acid sequence encoding a Cas9 molecule of *S. pyogenes* is set forth in SEQ ID NO:3. The corresponding amino acid sequence of an *S. pyogenes* Cas9 molecule is set forth in SEQ ID NO:2. In certain embodiments, the *S. pyogenes* Cas9 molecule is an *S. pyogenes* Cas9 variant. In certain embodiments, the *S. pyogenes* Cas9 variant is a EQR variant that has a sequence set forth in SEQ ID NO: 208. In certain embodiments, the *S. pyogenes* Cas9 variant is a VRER variant that has a sequence set forth in SEQ ID NO: 209.

Exemplary codon optimized nucleic acid sequences encoding an *S. aureus* Cas9 molecule are set forth in SEQ ID NOs:7-9, 206 and 207. In certain embodiments, the Cas9 molecule is a mutant *S. aureus* Cas9 molecule comprising a D10A mutation. In certain embodiments, the mutant *S.* aureus Cas9 molecule comprising a D10A mutation has a sequence set forth in SEQ ID NO: 10. In certain embodiments, the Cas9 molecule is a mutant *S. aureus* Cas9 molecule comprising a N580 mutation. In certain embodiments, the mutant *S. aureus* Cas9 molecule comprising a N580 mutation has a sequence set forth in SEQ ID NO: 11. An amino acid sequence of an *S. aureus* Cas9 molecule is set forth in SEQ ID NO:6.

If any of the above Cas9 sequences are fused with a peptide or polypeptide at the C-terminus, it is understood that the stop codon can be removed.

7.10 Other Cas Molecules and Cas Polypeptides

Various types of Cas molecules or Cas polypeptides can be used to practice the inventions disclosed herein. In certain embodiments, Cas molecules of Type II Cas systems are used. In certain embodiments, Cas molecules of other Cas systems are used. For example, Type I or Type III Cas molecules may be used. Exemplary Cas molecules (and Cas systems) have been described previously (see, e.g., Haft 2005 and Makarova 2011). Exemplary Cas molecules (and Cas systems) are also shown in Table 13.

TABLE 13

Cas Systems

| Gene name[‡] | System type or subtype | Name from Haft 2005[§] | Structure of encoded protein (PDB accessions)[¶] | Families (and superfamily) of encoded protein[#][**] | Representatives |
|---|---|---|---|---|---|
| cas1 | Type I<br>Type II<br>Type III | cas1 | 3GOD, 3LFX and 2YZS | COG1518 | SERP2463, SPy1047 and ygbT |
| cas2 | Type I<br>Type II<br>Type III | cas2 | 2IVY, 2I8E and 3EXC | COG1343 and COG3512 | SERP2462, SPy1048, SPy1723 (N-terminal domain) and ygbF |
| cas3' | Type I[‡‡] | cas3 | NA | COG1203 | APE1232 and ygcB |
| cas3" | Subtype I-A<br>Subtype I-B | NA | NA | COG2254 | APE1231 and BH0336 |
| cas4 | Subtype I-A<br>Subtype I-B<br>Subtype I-C<br>Subtype I-D<br>Subtype II-B | cas4 and csa1 | NA | COG1468 | APE1239 and BH0340 |
| cas5 | Subtype I-A<br>Subtype I-B<br>Subtype I-C<br>Subtype I-E | cas5a, cas5d, cas5e, cas5h, cas5p, cas5t and cmx5 | 3KG4 | COG1688 (RAMP) | APE1234, BH0337, devS and ygcI |
| cas6 | Subtype I-A<br>Subtype I-B<br>Subtype I-D<br>Subtype III-A<br>Subtype III-B | cas6 and cmx6 | 3I4H | COG1583 and COG5551 (RAMP) | PF1131 and slr7014 |
| cas6e | Subtype I-E | cse3 | 1WJ9 | (RAMP) | ygcH |
| cas6f | Subtype I-F | csy4 | 2XLJ | (RAMP) | y1727 |
| cas7 | Subtype I-A<br>Subtype I-B<br>Subtype I-C<br>Subtype I-E | csa2, csd2, cse4, csh2, csp1 and cst2 | NA | COG1857 and COG3649 (RAMP) | devR and ygcJ |

TABLE 13-continued

| Cas Systems | | | | | |
|---|---|---|---|---|---|
| Gene name‡ | System type or subtype | Name from Haft 2005§ | Structure of encoded protein (PDB accessions)¶ | Families (and superfamily) of encoded protein#** | Representatives |
| cas8a1 | Subtype I-A‡‡ | cmx1, cst1, csx8, csx13 and CXXC-CXXC | NA | BH0338-like | LA3191§§ and PG2018§§ |
| cas8a2 | Subtype I-A‡‡ | csa4 and csx9 | NA | PH0918 | AF0070, AF1873, MJ0385, PF0637, PH0918 and SSO1401 |
| cas8b | Subtype I-B‡‡ | csh1 and TM1802 | NA | BH0338-like | MTH1090 and TM1802 |
| cas8c | Subtype I-C‡‡ | csd1 and csp2 | NA | BH0338-like | BH0338 |
| cas9 | Type II‡‡ | csn1 and csx12 | NA | COG3513 | FTN_0757 and SPy1046 |
| cas10 | Type III‡‡ | cmr2, csm1 and csx11 | NA | COG1353 | MTH326, Rv2823c§§ and TM1794§§ |
| cas10d | Subtype I-D‡‡ | csc3 | NA | COG1353 | slr7011 |
| csy1 | Subtype I-F‡‡ | csy1 | NA | y1724-like | y1724 |
| csy2 | Subtype I-F | csy2 | NA | (RAMP) | y1725 |
| csy3 | Subtype I-F | csy3 | NA | (RAMP) | y1726 |
| cse1 | Subtype I-E‡‡ | cse1 | NA | YgcL-like | ygcL |
| cse2 | Subtype I-E | cse2 | 2ZCA | YgcK-like | ygcK |
| csc1 | Subtype I-D | csc1 | NA | alr1563-like (RAMP) | alr1563 |
| csc2 | Subtype I-D | csc1 and csc2 | NA | COG1337 (RAMP) | slr7012 |
| csa5 | Subtype I-A | csa5 | NA | AF1870 | AF1870, MJ0380, PF0643 and SSO1398 |
| csn2 | Subtype II-A | csn2 | NA | SPy1049-like | SPy1049 |
| csm2 | Subtype III-A‡‡ | csm2 | NA | COG1421 | MTH1081 and SERP2460 |
| csm3 | Subtype III-A | csc2 and csm3 | NA | COG1337 (RAMP) | MTH1080 and SERP2459 |
| csm4 | Subtype III-A | csm4 | NA | COG1567 (RAMP) | MTH1079 and SERP2458 |
| csm5 | Subtype III-A | csm5 | NA | COG1332 (RAMP) | MTH1078 and SERP2457 |
| csm6 | Subtype III-A | APE2256 and csm6 | 2WTE | COG1517 | APE2256 and SSO1445 |
| cmr1 | Subtype III-B | cmr1 | NA | COG1367 (RAMP) | PF1130 |
| cmr3 | Subtype III-B | cmr3 | NA | COG1769 (RAMP) | PF1128 |
| cmr4 | Subtype III-B | cmr4 | NA | COG1336 (RAMP) | PF1126 |
| cmr5 | Subtype III-B‡‡ | cmr5 | 2ZOP and 2OEB | COG3337 | MTH324 and PF1125 |
| cmr6 | Subtype III-B | cmr6 | NA | COG1604 (RAMP) | PF1124 |
| csb1 | Subtype I-U | GSU0053 | NA | (RAMP) | Balac_1306 and GSU0053 |

TABLE 13-continued

Cas Systems

| Gene name‡ | System type or subtype | Name from Haft 2005§ | Structure of encoded protein (PDB accessions)¶ | Families (and superfamily) of encoded protein#** | Representatives |
|---|---|---|---|---|---|
| csb2 | Subtype I-U§§ | NA | NA | (RAMP) | Balac_1305 and GSU0054 |
| csb3 | Subtype I-U | NA | NA | (RAMP) | Balac_1303§§ |
| csx17 | Subtype I-U | NA | NA | NA | Btus_2683 |
| csx14 | Subtype I-U | NA | NA | NA | GSU0052 |
| csx10 | Subtype I-U | csx10 | NA | (RAMP) | Caur_2274 |
| csx16 | Subtype I-U | VVA1548 | NA | NA | VVA1548 |
| csaX | Subtype III-U | csaX | NA | NA | SSO1438 |
| csx3 | Subtype III-U | csx3 | NA | NA | AF1864 |
| csx1 | Subtype III-U | csa3, csx1, csx2, DXTHG, NE0113 and TIGR02710 | 1XMX and 2171 | COG1517 and COG4006 | MJ1666, NE0113, PF1127 and TM1812 |
| csx15 | Unknown | NA | NA | TTE2665 | TTE2665 |
| csf1 | Type U | csf1 | NA | NA | AFE_1038 |
| csf2 | Type U | csf2 | NA | (RAMP) | AFE_1039 |
| csf3 | Type U | csf3 | NA | (RAMP) | AFE_1040 |
| csf4 | Type U | csf4 | NA | NA | AFE_1037 |

8. Functional Analysis of Candidate Molecules

Candidate Cas9 molecules, candidate gRNA molecules, candidate Cas9 molecule/gRNA molecule complexes, can be evaluated by art-known methods or as described herein. For example, exemplary methods for evaluating the endonuclease activity of Cas9 molecule have been described previously (Jinek 2012).

8.1 Binding and Cleavage Assay: Testing Cas9 Endonuclease Activity

The ability of a Cas9 molecule/gRNA molecule complex to bind to and cleave a target nucleic acid can be evaluated in a plasmid cleavage assay. In this assay, synthetic or in vitro-transcribed gRNA molecule is pre-annealed prior to the reaction by heating to 95° C. and slowly cooling down to room temperature. Native or restriction digest-linearized plasmid DNA (300 ng (~8 nM)) is incubated for 60 min at 37° C. with purified Cas9 protein molecule (50-500 nM) and gRNA (50-500 nM, 1:1) in a Cas9 plasmid cleavage buffer (20 mM HEPES pH 7.5, 150 mM KCl, 0.5 mM DTT, 0.1 mM EDTA) with or without 10 mM $MgCl_2$. The reactions are stopped with 5×DNA loading buffer (30% glycerol, 1.2% SDS, 250 mM EDTA), resolved by a 0.8 or 1% agarose gel electrophoresis and visualized by ethidium bromide staining. The resulting cleavage products indicate whether the Cas9 molecule cleaves both DNA strands, or only one of the two strands. For example, linear DNA products indicate the cleavage of both DNA strands. Nicked open circular products indicate that only one of the two strands is cleaved.

Alternatively, the ability of a Cas9 molecule/gRNA molecule complex to bind to and cleave a target nucleic acid can be evaluated in an oligonucleotide DNA cleavage assay. In this assay, DNA oligonucleotides (10 pmol) are radiolabeled by incubating with 5 units T4 polynucleotide kinase and ~3-6 pmol (~20-40 mCi) [γ-32P]-ATP in 1×T4 polynucleotide kinase reaction buffer at 37° C. for 30 min, in a 50 μL reaction. After heat inactivation (65° C. for 20 min), reactions are purified through a column to remove unincorporated label. Duplex substrates (100 nM) are generated by annealing labeled oligonucleotides with equimolar amounts of unlabeled complementary oligonucleotide at 95° C. for 3 min, followed by slow cooling to room temperature. For cleavage assays, gRNA molecules are annealed by heating to 95° C. for 30 s, followed by slow cooling to room temperature. Cas9 (500 nM final concentration) is pre-incubated with the annealed gRNA molecules (500 nM) in cleavage assay buffer (20 mM HEPES pH 7.5, 100 mM KCl, 5 mM MgCl2, 1 mM DTT, 5% glycerol) in a total volume of 9 μL. Reactions are initiated by the addition of 1 μL target DNA (10 nM) and incubated for 1 h at 37° C. Reactions are quenched by the addition of 20 μL of loading dye (5 mM EDTA, 0.025% SDS, 5% glycerol in formamide) and heated to 95° C. for 5 min. Cleavage products are resolved on 12% denaturing polyacrylamide gels containing 7 M urea and visualized by phosphorimaging. The resulting cleavage products indicate that whether the complementary strand, the non-complementary strand, or both, are cleaved.

One or both of these assays can be used to evaluate the suitability of a candidate gRNA molecule or candidate Cas9 molecule.

8.2 Binding Assay: Testing the Binding of Cas9 Molecule to Target DNA

Exemplary methods for evaluating the binding of Cas9 molecule to target DNA have been described previously, e.g., in Jinek et al., SCIENCE 2012; 337(6096):816-821.

For example, in an electrophoretic mobility shift assay, target DNA duplexes are formed by mixing of each strand (10 nmol) in deionized water, heating to 95° C. for 3 min and slow cooling to room temperature. All DNAs are purified on 8% native gels containing 1×TBE. DNA bands are visualized by UV shadowing, excised, and eluted by soaking gel pieces in DEPC-treated $H_2O$. Eluted DNA is ethanol precipitated and dissolved in DEPC-treated $H_2O$. DNA samples are 5' end labeled with [γ-32P]-ATP using T4 polynucleotide kinase for 30 min at 37° C. Polynucleotide kinase is heat denatured at 65° C. for 20 min, and unincorporated radiolabel is removed using a column. Binding assays are performed in buffer containing 20 mM HEPES pH 7.5, 100 mM KCl, 5 mM $MgCl_2$, 1 mM DTT and 10% glycerol in a total volume of 10 µL. Cas9 protein molecule is programmed with equimolar amounts of pre-annealed gRNA molecule and titrated from 100 µM to 1 µM. Radiolabeled DNA is added to a final concentration of 20 µM. Samples are incubated for 1 h at 37° C. and resolved at 4° C. on an 8% native polyacrylamide gel containing 1×TBE and 5 mM $MgCl_2$. Gels are dried and DNA visualized by phosphorimaging.

8.3 Differential Scanning Flourimetry (DSF)

The thermostability of Cas9-gRNA ribonucleoprotein (RNP) complexes can be measured via DSF. This technique measures the thermostability of a protein, which can increase under favorable conditions such as the addition of a binding RNA molecule, e.g., a gRNA.

The assay is performed using two different protocols, one to test the best stoichiometric ratio of gRNA:Cas9 protein and another to determine the best solution conditions for RNP formation.

To determine the best solution to form RNP complexes, a 2 uM solution of Cas9 in water+10×SYPRO Orange® (Life Technologies cat #S-6650) and dispensed into a 384 well plate. An equimolar amount of gRNA diluted in solutions with varied pH and salt is then added. After incubating at room temperature for 10' and brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

The second assay consists of mixing various concentrations of gRNA with 2 uM Cas9 in optimal buffer from assay 1 above and incubating at RT for 10' in a 384 well plate. An equal volume of optimal buffer+10×SYPRO Orange® (Life Technologies cat #S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° increase in temperature every 10 seconds.

9. Genome Editing Approaches

Described herein are compositions, genome editing systems and methods for targeted alteration (e.g., knockout) of the RS1, RL2, and/or LAT gene(s), e.g., one or both alleles of the RS1, RL2, and/or LAT gene(s), e.g., using one or more of the approaches or pathways described herein, e.g., using NHEJ. Described herein are also methods for targeted knockdown of the RS1, RL2, and/or LAT gene(s).

9.1 NHEJ Approaches for Gene Targeting

In certain embodiments of the methods provided herein, NHEJ-mediated alteration is used to alter an HSV RS1 target position, an HSV RL2 target position, or an HSV LAT target position. As described herein, nuclease-induced non-homologous end-joining (NHEJ) can be used to target gene-specific knockouts. Nuclease-induced NHEJ can also be used to remove (e.g., delete) sequence insertions in a gene of interest.

In certain embodiments, the genomic alterations associated with the methods described herein rely on nuclease-induced NHEJ and the error-prone nature of the NHEJ repair pathway. NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein. The indel mutations generated by NHEJ are unpredictable in nature; however, at a given break site certain indel sequences are favored and are over represented in the population, likely due to small regions of microhomology. The lengths of deletions can vary widely; they are most commonly in the 1-50 bp range, but can reach greater than 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it can also be used to delete small sequence motifs (e.g., motifs less than or equal to 50 nucleotides in length) as long as the generation of a specific final sequence is not required. If a double-strand break is targeted near to a target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. In this way, DNA segments as large as several hundred kilobases can be deleted. Both of these approaches can be used to delete specific DNA sequences; however, the error-prone nature of NHEJ may still produce indel mutations at the site of repair.

Both double strand cleaving eaCas9 molecules and single strand, or nickase, eaCas9 molecules can be used in the methods and compositions described herein to generate NHEJ-mediated indels. NHEJ-mediated indels targeted to the early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

9.1.1 Placement of Double Strand or Single Strand Breaks Relative to the Target Position In certain embodiments, in which a gRNA and Cas9 nuclease generate a double strand break for the purpose of inducing NHEJ-mediated indels, a gRNA, e.g., a unimolecular (or chimeric) or modular gRNA molecule, is configured to position one double-strand break in close proximity to a nucleotide of the target position. In certain embodiments, the cleavage site is between 0-30 bp away from the target position (e.g., less than 30, 25, 20, 15, 10, 9, 8, 7, 6, 5, 4, 3, 2 or 1 bp from the target position).

In certain embodiments, in which two gRNAs complexing with Cas9 nickases induce two single strand breaks for the purpose of inducing NHEJ-mediated indels, two gRNAs, e.g., independently, unimolecular (or chimeric) or modular gRNA, are configured to position two single-strand breaks to provide for NHEJ repair a nucleotide of the target position. In certain embodiments, the gRNAs are configured to position cuts at the same position, or within a few nucleotides of one another, on different strands, essentially mimicking a double strand break. In certain embodiments, the closer nick is between 0-30 bp away from the target position (e.g., less than 30, 25, 20, 15, 10, 9, 8, 7, 6, 5, 4, 3, 2 or 1 bp from the target position), and the two nicks are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp). In certain embodiments, the gRNAs are configured to place a single strand break on either side of a nucleotide of the target position.

Both double strand cleaving eaCas9 molecules and single strand, or nickase, eaCas9 molecules can be used in the methods and compositions described herein to generate breaks both sides of a target position. Double strand or paired single strand breaks may be generated on both sides of a target position to remove the nucleic acid sequence between the two cuts (e.g., the region between the two breaks in deleted). In certain embodiments, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a cas9 nuclease) and two single strand breaks or paired single stranded breaks (i.e., two gRNAs complex with Cas9 nickases) on either side of the target position. In certain embodiments, four gRNAs, e.g., independently, unimolecular (or chimeric) or modular gRNA, are configured to generate two pairs of single stranded breaks (i.e., two pairs of two gRNAs complex with Cas9 nickases) on either side of the target position. The double strand break(s) or the closer of the two single strand nicks in a pair can ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20, or 10 bp).

9.2 HDR Repair, HDR-Mediated Knock-in, and Template Nucleic Acids

In certain embodiments of the methods provided herein, HDR-mediated sequence alteration is used to alter the sequence of one or more nucleotides in a RS1, RL2 or LAT gene using an exogenously provided template nucleic acid (also referred to herein as a donor construct). In certain embodiments, HDR-mediated alteration of an HSV RS1 target position, an HSV RL2 target position, or an HSV LAT target position occurs by HDR with an exogenously provided donor template or template nucleic acid. For example, the donor construct or template nucleic acid provides for alteration of an HSV RS1 target position, an HSV RL2 target position, or an HSV LAT target position. In certain embodiments, a plasmid donor is used as a template for homologous recombination. In certain embodiments, a single stranded donor template is used as a template for alteration of the HSV RS1 target position, HSV RL2 target position, or HSV LAT target position sition by alternate methods of HDR (e.g., single strand annealing) between the target sequence and the donor template. Donor template-effected alteration of an HSV RS1 target position, an HSV RL2 target position, or an HSV LAT target position depends on cleavage by a Cas9 molecule. Cleavage by Cas9 can comprise a double strand break or two single strand breaks.

In certain embodiments, HDR-mediated sequence alteration is used to alter the sequence of one or more nucleotides in a RS1, RL2 or LAT gene without using an exogenously provided template nucleic acid. In certain embodiments, alteration of an HSV RS1 target position, an HSV RL2 target position, or an HSV LAT target position target position occurs by HDR with endogenous genomic donor sequence. For example, the endogenous genomic donor sequence provides for alteration of the RL2, LAT, or RS1 target position. In certain embodiments, the endogenous genomic donor sequence is located on the same chromosome as the target sequence. In certain embodiments, the endogenous genomic donor sequence is located on a different chromosome from the target sequence. Alteration of an HSV RS1 target position, an HSV RL2 target position, or an HSV LAT target position by endogenous genomic donor sequence depends on cleavage by a Cas9 molecule. Cleavage by Cas9 can comprise a double strand break or two single strand breaks.

In certain embodiments of the methods provided herein, HDR-mediated alteration is used to alter a single nucleotide in a RL2, LAT, or RS1 gene. These embodiments may utilize either one double-strand break or two single-strand breaks. In certain embodiments, a single nucleotide alteration is incorporated using (1) one double-strand break, (2) two single-strand breaks, (3) two double-strand breaks with a break occurring on each side of the target position, (4) one double-strand break and two single strand breaks with the double strand break and two single strand breaks occurring on each side of the target position, (5) four single-strand breaks with a pair of single-strand breaks occurring on each side of the target position, or (6) one single-strand break.

In certain embodiments, wherein a single-stranded template nucleic acid (e.g., a donor template) is used, the target position can be altered by alternative HDR.

Donor template-effected alteration of an HSV RS1 target position, an HSV RL2 target position, or an HSV LAT target position depends on cleavage by a Cas9 molecule. Cleavage by Cas9 can comprise a nick, a double-strand break, or two single-strand breaks, e.g., one on each strand of the target nucleic acid. After introduction of the breaks on the target nucleic acid, resection occurs at the break ends resulting in single stranded overhanging DNA regions.

In canonical HDR, a double-stranded donor template is introduced, comprising homologous sequence to the target nucleic acid that can either be directly incorporated into the target nucleic acid or used as a template to change the sequence of the target nucleic acid. After resection at the break, repair can progress by different pathways, e.g., by the double Holliday junction model (or double-strand break repair, DSBR, pathway) or the synthesis-dependent strand annealing (SDSA) pathway. In the double Holliday junction model, strand invasion by the two single stranded overhangs of the target nucleic acid to the homologous sequences in the donor template occurs, resulting in the formation of an intermediate with two Holliday junctions. The junctions migrate as new DNA is synthesized from the ends of the invading strand to fill the gap resulting from the resection. The end of the newly synthesized DNA is ligated to the resected end, and the junctions are resolved, resulting in alteration of the target nucleic acid. Crossover with the donor template may occur upon resolution of the junctions. In the SDSA pathway, only one single stranded overhang invades the donor template and new DNA is synthesized from the end of the invading strand to fill the gap resulting from resection. The newly synthesized DNA then anneals to the remaining single stranded overhang, new DNA is synthesized to fill in the gap, and the strands are ligated to produce the altered DNA duplex.

In alternative HDR, a single strand donor template, e.g., template nucleic acid, is introduced. A nick, single strand break, or double strand break at the target nucleic acid, for altering a desired target position, is mediated by a Cas9 molecule, e.g., described herein, and resection at the break occurs to reveal single stranded overhangs. Incorporation of the sequence of the template nucleic acid to alter an HSV RS1 target position, an HSV RL2 target position, or an HSV LAT target position typically occurs by the SDSA pathway, as described above.

Additional details on template nucleic acids are provided in Section IV entitled "Template nucleic acids" in International Application PCT/US2014/057905.

In certain embodiments, double strand cleavage is effected by a Cas9 molecule having cleavage activity associated with an HNH-like domain and cleavage activity associated with a RuvC-like domain, e.g., an N-terminal RuvC-like domain, e.g., a wild-type Cas9. Such embodiments require only a single gRNA.

In certain embodiments, one single-strand break, or nick, is effected by a Cas9 molecule having nickase activity, e.g., a Cas9 nickase as described herein (such as a D10A Cas9 nickase). A nicked target nucleic acid can be a substrate for alt-HDR.

In certain embodiments, two single-strand breaks, or nicks, are effected by a Cas9 molecule having nickase activity, e.g., cleavage activity associated with an HNH-like domain or cleavage activity associated with an N-terminal RuvC-like domain. Such embodiments usually require two gRNAs, one for placement of each single-strand break. In certain embodiments, the Cas9 molecule having nickase activity cleaves the strand to which the gRNA hybridizes, but not the strand that is complementary to the strand to which the gRNA hybridizes. In certain embodiments, the Cas9 molecule having nickase activity does not cleave the strand to which the gRNA hybridizes, but rather cleaves the strand that is complementary to the strand to which the gRNA hybridizes.

In certain embodiments, the nickase has HNH activity, e.g., a Cas9 molecule having the RuvC activity inactivated, e.g., a Cas9 molecule having a mutation at D10, e.g., the D10A mutation (see, e.g., SEQ ID NO:10). D10A inactivates RuvC; therefore, the Cas9 nickase has (only) HNH activity and can cut on the strand to which the gRNA hybridizes (e.g., the complementary strand, which does not have the NGG PAM on it). In certain embodiments, a Cas9 molecule having an H840, e.g., an H840A, mutation can be used as a nickase. H840A inactivates HNH; therefore, the Cas9 nickase has (only) RuvC activity and cuts on the non-complementary strand (e.g., the strand that has the NGG PAM and whose sequence is identical to the gRNA). In certain embodiments, a Cas9 molecule having an N863 mutation, e.g., the N863A mutation, mutation can be used as a nickase. N863A inactivates HNH therefore the Cas9 nickase has (only) RuvC activity and cuts on the non-complementary strand (the strand that has the NGG PAM and whose sequence is identical to the gRNA). In certain embodiments, a Cas9 molecule having an N580 mutation, e.g., the N580A mutation, mutation can be used as a nickase. N580A inactivates HNH therefore the Cas9 nickase has (only) RuvC activity and cuts on the non-complementary strand (the strand that has the NGG PAM and whose sequence is identical to the gRNA).

In certain embodiments, in which a nickase and two gRNAs are used to position two single strand nicks, one nick is on the + strand and one nick is on the − strand of the target nucleic acid. The PAMs can be outwardly facing. The gRNAs can be selected such that the gRNAs are separated by, from about 0-50, 0-100, or 0-200 nucleotides. In certain embodiments, there is no overlap between the target sequences that are complementary to the targeting domains of the two gRNAs. In certain embodiments, the gRNAs do not overlap and are separated by as much as 50, 100, or 200 nucleotides. In certain embodiments, the use of two gRNAs can increase specificity, e.g., by decreasing off-target binding (Ran 2013).

In certain embodiments, a single nick can be used to induce HDR, e.g., alt-HDR. In certain embodiments, a single nick can be used to increase the ratio of HR to NHEJ at a given cleavage site. In certain embodiments, a single strand break is formed in the strand of the target nucleic acid to which the targeting domain of said gRNA is complementary. In certain embodiments, a single strand break is formed in the strand of the target nucleic acid other than the strand to which the targeting domain of said gRNA is complementary.

9.2.1 Placement of Double Strand or Single Strand Breaks Relative to the Target Position A double strand break or single strand break in one of the strands should be sufficiently close to an HSV RS1 target position, an HSV RL2 target position, or an HSV LAT target position that an alteration is produced in the desired region. In certain embodiments, the distance is not more than 50, 100, 200, 300, 350 or 400 nucleotides. In certain embodiments, the break should be sufficiently close to target position such that the target position is within the region that is subject to exonuclease-mediated removal during end resection. If the distance between the HSV RS1 target position, HSV RL2 target position, or HSV LAT target position and a break is too great, the sequence desired to be altered may not be included in the end resection and, therefore, may not be altered, as donor sequence, either exogenously provided donor sequence or endogenous genomic donor sequence, in certain embodiments is only used to alter sequence within the end resection region.

In certain embodiments, the methods described herein introduce one or more breaks near an HSV RS1 target position, an HSV RL2 target position, or an HSV LAT target position. In certain of these embodiments, two or more breaks are introduced that flank an HSV RS1 target position, an HSV RL2 target position, or an HSV LAT target position. The two or more breaks remove (e.g., delete) a genomic sequence including an HSV RS1 target position, an HSV RL2 target position, or an HSV LAT target position. All methods described herein result in altering an HSV RS1 target position, an HSV RL2 target position, or an HSV LAT target position within a RS1, RL2, or LAT gene.

In certain embodiments, the gRNA targeting domain is configured such that a cleavage event, e.g., a double strand or single strand break, is positioned within 1, 2, 3, 4, 5, 10, 15, 20, 25, 30, 35, 40, 45, 50, 60, 70, 80, 90, 100, 150, or 200 nucleotides of the region desired to be altered, e.g., a mutation. The break, e.g., a double strand or single strand break, can be positioned upstream or downstream of the region desired to be altered, e.g., a mutation. In certain embodiments, a break is positioned within the region desired to be altered, e.g., within a region defined by at least two mutant nucleotides. In certain embodiments, a break is positioned immediately adjacent to the region desired to be altered, e.g., immediately upstream or downstream of a mutation.

In certain embodiments, a single strand break is accompanied by an additional single strand break, positioned by a second gRNA molecule, as discussed below. For example, the targeting domains bind configured such that a cleavage event, e.g., the two single strand breaks, are positioned within 1, 2, 3, 4, 5, 10, 15, 20, 25, 30, 35, 40, 45, 50, 60, 70, 80, 90, 100, 150, or 200 nucleotides of a target position. In certain embodiments, the first and second gRNA molecules are configured such that, when guiding a Cas9 nickase, a single strand break can be accompanied by an additional single strand break, positioned by a second gRNA, sufficiently close to one another to result in alteration of the desired region. In certain embodiments, the first and second gRNA molecules are configured such that a single strand break positioned by said second gRNA is within 10, 20, 30, 40, or 50 nucleotides of the break positioned by said first gRNA molecule, e.g., when the Cas9 is a nickase. In certain embodiments, the two gRNA molecules are configured to position cuts at the same position, or within a few nucleotides of one another, on different strands, e.g., essentially mimicking a double strand break.

In certain embodiments in which a gRNA (unimolecular (or chimeric) or modular gRNA) and Cas9 nuclease induce a double strand break for the purpose of inducing HDR-mediated sequence alteration, the cleavage site is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position. In certain embodiments, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In certain embodiments, one can promote HDR by using nickases to generate a break with overhangs. While not wishing to be bound by theory, the single stranded nature of the overhangs can enhance the cell's likelihood of repairing the break by HDR as opposed to, e.g., NHEJ. Specifically, in certain embodiments, HDR is promoted by selecting a first gRNA that targets a first nickase to a first target sequence, and a second gRNA that targets a second nickase to a second target sequence which is on the opposite DNA strand from the first target sequence and offset from the first nick.

In certain embodiments, the targeting domain of a gRNA molecule is configured to position a cleavage event sufficiently far from a preselected nucleotide that the nucleotide is not altered. In certain embodiments, the targeting domain of a gRNA molecule is configured to position an intronic cleavage event sufficiently far from an intron/exon border, or naturally occurring splice signal, to avoid alteration of the exonic sequence or unwanted splicing events. The gRNA molecule may be a first, second, third and/or fourth gRNA molecule, as described herein.

9.2.2 Placement of a First Break and a Second Break Relative to Each Other

In certain embodiments, a double strand break can be accompanied by an additional double strand break, positioned by a second gRNA molecule, as is discussed below.

In certain embodiments, a double strand break can be accompanied by two additional single strand breaks, positioned by a second gRNA molecule and a third gRNA molecule.

In certain embodiments, a first and second single strand breaks can be accompanied by two additional single strand breaks positioned by a third gRNA molecule and a fourth gRNA molecule.

When two or more gRNAs are used to position two or more cleavage events, e.g., double strand or single strand breaks, in a target nucleic acid, the two or more cleavage events may be made by the same or different Cas9 proteins. For example, when two gRNAs are used to position two double stranded breaks, a single Cas9 nuclease may be used to create both double stranded breaks. When two or more gRNAs are used to position two or more single stranded breaks (nicks), a single Cas9 nickase may be used to create the two or more nicks. When two or more gRNAs are used to position at least one double stranded break and at least one single stranded break, two Cas9 proteins may be used, e.g., one Cas9 nuclease and one Cas9 nickase. In certain embodiments, two or more Cas9 proteins are used, and the two or more Cas9 proteins may be delivered sequentially to control specificity of a double stranded versus a single stranded break at the desired position in the target nucleic acid.

In certain embodiments, the targeting domain of the first gRNA molecule and the targeting domain of the second gRNA molecules are complementary to opposite strands of the target nucleic acid molecule. In certain embodiments, the gRNA molecule and the second gRNA molecule are configured such that the PAMs are oriented outward.

In certain embodiments, two gRNA are selected to direct Cas9-mediated cleavage at two positions that are a preselected distance from each other. In certain embodiments, the two points of cleavage are on opposite strands of the target nucleic acid. In certain embodiments, the two cleavage points form a blunt ended break, and in other embodiments, they are offset so that the DNA ends comprise one or two overhangs (e.g., one or more 5' overhangs and/or one or more 3' overhangs). In certain embodiments, each cleavage event is a nick. In certain embodiments, the nicks are close enough together that they form a break that is recognized by the double stranded break machinery (as opposed to being recognized by, e.g., the SSBr machinery). In certain embodiments, the nicks are far enough apart that they create an overhang that is a substrate for HDR, i.e., the placement of the breaks mimics a DNA substrate that has experienced some resection. For instance, in certain embodiments the nicks are spaced to create an overhang that is a substrate for processive resection. In certain embodiments, the two breaks are spaced within 25-65 nucleotides of each other. The two breaks may be, e.g., about 25, 30, 35, 40, 45, 50, 55, 60, or 65 nucleotides of each other. The two breaks may be, e.g., at least about 25, 30, 35, 40, 45, 50, 55, 60, or 65 nucleotides of each other. The two breaks may be, e.g., at most about 30, 35, 40, 45, 50, 55, 60, or 65 nucleotides of each other. In certain embodiments, the two breaks are about 25-30, 30-35, 35-40, 40-45, 45-50, 50-55, 55-60, or 60-65 nucleotides of each other.

In certain embodiments, the break that mimics a resected break comprises a 3' overhang (e.g., generated by a DSB and a nick, where the nick leaves a 3' overhang), a 5' overhang (e.g., generated by a DSB and a nick, where the nick leaves a 5' overhang), a 3' and a 5' overhang (e.g., generated by three cuts), two 3' overhangs (e.g., generated by two nicks that are offset from each other), or two 5' overhangs (e.g., generated by two nicks that are offset from each other).

In certain embodiments in which two gRNAs (independently, unimolecular (or chimeric) or modular gRNA) complexing with Cas9 nickases induce two single strand breaks for the purpose of inducing HDR-mediated alteration, the closer nick is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, or 75 to 100 bp) away from the target position and the two nicks can ideally be within 25-65 bp of each other (e.g., 25 to 50, 25 to 45, 25 to 40, 25 to 35, 25 to 30, 30 to 55, 30 to 50, 30 to 45, 30 to 40, 30 to 35, 35 to 55, 35 to 50, 35 to 45, 35 to 40, 40 to 55, 40 to 50, 40 to 45 bp, 45 to 50 bp, 50 to 55 bp, 55 to 60 bp, or 60 to 65 bp) and no more than 100 bp away from each other (e.g., no more than 90, 80, 70, 60, 50, 40, 30, 20, 10, or 5 bp away from each other). In certain embodiments, the cleavage site is between 0-100 bp (e.g., 0 to 75, 0 to 50, 0 to 25, 25 to 100, 25 to 75, 25 to 50, 50 to 100, 50 to 75, or 75 to 100 bp) away from the target position.

In certain embodiments, two gRNAs, e.g., independently, unimolecular (or chimeric) or modular gRNA, are configured to position a double-strand break on both sides of a target position. In certain embodiments, three gRNAs, e.g., independently, unimolecular (or chimeric) or modular gRNA, are configured to position a double strand break (i.e., one gRNA complexes with a cas9 nuclease) and two single strand breaks or paired single stranded breaks (i.e., two gRNAs complex with Cas9 nickases) on either side of the target position. In certain embodiments, four gRNAs, e.g., independently, unimolecular (or chimeric) or modular gRNA, are configured to generate two pairs of single stranded breaks (i.e., two pairs of two gRNAs complex with Cas9 nickases) on either side of the target position. The double strand break(s) or the closer of the two single strand nicks in a pair can ideally be within 0-500 bp of the target position (e.g., no more than 450, 400, 350, 300, 250, 200, 150, 100, 50 or 25 bp from the target position). When nickases are used, the two nicks in a pair are, in certain embodiments, within 25-65 bp of each other (e.g., between 25 to 55, 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, 40 to 45 bp, 45 to 50 bp, 50 to 55 bp, 55 to 60 bp, or 60 to 65 bp) and no more than 100 bp away from each other (e.g., no more than 90, 80, 70, 60, 50, 40, 30, or 20 or 10 bp).

When two gRNAs are used to target Cas9 molecules to breaks, different combinations of Cas9 molecules are envisioned. In certain embodiments, a first gRNA is used to target a first Cas9 molecule to a first target position, and a second gRNA is used to target a second Cas9 molecule to a second target position. In certain embodiments, the first Cas9 molecule creates a nick on the first strand of the target nucleic acid, and the second Cas9 molecule creates a nick on the opposite strand, resulting in a double stranded break (e.g., a blunt ended cut or a cut with overhangs).

Different combinations of nickases can be chosen to target one single stranded break to one strand and a second single stranded break to the opposite strand. When choosing a combination, one can take into account that there are nickases having one active RuvC-like domain, and nickases having one active HNH domain. In certain embodiments, a RuvC-like domain cleaves the non-complementary strand of the target nucleic acid molecule. In certain embodiments, an HNH-like domain cleaves a single stranded complementary domain, e.g., a complementary strand of a double stranded nucleic acid molecule. Generally, if both Cas9 molecules have the same active domain (e.g., both have an active RuvC domain or both have an active HNH domain), one can choose two gRNAs that bind to opposite strands of the target. In more detail, in certain embodiments a first gRNA is complementary with a first strand of the target nucleic acid and binds a nickase having an active RuvC-like domain and causes that nickase to cleave the strand that is non-complementary to that first gRNA, i.e., a second strand of the target nucleic acid; and a second gRNA is complementary with a second strand of the target nucleic acid and binds a nickase having an active RuvC-like domain and causes that nickase to cleave the strand that is non-complementary to that second gRNA, i.e., the first strand of the target nucleic acid. Conversely, in certain embodiments, a first gRNA is complementary with a first strand of the target nucleic acid and binds a nickase having an active HNH domain and causes that nickase to cleave the strand that is complementary to that first gRNA, i.e., a first strand of the target nucleic acid; and a second gRNA is complementary with a second strand of the target nucleic acid and binds a nickase having an active HNH domain and causes that nickase to cleave the strand that is complementary to that second gRNA, i.e., the second strand of the target nucleic acid. In another arrangement, if one Cas9 molecule has an active RuvC-like domain and the other Cas9 molecule has an active HNH domain, the gRNAs for both Cas9 molecules can be complementary to the same strand of the target nucleic acid, so that the Cas9 molecule with the active RuvC-like domain can cleave the non-complementary strand and the Cas9 molecule with the HNH domain can cleave the complementary strand, resulting in a double stranded break.

9.2.3 Homology Arms of the Donor Template

A homology arm should extend at least as far as the region in which end resection may occur, e.g., in order to allow the resected single stranded overhang to find a complementary region within the donor template. The overall length could be limited by parameters such as plasmid size or viral packaging limits. In certain embodiments, a homology arm does not extend into repeated elements, e.g., Alu repeats or LINE repeats.

Exemplary homology arm lengths include at least 50, 100, 250, 500, 750, 1000, 2000, 3000, 4000, or 5000 nucleotides. In certain embodiments, the homology arm length is 50-100, 100-250, 250-500, 500-750, 750-1000, 1000-2000, 2000-3000, 3000-4000, or 4000-5000 nucleotides.

A template nucleic acid, as that term is used herein, refers to a nucleic acid sequence which can be used in conjunction with a Cas9 molecule and a gRNA molecule to alter the structure of an HSV RS1 target position, an HSV RL2 target position, or an HSV LAT target position. In certain embodiments, the HSV RS1 target position, HSV RL2 target position, or HSV LAT target position target position can be a site between two nucleotides, e.g., adjacent nucleotides, on the target nucleic acid into which one or more nucleotides is added. Alternatively, the HSV RS1 target position, HSV RL2 target position, or HSV LAT target position target position may comprise one or more nucleotides that are altered by a template nucleic acid.

In certain embodiments, the target nucleic acid is modified to have some or all of the sequence of the template nucleic acid, typically at or near cleavage site(s). In certain embodiments, the template nucleic acid is single stranded. In certain embodiments, the template nucleic acid is double stranded. In certain embodiments, the template nucleic acid is DNA, e.g., double stranded DNA. In certain embodiments, the template nucleic acid is single stranded DNA. In certain embodiments, the template nucleic acid is encoded on the same vector backbone, e.g. AAV genome, plasmid DNA, as the Cas9 and gRNA. In certain embodiments, the template nucleic acid is excised from a vector backbone in vivo, e.g., it is flanked by gRNA recognition sequences. In certain embodiments, the template nucleic acid comprises endogenous genomic sequence.

In certain embodiments, the template nucleic acid alters the structure of the target position by participating in an HDR event. In certain embodiments, the template nucleic acid alters the sequence of the target position. In certain embodiments, the template nucleic acid results in the incorporation of a modified, or non-naturally occurring base into the target nucleic acid.

Typically, the template sequence undergoes a breakage mediated or catalyzed recombination with the target sequence. In certain embodiments, the template nucleic acid includes sequence that corresponds to a site on the target sequence that is cleaved by an eaCas9 mediated cleavage event. In certain embodiments, the template nucleic acid includes sequence that corresponds to both a first site on the target sequence that is cleaved in a first Cas9 mediated event, and a second site on the target sequence that is cleaved in a second Cas9 mediated event.

A template nucleic acid typically comprises the following components:

[5' homology arm]-[replacement sequence]-[3' homology arm].

The homology arms provide for recombination into the chromosome, thus replacing the undesired element, e.g., a mutation or signature, with the replacement sequence. In certain embodiments, the homology arms flank the most distal cleavage sites.

In certain embodiments, the 3' end of the 5' homology arm is the position next to the 5' end of the replacement sequence. In certain embodiments, the 5' homology arm can extend at least 10, 20, 30, 40, 50, 100, 200, 300, 400, 500, 600, 700, 800, 900, 1000, 1500, 2000, 3000, 4000, or 5000 nucleotides 5' from the 5' end of the replacement sequence.

In certain embodiments, the 5' end of the 3' homology arm is the position next to the 3' end of the replacement sequence. In certain embodiments, the 3' homology arm can extend at least 10, 20, 30, 40, 50, 100, 200, 300, 400, 500, 600, 700, 800, 900, 1000, 1500, 2000, 3000, 4000, or 5000 nucleotides 3' from the 3' end of the replacement sequence.

In certain embodiments, to alter one or more nucleotides at an HSV RS1 target position, an HSV RL2 target position, or an HSV LAT target position, the homology arms, e.g., the 5' and 3' homology arms, may each comprise about 1000 bp of sequence flanking the most distal gRNAs (e.g., 1000 bp of sequence on either side of the HSV RS1 target position, HSV RL2 target position, or HSV LAT target position).

In certain embodiments, one or both homology arms may be shortened to avoid including certain sequence repeat elements, e.g., Alu repeats or LINE elements. For example, a 5' homology arm may be shortened to avoid a sequence repeat element. In certain embodiments, a 3' homology arm may be shortened to avoid a sequence repeat element. In certain embodiments, both the 5' and the 3' homology arms may be shortened to avoid including certain sequence repeat elements.

In certain embodiments, template nucleic acids for altering the sequence of an HSV RS1 target position, an HSV RL2 target position, or an HSV LAT target position may be designed for use as a single-stranded oligonucleotide, e.g., a single-stranded oligodeoxynucleotide (ssODN). When using a ssODN, 5' and 3' homology arms may range up to about 200 bp in length, e.g., at least 25, 50, 75, 100, 125, 150, 175, or 200 bp in length. Longer homology arms can also be for ssODNs as improvements in oligonucleotide synthesis continue to be made. In certain embodiments, a longer homology arm is made by a method other than chemical synthesis, e.g., by denaturing a long double stranded nucleic acid and purifying one of the strands, e.g., by affinity for a strand-specific sequence anchored to a solid substrate.

In certain embodiments, alt-HDR proceeds more efficiently when the template nucleic acid has extended homology 5' to the nick (i.e., in the 5' direction of the nicked strand). Accordingly, in certain embodiments, the template nucleic acid has a longer homology arm and a shorter homology arm, wherein the longer homology arm can anneal 5' of the nick. In certain embodiments, the arm that can anneal 5' to the nick is at least 25, 50, 75, 100, 125, 150, 175, or 200, 300, 400, 500, 600, 700, 800, 900, 1000, 1500, 2000, 3000, 4000, or 5000 nucleotides from the nick or the 5' or 3' end of the replacement sequence. In certain embodiments, the arm that can anneal 5' to the nick is at least about 10%, about 20%, about 30%, about 40%, or about 50% longer than the arm that can anneal 3' to the nick. In certain embodiments, the arm that can anneal 5' to the nick is at least 2×, 3×, 4×, or 5× longer than the arm that can anneal 3' to the nick. Depending on whether a ssDNA template can anneal to the intact strand or the nicked strand, the homology arm that anneals 5' to the nick may be at the 5' end of the ssDNA template or the 3' end of the ssDNA template, respectively.

Similarly, in certain embodiments, the template nucleic acid has a 5' homology arm, a replacement sequence, and a 3' homology arm, such that the template nucleic acid has extended homology to the 5' of the nick. For example, the 5' homology arm and 3' homology arm may be substantially the same length, but the replacement sequence may extend farther 5' of the nick than 3' of the nick. In certain embodiments, the replacement sequence extends at least about 10%, about 20%, about 30%, about 40%, about 50%, 2×, 3×, 4×, or 5× further to the 5' end of the nick than the 3' end of the nick.

In certain embodiments, alt-HDR proceeds more efficiently when the template nucleic acid is centered on the nick. Accordingly, in certain embodiments, the template nucleic acid has two homology arms that are essentially the same size. For instance, the first homology arm of a template nucleic acid may have a length that is within about 10%, about 9%, about 8%, about 7%, about 6%, about 5%, about 4%, about 3%, about 2%, or about 1% of the second homology arm of the template nucleic acid.

Similarly, in certain embodiments, the template nucleic acid has a 5' homology arm, a replacement sequence, and a 3' homology arm, such that the template nucleic acid extends substantially the same distance on either side of the nick. For example, the homology arms may have different lengths, but the replacement sequence may be selected to compensate for this. For example, the replacement sequence may extend further 5' from the nick than it does 3' of the nick, but the homology arm 5' of the nick is shorter than the homology arm 3' of the nick, to compensate. The converse is also possible, e.g., that the replacement sequence may extend further 3' from the nick than it does 5' of the nick, but the homology arm 3' of the nick is shorter than the homology arm 5' of the nick, to compensate.

9.2.4 Template Nucleic Acids

In certain embodiments, the template nucleic acid is double stranded. In certain embodiments, the template nucleic acid is single stranded. In certain embodiments, the template nucleic acid comprises a single stranded portion and a double stranded portion. In certain embodiments, the template nucleic acid comprises about 50 to 100 bp, e.g., 55 to 95, 60 to 90, 65 to 85, or 70 to 80 bp, homology on either side of the nick and/or replacement sequence. In certain embodiments, the template nucleic acid comprises about 50, 55, 60, 65, 70, 75, 80, 85, 90, 95, or 100 bp homology 5' of the nick or replacement sequence, 3' of the nick or replacement sequence, or both 5' and 3' of the nick or replacement sequences.

In certain embodiments, the template nucleic acid comprises about 150 to 200 bp, e.g., 155 to 195, 160 to 190, 165 to 185, or 170 to 180 bp, homology 3' of the nick and/or replacement sequence. In certain embodiments, the template nucleic acid comprises about 150, 155, 160, 165, 170, 175, 180, 185, 190, 195, or 200 bp homology 3' of the nick or replacement sequence. In certain embodiments, the template nucleic acid comprises less than about 100, 90, 80, 70, 60, 50, 40, 30, 20, 15, or 10 bp homology 5' of the nick or replacement sequence.

In certain embodiment, the template nucleic acid comprises about 150 to 200 bp, e.g., 155 to 195, 160 to 190, 165 to 185, or 170 to 180 bp, homology 5' of the nick and/or replacement sequence. In certain embodiment, the template nucleic acid comprises about 150, 155, 160, 165, 170, 175, 180, 185, 190, 195, or 200 bp homology 5' of the nick or replacement sequence. In certain embodiments, the template nucleic acid comprises less than about 100, 90, 80, 70, 60, 50, 40, 30, 20, 15, or 10 bp homology 3' of the nick or replacement sequence.

In certain embodiments, the template nucleic acid comprises a nucleotide sequence, e.g., of one or more nucleotides, that can be added to or can template a change in the target nucleic acid. In other embodiments, the template nucleic acid comprises a nucleotide sequence that may be used to modify the target position.

The template nucleic acid may comprise a replacement sequence. In certain embodiments, the template nucleic acid comprises a 5' homology arm. In certain embodiments, the template nucleic acid comprises a 3' homology arm.

In certain embodiments, the template nucleic acid is linear double stranded DNA. The length may be, e.g., about 150-200 bp, e.g., about 150, 160, 170, 180, 190, or 200 bp. The length may be, e.g., at least 150, 160, 170, 180, 190, or 200 bp. In certain embodiments, the length is no greater than 150, 160, 170, 180, 190, or 200 bp. In certain embodiments, a double stranded template nucleic acid has a length of about 160 bp, e.g., about 155-165, 150-170, 140-180, 130-190, 120-200, 110-210, 100-220, 90-230, or 80-240 bp.

The template nucleic acid can be linear single stranded DNA. In certain embodiments, the template nucleic acid is (i) linear single stranded DNA that can anneal to the nicked strand of the target nucleic acid, (ii) linear single stranded DNA that can anneal to the intact strand of the target nucleic acid, (iii) linear single stranded DNA that can anneal to the plus strand of the target nucleic acid, (iv) linear single stranded DNA that can anneal to the minus strand of the target nucleic acid, or more than one of the preceding. The length may be, e.g., about 150-200 nucleotides, e.g., about 150, 160, 170, 180, 190, or 200 nucleotides. The length may be, e.g., at least 150, 160, 170, 180, 190, or 200 nucleotides. In certain embodiments, the length is no greater than 150, 160, 170, 180, 190, or 200 nucleotides. In certain embodiments, a single stranded template nucleic acid has a length of about 160 nucleotides, e.g., about 155-165, 150-170, 140-180, 130-190, 120-200, 110-210, 100-220, 90-230, or 80-240 nucleotides.

In certain embodiments, the template nucleic acid is circular double stranded DNA, e.g., a plasmid. In certain embodiments, the template nucleic acid comprises about 500 to 1000 bp of homology on either side of the replacement sequence and/or the nick. In certain embodiments, the template nucleic acid comprises about 300, 400, 500, 600, 700, 800, 900, 1000, 1500, or 2000 bp of homology 5' of the nick or replacement sequence, 3' of the nick or replacement sequence, or both 5' and 3' of the nick or replacement sequence. In certain embodiments, the template nucleic acid comprises at least 300, 400, 500, 600, 700, 800, 900, 1000, 1500, or 2000 bp of homology 5' of the nick or replacement sequence, 3' of the nick or replacement sequence, or both 5' and 3' of the nick or replacement sequence. In certain embodiments, the template nucleic acid comprises no more than 300, 400, 500, 600, 700, 800, 900, 1000, 1500, or 2000 bp of homology 5' of the nick or replacement sequence, 3' of the nick or replacement sequence, or both 5' and 3' of the nick or replacement sequence.

In certain embodiments, one or both homology arms may be shortened to avoid including certain sequence repeat elements, e.g., Alu repeats, LINE elements. For example, a 5' homology arm may be shortened to avoid a sequence repeat element, while a 3' homology arm may be shortened to avoid a sequence repeat element. In certain embodiments, both the 5' and the 3' homology arms may be shortened to avoid including certain sequence repeat elements.

In certain embodiments, the template nucleic acid is an adenovirus vector, e.g., an AAV vector, e.g., a ssDNA molecule of a length and sequence that allows it to be packaged in an AAV capsid. The vector may be, e.g., less than 5 kb and may contain an ITR sequence that promotes packaging into the capsid. The vector may be integration-deficient. In certain embodiments, the template nucleic acid comprises about 150 to 1000 nucleotides of homology on either side of the replacement sequence and/or the nick. In certain embodiments, the template nucleic acid comprises about 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence. In certain embodiments, the template nucleic acid comprises at least 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence. In certain embodiments, the template nucleic acid comprises at most 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence.

In certain embodiments, the template nucleic acid is a lentiviral vector, e.g., an DLV (integration deficiency lentivirus). In certain embodiments, the template nucleic acid comprises about 500 to 1000 bp of homology on either side of the replacement sequence and/or the nick. In certain embodiments, the template nucleic acid comprises about 300, 400, 500, 600, 700, 800, 900, 1000, 1500, or 2000 bp of homology 5' of the nick or replacement sequence, 3' of the nick or replacement sequence, or both 5' and 3' of the nick or replacement sequence. In certain embodiments, the template nucleic acid comprises at least 300, 400, 500, 600, 700, 800, 900, 1000, 1500, or 2000 bp of homology 5' of the nick or replacement sequence, 3' of the nick or replacement sequence, or both 5' and 3' of the nick or replacement sequence. In certain embodiments, the template nucleic acid comprises no more than 300, 400, 500, 600, 700, 800, 900, 1000, 1500, or 2000 bp of homology 5' of the nick or replacement sequence, 3' of the nick or replacement sequence, or both 5' and 3' of the nick or replacement sequence.

In certain embodiments, the template nucleic acid comprises one or more mutations, e.g., silent mutations, which prevent Cas9 from recognizing and cleaving the template nucleic acid. The template nucleic acid may comprise, e.g., at least 1, 2, 3, 4, 5, 10, 20, or 30 silent mutations relative to the corresponding sequence in the genome of the cell to be altered. In certain embodiments, the template nucleic acid comprises at most 2, 3, 4, 5, 10, 20, 30, or 50 silent mutations relative to the corresponding sequence in the genome of the cell to be altered. In certain embodiments, the cDNA comprises one or more mutations, e.g., silent mutations that prevent Cas9 from recognizing and cleaving the template nucleic acid. The template nucleic acid may comprise, e.g., at least 1, 2, 3, 4, 5, 10, 20, or 30 silent mutations relative to the corresponding sequence in the genome of the cell to be altered. In certain embodiments, the template nucleic acid comprises at most 2, 3, 4, 5, 10, 20, 30, or 50 silent mutations relative to the corresponding sequence in the genome of the cell to be altered.

In certain embodiments, the 5' and 3' homology arms each comprise a length of sequence flanking the nucleotides corresponding to the replacement sequence. In certain embodiments, a template nucleic acid comprises a replacement sequence flanked by a 5' homology arm and a 3' homology arm each independently comprising 10 or more, 20 or more, 50 or more, 100 or more, 150 or more, 200 or more, 250 or more, 300 or more, 350 or more, 400 or more, 450 or more, 500 or more, 550 or more, 600 or more, 650 or more, 700 or more, 750 or more, 800 or more, 850 or more, 900 or more, 1000 or more, 1100 or more, 1200 or more, 1300 or more, 1400 or more, 1500 or more, 1600 or more, 1700 or more, 1800 or more, 1900 or more, or 2000 or more nucleotides. In certain embodiments, a template nucleic acid comprises a replacement sequence flanked by a 5' homology arm and a 3' homology arm each independently comprising at least 50, 100, or 150 nucleotides, but not long enough to include a repeated element. In certain embodiments, a template nucleic acid comprises a replacement sequence flanked by a 5' homology arm and a 3' homology arm each independently comprising 5 to 100, 10 to 150, or 20 to 150 nucleotides. In certain embodiments, the replacement sequence optionally comprises a promoter and/or polyA signal.

9.3 Single-Strand Annealing

Single strand annealing (SSA) is another DNA repair process that repairs a double-strand break between two repeat sequences present in a target nucleic acid. Repeat sequences utilized by the SSA pathway are generally greater than 30 nucleotides in length. Resection at the break ends occurs to reveal repeat sequences on both strands of the target nucleic acid. After resection, single strand overhangs containing the repeat sequences are coated with RPA protein to prevent the repeats sequences from inappropriate annealing, e.g., to themselves. RAD52 binds to and each of the repeat sequences on the overhangs and aligns the sequences to enable the annealing of the complementary repeat sequences. After annealing, the single-strand flaps of the overhangs are cleaved. New DNA synthesis fills in any gaps, and ligation restores the DNA duplex. As a result of the processing, the DNA sequence between the two repeats is deleted. The length of the deletion can depend on many factors including the location of the two repeats utilized, and the pathway or processivity of the resection.

In contrast to HDR pathways, SSA does not require a template nucleic acid to alter a target nucleic acid sequence. Instead, the complementary repeat sequence is utilized.

9.4 Other DNA Repair Pathways 9.4.1 SSBR (Single Strand Break Repair)

Single-stranded breaks (SSB) in the genome are repaired by the SSBR pathway, which is a distinct mechanism from the DSB repair mechanisms discussed above. The SSBR pathway has four major stages: SSB detection, DNA end processing, DNA gap filling, and DNA ligation. A more detailed explanation is given in Caldecott 2008, and a summary is given here.

In the first stage, when a SSB forms, PARP1 and/or PARP2 recognize the break and recruit repair machinery. The binding and activity of PARP1 at DNA breaks is transient and it seems to accelerate SSBr by promoting the focal accumulation or stability of SSBr protein complexes at the lesion. Arguably the most important of these SSBr proteins is XRCC1, which functions as a molecular scaffold that interacts with, stabilizes, and stimulates multiple enzymatic components of the SSBr process including the protein responsible for cleaning the DNA 3' and 5' ends. For instance, XRCC1 interacts with several proteins (DNA polymerase beta, PNK, and three nucleases, APE1, APTX, and APLF) that promote end processing. APE1 has endonuclease activity. APLF exhibits endonuclease and 3' to 5' exonuclease activities. APTX has endonuclease and 3' to 5' exonuclease activity.

This end processing is an important stage of SSBR since the 3'- and/or 5'-termini of most, if not all, SSBs are 'damaged.' End processing generally involves restoring a damaged 3'-end to a hydroxylated state and and/or a damaged 5' end to a phosphate moiety, so that the ends become ligation-competent. Enzymes that can process damaged 3' termini include PNKP, APE1, and TDP1. Enzymes that can process damaged 5' termini include PNKP, DNA polymerase beta, and APTX. LIG3 (DNA ligase III) can also participate in end processing. Once the ends are cleaned, gap filling can occur.

At the DNA gap filling stage, the proteins typically present are PARP1, DNA polymerase beta, XRCC1, FEN1 (flap endonuclease 1), DNA polymerase delta/epsilon, PCNA, and LIG1. There are two ways of gap filling, the short patch repair and the long patch repair. Short patch repair involves the insertion of a single nucleotide that is missing. At some SSBs, "gap filling" might continue displacing two or more nucleotides (displacement of up to 12 bases have been reported). FEN1 is an endonuclease that removes the displaced 5'-residues. Multiple DNA polymerases, including Polβ, are involved in the repair of SSBs, with the choice of DNA polymerase influenced by the source and type of SSB.

In the fourth stage, a DNA ligase such as LIG1 (Ligase I) or LIG3 (Ligase III) catalyzes joining of the ends. Short patch repair uses Ligase III and long patch repair uses Ligase I. Sometimes, SSBR is replication-coupled. This pathway can involve one or more of CtIP, MRN, ERCC1, and FEN1. Additional factors that may promote SSBR include: aPARP, PARP1, PARP2, PARG, XRCC1, DNA polymerase b, DNA polymerase d, DNA polymerase e, PCNA, LIG1, PNK, PNKP, APE1, APTX, APLF, TDP1, LIG3, FEN1, CtIP, MRN, and ERCC1.

9.4.2 MMR (Mismatch Repair)

Cells contain three excision repair pathways: MMR, BER, and NER. The excision repair pathways have a common feature in that they typically recognize a lesion on one strand of the DNA, then exo/endonucleases remove the lesion and leave a 1-30 nucleotide gap that is sub-sequentially filled in by DNA polymerase and finally sealed with ligase. A more complete picture is given in Li, Cell Research (2008) 18:85-98, and a summary is provided here.

Mismatch repair (MMR) operates on mispaired DNA bases.

The MSH2/6 or MSH2/3 complexes both have ATPases activity that plays an important role in mismatch recognition and the initiation of repair. MSH2/6 preferentially recognizes base-base mismatches and identifies mispairs of 1 or 2 nucleotides, while MSH2/3 preferentially recognizes larger ID mispairs.

hMLH1 heterodimerizes with hPMS2 to form hMutLa which possesses an ATPase activity and is important for multiple steps of MMR. It possesses a PCNA/replication factor C (RFC)-dependent endonuclease activity which plays an important role in 3' nick-directed MMR involving EXO1. (EXO1 is a participant in both HR and MMR.) It regulates termination of mismatch-provoked excision. Ligase I is the relevant ligase for this pathway. Additional factors that may promote MMR include: EXO1, MSH2, MSH3, MSH6, MLH1, PMS2, MLH3, DNA Pol d, RPA, HMGB1, RFC, and DNA ligase I.

9.4.3 Base Excision Repair (BER)

The base excision repair (BER) pathway is active throughout the cell cycle; it is responsible primarily for removing small, non-helix-distorting base lesions from the genome. In contrast, the related Nucleotide Excision Repair pathway (discussed in the next section) repairs bulky helix-distorting lesions. A more detailed explanation is given in Caldecott, Nature Reviews Genetics 9, 619-631 (August 2008), and a summary is given here.

Upon DNA base damage, base excision repair (BER) is initiated and the process can be simplified into five major steps: (a) removal of the damaged DNA base; (b) incision of the subsequent a basic site; (c) clean-up of the DNA ends; (d) insertion of the desired nucleotide into the repair gap; and (e) ligation of the remaining nick in the DNA backbone. These last steps are similar to the SSBR.

In the first step, a damage-specific DNA glycosylase excises the damaged base through cleavage of the N-glycosidic bond linking the base to the sugar phosphate backbone. Then AP endonuclease-1 (APE1) or bifunctional DNA glycosylases with an associated lyase activity incised the phosphodiester backbone to create a DNA single strand break (SSB). The third step of BER involves cleaning-up of the DNA ends. The fourth step in BER is conducted by Polβ that adds a new complementary nucleotide into the repair gap and in the final step XRCC1/Ligase III seals the remaining nick in the DNA backbone. This completes the short-patch BER pathway in which the majority (~80%) of damaged DNA bases are repaired. However, if the 5' ends in step 3 are resistant to end processing activity, following one nucleotide insertion by Pol β there is then a polymerase switch to the replicative DNA polymerases, Pol δ/ε, which then add ~2-8 more nucleotides into the DNA repair gap. This creates a 5' flap structure, which is recognized and excised by flap endonuclease-1 (FEN-1) in association with the processivity factor proliferating cell nuclear antigen (PCNA). DNA ligase I then seals the remaining nick in the DNA backbone and completes long-patch BER. Additional factors that may promote the BER pathway include: DNA glycosylase, APE1, Polb, Pold, Pole, XRCC1, Ligase III, FEN-1, PCNA, RECQL4, WRN, MYH, PNKP, and APTX.

9.4.4 Nucleotide Excision Repair (NER)

Nucleotide excision repair (NER) is an important excision mechanism that removes bulky helix-distorting lesions from DNA. Additional details about NER are given in Marteijn et al., Nature Reviews Molecular Cell Biology 15, 465-481 (2014), and a summary is given here. NER a broad pathway encompassing two smaller pathways: global genomic NER (GG-NER) and transcription coupled repair NER (TC-NER). GG-NER and TC-NER use different factors for recognizing DNA damage. However, they utilize the same machinery for lesion incision, repair, and ligation.

Once damage is recognized, the cell removes a short single-stranded DNA segment that contains the lesion. Endonucleases XPF/ERCC1 and XPG (encoded by ERCC5) remove the lesion by cutting the damaged strand on either side of the lesion, resulting in a single-strand gap of 22-30 nucleotides. Next, the cell performs DNA gap filling synthesis and ligation. Involved in this process are: PCNA, RFC, DNA Pol δ, DNA Pol ε or DNA Pol κ, and DNA ligase I or XRCC1/Ligase III. Replicating cells tend to use DNA pol ε and DNA ligase I, while non-replicating cells tend to use DNA Pol δ, DNA Pol κ, and the XRCC1/Ligase III complex to perform the ligation step.

NER can involve the following factors: XPA-G, POLH, XPF, ERCC1, XPA-G, and LIG1. Transcription-coupled NER (TC-NER) can involve the following factors: CSA, CSB, XPB, XPD, XPG, ERCC1, and TTDA. Additional factors that may promote the NER repair pathway include XPA-G, POLH, XPF, ERCC1, XPA-G, LIG1, CSA, CSB, XPA, XPB, XPC, XPD, XPF, XPG, TTDA, UVSSA, USP7, CETN2, RAD23B, UV-DDB, CAK subcomplex, RPA, and PCNA.

9.4.5 Interstrand Crosslink (ICL)

A dedicated pathway called the ICL repair pathway repairs interstrand crosslinks. Interstrand crosslinks, or covalent crosslinks between bases in different DNA strand, can occur during replication or transcription. ICL repair involves the coordination of multiple repair processes, in particular, nucleolytic activity, translesion synthesis (TLS), and HDR. Nucleases are recruited to excise the ICL on either side of the crosslinked bases, while TLS and HDR are coordinated to repair the cut strands. ICL repair can involve the following factors: endonucleases, e.g., XPF and RAD51C, endonucleases such as RAD51, translesion polymerases, e.g., DNA polymerase zeta and Rev1), and the Fanconi anemia (FA) proteins, e.g., FancJ.

9.4.6 Other Pathways

Several other DNA repair pathways exist in mammals.

Translesion synthesis (TLS) is a pathway for repairing a single stranded break left after a defective replication event and involves translesion polymerases, e.g., DNA polβ and Rev1.

Error-free postreplication repair (PRR) is another pathway for repairing a single stranded break left after a defective replication event.

9.5 Targeted Knockdown

Unlike CRISPR/Cas-mediated gene knockout, which permanently eliminates expression by mutating the gene (e.g., a RS1, RL2, or LAT gene) at the DNA level, CRISPR/Cas knockdown allows for temporary reduction of gene expression through the use of artificial transcription factors. Mutating key residues in both DNA cleavage domains of the Cas9 protein (e.g. the D10A and H840A mutations) results in the generation of a catalytically inactive Cas9 (eiCas9 which is also known as dead Cas9 or dCas9) molecule. A catalytically inactive Cas9 complexes with a gRNA and localizes to the DNA sequence specified by that gRNA's targeting domain, however, it does not cleave the target DNA. Fusion of the dCas9 to an effector domain, e.g., a transcription repression domain, enables recruitment of the effector to any DNA site specified by the gRNA. Although an enzymatically inactive (eiCas9) Cas9 molecule itself can block transcription when recruited to early regions in the coding sequence, more robust repression can be achieved by fusing a transcriptional repression domain (for example KRAB, SID or ERD) to the Cas9 and recruiting it to the target knockdown position, e.g., within 1000 bp of sequence 3' of the start codon or within 500 bp of a promoter region 5' of the start codon of a gene (e.g., a RL2, LAT, or RS1 gene). It is likely that targeting DNAseI hypersensitive sites (DHSs) of the promoter may yield more efficient gene repression or activation because these regions are more likely to be accessible to the Cas9 protein and are also more likely to harbor sites for endogenous transcription factors. Especially for gene repression, blocking the binding site of an endogenous transcription factor would aid in downregulating gene expression. In certain embodiments, one or more eiCas9 molecules may be used to block binding of one or more endogenous transcription factors. In certain embodiments, an eiCas9 molecule can be fused to a chromatin modifying protein. Altering chromatin status can result in decreased expression of the target gene. One or more eiCas9 molecules fused to one or more chromatin modifying proteins may be used to alter chromatin status.

In certain embodiments, a gRNA molecule can be targeted to a known transcription response elements (e.g., promoters, enhancers, etc.), a known upstream activating sequences (UAS), and/or sequences of unknown or known function that are suspected of being able to control expression of the target DNA.

CRISPR/Cas-mediated gene knockdown can be used to reduce expression of an unwanted allele or transcript. In certain embodiments, permanent destruction of the gene is not ideal. In these embodiments, site-specific repression may be used to temporarily reduce or eliminate expression. In certain embodiments, the off-target effects of a Cas-repressor may be less severe than those of a Cas-nuclease as a nuclease can cleave any DNA sequence and cause mutations whereas a Cas-repressor may only have an effect if it targets the promoter region of an actively transcribed gene. However, while nuclease-mediated knockout is permanent, repression may only persist as long as the Cas-repressor is present in the cells. Once the repressor is no longer present, it is likely that endogenous transcription factors and gene regulatory elements would restore expression to its natural state.

9.6 Examples of gRNAs in Genome Editing Methods gRNA molecules as described herein can be used with Cas9 molecules that generate a double strand break or a single strand break to alter the sequence of a target nucleic acid, e.g., a target position or target genetic signature. gRNA molecules useful in these methods are described below.

In certain embodiments, the gRNA, e.g., a chimeric gRNA, is configured such that it comprises one or more of the following properties;

(a) it can position, e.g., when targeting a Cas9 molecule that makes double strand breaks, a double strand break (i) within 50, 100, 150, 200, 250, 300, 350, 400, 450, or 500 nucleotides of a target position, or (ii) sufficiently close that the target position is within the region of end resection;

(b) it has a targeting domain of at least 16 nucleotides, e.g., a targeting domain of (i) 16, (ii), 17, (iii) 18, (iv) 19, (v) 20, (vi) 21, (vii) 22, (viii) 23, (ix) 24, (x) 25, or (xi) 26 nucleotides; and (c)(i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring *S. pyogenes, S. aureus*, or *N. meningitidis* tail and proximal domain, or a sequence that differs by no more than 1, 2, 3, 4, 5; 6, 7, 8, 9 or 10 nucleotides therefrom;

(c)(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring *S. pyogenes, S. aureus*, or *N. meningitidis* gRNA, or a sequence that differs by no more than 1, 2, 3, 4, 5; 6, 7, 8, 9 or 10 nucleotides therefrom;

(c)(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring *S. pyogenes, S. aureus*, or *N. meningitidis* gRNA, or a sequence that differs by no more than 1, 2, 3, 4, 5; 6, 7, 8, 9 or 10 nucleotides therefrom;

(c)(iv) the tail domain is at least 10, 15, 20, 25, 30, 35 or 40 nucleotides in length, e.g., it comprises at least 10, 15, 20, 25, 30, 35 or 40 nucleotides from a naturally occurring *S. pyogenes, S. aureus*, or *N. meningitidis* tail domain, or a sequence that differs by no more than 1, 2, 3, 4, 5; 6, 7, 8, 9 or 10 nucleotides therefrom; or (c)(v) the tail domain comprises 15, 20, 25, 30, 35, 40 nucleotides or all of the corresponding portions of a naturally occurring tail domain, e.g., a naturally occurring *S. pyogenes, S. aureus*, or *N. meningitidis* tail domain.

In certain embodiments, the gRNA is configured such that it comprises properties: a and b(i); a and b(ii); a and b(iii); a and b(iv); a and b(v); a and b(vi); a and b(vii); a and b(viii); a and b(ix); a and b(x); a and b(xi); a and c; a, b, and c; a(i), b(i), and c(i); a(i), b(i), and c(ii); a(i), b(ii), and c(i); a(i), b(ii), and c(ii); a(i), b(iii), and c(i); a(i), b(iii), and c(ii); a(i), b(iv), and c(i); a(i), b(iv), and c(ii); a(i), b(v), and c(i); a(i), b(v), and c(ii); a(i), b(vi), and c(i); a(i), b(vi), and c(ii); a(i), b(vii), and c(i); a(i), b(vii), and c(ii); a(i), b(viii), and c(i); a(i), b(viii), and c(ii); a(i), b(ix), and c(i); a(i), b(ix), and c(ii); a(i), b(x), and c(i); a(i), b(x), and c(ii); a(i), b(xi), or c(i); a(i), b(xi), and c(ii).

In certain embodiments, the gRNA, e.g., a chimeric gRNA, is configured such that it comprises one or more of the following properties:

(a) one or both of the gRNAs can position, e.g., when targeting a Cas9 molecule that makes single strand breaks, a single strand break within (i) 50, 100, 150, 200, 250, 300, 350, 400, 450, or 500 nucleotides of a target position, or (ii) sufficiently close that the target position is within the region of end resection;

(b) one or both have a targeting domain of at least 16 nucleotides, e.g., a targeting domain of (i) 16, (ii), 17, (iii) 18, (iv) 19, (v) 20, (vi) 21, (vii) 22, (viii) 23, (ix) 24, (x) 25, or (xi) 26 nucleotides; and (c)(i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring *S. pyogenes, S. aureus*, or *N. meningitidis* tail and proximal domain, or a sequence that differs by no more than 1, 2, 3, 4, 5, 6, 7, 8, 9 or 10 nucleotides therefrom;

(c)(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring *S. pyogenes, S. aureus*, or *N. meningitidis* gRNA, or a sequence that differs by no more than 1, 2, 3, 4, 5; 6, 7, 8, 9 or 10 nucleotides therefrom;

(c)(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring *S. pyogenes, S. aureus*, or *N. meningitidis* gRNA, or a sequence that differs by no more than 1, 2, 3, 4, 5; 6, 7, 8, 9 or 10 nucleotides therefrom;

(c)(iv) the tail domain is at least 10, 15, 20, 25, 30, 35 or 40 nucleotides in length, e.g., it comprises at least 10, 15, 20, 25, 30, 35 or 40 nucleotides from a naturally occurring *S. pyogenes, S. aureus*, or *N. meningitidis* tail domain, or a sequence that differs by no more than 1, 2, 3, 4, 5; 6, 7, 8, 9 or 10 nucleotides therefrom; or (c)(v) the tail domain comprises 15, 20, 25, 30, 35, 40 nucleotides or all of the corresponding portions of a naturally occurring tail domain, e.g., a naturally occurring *S. pyogenes, S. aureus*, or *N. meningitidis* tail domain.

In certain embodiments, the gRNA is configured such that it comprises properties: a and b(i); a and b(ii); a and b(iii); a and b(iv); a and b(v); a and b(vi); a and b(vii); a and b(viii); a and b(ix); a and b(x); a and b(xi); a and c; a, b, and c; a(i), b(i), and c(i); a(i), b(i), and c(ii); a(i), b(ii), and c(i); a(i), b(ii), and c(ii); a(i), b(iii), and c(i); a(i), b(iii), and c(ii); a(i), b(iv), and c(i); a(i), b(iv), and c(ii); a(i), b(v), and c(i); a(i), b(v), and c(ii); a(i), b(vi), and c(i); a(i), b(vi), and c(ii); a(i), b(vii), and c(i); a(i), b(vii), and c(ii); a(i), b(viii), and c(i); a(i), b(viii), and c(ii); a(i), b(ix), and c(i); a(i), b(ix), and c(ii); a(i), b(x), and c(i); a(i), b(x), and c(ii); a(i), b(xi), and c(i); a(i), b(xi), and c(ii).

In certain embodiments, the gRNA is used with a Cas9 nickase molecule having HNH activity, e.g., a Cas9 molecule having the RuvC activity inactivated, e.g., a Cas9 molecule having a mutation at D10, e.g., the D10A mutation. In certain embodiments, the gRNA is used with a Cas9 nickase molecule having RuvC activity, e.g., a Cas9 molecule having the HNH activity inactivated, e.g., a Cas9 molecule having a mutation at 840, e.g., the H840A. In certain embodiments, the gRNAs are used with a Cas9 nickase molecule having RuvC activity, e.g., a Cas9 molecule having the HNH activity inactivated, e.g., a Cas9 molecule having a mutation at N863, e.g., the N863A mutation. In certain embodiments, the gRNAs are used with a Cas9 nickase molecule having RuvC activity, e.g., a Cas9 molecule having the HNH activity inactivated, e.g., a Cas9 molecule having a mutation at N580, e.g., the N580A mutation.

In certain embodiments, a pair of gRNAs, e.g., a pair of chimeric gRNAs, comprising a first and a second gRNA, is configured such that they comprise one or more of the following properties;

(a) one or both of the gRNAs can position, e.g., when targeting a Cas9 molecule that makes single strand breaks, a single strand break within (i) 50, 100, 150, 200, 250, 300, 350, 400, 450, or 500 nucleotides of a target position, or (ii) sufficiently close that the target position is within the region of end resection;

(b) one or both have a targeting domain of at least 16 nucleotides, e.g., a targeting domain of (i) 16, (ii), 17, (iii) 18, (iv) 19, (v) 20, (vi) 21, (vii) 22, (viii) 23, (ix) 24, (x) 25, or (xi) 26 nucleotides;

(c) (i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring *S. pyogenes, S. aureus*, or *N. meningitidis* tail and proximal domain, or a sequence that differs by no more than 1, 2, 3, 4, 5; 6, 7, 8, 9 or 10 nucleotides therefrom;

(c)(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring *S. pyogenes, S. aureus*, or *N. meningitidis* gRNA, or a sequence that differs by no more than 1, 2, 3, 4, 5; 6, 7, 8, 9 or 10 nucleotides therefrom;

(c)(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring *S. pyogenes, S. aureus*, or *N. meningitidis* gRNA, or a sequence that differs by no more than 1, 2, 3, 4, 5; 6, 7, 8, 9 or 10 nucleotides therefrom;

(c)(iv) the tail domain is at least 10, 15, 20, 25, 30, 35 or 40 nucleotides in length, e.g., it comprises at least 10, 15, 20, 25, 30, 35 or 40 nucleotides from a naturally occurring *S. pyogenes, S. aureus*, or *N. meningitidis* tail domain; or, or a sequence that differs by no more than 1, 2, 3, 4, 5; 6, 7, 8, 9 or 10 nucleotides therefrom; or (c)(v) the tail domain comprises 15, 20, 25, 30, 35, 40 nucleotides or all of the corresponding portions of a naturally occurring tail domain, e.g., a naturally occurring *S. pyogenes, S. aureus*, or *N. meningitidis* tail domain;

(d) the gRNAs are configured such that, when hybridized to target nucleic acid, they are separated by 0-50, 0-100, 0-200, at least 10, at least 20, at least 30 or at least 50 nucleotides;

(e) the breaks made by the first gRNA and second gRNA are on different strands; and (f) the PAMs are facing outwards.

In certain embodiments, one or both of the gRNAs is configured such that it comprises properties: a and b(i); a and b(ii); a and b(iii); a and b(iv); a and b(v); a and b(vi); a and b(vii); a and b(viii); a and b(ix); a and b(x); a and b(xi); a and c; a, b, and c; a(i), b(i), and c(i); a(i), b(i), and c(ii); a(i), b(i), c, and d; a(i), b(i), c, and e; a(i), b(i), c, d, and e; a(i), b(ii), and c(i); a(i), b(ii), and c(ii); a(i), b(ii), c, and d; a(i), b(ii), c, and e; a(i), b(ii), c, d, and e; a(i), b(iii), and c(i); a(i), b(iii), and c(ii); a(i), b(iii), c, and d; a(i), b(iii), c, and e; a(i), b(iii), c, d, and e; a(i), b(iv), and c(i); a(i), b(iv), and c(ii); a(i), b(iv), c, and d; a(i), b(iv), c, and e; a(i), b(iv), c, d, and e; a(i), b(v), and c(i); a(i), b(v), and c(ii); a(i), b(v), c, and d; a(i), b(v), c, and e; a(i), b(v), c, d, and e; a(i), b(vi), and c(i); a(i), b(vi), and c(ii); a(i), b(vi), c, and d; a(i), b(vi), c, and e; a(i), b(vi), c, d, and e; a(i), b(vii), and c(i); a(i), b(vii), and c(ii); a(i), b(vii), c, and d; a(i), b(vii), c, and e; a(i), b(vii), c, d, and e; a(i), b(viii), and c(i); a(i), b(viii), and c(ii); a(i), b(viii), c, and d; a(i), b(viii), c, and e; a(i), b(viii), c, d, and e; a(i), b(ix), and c(i); a(i), b(ix), and c(ii); a(i), b(ix), c, and d; a(i), b(ix), c, and e; a(i), b(ix), c, d, and e; a(i), b(x), and c(i); a(i), b(x), and c(ii); a(i), b(x), c, and d; a(i), b(x), c, and e; a(i), b(x), c, d, and e; a(i), b(xi), and c(i); a(i), b(xi), and c(ii); a(i), b(xi), c, and d; a(i), b(xi), c, and e; a(i), b(xi), c, d, and e.

In certain embodiments, the gRNAs are used with a Cas9 nickase molecule having HNH activity, e.g., a Cas9 molecule having the RuvC activity inactivated, e.g., a Cas9 molecule having a mutation at D10, e.g., the D10A mutation. In certain embodiments, the gRNAs are used with a Cas9 nickase molecule having RuvC activity, e.g., a Cas9 molecule having the HNH activity inactivated, e.g., a Cas9 molecule having a mutation at H840, e.g., the H840A mutation. In certain embodiments, the gRNAs are used with a Cas9 nickase molecule having RuvC activity, e.g., a Cas9 molecule having the HNH activity inactivated, e.g., a Cas9 molecule having a mutation at N863, e.g., the N863A mutation. In certain embodiments, the gRNAs are used with a Cas9 nickase molecule having RuvC activity, e.g., a Cas9 molecule having the HNH activity inactivated, e.g., a Cas9 molecule having a mutation at N580, e.g., the N580A mutation.

10. Target Cells

Cas9 molecules (e.g., an eaCas9 molecule or an eiCas9 molecule) or Cas9 fusion protein and gRNA molecules, e.g., a Cas9 molecule/gRNA molecule complex, can be used to manipulate a cell, e.g., to edit a target nucleic acid, in a wide variety of cells.

In certain embodiments, a cell is manipulated by editing (e.g., introducing a mutation in) one or more target genes, e.g., an HSV-1 or HSV-2 genes, e.g., one, two, or three of RS1, RL2 and/or LAT genes. In certain embodiments, the cell is infected with HSV-1 and/or HSV-2. In certain embodiments, the cell is from a subject having an HSV-1 and/or HSV-2 infection. In certain embodiments, the cell or subject has a latent HSV-1 and/or HSV-2 infection. In certain embodiments, the expression of one or more target genes (e.g., one or more target genes described herein, e.g., one, two, or three of RS1, RL2 and/or LAT genes) is modulated, e.g., in vivo.

The Cas9 and gRNA molecules described herein can be delivered to a target cell, e.g., a cell described herein. In certain embodiments, the target cell is an epithelial cell, e.g., an epithelial cell of the oropharynx (including, e.g., an epithelial cell of the nose, gums, lips, tongue or pharynx), an epithelial cell of the finger or fingernail bed, or an epithelial cell of the ano-genital area (including, e.g., an epithelial cell of the penis, scrotum, vulva, vagina, cervix, anus or thighs). In certain embodiments, the target cell is a neuronal cell, e.g., a cranial ganglion neuron (e.g. a trigeminal ganglion neuron, e.g., an oculomotor nerve ganglion neuron, e.g., an abducens nerve ganglion neuron, e.g., a trochlear nerve ganglion neuron), e.g. a cervical ganglion neuron, e.g., a sacral ganglion neuron, a sensory ganglion neuron, a cortical neuron, a cerebellar neuron or a hippocampal neuron. In certain embodiments, the target cell is an optic cell, e.g. an epithelial cell of the eye, e.g. an epithelial cell of the eyelid, e.g., a conjunctival cell, e.g., a conjunctival epithelial cell, e.g., a corneal keratocyte, e.g., a limbus cell, e.g., a corneal epithelial cell, e.g., a corneal stromal cell, e.g., a ciliary body cell, e.g., a scleral cell, e.g., a lens cell, e.g., a choroidal cell, e.g., a retinal cell, e.g., a rod photoreceptor cell, e.g., a cone photoreceptor cell, e.g., a retinal pigment epithelium cell, e.g., a horizontal cell, e.g., an amacrine cell, e.g., a ganglion cell.

11. Delivery, Formulations and Routes of Administration

The components, e.g., a Cas9 molecule, one or more gRNA molecules (e.g., a Cas9 molecule/gRNA molecule complex), and a donor template nucleic acid, or all three, can be delivered, formulated, or administered in a variety of forms, see, e.g., Tables 14 and 15. In certain embodiments, the Cas9 molecule, one or more gRNA molecules (e.g., two gRNA molecules) are present together in a genome editing system. In certain embodiments, the sequence encoding the Cas9 molecule and the sequence(s) encoding the two or more (e.g., 2, 3, 4, or more) different gRNA molecules are present on the same nucleic acid molecule, e.g., an AAV vector. In certain embodiments, two sequences encoding the Cas9 molecules and the sequences encoding the two or more (e.g., 2, 3, 4, or more) different gRNA molecules are present on the same nucleic acid molecule, e.g., an AAV vector. When a Cas9 or gRNA component is encoded as DNA for delivery, the DNA can typically include a control region, e.g., comprising a promoter, to effect expression. Useful promoters for Cas9 molecule sequences include CMV, EFS, EF-1a, MSCV, PGK, and CAG, the Skeletal Alpha Actin promoter, the Muscle Creatine Kinase promoter, the Dystrophin promoter, the Alpha Myosin Heavy Chain promoter, and the Smooth Muscle Actin promoter. In certain embodiments, the promoter is a constitutive promoter. In certain embodiments, the promoter is a tissue specific promoter. Useful promoters for gRNAs include T7.H1, EF-1a, 7SK, U6, U1 and tRNA promoters. Promoters with similar or dissimilar strengths can be selected to tune the expression of components. Sequences encoding a Cas9 molecule can comprise a nuclear localization signal (NLS), e.g., an SV40 NLS. In certain embodiments, the sequence encoding a Cas9 molecule comprise at least two nuclear localization signals. In certain embodiments a promoter for a Cas9 molecule or a gRNA molecule can be, independently, inducible, tissue specific, or cell specific. Table 14 provides examples of how the components can be formulated, delivered, or administered.

TABLE 14

| | | Elements | |
|---|---|---|---|
| Cas9 Molecule(s) | gRNA Molecule(s) | Donor Template Nucleic Acid | Comments |
| DNA | DNA | DNA | In certain embodiments, a Cas9 molecule (e.g., an eaCas9 or eiCas9 molecule) and a gRNA are transcribed from DNA. In certain embodiments, they are encoded on separate molecules. In certain embodiments, the donor template is provided as a separate DNA molecule. |
| DNA | DNA | | In certain embodiments, a Cas9 molecule (e.g., an eaCas9 or eiCas9 molecule) and a gRNA are transcribed from DNA. In certain embodiments, they are encoded on separate molecules. In certain embodiments, the donor template is |

TABLE 14-continued

| Cas9 Molecule(s) | gRNA Molecule(s) | Donor Template Nucleic Acid | Comments |
|---|---|---|---|
| | DNA | DNA | provided on the same DNA molecule that encodes the gRNA. In certain embodiments, a Cas9 molecule (e.g., an eaCas9 or eiCas9 molecule) and a gRNA are transcribed from DNA, here from a single molecule. In certain embodiments, the donor template is provided as a separate DNA molecule. |
| DNA | | DNA | In certain embodiments, a Cas9 molecule (e.g., an eaCas9 or eiCas9 molecule), and a gRNA are transcribed from DNA. In certain embodiments, they are encoded on separate molecules. In certain embodiments, the donor template is provided on the same DNA molecule that encodes the Cas9. |
| DNA | RNA | DNA | In certain embodiments, a Cas9 molecule (e.g., an eaCas9 or eiCas9 molecule) is transcribed from DNA, and a gRNA is provided as in vitro transcribed or synthesized RNA. In certain embodiments, the donor template is provided as a separate DNA molecule. |
| DNA | | RNA | In certain embodiments, a Cas9 molecule (e.g., an eaCas9 or eiCas9 molecule) is transcribed from DNA, and a gRNA is provided as in vitro transcribed or synthesized RNA. In certain embodiments, the donor template is provided on the same DNA molecule that encodes the Cas9. |
| mRNA | RNA | DNA | In certain embodiments, a Cas9 molecule (e.g., an eaCas9 or eiCas9 molecule) is translated from in vitro transcribed mRNA, and a gRNA is provided as in vitro transcribed or synthesized RNA. In certain embodiments, the donor template is provided as a DNA molecule. |
| mRNA | DNA | DNA | In certain embodiments, a Cas9 molecule (e.g., an eaCas9 or eiCas9 molecule) is translated from in vitro transcribed mRNA, and a gRNA is transcribed from DNA. In certain embodiments, the donor template is provided as a separate DNA molecule. |
| mRNA | DNA | | In certain embodiments, a Cas9 molecule (e.g., an eaCas9 or eiCas9 molecule) is translated from in vitro transcribed mRNA, and a gRNA is transcribed from DNA. In certain embodiments, the donor template is provided on the same DNA molecule that encodes the gRNA. |
| Protein | DNA | DNA | In certain embodiments, a Cas9 molecule (e.g., an eaCas9 or eiCas9 molecule) is provided as a protein, and a gRNA is transcribed from DNA. In certain embodiments, the donor template is provided as a separate DNA molecule. |
| Protein | | DNA | In certain embodiments, a Cas9 molecule (e.g., an eaCas9 or eiCas9 molecule) is provided as a protein, and a gRNA is transcribed from DNA. In certain embodiments, the donor template is provided on the same DNA molecule that encodes the gRNA. |
| Protein | RNA | DNA | In certain embodiments (e.g., an eaCas9 or eiCas9 molecule) is provided as a protein, and a gRNA is provided as transcribed or synthesized RNA. This delivery method is referred to as "RNP delivery". In certain embodiments, the donor template is provided as a DNA molecule. |

Table 15 summarizes various delivery methods for the components of a Cas system, e.g., the Cas9 molecule component and the gRNA molecule component, as described herein.

TABLE 15

| Delivery Vector/Mode | | Delivery into Non-Dividing Cells | Duration of Expression | Genome Integration | Type of Molecule Delivered |
|---|---|---|---|---|---|
| Physical (e.g., electroporation, particle gun, Calcium Phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |

TABLE 15-continued

| | Delivery Vector/Mode | Delivery into Non-Dividing Cells | Duration of Expression | Genome Integration | Type of Molecule Delivered |
|---|---|---|---|---|---|
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

11.1 DNA-Based Delivery of a Cas9 Molecule and or One or More gRNA Molecule

Nucleic acid compositions encoding Cas9 molecules (e.g., eaCas9 molecules or eiCas9 molecules), gRNA molecules, a donor template nucleic acid, or any combination (e.g., two or all) thereof can be administered to subjects or delivered into cells by art-known methods or as described herein. For example, Cas9-encoding and/or gRNA-encoding DNA, as well as donor template nucleic acids can be delivered, e.g., by vectors (e.g., viral or non-viral vectors), non-vector based methods (e.g., using naked DNA or DNA complexes), or a combination thereof.

Nucleic acid compositions encoding Cas9 molecules (e.g., eaCas9 molecules or eiCas9 molecules) and/or gRNA molecules can be conjugated to molecules (e.g., N-acetylgalactosamine) promoting uptake by the target cells (e.g., the target cells described herein). Donor template molecules can likewise be conjugated to molecules (e.g., N-acetylgalactosamine) promoting uptake by the target cells (e.g., the target cells described herein).

In certain embodiments, the Cas9- and/or gRNA-encoding DNA is delivered by a vector (e.g., viral vector/virus or plasmid).

Vectors can comprise a sequence that encodes a Cas9 molecule and/or a gRNA molecule, and/or a donor template with high homology to the region (e.g., target sequence) being targeted. In certain embodiments, the donor template comprises all or part of a target sequence. Exemplary donor templates are a repair template, e.g., a gene correction template, or a gene mutation template, e.g., point mutation (e.g., single nucleotide (nt) substitution) template). A vector can also comprise a sequence encoding a signal peptide (e.g., for nuclear localization, nucleolar localization, or mitochondrial localization), fused, e.g., to a Cas9 molecule sequence. For example, the vectors can comprise a nuclear localization sequence (e.g., from SV40) fused to the sequence encoding the Cas9 molecule.

One or more regulatory/control elements, e.g., promoters, enhancers, introns, polyadenylation signals, a Kozak consensus sequences, internal ribosome entry sites (IRES), a 2A sequence, and splice acceptor or donor can be included in the vectors. In certain embodiments, the promoter is recognized by RNA polymerase II (e.g., a CMV promoter). In other embodiments, the promoter is recognized by RNA polymerase III (e.g., a U6 promoter). In certain embodiments, the promoter is a regulated promoter (e.g., inducible promoter). In certain embodiments, the promoter is a constitutive promoter. In certain embodiments, the promoter is a tissue specific promoter. In certain embodiments, the promoter is a viral promoter. In certain embodiments, the promoter is a non-viral promoter.

In certain embodiments, the vector or delivery vehicle is a viral vector (e.g., for generation of recombinant viruses). In certain embodiments, the virus is a DNA virus (e.g., dsDNA or ssDNA virus). In certain embodiments, the virus is an RNA virus (e.g., an ssRNA virus). In certain embodiments, the virus infects dividing cells. In other embodiments, the virus infects non-dividing cells. Exemplary viral vectors/viruses include, e.g., retroviruses, lentiviruses, adenovirus, adeno-associated virus (AAV), vaccinia viruses, poxviruses, and herpes simplex viruses.

In certain embodiments, the virus infects dividing cells. In other embodiments, the virus infects non-dividing cells. In certain embodiments, the virus infects both dividing and non-dividing cells. In certain embodiments, the virus can integrate into the host genome. In certain embodiments, the virus is engineered to have reduced immunity, e.g., in human. In certain embodiments, the virus is replication-competent. In other embodiments, the virus is replication-defective, e.g., having one or more coding regions for the genes necessary for additional rounds of virion replication and/or packaging replaced with other genes or deleted. In certain embodiments, the virus causes transient expression of the Cas9 molecule or molecules and/or the gRNA molecule or molecules. In other embodiments, the virus causes long-lasting, e.g., at least 1 week, 2 weeks, 1 month, 2 months, 3 months, 6 months, 9 months, 1 year, 2 years, or permanent expression, of the Cas9 molecule or molecules and/or the gRNA molecule or molecules. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, 45 kb, or 50 kb.

In certain embodiments, the viral vector recognizes a specific cell type or tissue. For example, the viral vector can be pseudotyped with a different/alternative viral envelope glycoprotein; engineered with a cell type-specific receptor (e.g., genetic modification(s) of one or more viral envelope glycoproteins to incorporate a targeting ligand such as a peptide ligand, a single chain antibody, or a growth factor); and/or engineered to have a molecular bridge with dual specificities with one end recognizing a viral glycoprotein and the other end recognizing a moiety of the target cell surface (e.g., a ligand-receptor, monoclonal antibody, avidin-biotin and chemical conjugation).

Exemplary viral vectors/viruses include, e.g., retroviruses, lentiviruses, adenovirus, adeno-associated virus (AAV), vaccinia viruses, poxviruses, and herpes simplex viruses.

In certain embodiments, the Cas9- and/or gRNA-encoding sequence is delivered by a recombinant retrovirus. In certain embodiments, the retrovirus (e.g., Moloney murine leukemia virus) comprises a reverse transcriptase, e.g., that allows integration into the host genome. In certain embodiments, the retrovirus is replication-competent. In other embodiments, the retrovirus is replication-defective, e.g., having one of more coding regions for the genes necessary for additional rounds of virion replication and packaging replaced with other genes, or deleted.

In certain embodiments, the Cas9- and/or gRNA-encoding nucleic acid sequence is delivered by a recombinant lentivirus. In certain embodiments, the donor template nucleic acid is delivered by a recombinant retrovirus. For example, the lentivirus is replication-defective, e.g., does not comprise one or more genes required for viral replication.

In certain embodiments, the Cas9- and/or gRNA-encoding nucleic acid sequence is delivered by a recombinant adenovirus. In certain embodiments, the donor template nucleic acid is delivered by a recombinant adenovirus. In certain embodiments, the adenovirus is engineered to have reduced immunity in human.

In certain embodiments, the Cas9- and/or gRNA-encoding nucleic acid sequence is delivered by a recombinant AAV. In certain embodiments, the donor template nucleic acid is delivered by a recombinant AAV. In certain embodiments, the AAV does not incorporate its genome into that of a host cell, e.g., a target cell as describe herein. In certain embodiments, the AAV can incorporate at least part of its genome into that of a host cell, e.g., a target cell as described herein. In certain embodiments, the AAV is a self-complementary adeno-associated virus (scAAV), e.g., a scAAV that packages both strands which anneal together to form double stranded DNA. AAV serotypes that may be used in the disclosed methods, include AAV1, AAV2, modified AAV2 (e.g., modifications at Y444F, Y500F, Y730F and/or S662V), AAV3, modified AAV3 (e.g., modifications at Y705F, Y731F and/or T492V), AAV4, AAV5, AAV6, modified AAV6 (e.g., modifications at S663V and/or T492V), AAV8, AAV 8.2, AAV9, AAV rh10, and pseudotyped AAV, such as AAV2/8, AAV2/5 and AAV2/6 can also be used in the disclosed methods. In certain embodiments, an AAV capsid that can be used in the methods described herein is a capsid sequence from serotype AAV1, AAV2, AAV3, AAV4, AAV5, AAV6, AAV7, AAV8, AAV9, AAV.rh8, AAV.rh10, AAV.rh32/33, AAV.rh43, AAV.rh64R1, or AAV7m8.

In certain embodiments, the Cas9- and/or gRNA-encoding nucleic acid sequence is delivered in a re-engineered AAV capsid, e.g., with about 50% or greater, e.g., about 60% or greater, about 70% or greater, about 80% or greater, about 90% or greater, or about 95% or greater, sequence homology with a capsid sequence from serotypes AAV1, AAV2, AAV3, AAV4, AAV5, AAV6, AAV7, AAV8, AAV9, AAV.rh8, AAV.rh10, AAV.rh32/33, AAV.rh43, or AAV.rh64R1.

In certain embodiments, the Cas9- and/or gRNA-encoding nucleic acid sequence is delivered by a chimeric AAV capsid. In certain embodiments, the donor template nucleic acid is delivered by a chimeric AAV capsid. Exemplary chimeric AAV capsids include, but are not limited to, AAV9i1, AAV2i8, AAV-DJ, AAV2G9, AAV2i8G9, or AAV8G9.

In certain embodiments, the AAV is a self-complementary adeno-associated virus (scAAV), e.g., a scAAV that packages both strands which anneal together to form double stranded DNA.

In certain embodiments, the Cas9- and/or gRNA-encoding DNA is delivered by a hybrid virus, e.g., a hybrid of one or more of the viruses described herein. In certain embodiments, the hybrid virus is hybrid of an AAV (e.g., of any AAV serotype), with a Bocavirus, B19 virus, porcine AAV, goose AAV, feline AAV, canine AAV, or MVM.

A packaging cell is used to form a virus particle that is capable of infecting a target cell. Exemplary packaging cells include 293 cells, which can package adenovirus, and ψ2 or PA317 cells, which can package retrovirus. A viral vector used in gene therapy is usually generated by a producer cell line that packages a nucleic acid vector into a viral particle. The vector typically contains the minimal viral sequences required for packaging and subsequent integration into a host or target cell (if applicable), with other viral sequences being replaced by an expression cassette encoding the protein to be expressed, e.g., components for a Cas9 molecule, e.g., two Cas9 components. For example, an AAV vector used in gene therapy typically only possesses inverted terminal repeat (ITR) sequences from the AAV genome which are required for packaging and gene expression in the host or target cell. The missing viral functions can be supplied in trans by the packaging cell line and/or plasmid containing E2A, E4, and VA genes from adenovirus, and plasmid encoding Rep and Cap genes from AAV, as described in "Triple Transfection Protocol." Henceforth, the viral DNA is packaged in a cell line, which contains a helper plasmid encoding the other AAV genes, namely rep and cap, but lacking ITR sequences. In certain embodiments, the viral DNA is packaged in a producer cell line, which contains E1A and/or E1B genes from adenovirus. The cell line is also infected with adenovirus as a helper. The helper virus (e.g., adenovirus or HSV) or helper plasmid promotes replication of the AAV vector and expression of AAV genes from the helper plasmid with ITRs. The helper plasmid is not packaged in significant amounts due to a lack of ITR sequences. Contamination with adenovirus can be reduced by, e.g., heat treatment to which adenovirus is more sensitive than AAV.

In certain embodiments, the viral vector is capable of cell type and/or tissue type recognition. For example, the viral vector can be pseudotyped with a different/alternative viral envelope glycoprotein; engineered with a cell type-specific receptor (e.g., genetic modification of the viral envelope glycoproteins to incorporate targeting ligands such as peptide ligands, single chain antibodies, growth factors); and/or engineered to have a molecular bridge with dual specificities with one end recognizing a viral glycoprotein and the other end recognizing a moiety of the target cell surface (e.g., ligand-receptor, monoclonal antibody, avidin-biotin and chemical conjugation).

In certain embodiments, the viral vector achieves cell type specific expression. For example, a tissue-specific promoter can be constructed to restrict expression of the transgene (Cas9 and gRNA) to only the target cell. The specificity of the vector can also be mediated by microRNA-dependent control of transgene expression. In certain embodiments, the viral vector has increased efficiency of fusion of the viral vector and a target cell membrane. For example, a fusion protein such as fusion-competent hemagglutin (HA) can be incorporated to increase viral uptake into cells. In certain embodiments, the viral vector has the ability of nuclear localization. For example, a virus that requires the breakdown of the nuclear envelope (during cell division) and therefore can not infect a non-diving cell can be altered to incorporate a nuclear localization peptide in the matrix protein of the virus thereby enabling the transduction of non-proliferating cells.

In certain embodiments, the Cas9- and/or gRNA-encoding nucleic acid sequence is delivered by a non-vector based method (e.g., using naked DNA or DNA complexes). For example, the DNA can be delivered, e.g., by organically modified silica or silicate (Ormosil), electroporation, transient cell compression or squeezing (e.g., as described in Lee, et al, 2012, Nano Lett 12: 6322-27), gene gun, sonoporation, magnetofection, lipid-mediated transfection, dendrimers, inorganic nanoparticles, calcium phosphates, or a combination thereof.

In certain embodiments, delivery via electroporation comprises mixing the cells with the Cas9- and/or gRNA-encoding DNA in a cartridge, chamber or cuvette and applying one or more electrical impulses of defined duration and amplitude. In certain embodiments, delivery via electroporation is performed using a system in which cells are mixed with the Cas9- and/or gRNA-encoding DNA in a vessel connected to a device (e.g., a pump) which feeds the mixture into a cartridge, chamber or cuvette wherein one or more electrical impulses of defined duration and amplitude are applied, after which the cells are delivered to a second vessel.

In certain embodiments, the Cas9- and/or gRNA-encoding nucleic acid sequence is delivered by a combination of a vector and a non-vector based method. In certain embodiments, the donor template nucleic acid is delivered by a combination of a vector and a non-vector based method. For example, virosomes combine liposomes combined with an inactivated virus (e.g., HIV or influenza virus), which can result in more efficient gene transfer, e.g., in respiratory epithelial cells than either viral or liposomal methods alone.

In certain embodiments, the delivery vehicle is a non-viral vector. In certain embodiments, the non-viral vector is an inorganic nanoparticle. Exemplary inorganic nanoparticles include, e.g., magnetic nanoparticles (e.g., $Fe_3MnO_2$) and silica. The outer surface of the nanoparticle can be conjugated with a positively charged polymer (e.g., polyethylenimine, polylysine, polyserine) which allows for attachment (e.g., conjugation or entrapment) of payload. In certain embodiments, the non-viral vector is an organic nanoparticle (e.g., entrapment of the payload inside the nanoparticle). Exemplary organic nanoparticles include, e.g., SNALP liposomes that contain cationic lipids together with neutral helper lipids which are coated with polyethylene glycol (PEG) and protamine and nucleic acid complex coated with lipid coating.

Exemplary lipids for gene transfer are shown below in Table 16.

TABLE 16

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |

TABLE 16-continued

Lipids Used for Gene Transfer

| Lipid | Abbreviation | Feature |
|---|---|---|
| Cholesterol | | Helper |
| N-[1-(2,3-Dioleyloxy)propyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysylaspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

Exemplary polymers for gene transfer are shown below in Table 17.

TABLE 17

Polymers Used for Gene Transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |

TABLE 17-continued

Polymers Used for Gene Transfer

| Polymer | Abbreviation |
| --- | --- |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

In certain embodiments, the vehicle has targeting modifications to increase target cell update of nanoparticles and liposomes, e.g., cell specific antigens, monoclonal antibodies, single chain antibodies, aptamers, polymers, sugars (e.g., N-acetylgalactosamine (GalNAc)), and cell penetrating peptides. In certain embodiments, the vehicle uses fusogenic and endosome-destabilizing peptides/polymers. In certain embodiments, the vehicle undergoes acid-triggered conformational changes (e.g., to accelerate endosomal escape of the cargo). In certain embodiments, a stimuli-cleavable polymer is used, e.g., for release in a cellular compartment. For example, disulfide-based cationic polymers that are cleaved in the reducing cellular environment can be used.

In certain embodiments, the delivery vehicle is a biological non-viral delivery vehicle. In certain embodiments, the vehicle is an attenuated bacterium (e.g., naturally or artificially engineered to be invasive but attenuated to prevent pathogenesis and expressing the transgene (e.g., *Listeria monocytogenes*, certain *Salmonella* strains, *Bifidobacterium longum*, and modified *Escherichia coli*), bacteria having nutritional and tissue-specific tropism to target specific tissues, bacteria having modified surface proteins to alter target tissue specificity). In certain embodiments, the vehicle is a genetically modified bacteriophage (e.g., engineered phages having large packaging capacity, less immunogenic, containing mammalian plasmid maintenance sequences and having incorporated targeting ligands). In certain embodiments, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In certain embodiments, the vehicle is a biological liposome. For example, the biological liposome is a phospholipid-based particle derived from human cells (e.g., erythrocyte ghosts, which are red blood cells broken down into spherical structures derived from the subject (e.g., tissue targeting can be achieved by attachment of various tissue or cell-specific ligands), or secretory exosomes-subject (i.e., patient) derived membrane-bound nanovesicle (30-100 nm) of endocytic origin (e.g., can be produced from various cell types and can therefore be taken up by cells without the need of for targeting ligands).

In certain embodiments, one or more nucleic acid molecules (e.g., DNA molecules) other than the components of a Cas system, e.g., the Cas9 molecule component or components and/or the gRNA molecule component or components described herein, are delivered. In certain embodiments, the nucleic acid molecule is delivered at the same time as one or more of the components of the Cas system are delivered. In certain embodiments, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Cas system are delivered. In certain embodiments, the nucleic acid molecule is delivered by a different means than one or more of the components of the Cas system, e.g., the Cas9 molecule component and/or the gRNA molecule component, are delivered. The nucleic acid molecule can be delivered by any of the delivery methods described herein. For example, the nucleic acid molecule can be delivered by a viral vector, e.g., an integration-deficient lentivirus, and the Cas9 molecule component or components and/or the gRNA molecule component or components can be delivered by electroporation, e.g., such that the toxicity caused by nucleic acids (e.g., DNAs) can be reduced. In certain embodiments, the nucleic acid molecule encodes a therapeutic protein, e.g., a protein described herein. In certain embodiments, the nucleic acid molecule encodes an RNA molecule, e.g., an RNA molecule described herein.

11.2 Delivery of a RNA Encoding a Cas9 Molecule

RNA encoding Cas9 molecules (e.g., eaCas9 molecules or eiCas9 molecules) and/or gRNA molecules, can be delivered into cells, e.g., target cells described herein, by art-known methods or as described herein. For example, Cas9-encoding and/or gRNA-encoding RNA can be delivered, e.g., by microinjection, electroporation, transient cell compression or squeezing (e.g., as described in Lee, et al., 2012, Nano Lett 12: 6322-27), lipid-mediated transfection, peptide-mediated delivery, or a combination thereof. Cas9-encoding and/or gRNA-encoding RNA can be conjugated to molecules to promote uptake by the target cells (e.g., target cells described herein).

In certain embodiments, delivery via electroporation comprises mixing the cells with the RNA encoding Cas9 molecules (e.g., eaCas9 molecules, eiCas9 molecules or eiCas9 fusion proteins) and/or gRNA molecules with or without donor template nucleic acid molecules, in a cartridge, chamber or cuvette and applying one or more electrical impulses of defined duration and amplitude. In certain embodiments, delivery via electroporation is performed using a system in which cells are mixed with the RNA encoding Cas9 molecules (e.g., eaCas9 molecules, eiCas9 molecules or eiCas9 fusion proteins) and/or gRNA molecules with or without donor template nucleic acid molecules, in a vessel connected to a device (e.g., a pump) which feeds the mixture into a cartridge, chamber or cuvette wherein one or more electrical impulses of defined duration and amplitude are applied, after which the cells are delivered to a second vessel. Cas9-encoding and/or gRNA-encoding RNA can be conjugated to molecules to promote uptake by the target cells (e.g., target cells described herein).

11.3 Delivery of a Cas9 Molecule Protein

Cas9 molecules (e.g., eaCas9 molecules or eiCas9 molecules) can be delivered into cells by art-known methods or as described herein. For example, Cas9 protein molecules can be delivered, e.g., by microinjection, electroporation, transient cell compression or squeezing (e.g., as described in Lee, et al, 2012, Nano Lett 12: 6322-27), lipid-mediated transfection, peptide-mediated delivery, or a combination thereof. Delivery can be accompanied by DNA encoding a gRNA or by a gRNA. Cas9 protein can be conjugated to molecules promoting uptake by the target cells (e.g., target cells described herein).

In certain embodiments, delivery via electroporation comprises mixing the cells with the Cas9 molecules (e.g., eaCas9 molecules, eiCas9 molecules or eiCas9 fusion proteins) and/or gRNA molecules with or without donor nucleic acid, in a cartridge, chamber or cuvette and applying one or more electrical impulses of defined duration and amplitude. In certain embodiments, delivery via electroporation is performed using a system in which cells are mixed with the Cas9 molecules (e.g., eaCas9 molecules, eiCas9 molecules or eiCas9 fusion proteins) and/or gRNA molecules in a vessel connected to a device (e.g., a pump) which feeds the mixture into a cartridge, chamber or cuvette wherein one or more electrical impulses of defined duration and amplitude are applied, after which the cells are delivered to a second vessel. Cas9-encoding and/or gRNA-encoding RNA can be conjugated to molecules to promote uptake by the target cells (e.g., target cells described herein).

11. 4 RNP Delivery of Cas9 Molecule Protein and gRNA

In certain embodiments, the Cas9 molecule and gRNA molecule are delivered to target cells via Ribonucleoprotein (RNP) delivery. In certain embodiments, the Cas9 molecule is provided as a protein, and the gRNA molecule is provided as transcribed or synthesized RNA. The gRNA molecule can be generated by chemical synthesis. In certain embodiments, the gRNA molecule forms a RNP complex with the Cas9 molecule protein under suitable condition prior to delivery to the target cells. The RNP complex can be delivered to the target cells by any suitable methods known in the art, e.g., by electroporation, lipid-mediated transfection, protein or DNA-based shuttle, mechanical force, or hydraulic force. In certain embodiments, the RNP complex is delivered to the target cells by electroporation.

11.5 Route of Administration

Systemic modes of administration include oral and parenteral routes. Parenteral routes include, by way of example, intravenous, intrarterial, intraosseous, intramuscular, intradermal, subcutaneous, intranasal and intraperitoneal routes. Components administered systemically may be modified or formulated to target the components to epithelial or neuronal cells.

Local modes of administration include, by way of example, intrathecal, intraspinal, intra-cerebroventricular, and intraparenchymal (e.g., into the parenchyma of the brain or spinal cord).

In certain embodiments, local modes of administration include intra-parenchymal into the dorsal root ganglion at the level of the trigeminal nerve. In certain embodiments, local modes of administration include intra-parenchymal into the dorsal root ganglion at the level of the sacral ganglia. In certain embodiments, local modes of administration include intra-parenchymal into the dorsal root ganglion at the level of the lumbar ganglia. In certain embodiments, local modes of administration include intra-parenchymal into the dorsal root ganglion at the level of the thoracic ganglia. In certain embodiments, local modes of administration include intra-parenchymal into the dorsal root ganglion at the level of the cervical ganglia, e.g., superior cervical ganglion, e.g., middle cervical ganglion, e.g., inferior cervical ganglion. In certain embodiments, local modes of administration include intra-parenchymal into the dorsal root ganglion at the level of the cranial nerve ganglia, e.g. cranial nerve ganglia I-XII.

In certain embodiments, significantly smaller amounts of the components (compared with systemic approaches) may exert an effect when administered locally compared to when administered systemically (for example, intravenously). Local modes of administration can reduce or eliminate the incidence of potentially toxic side effects that may occur when therapeutically effective amounts of a component are administered systemically.

In certain embodiments, components described herein are delivered to epithelial cells, e.g., epithelial cells of the oropharynx (including, e.g., epithelial cells of the nose, gums, lips, tongue or pharynx), epithelial cells of the finger or fingernail bed, or epithelial cells of the ano-genital area (including, e.g., epithelial cells of the penis, vulva, vagina or anus). In certain embodiments, components described herein are delivered to the eye (including, e.g., corneal epithelium, e.g., corneal stroma, e.g., epithelium of upper and lower eyelid, e.g., lens).

Administration may be provided as a periodic bolus or as continuous infusion from an internal reservoir or from an external reservoir (for example, from an intravenous bag). Components may be administered locally, for example, by continuous release from a sustained release drug delivery device.

Administration may be provided as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag). Components may be administered locally, for example, by continuous release from a sustained release drug delivery device immobilized to an inner wall of the eye or via targeted transscleral controlled release into the choroid (see, for example, PCT/US00/00207, PCT/US02/14279, Ambati et al. (2000) Invest. Ophthalmol. Vis. Sci. 41:1181-1185, and Ambati et al. (2000) Invest. Ophthalmol. Vis. Sci. 41:1186-1191). A variety of devices suitable for administering components locally to the inside of the eye are known in the art. See, for example, U.S. Pat. Nos. 6,251,090, 6,299,895, 6,416,777, 6,413,540, and PCT/US00/28187.

In certain embodiments, components may be formulated to permit release over a prolonged period of time. A release system can include a matrix of a biodegradable material or a material which releases the incorporated components by diffusion. The components can be homogeneously or heterogeneously distributed within the release system. A variety of release systems may be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used for injection. Typically the microspheres are composed of a polymer of lactic acid and glycolic acid, which are structured to form hollow spheres. The spheres can be approximately 15-30 microns in diameter and can be loaded with components described herein.

11.6 Bi-Modal or Differential Delivery of Components

Separate delivery of the components of a Cas system, e.g., the Cas9 molecule or Cas9-fusion protein component and the gRNA molecule component, and more particularly, delivery of the components by differing modes, can enhance performance, e.g., by improving tissue specificity and safety. In certain embodiments, the Cas9 molecule is a Cas9 variant. For example, and not by way of limitation, the Cas9 variant can be a S. pyogenes Cas9 variant or a S. aureus Cas9 variant. In certain embodiments, the S. pyogenes Cas9 variant is the EQR variant. In certain embodiments, the S. pyogenes Cas9 variant is the VRER variant.

In certain embodiments, the Cas9 molecule (e.g., eaCas9 or eiCas9 molecule) or Cas9-fusion protein and the gRNA molecule are delivered by different modes, or as sometimes referred to herein as differential modes. Different or differential modes, as used herein, refer modes of delivery that confer different pharmacodynamic or pharmacokinetic properties on the subject component molecule, e.g., a Cas9 molecule, or gRNA molecule. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., adeno-associated virus or lentivirus, delivery.

By way of example, the components, e.g., a Cas9 molecule and a gRNA molecule, can be delivered by modes that differ in terms of resulting half-life or persistent of the delivered component the body, or in a particular compartment, tissue or organ. In certain embodiments, a gRNA molecule can be delivered by such modes. The Cas9 molecule component can be delivered by a mode which results in less persistence or less exposure to the body or a particular compartment or tissue or organ.

More generally, in certain embodiments, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In certain embodiments, the first pharmacodynamic or pharmacokinetic property, e.g., distribution, persistence or exposure, is more limited than the second pharmacodynamic or pharmacokinetic property.

In certain embodiments, the first mode of delivery is selected to optimize, e.g., minimize, a pharmacodynamic or pharmacokinetic property, e.g., distribution, persistence or exposure.

In certain embodiments, the second mode of delivery is selected to optimize, e.g., maximize, a pharmacodynamic or pharmcokinetic property, e.g., distribution, persistence or exposure.

In certain embodiments, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In certain embodiments, the second mode of delivery comprises a relatively transient element, e.g., an RNA or protein.

In certain embodiments, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a Cas9 molecule (e.g., an eaCas9 molecule or an eiCas9 molecule), is delivered in a transient manner, for example as mRNA or as protein, ensuring that the full Cas9 molecule/gRNA molecule complex is only present and active for a short period of time.

Furthermore, the components can be delivered in different molecular form or with different delivery vectors that complement one another to enhance safety and tissue specificity.

Use of differential delivery modes can enhance performance, safety and efficacy. E.g., the likelihood of an eventual off-target modification can be reduced. Delivery of immunogenic components, e.g., Cas9 molecules (e.g., eaCas9 or eiCas9 molecules) or Cas9-fusion proteins, by less persistent modes can reduce immunogenicity, as peptides from the bacterially-derived Cas enzyme are displayed on the surface of the cell by MEW molecules. A two-part delivery system can alleviate these drawbacks.

Differential delivery modes can be used to deliver components to different, but overlapping target regions. The formation active complex is minimized outside the overlap of the target regions. Thus, in certain embodiments, a first component, e.g., a gRNA molecule is delivered by a first delivery mode that results in a first spatial, e.g., tissue, distribution. A second component, e.g., a Cas9 molecule (e.g., an eaCas9 molecule or an eiCas9 molecule) is delivered by a second delivery mode that results in a second spatial, e.g., tissue, distribution. In certain embodiments, the first mode comprises a first element selected from a liposome, nanoparticle, e.g., polymeric nanoparticle, and a nucleic acid, e.g., viral vector. The second mode comprises a second element selected from the group. In certain embodiments, the first mode of delivery comprises a first targeting element, e.g., a cell specific receptor or an antibody, and the second mode of delivery does not include that element. In embodiment, the second mode of delivery comprises a second targeting element, e.g., a second cell specific receptor or second antibody.

When the Cas9 molecule (e.g., eaCas9 molecule or eiCas9 molecule) is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA molecule and the Cas9 molecule are packaged in separated delivery vehicles with distinct but overlapping tissue tropism, the fully functional complex is only be formed in the tissue that is targeted by both vectors.

11. 7 Ex Vivo Delivery

In certain embodiments, each component of the genome editing system described in Table 14 are introduced into a cell which is then introduced into the subject, e.g., cells are removed from a subject, manipulated ex vivo and then introduced into the subject. Methods of introducing the components can include, e.g., any of the delivery methods described in Table 15.

12. Modified Nucleosides, Nucleotides, and Nucleic Acids

Modified nucleosides and modified nucleotides can be present in nucleic acids, e.g., particularly gRNA, but also other forms of RNA, e.g., mRNA, RNAi, or siRNA. As described herein, "nucleoside" is defined as a compound containing a five-carbon sugar molecule (a pentose or ribose) or derivative thereof, and an organic base, purine or pyrimidine, or a derivative thereof. As described herein, "nucleotide" is defined as a nucleoside further comprising a phosphate group.

Modified nucleosides and nucleotides can include one or more of:

(i) alteration, e.g., replacement, of one or both of the non-linking phosphate oxygens and/or of one or more of the linking phosphate oxygens in the phosphodiester backbone linkage;

(ii) alteration, e.g., replacement, of a constituent of the ribose sugar, e.g., of the 2' hydroxyl on the ribose sugar;

(iii) wholesale replacement of the phosphate moiety with "dephospho" linkers;

(iv) modification or replacement of a naturally occurring nucleobase;

(v) replacement or modification of the ribose-phosphate backbone;

(vi) modification of the 3' end or 5' end of the oligonucleotide, e.g., removal, modification or replacement of a terminal phosphate group or conjugation of a moiety; and (vii) modification of the sugar.

The modifications listed above can be combined to provide modified nucleosides and nucleotides that can have two, three, four, or more modifications. For example, a modified nucleoside or nucleotide can have a modified sugar and a modified nucleobase. In certain embodiments, every base of a gRNA is modified, e.g., all bases have a modified phosphate group, e.g., all are phosphorothioate groups. In certain embodiments, all, or substantially all, of the phosphate groups of a unimolecular or modular gRNA molecule are replaced with phosphorothioate groups.

In certain embodiments, modified nucleotides, e.g., nucleotides having modifications as described herein, can be incorporated into a nucleic acid, e.g., a "modified nucleic acid." In certain embodiments, the modified nucleic acids comprise one, two, three or more modified nucleotides. In certain embodiments, at least 5% (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%) of the positions in a modified nucleic acid are a modified nucleotides.

Unmodified nucleic acids can be prone to degradation by, e.g., cellular nucleases. For example, nucleases can hydrolyze nucleic acid phosphodiester bonds. Accordingly, in certain embodiments, the modified nucleic acids described herein can contain one or more modified nucleosides or nucleotides, e.g., to introduce stability toward nucleases.

In certain embodiments, the modified nucleosides, modified nucleotides, and modified nucleic acids described herein can exhibit a reduced innate immune response when introduced into a population of cells, both in vivo and ex vivo. The term "innate immune response" includes a cellular response to exogenous nucleic acids, including single stranded nucleic acids, generally of viral or bacterial origin, which involves the induction of cytokine expression and release, particularly the interferons, and cell death. In certain embodiments, the modified nucleosides, modified nucleotides, and modified nucleic acids described herein can disrupt binding of a major groove interacting partner with the nucleic acid. In certain embodiments, the modified nucleosides, modified nucleotides, and modified nucleic acids described herein can exhibit a reduced innate immune response when introduced into a population of cells, both in vivo and ex vivo, and also disrupt binding of a major groove interacting partner with the nucleic acid.

12.1 Definitions of Chemical Groups

As used herein, "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 12, from 1 to about 8, from 1 to about 6, from 1 to about 4, or from 1 to about 3 carbon atoms.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In certain embodiments, aryl groups have from 6 to about 20 carbon atoms.

As used herein, "alkenyl" refers to an aliphatic group containing at least one double bond.

As used herein, "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl.

As used herein, "arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

As used herein, "cycloalkyl" refers to a cyclic, bicyclic, tricyclic, or polycyclic non-aromatic hydrocarbon groups having 3 to 12 carbons. Examples of cycloalkyl moieties include, but are not limited to, cyclopropyl, cyclopentyl, and cyclohexyl.

As used herein, "heterocyclyl" refers to a monovalent radical of a heterocyclic ring system. Representative heterocyclyls include, without limitation, tetrahydrofuranyl, tetrahydrothienyl, pyrrolidinyl, pyrrolidonyl, piperidinyl, pyrrolinyl, piperazinyl, dioxanyl, dioxolanyl, diazepinyl, oxazepinyl, thiazepinyl, and morpholinyl.

As used herein, "heteroaryl" refers to a monovalent radical of a heteroaromatic ring system. Examples of heteroaryl moieties include, but are not limited to, imidazolyl, oxazolyl, thiazolyl, triazolyl, pyrrolyl, furanyl, indolyl, thiophenyl pyrazolyl, pyridinyl, pyrazinyl, pyridazinyl, pyrimidinyl, indolizinyl, purinyl, naphthyridinyl, quinolyl, and pteridinyl.

12.2 Phosphate Backbone Modifications 12.2.1 the Phosphate Group

In certain embodiments, the phosphate group of a modified nucleotide can be modified by replacing one or more of the oxygens with a different substituent. Further, the modified nucleotide, e.g., modified nucleotide present in a modified nucleic acid, can include the wholesale replacement of an unmodified phosphate moiety with a modified phosphate as described herein. In certain embodiments, the modification of the phosphate backbone can include alterations that result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. In certain embodiments, one of the non-bridging phosphate oxygen atoms in the phosphate backbone moiety can be replaced by any of the following groups: sulfur (S), selenium (Se), $BR_3$ (wherein R can be, e.g., hydrogen, alkyl, or aryl), C (e.g., an alkyl group, an aryl group, and the like), H, $NR_2$ (wherein R can be, e.g., hydrogen, alkyl, or aryl), or OR (wherein R can be, e.g., alkyl or aryl). The phosphorous atom in an unmodified phosphate group is achiral. However, replacement of one of the non-bridging oxygens with one of the above atoms or groups of atoms can render the phosphorous atom chiral; that is to say that a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotide diastereomers. In certain embodiments, modifications to one or both non-bridging oxygens can also include the replacement of the non-bridging oxygens with a group independently selected from S, Se, B, C, H, N, and OR (R can be, e.g., alkyl or aryl).

The phosphate linker can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens.

12.2.2 Replacement of the Phosphate Group

The phosphate group can be replaced by non-phosphorus containing connectors. In certain embodiments, the charge phosphate group can be replaced by a neutral moiety.

Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methyl enedimethylhydrazo and methyleneoxymethylimino.

12.2.3 Replacement of the Ribophosphate Backbone

Scaffolds that can mimic nucleic acids can also be constructed wherein the phosphate linker and ribose sugar are replaced by nuclease resistant nucleoside or nucleotide surrogates. In certain embodiments, the nucleobases can be tethered by a surrogate backbone. Examples can include, without limitation, the morpholino, cyclobutyl, pyrrolidine and peptide nucleic acid (PNA) nucleoside surrogates.

12.3 Sugar Modifications

The modified nucleosides and modified nucleotides can include one or more modifications to the sugar group. For example, the 2' hydroxyl group (OH) can be modified or replaced with a number of different "oxy" or "deoxy" substituents. In certain embodiments, modifications to the 2' hydroxyl group can enhance the stability of the nucleic acid since the hydroxyl can no longer be deprotonated to form a 2'-alkoxide ion. The 2'-alkoxide can catalyze degradation by intramolecular nucleophilic attack on the linker phosphorus atom.

Examples of "oxy"-2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), $O(CH_2CH_2O)_nCH_2CH_2OR$ wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20). In certain embodiments, the "oxy"-2' hydroxyl group modification can include "locked" nucleic acids (LNA) in which the 2' hydroxyl can be connected, e.g., by a $C_{1-6}$ alkylene or $C_{1-6}$ heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy, $O(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). In certain embodiments, the "oxy"-2' hydroxyl group modification can include the methoxyethyl group (MOE), ($OCH_2CH_2OCH_3$, e.g., a PEG derivative).

"Deoxy" modifications can include hydrogen (i.e. deoxyribose sugars, e.g., at the overhang portions of partially ds RNA); halo (e.g., bromo, chloro, fluoro, or iodo); amino (wherein amino can be, e.g., $NH_2$; alkylamino, dialkylamino, heterocyclyl, arylamino, diarylamino, heteroarylamino, diheteroarylamino, or amino acid); $NH(CH_2CH_2NH)_nCH_2CH_2$-amino (wherein amino can be, e.g., as described herein), —NHC(O)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino as described herein.

The sugar group can also contain one or more carbons that possess the opposite stereochemical configuration than that of the corresponding carbon in ribose. Thus, a modified nucleic acid can include nucleotides containing e.g., arabinose, as the sugar. The nucleotide "monomer" can have an alpha linkage at the 1' position on the sugar, e.g., alpha-nucleosides. The modified nucleic acids can also include "abasic" sugars, which lack a nucleobase at C-1'. These abasic sugars can also be further modified at one or more of the constituent sugar atoms. The modified nucleic acids can also include one or more sugars that are in the L form, e.g. L-nucleosides.

Generally, RNA includes the sugar group ribose, which is a 5-membered ring having an oxygen. Exemplary modified nucleosides and modified nucleotides can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). In certain embodiments, the modified nucleotides can include multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replaced with α-L-threofuranosyl-(3'→2')).

12.4 Modifications on the Nucleobase

The modified nucleosides and modified nucleotides described herein, which can be incorporated into a modified nucleic acid, can include a modified nucleobase. Examples of nucleobases include, but are not limited to, adenine (A), guanine (G), cytosine (C), and uracil (U). These nucleobases can be modified or wholly replaced to provide modified nucleosides and modified nucleotides that can be incorporated into modified nucleic acids. The nucleobase of the nucleotide can be independently selected from a purine, a pyrimidine, a purine or pyrimidine analog. In certain embodiments, the nucleobase can include, for example, naturally-occurring and synthetic derivatives of a base.

12.4.1 Uracil

In certain embodiments, the modified nucleobase is a modified uracil. Exemplary nucleobases and nucleosides having a modified uracil include without limitation pseudouridine (w), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho$^5$U), 5-aminoallyl-uridine, 5-halo-uridine (e.g., 5-iodo-uridine or 5-bromo-uridine), 3-methyl-uridine (m$^3$U), 5-methoxy-uridine (mo$^5$U), uridine 5-oxyacetic acid (cmo$^5$U), uridine 5-oxyacetic acid methyl ester (mcmo$^5$U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$s2U), 5-aminomethyl-2-thio-uridine (nm$^5$s2U), 5-methylaminomethyl-uridine (mnm$^5$U), 5-methylaminomethyl-2-thio-uridine (mnm$^5$s2U), 5-methylaminomethyl-2-seleno-uridine (mnm$^5$se$^2$U), 5-carbamoylmethyl-uridine (ncm$^5$U), 5-carboxymethylaminomethyl-uridine (cmnm$^5$U), 5-carboxymethylaminomethyl-2-thio-uridine (cmnm$^5$s2U), 5-propynyl-uridine, 1-propynyl-pseudouridine, 5-taurinomethyl-uridine (τcm$^5$U), 1-taurinomethyl-pseudouridine, 5-taurinomethyl-2-thio-uridine(τm$^5$s2U), 1-taurinomethyl-4-thio-pseudouridine, 5-methyl-uridine (m$^5$U, i.e., having the nucleobase deoxythymine), 1-methyl-pseudouridine (m$^1$ψ), 5-methyl-2-thio-uridine (m$^5$s2U), 1-methyl-4-thio-pseudouridine (m$^1$s$^4$ψ), 4-thio-1-methyl-pseudouridine, 3-methyl-pseudouridine (m$^3$ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m$^5$D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine (acp$^3$U), 1-methyl-3-(3-amino-3-carboxypropyl) pseudouridine (acp$^3$ψ), 5-(isopentenylaminomethyl)uridine (inm$^5$U), 5-(isopentenylaminomethyl)-2-thio-uridine (inm$^5$s2U), α-thio-uridine, 2'-O-methyl-uridine (Um), 5,2'-O-dimethyl-uridine (m$^5$Um), 2'-O-methyl-pseudouridine (ψm), 2-thio-2'-O-methyl-uridine (s2Um), 5-methoxycarbonylmethyl-2'-O-methyl-uridine (mcm$^5$Um), 5-carbamoylmethyl-2'-O-methyl-uridine (ncm$^5$Um), 5-carboxymethylaminomethyl-2'-O-methyl-uridine (cmnm$^5$Um), 3,2'-O-dimethyl-uridine (m$^3$Um), 5-(isopentenylaminomethyl)-2'-O-methyl-uridine (inm$^5$Um), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, pyrazolo[3,4-d]pyrimidines, xanthine, and hypoxanthine.

12.4.2 Cytosine

In certain embodiments, the modified nucleobase is a modified cytosine. Exemplary nucleobases and nucleosides having a modified cytosine include without limitation 5-aza-cytidine, 6-aza-cytidine, pseudoisocytidine, 3-methyl-cytidine (m$^3$C), N4-acetyl-cytidine (act), 5-formyl-cytidine (f$^5$C), N4-methyl-cytidine (m$^4$C), 5-methyl-cytidine (m$^5$C), 5-halo-cytidine (e.g., 5-iodo-cytidine), 5-hydroxymethyl-cytidine (hm$^5$C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k$^2$C), α-thio-cytidine, 2'-O-methyl-cytidine (Cm), 5,2'-O-dimethyl-cytidine (m$^5$Cm), N4-acetyl-2'-O-methyl-cytidine (ac$^4$Cm), N4,2'-O-dimethyl-cytidine (m$^4$Cm), 5-formyl-2'-O-methyl-cytidine (f$^5$Cm), N4,N4,2'-O-trimethyl-cytidine (m$^4_2$Cm), 1-thio-cytidine, 2'-F-ara-cytidine, 2'-F-cytidine, and 2'-OH-ara-cytidine.

12.4.3 Adenine

In certain embodiments, the modified nucleobase is a modified adenine. Exemplary nucleobases and nucleosides having a modified adenine include without limitation 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenosine, 7-deaza-8-aza-adenosine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m$^1$A), 2-methyl-adenosine (m$^2$A), N6-methyl-adenosine (m$^6$A), 2-methylthio-N6-methyl-adenosine (ms$^2$m$^6$A), N6-isopentenyl-adenosine (i$^6$A), 2-methylthio-N6-isopentenyl-adenosine (ms$^2$i$^6$A), N6-(cis-hydroxyisopentenyl)adenosine (io$^6$A), 2-methyl-thio-N6-(cis-hydroxyisopentenyl)adenosine (ms2io$^6$A), N6-glycinylcarbamoyl-adenosine (g$^6$A), N6-threonylcarbamoyl-adenosine (t$^6$A), N6-methyl-N6-threonylcarbamoyl-adenosine (m⁶t⁶A), 2-methylthio-N6-threonylcarbamoyl-adenosine (ms²g⁶A), N6,N6-dimethyl-adenosine (m⁶₂A), N6-hydroxynorvalylcarbamoyl-adenosine (hn⁶A), 2-methylthio-N6-hydroxynorvalylcarbamoyl-adenosine (ms2hn⁶A), N6-acetyl-adenosine (ac⁶A), 7-methyl-adenosine, 2-methylthio-adenosine, 2-methoxy-adenosine, α-thio-adenosine, 2'-O-methyl-adenosine (Am), N⁶,2'-O-dimethyl-adenosine (m⁶Am), N⁶-Methyl-2'-deoxyadenosine, N6,N6,2'-O-trimethyl-adenosine (m⁶₂Am), 1,2'-O-dimethyl-adenosine (m¹Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

12.4.4 Guanine

In certain embodiments, the modified nucleobase is a modified guanine. Exemplary nucleobases and nucleosides having a modified guanine include without limitation inosine (I), 1-methyl-inosine (m¹I), wyosine (imG), methylwyosine (mimG), 4-demethyl-wyosine (imG-14), isowyosine (imG2), wybutosine (yW), peroxywybutosine (o₂yW), hydroxywybutosine (OHyW), undermodified hydroxywybutosine (OHyW*), 7-deaza-guanosine, queuosine (Q), epoxyqueuosine (oQ), galactosyl-queuosine (galQ), mannosyl-queuosine (manQ), 7-cyano-7-deaza-guanosine (preQ₀), 7-aminomethyl-7-deaza-guanosine (preQ₁), archaeosine (G⁺), 7-deaza-8-aza-guanosine, 6-thio-guanosine, 6-thio-7-deaza-guanosine, 6-thio-7-deaza-8-aza-guanosine, 7-methyl-guanosine (m⁷G), 6-thio-7-methyl-guanosine, 7-methyl-inosine, 6-methoxy-guanosine, 1-methyl-guanosine (m'G), N2-methyl-guanosine (m²G), N2,N2-dimethyl-guanosine (m²₂G), N2,7-dimethyl-guanosine (m²,7G), N2, N2,7-dimethyl-guanosine (m²,2,7G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m²Gm), N2,N2-dimethyl-2'-O-methyl-guanosine (m²₂Gm), 1-methyl-2'-O-methyl-guanosine (m'Gm), N2,7-dimethyl-2'-O-methyl-guanosine (m²,7Gm), 2'-O-methyl-inosine (Im), 1,2'-O-dimethyl-inosine (m'Im), O⁶-phenyl-2'-deoxyinosine, 2'-O-ribosylguanosine (phosphate) (Gr(p)), 1-thio-guanosine, O⁶-methyl-guanosine, O⁶-Methyl-2'-deoxyguanosine, 2'-F-ara-guanosine, and 2'-F-guanosine.

12.5 Exemplary Modified gRNAs

In certain embodiments, the modified nucleic acids can be modified gRNAs. It is to be understood that any of the gRNAs described herein can be modified in accordance with this section, including any gRNA that comprises a targeting domain comprising a nucleotide sequence selected from SEQ ID NOS: 208 to 58749.

As discussed above, transiently expressed or delivered nucleic acids can be prone to degradation by, e.g., cellular nucleases. Accordingly, in one aspect the modified gRNA molecules described herein can contain one or more modified nucleosides or nucleotides which introduce stability toward nucleases. In certain embodiments, certain modified gRNA molecules described herein can exhibit a reduced innate immune response when introduced into a population of cells, particularly the cells disclosed herein. As noted above, the term "innate immune response" includes a cellular response to exogenous nucleic acids, including single stranded nucleic acids, generally of viral or bacterial origin, which involves the induction of cytokine expression and release, particularly the interferons, and cell death.

While some of the exemplary modification discussed in this section may be included at any position within the gRNA sequence, in certain embodiments, a gRNA molecule comprises a modification at or near its 5' end (e.g., within 1-10, 1-5, or 1-2 nucleotides of its 5' end). In certain embodiments, a gRNA comprises a modification at or near its 3' end (e.g., within 1-10, 1-5, or 1-2 nucleotides of its 3' end). In certain embodiments, a gRNA molecule comprises both a modification at or near its 5' end and a modification at or near its 3' end.

In certain embodiments, the 5' end of the gRNA molecule lacks a 5' triphosphate group. In certain embodiments, the 5' end of the targeting domain lacks a 5' triphosphate group. In certain embodiments, the 5' end of the gRNA molecule includes a 5' cap. In certain embodiments, the 5' end of the targeting domain includes a 5' cap. In certain embodiments, the gRNA molecule lacks a 5' triphosphate group. In certain embodiments, the gRNA molecule comprises a targeting domain and the 5' end of the targeting domain lacks a 5' triphosphate group. In certain embodiments, gRNA molecule includes a 5' cap. In certain embodiments, the gRNA molecule comprises a targeting domain and the 5' end of the targeting domain includes a 5' cap.

In certain embodiments, the 5' end of a gRNA is modified by the inclusion of a eukaryotic mRNA cap structure or cap analog (e.g., without limitation, a G(5)ppp(5)G cap analog, a m7G(5)ppp(5)G cap analog, or a 3'-O-Me-m7G(5)ppp(5)G anti reverse cap analog (ARCA)). In certain embodiments, the 5' cap comprises a modified guanine nucleotide that is linked to the remainder of the gRNA molecule via a 5'-5' triphosphate linkage. In certain embodiments, the 5' cap analog comprises two optionally modified guanine nucleotides that are linked via a 5'-5' triphosphate linkage. In certain embodiments, the 5' end of the gRNA molecule has the chemical formula:

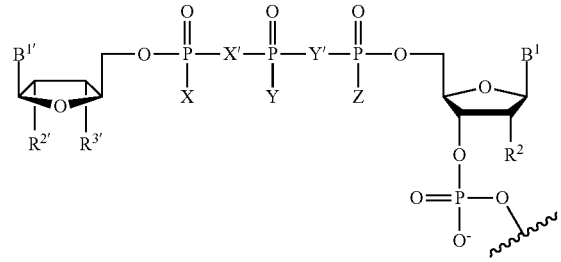

wherein:
each of $R^1$ and $B^{1'}$ is independently

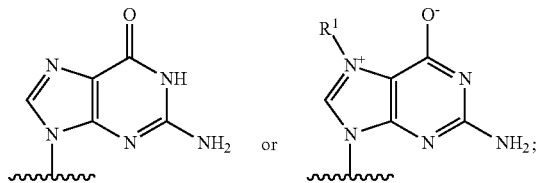

each $R^1$ is independently $C_{1-4}$ alkyl, optionally substituted by a phenyl or a 6-membered heteroaryl;
each of $R^2$, $R^{2'}$, and $R^{3'}$ is independently H, F, OH, or $O-C_{1-4}$ alkyl;
each of X, Y, and Z is independently O or S; and
each of X' and Y' is independently O or $CH_2$.

In certain embodiments, each $R^1$ is independently $-CH_3$, $-CH_2CH_3$, or $-CH_2C_6H_5$.

In certain embodiments, R¹ is —CH₃.
In certain embodiments, B¹' is

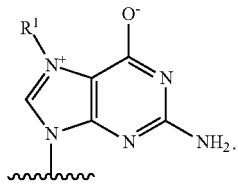

In certain embodiments, each of R², R²', and R³' is independently H, OH, or O—CH₃.

In certain embodiments, each of X, Y, and Z is O.

In certain embodiments, X' and Y' are O.

In certain embodiments, the 5' end of the gRNA molecule has the chemical formula:

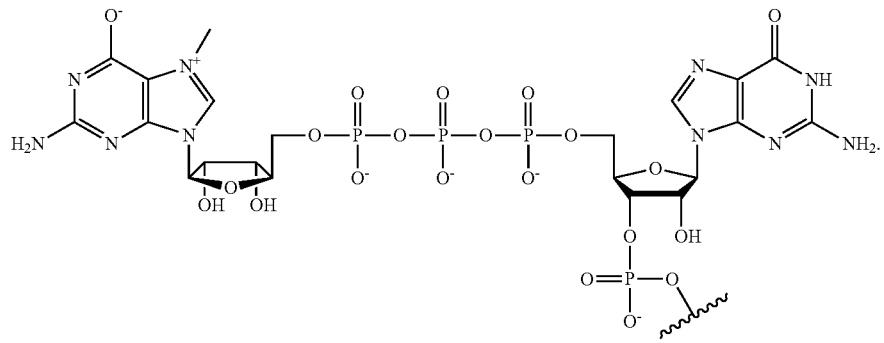

In certain embodiments, the 5' end of the gRNA molecule has the chemical formula:

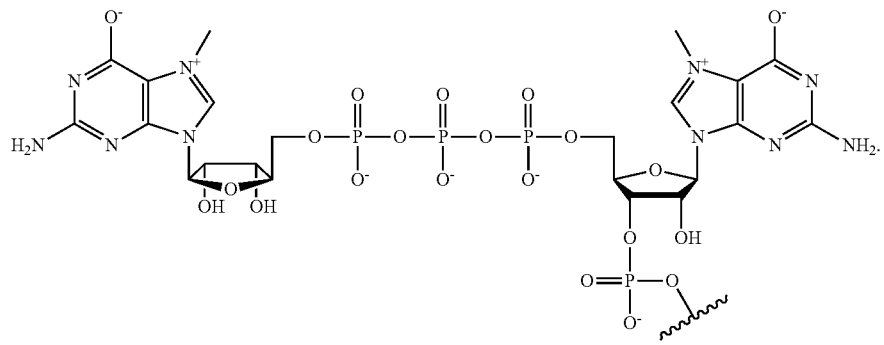

In certain embodiments, the 5' end of the gRNA molecule has the chemical formula:

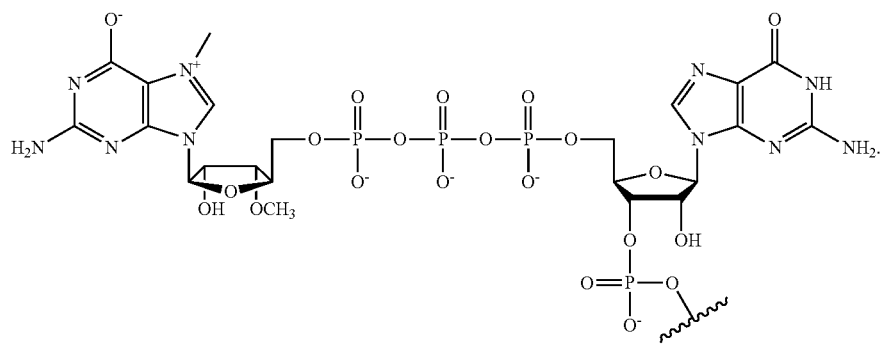

In certain embodiments, the 5' end of the gRNA molecule has the chemical formula:

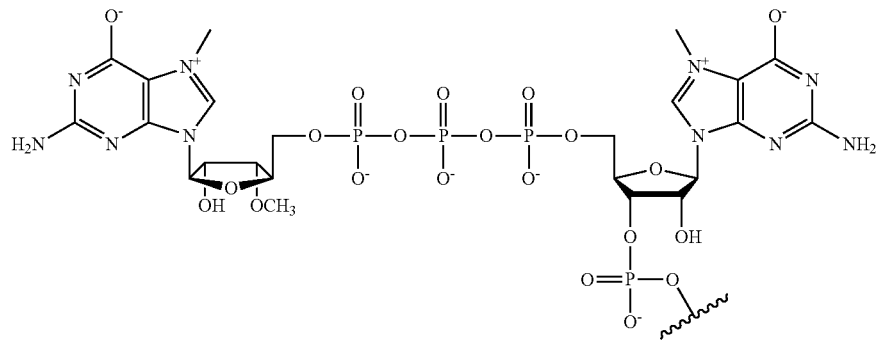

In certain embodiments, X is S, and Y and Z are O.
In certain embodiments, Y is S, and X and Z are O.
In certain embodiments, Z is S, and X and Y are O.
In certain embodiments, the phosphorothioate is the Sp diastereomer.
In certain embodiments, X' is CH$_2$, and Y' is O.
In certain embodiments, X' is O, and Y' is CH$_2$.
In certain embodiments, the 5' cap comprises two optionally modified guanine nucleotides that are linked via an optionally modified 5'-5' tetraphosphate linkage.
In certain embodiments, the 5' end of the gRNA molecule has the chemical formula:

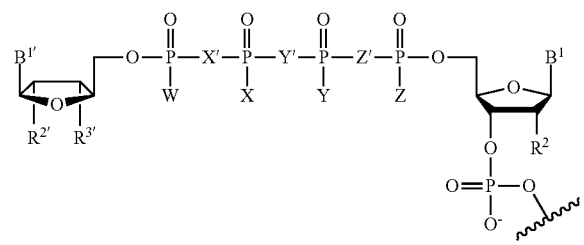

wherein:
each of R$^1$ and B$^{1'}$ is independently

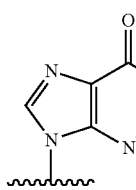 or 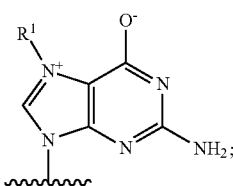

each R$^1$ is independently C$_{1-4}$ alkyl, optionally substituted by a phenyl or a 6-membered heteroaryl;
each of R$^2$, R$^{2'}$, and R$^{3'}$ is independently H, F, OH, or O—C$_{1-4}$ alkyl;
each of W, X, Y, and Z is independently O or S; and
each of X', Y', and Z' is independently O or CH$_2$.
In certain embodiments, each R$^1$ is independently —CH$_3$, —CH$_2$CH$_3$, or —CH$_2$C$_6$H$_5$.
In certain embodiments, R$^1$ is —CH$_3$.

In certain embodiments, B$^{1'}$ is

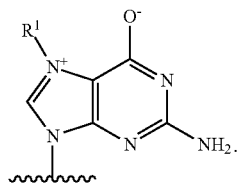

In certain embodiments, each of R$^2$, R$^{2'}$, and R$^{3'}$ is independently H, OH, or O—CH$_3$.
In certain embodiments, each of W, X, Y, and Z is O.
In certain embodiments, each of X', Y', and Z' are O.
In certain embodiments, X' is CH$_2$, and Y' and Z' are O.
In certain embodiments, Y' is CH$_2$, and X' and Z' are O.
In certain embodiments, Z' is CH$_2$, and X' and Y' are O.
In certain embodiments, the 5' cap comprises two optionally modified guanine nucleotides that are linked via an optionally modified 5'-5' pentaphosphate linkage.
In certain embodiments, the 5' end of the gRNA molecule has the chemical formula:

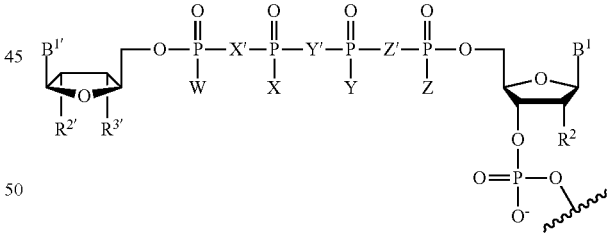

wherein:
each of B$^1$ and B$^{1'}$ is independently

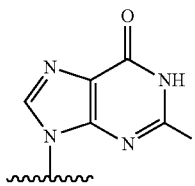 or 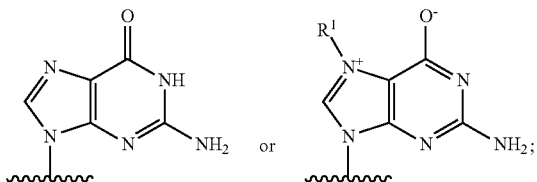

each R$^1$ is independently C$_{1-4}$ alkyl, optionally substituted by a phenyl or a 6-membered heteroaryl;

each of $R^2$, $R^{2'}$, and $R^{3'}$ is independently H, F, OH, or O—$C_{1-4}$ alkyl;

each of V, W, X, Y, and Z is independently O or S; and each of W', X', Y', and Z' is independently O or $CH_2$.

In certain embodiments, each $R^1$ is independently —$CH_3$, —$CH_2CH_3$, or —$CH_2C_6H_5$.

In certain embodiments, $R^1$ is —$CH_3$.

In certain embodiments, $B^{1'}$ is

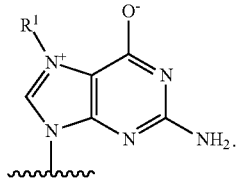

In certain embodiments, each of $R^2$, $R^{2'}$, and $R^{3'}$ is independently H, OH, or O—$CH_3$.

In certain embodiments, each of V, W, X, Y, and Z is O.

In certain embodiments, each of W', X', Y', and Z' is O.

As used herein, the term "5' cap" encompasses traditional mRNA 5' cap structures but also analogs of these. For example, in addition to the 5' cap structures that are encompassed by the chemical structures shown above, one may use, e.g., tetraphosphate analogs having a methylene-bis (phosphonate) moiety (e.g., see Rydzik, A M et al., (2009) Org Biomol Chem 7(22):4763-76), analogs having a sulfur substitution for a non-bridging oxygen (e.g., see Grudzien-Nogalska, E. et al, (2007) RNA 13(10): 1745-1755), N7-benzylated dinucleoside tetraphosphate analogs (e.g., see Grudzien, E. et al., (2004) RNA 10(9): 1479-1487), or anti-reverse cap analogs (e.g., see U.S. Pat. No. 7,074,596 and Jemielity, J. et al., (2003) RNA 9(9): 1 108-1 122 and Stepinski, J. et al., (2001) RNA 7(10):1486-1495). The present application also encompasses the use of cap analogs with halogen groups instead of OH or OMe (e.g., see U.S. Pat. No. 8,304,529); cap analogs with at least one phosphorothioate (PS) linkage (e.g., see U.S. Pat. No. 8,153,773 and Kowalska, J. et al., (2008) RNA 14(6): 1 1 19-1131); and cap analogs with at least one boranophosphate or phosphoroselenoate linkage (e.g., see U.S. Pat. No. 8,519,110); and alkynyl-derivatized 5' cap analogs (e.g., see U.S. Pat. No. 8,969,545).

In general, the 5' cap can be included during either chemical synthesis or in vitro transcription of the gRNA. In certain embodiments, a 5' cap is not used and the gRNA (e.g., an in vitro transcribed gRNA) is instead modified by treatment with a phosphatase (e.g., calf intestinal alkaline phosphatase) to remove the 5' triphosphate group.

The presently disclosed subject matter also provides for methods, genome editing system and compositions for gene editing by using gRNAs which comprise a 3' polyA tail (also called a polyA tract herein). Such gRNAs may, for example, be prepared by adding a polyA tail to a gRNA molecule precursor using a polyadenosine polymerase following in vitro transcription of the gRNA molecule precursor. For example, in certain embodiments, a polyA tail may be added enzymatically using a polymerase such as E. coli polyA polymerase (E-PAP). gRNAs including a polyA tail may also be prepared by in vitro transcription from a DNA template. In certain embodiments, a polyA tail of defined length is encoded on a DNA template and transcribed with the gRNA via an RNA polymerase (such as T7 RNA polymerase). gRNAs with a polyA tail may also be prepared by ligating a polyA oligonucleotide to a gRNA molecule precursor following in vitro transcription using an RNA ligase or a DNA ligase with or without a splinted DNA oligonucleotide complementary to the gRNA molecule precursor and the polyA oligonucleotide. For example, in certain embodiments, a polyA tail of defined length is synthesized as a synthetic oligonucleotide and ligated on the 3' end of the gRNA with either an RNA ligase or a DNA ligase with or without a splinted DNA oligonucleotide complementary to the guide RNA and the polyA oligonucleotide. gRNAs including the polyA tail may also be prepared synthetically, in one or several pieces that are ligated together by either an RNA ligase or a DNA ligase with or without one or more splinted DNA oligonucleotides.

In certain embodiments, the polyA tail is comprised of fewer than 50 adenine nucleotides, for example, fewer than 45 adenine nucleotides, fewer than 40 adenine nucleotides, fewer than 35 adenine nucleotides, fewer than 30 adenine nucleotides, fewer than 25 adenine nucleotides or fewer than 20 adenine nucleotides. In certain embodiments the polyA tail is comprised of between 5 and 50 adenine nucleotides, for example between 5 and 40 adenine nucleotides, between 5 and 30 adenine nucleotides, between 10 and 50 adenine nucleotides, or between 15 and 25 adenine nucleotides. In certain embodiments, the polyA tail is comprised of about 20 adenine nucleotides.

The presently disclosed subject matter also provides for methods, genome editing system and compositions for gene editing (e.g., ex vivo gene editing) by using gRNAs which include one or more modified nucleosides or nucleotides that are described herein.

While some of the exemplary modifications discussed in this section may be included at any position within the gRNA sequence, in certain embodiments, a gRNA comprises a modification at or near its 5' end (e.g., within 1-10, 1-5, or 1-2 nucleotides of its 5' end). In certain embodiments, a gRNA comprises a modification at or near its 3' end (e.g., within 1-10, 1-5, or 1-2 nucleotides of its 3' end). In certain embodiments, a gRNA comprises both a modification at or near its 5' end and a modification at or near its 3' end.

In certain embodiments, a gRNA molecule (e.g., an in vitro transcribed gRNA) comprises a targeting domain which is complementary with a target domain from a gene expressed in a eukaryotic cell, wherein the gRNA molecule is modified at its 5' end and comprises a 3' polyA tail. The gRNA molecule may, for example, lack a 5' triphosphate group (e.g., the 5' end of the targeting domain lacks a 5' triphosphate group). In certain embodiments, a gRNA (e.g., an in vitro transcribed gRNA) is modified by treatment with a phosphatase (e.g., calf intestinal alkaline phosphatase) to remove the 5' triphosphate group and comprises a 3' polyA tail as described herein. The gRNA molecule may alternatively include a 5' cap (e.g., the 5' end of the targeting domain includes a 5' cap). In certain embodiments, a gRNA (e.g., an in vitro transcribed gRNA) contains both a 5' cap structure or cap analog and a 3' polyA tail as described herein. In certain embodiments, the 5' cap comprises a modified guanine nucleotide that is linked to the remainder of the gRNA molecule via a 5'-5' triphosphate linkage. In certain embodiments, the 5' cap comprises two optionally modified guanine nucleotides that are linked via an optionally modified 5'-5' triphosphate linkage (e.g., as described above). In certain embodiments, the polyA tail is comprised of between 5 and 50 adenine nucleotides, for example between 5 and 40 adenine nucleotides, between 5 and 30 adenine nucleotides, between 10 and 50 adenine nucleotides, between 15 and 25 adenine nucleotides, fewer than 30 adenine nucleotides, fewer than 25 adenine nucleotides or about 20 adenine nucleotides.

In certain embodiments, the presently disclosed subject matter provides for a gRNA molecule comprising a targeting domain which is complementary with a target domain from a gene expressed in a eukaryotic cell, wherein the gRNA molecule comprises a 3' polyA tail which is comprised of fewer than 30 adenine nucleotides (e.g., fewer than 25 adenine nucleotides, between 15 and 25 adenine nucleotides, or about 20 adenine nucleotides). In certain embodiments, these gRNA molecules are further modified at their 5' end (e.g., the gRNA molecule is modified by treatment with a phosphatase to remove the 5' triphosphate group or modified to include a 5' cap as described herein).

In certain embodiments, gRNAs can be modified at a 3' terminal U ribose. In certain embodiments, the 5' end and a 3' terminal U ribose of the gRNA are modified (e.g., the gRNA is modified by treatment with a phosphatase to remove the 5' triphosphate group or modified to include a 5' cap as described herein).

For example, the two terminal hydroxyl groups of the U ribose can be oxidized to aldehyde groups and a concomitant opening of the ribose ring to afford a modified nucleoside as shown below:

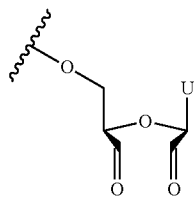

wherein "U" can be an unmodified or modified uridine.

In certain embodiments, the 3' terminal U can be modified with a 2'3' cyclic phosphate as shown below:

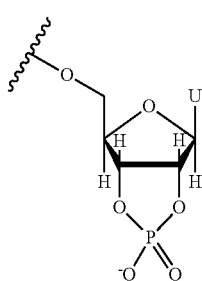

wherein "U" can be an unmodified or modified uridine.

In certain embodiments, the gRNA molecules may contain 3' nucleotides which can be stabilized against degradation, e.g., by incorporating one or more of the modified nucleotides described herein. In this embodiment, e.g., uridines can be replaced with modified uridines, e.g., 5-(2-amino)propyl uridine, and 5-bromo uridine, or with any of the modified uridines described herein; adenosines, cytidines and guanosines can be replaced with modified adenosines, cytidines and guanosines, e.g., with modifications at the 8-position, e.g., 8-bromo guanosine, or with any of the modified adenosines, cytidines or guanosines described herein.

In certain embodiments, sugar-modified ribonucleotides can be incorporated into the gRNA, e.g., wherein the 2' OH-group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., $NH_2$; alkylamino, dialkylamino, heterocyclylamino, arylamino, diarylamino, heteroarylamino, diheteroarylamino, or amino acid); or cyano (—CN). In certain embodiments, the phosphate backbone can be modified as described herein, e.g., with a phosphothioate group. In certain embodiments, one or more of the nucleotides of the gRNA can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aeo), 2'-O-methoxyethyl-5-methylcytidine (m5Ceo), and any combinations thereof.

In certain embodiments, a gRNA can include "locked" nucleic acids (LNA) in which the 2' OH-group can be connected, e.g., by a C1-6 alkylene or C1-6 heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclylamino, arylamino, diarylamino, heteroarylamino, or diheteroarylamino, ethylenediamine, or polyamino) and aminoalkoxy or $O(CH_2)_n$-amino (wherein amino can be, e.g., $NH_2$; alkylamino, dialkylamino, heterocyclylamino, arylamino, diarylamino, heteroarylamino, or diheteroarylamino, ethylenediamine, or polyamino).

In certain embodiments, a gRNA can include a modified nucleotide which is multicyclic (e.g., tricyclo; and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-(3'→2')).

Generally, gRNA molecules include the sugar group ribose, which is a 5-membered ring having an oxygen. Exemplary modified gRNAs can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In certain embodiments, a gRNA comprises a 4'-S, 4'-Se or a 4'-C-aminomethyl-2'-O-Me modification.

In certain embodiments, deaza nucleotides, e.g., 7-deaza-adenosine, can be incorporated into the gRNA. In certain embodiments, 0- and N-alkylated nucleotides, e.g., N6-methyl adenosine, can be incorporated into the gRNA. In certain embodiments, one or more or all of the nucleotides in a gRNA molecule are deoxynucleotides.

12.6 miRNA Binding Sites microRNAs (or miRNAs) are naturally occurring cellular 19-25 nucleotide long noncoding RNAs. They bind to nucleic acid molecules having an appropriate miRNA binding site, e.g., in the 3' UTR of an mRNA, and down-regulate gene expression. In certain embodiments, this down regulation occurs by either reducing nucleic acid molecule stability or inhibiting translation. An RNA species disclosed herein, e.g., an mRNA encoding Cas9 can comprise an miRNA binding site, e.g., in its 3'UTR. The miRNA binding site can be selected to promote down regulation of expression is a selected cell type. By way of example, the incorporation of a binding site for miR-122, a microRNA abundant in liver, can inhibit the expression of the gene of interest in the liver.

EXAMPLES

The following Examples are merely illustrative and are not intended to limit the scope or content of the invention in any way.

Example 1: Evaluation of Candidate Guide RNAs (gRNAs)

The suitability of candidate gRNAs can be evaluated as described in this example. Although described for a chimeric gRNA, the approach can also be used to evaluate modular gRNAs.

Cloning gRNAs into Vectors

For each gRNA, a pair of overlapping oligonucleotides is designed and obtained.

Oligonucleotides are annealed and ligated into a digested vector backbone containing an upstream U6 promoter and the remaining sequence of a long chimeric gRNA. Plasmid is sequence-verified and prepped to generate sufficient amounts of transfection-quality DNA. Alternate promoters maybe used to drive in vivo transcription (e.g. H1 promoter) or for in vitro transcription (e.g., a T7 promoter).

Cloning gRNAs in Linear dsDNA Molecule (STITCHR)

For each gRNA, a single oligonucleotide is designed and obtained. The U6 promoter and the gRNA scaffold (e.g. including everything except the targeting domain, e.g., including sequences derived from the crRNA and tracrRNA, e.g., including a first complementarity domain; a linking domain; a second complementarity domain; a proximal domain; and a tail domain) are separately PCR amplified and purified as dsDNA molecules. The gRNA-specific oligonucleotide is used in a PCR reaction to stitch together the U6 and the gRNA scaffold, linked by the targeting domain specified in the oligonucleotide. Resulting dsDNA molecule (STITCHR product) is purified for transfection. Alternate promoters may be used to drive in vivo transcription (e.g., H1 promoter) or for in vitro transcription (e.g., T7 promoter). Any gRNA scaffold may be used to create gRNAs compatible with Cas9s from any bacterial species.

Each gRNA to be tested is transfected, along with a plasmid expressing Cas9 and a small amount of a GFP-expressing plasmid into human cells. In preliminary experiments, these cells can be immortalized human cell lines such as 293T, K562 or U2OS. Alternatively, primary human cells may be used. In this case, cells may be relevant to the eventual therapeutic cell target. The use of primary cells similar to the potential therapeutic target cell population may provide important information on gene targeting rates in the context of endogenous chromatin and gene expression.

Transfection may be performed using lipid transfection (such as Lipofectamine or Fugene) or by electroporation (such as Lonza Nucleofection). Following transfection, GFP expression can be determined either by fluorescence microscopy or by flow cytometry to confirm consistent and high levels of transfection. These preliminary transfections can comprise different gRNAs and different targeting approaches (17-mers, 20-mers, nuclease, dual-nickase, etc.) to determine which gRNAs/combinations of gRNAs give the greatest activity.

Efficiency of cleavage with each gRNA may be assessed by measuring NHEJ-induced indel formation at the target locus by a T7E1-type assay or by sequencing. Alternatively, other mismatch-sensitive enzymes, such as Cell/Surveyor nuclease, may also be used.

For the T7E1 assay, PCR amplicons are approximately 500-700 bp with the intended cut site placed asymmetrically in the amplicon. Following amplification, purification and size-verification of PCR products, DNA is denatured and re-hybridized by heating to 95° C. and then slowly cooling. Hybridized PCR products are then digested with T7 Endonuclease I (or other mismatch-sensitive enzyme) which recognizes and cleaves non-perfectly matched DNA. If indels are present in the original template DNA, when the amplicons are denatured and re-annealed, this results in the hybridization of DNA strands harboring different indels and therefore lead to double-stranded DNA that is not perfectly matched. Digestion products may be visualized by gel electrophoresis or by capillary electrophoresis. The fraction of DNA that is cleaved (density of cleavage products divided by the density of cleaved and uncleaved) may be used to estimate a percent NHEJ using the following equation: % NHEJ=$(1-(1-\text{fraction cleaved})^{1/2})$. The T7E1 assay is sensitive down to about 2-5% NHEJ.

Sequencing may be used instead of, or in addition to, the T7E1 assay. For Sanger sequencing, purified PCR amplicons are cloned into a plasmid backbone, transformed, mini-prepped and sequenced with a single primer. Sanger sequencing may be used for determining the exact nature of indels after determining the NHEJ rate by T7E1.

Sequencing may also be performed using next generation sequencing techniques. When using next generation sequencing, amplicons may be 300-500 bp with the intended cut site placed asymmetrically. Following PCR, next generation sequencing adapters and barcodes (for example Illumina multiplex adapters and indexes) may be added to the ends of the amplicon, e.g., for use in high throughput sequencing (for example on an Illumina MiSeq). This method allows for detection of very low NHEJ rates.

Example 2: Assessment of Gene Targeting by NHEJ

The gRNAs that induce the greatest levels of NHEJ in initial tests can be selected for further evaluation of gene targeting efficiency. In this case, cells are derived from disease subjects and, therefore, harbor the relevant mutation.

Following transfection (usually 2-3 days post-transfection) genomic DNA may be isolated from a bulk population of transfected cells and PCR may be used to amplify the target region. Following PCR, gene targeting efficiency to generate the desired mutations (either knockout of a target gene or removal of a target sequence motif) may be determined by sequencing. For Sanger sequencing, PCR amplicons may be 500-700 bp long. For next generation sequencing, PCR amplicons may be 300-500 bp long. If the goal is to knockout gene function, sequencing may be used to assess what percent of viral copies have undergone NHEJ-induced indels that result in a frameshift or large deletion or insertion that would be expected to destroy gene function. If the goal is to remove a specific sequence motif, sequencing may be used to assess what percent of viral copies have undergone NHEJ-induced deletions that span this sequence.

Example 3: Assessment of Activity of Individual gRNAs Targeting a Synthetic HSV-1 Construct A plasmid containing HSV-1 sequences was constructed as a reporter to measure Cas9-mediated cleavage of target DNA. This reporter plasmid, pAF025, encodes a Green Fluorescent Protein (GFP) driven by a CMV promoter. The target HSV-1 sequences were inserted in frame with the GFP, at its N-terminus, with a P2A self-cleaving peptide sequence between them.

gRNA molecules were identified using a custom guide RNA design software based on the public tool cas-offinder (Bae et al. Bioinformatics. 2014; 30(10): 1473-1475). Each gRNA molecules tested in this example and listed in Tables 18 and 19 were generated as a STITCHR product and co-transfected with a plasmid expressing the *S. aureus* Cas9 (pAF003) into HEK293FT cells. The pAF003 plasmid encodes the *S. aureus* Cas9, with N-terminal and C-terminal nuclear localization signals (NLS) and a C-terminal triple flag tag, driven by a CMV promoter. gRNA and Cas9-encoding DNA were introduced into cells along with target plasmid pAF025 by Minis TransIT-293 transfection reagent. Two days post-transfection, cells were removed from their growth plates by trypsinization, washed in PBS buffer, and analyzed with a BD Accuri Flow Cytometer.

Figure 9:
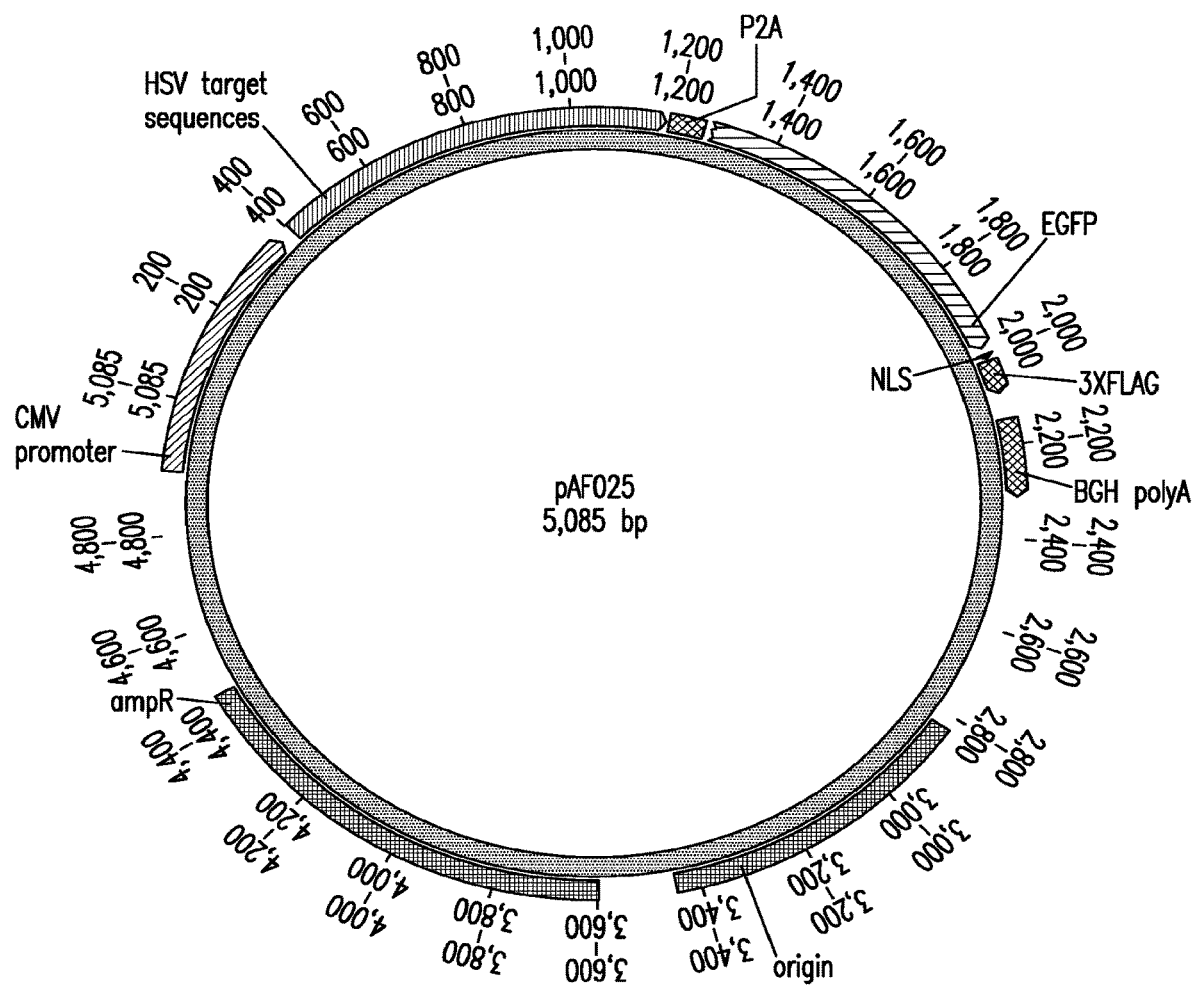
FIG. 9 is a schematic representation of the pAF025 plasmid map.
Figure 10A:
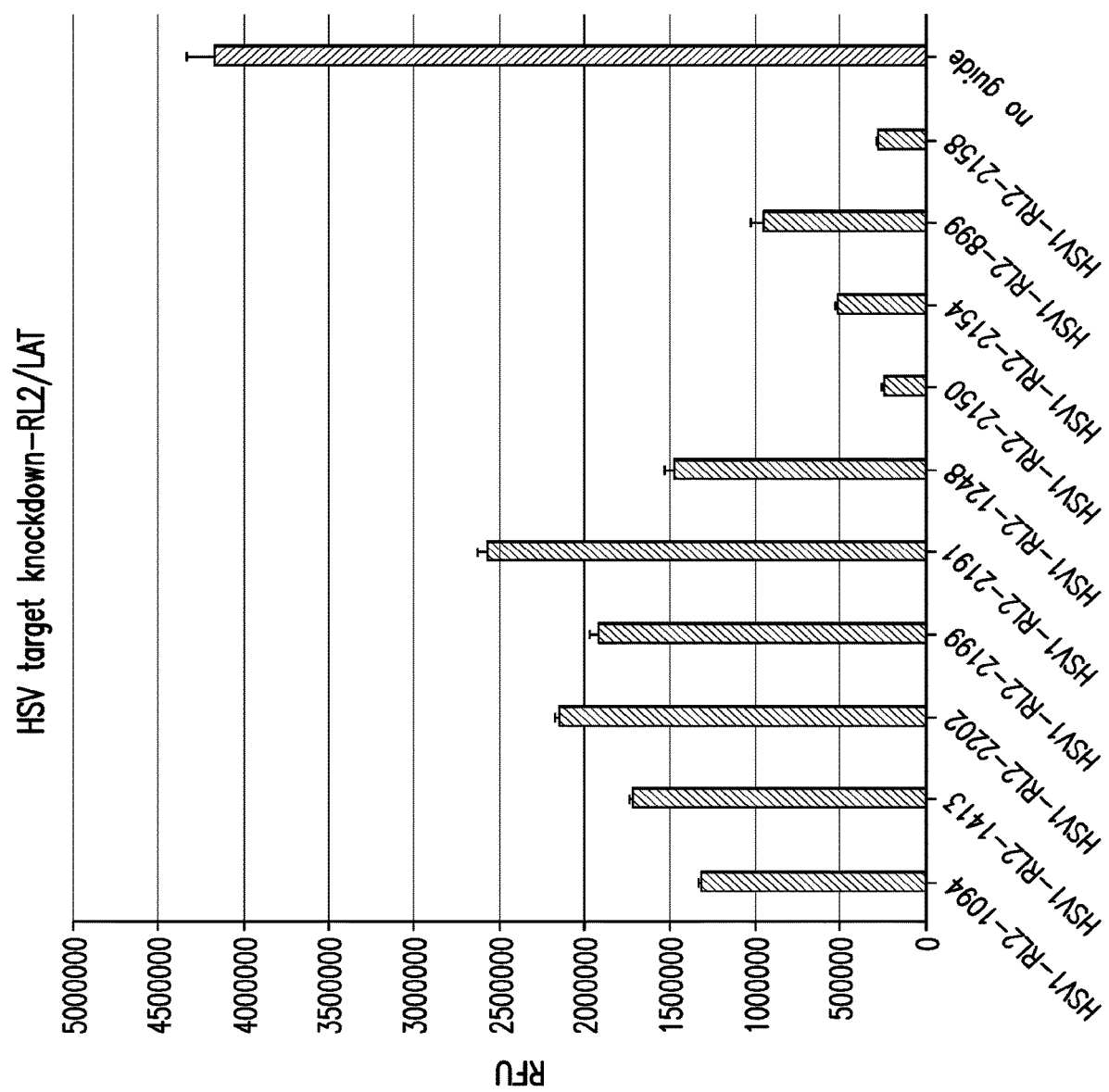
FIGS. 10A-10B show Cas9-mediated cleavage of HSV-1 target sequences in plasmid pAF025. (A) shows HSV1 target knockdown of RL2/LAT by gRNAs listed in Table 18
Figure 10B:
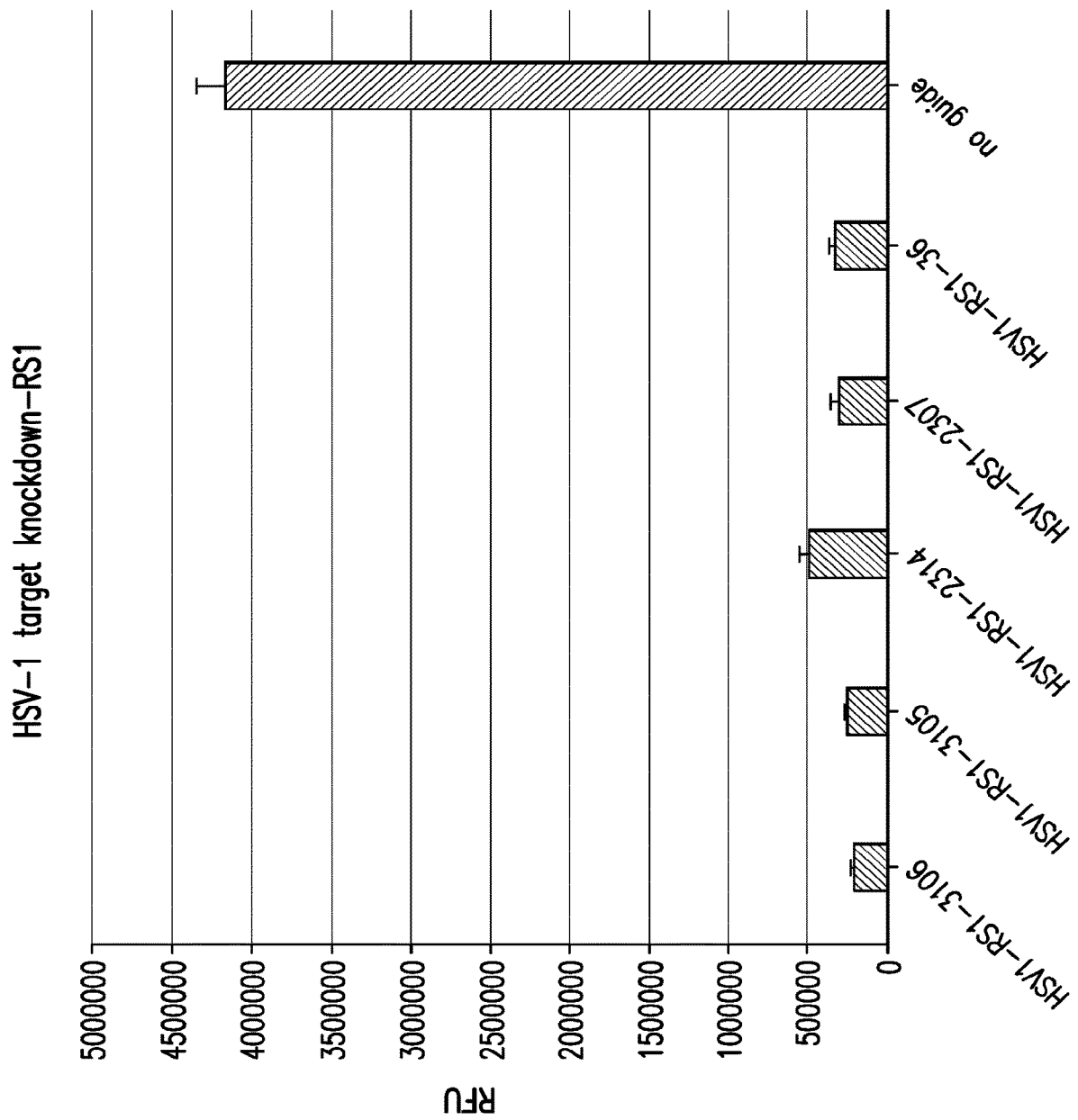

FIG. 9 shows the plasmid map for pAF025. FIGS. 10A-10B show the reduction in GFP expression as measured by mean fluorescence (or relative fluorescence units, RFU) of the transfected cell population due to Cas9-mediated cleavage of the HSV-1 target sequences in plasmid pAF025. Table 18 lists the gRNAs shown in FIG. 10A, and Table 19 lists the gRNAs shown in FIG. 10B.

TABLE 18

(gRNAs shown in FIG. 10A)

| gRNA name | SEQ ID NO. for the nucleotide sequence of the targeting domain of the gRNA |
|---|---|
| HSV1-RL2-1094 | GAGGCCGCCGAGGACGUCAG (SEQ ID NO: 23519) |
| HSV1-RL2-1413 | GGGGGGGUUGGGGUUGGGGU (SEQ ID NO: 23587) |
| HSV1-RL2-2202 | GCCCCUCCGGGGGGUUGGGGU (SEQ ID NO: 23583) |
| HSV1-RL2-2199 | GUCUGGCCCCUCCGGGGGGU (SEQ ID NO: 23580) |
| HSV1-RL2-2191 | GGGGGGCGUCUGGCCCCUCCGG (SEQ ID NO: 23571) |

TABLE 18-continued (gRNAs shown in FIG. 10A)

| gRNA name | SEQ ID NO. for the nucleotide sequence of the targeting domain of the gRNA |
|---|---|
| HSV1-RL2-1248 | GGGGCGUCUGGCCCCUCCGG (SEQ ID NO: 23569) |
| HSV1-RL2-2150 | GCCCCCCCGGCCCUGAGUCGGAGG (SEQ ID NO: 23527) |
| HSV1-RL2-2154 | GCCUGUGGGGAGAGGCCGGGG (SEQ ID NO: 23531) |
| HSV1-RL2-899 | GGGGGAGUCGCUGAUCACUA (SEQ ID NO: 23489) |
| HSV1-RL2-2158 | GUCUCUGUUGUUUGCAAGGGGG (SEQ ID NO: 23535) |

TABLE 19

(gRNAs shown in FIG. 10B)

| gRNA name | SEQ ID NO. for the nucleotide sequence of the targeting domain of the gRNA |
|---|---|
| HSV1-RS1-3106 | GCGUCAUCGACCUCGUCGGACU (SEQ ID NO: 3363) |
| HSV1-RS1-3105 | GUCAUCGACCUCGUCGGACU (SEQ ID NO: 3362) |
| HSV1-RS1-2314 | GCGACAGGCGGUCCGUGGGGU (SEQ ID NO: 2522) |
| HSV1-RS1-2307 | GGGCGCGGCGACAGGCGGUCCG (SEQ ID NO: 2515) |
| HSV1-RS1-36 | GCGCGGCGACAGGCGGUCCG (SEQ ID NO: 243) |

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11001844B2). An electronic copy of the "Sequence Listing" will also be available from the USPTO upon request and payment of the fee set forth in 37 CFR 1.19(b)(3).

What is claimed is:

1. A genome editing system comprising:
a gRNA molecule comprising a targeting domain that is complementary with a target sequence of a Herpes simplex virus (HSV) viral gene selected from the group consisting of a RS1 gene, a RL2 gene, and a LAT gene, wherein the targeting domain consists of a nucleotide sequence that is identical to, or differs by no more than 3 nucleotides from, a nucleotide sequence selected from the nucleotide sequences set forth in SEQ ID NOS: 208 to 58749; and
a Cas9 molecule.

2. The genome editing system of claim 1, wherein said targeting domain is configured to form a double strand break or a single strand break within about 500 bp, about 450 bp, about 400 bp, about 350 bp, about 300 bp, about 250 bp, about 200 bp, about 150 bp, about 100 bp, about 50 bp, about 25 bp, or about 10 bp of an HSV target position, thereby altering said HSV viral gene.

3. The genome editing system of claim 2, wherein said altering said HSV viral gene comprises knockout of said HSV viral gene, knockdown of said HSV viral gene, or concomitant knockout and knockdown of said HSV viral gene.

4. The genome editing system of claim 1, wherein said targeting domain is configured to target a coding region or a non-coding region of said HSV viral gene, wherein said non-coding region comprises a promoter region, an enhancer region, an intron, the 3' UTR, the 5' UTR, or a polyadenylation signal region of said HSV viral gene; and said coding region comprises an early coding region of said HSV viral gene.

5. The genome editing system of claim 1, wherein said Cas9 molecule is an *S. pyogenes* Cas9 molecule, said genome editing system knocks out said HSV-1 RS1 gene, and said targeting domain consists of a nucleotide sequence that is identical to, or differs by no more than 3 nucleotides from, a nucleotide sequence selected from the nucleotide sequences set forth in SEQ ID NOS: 208 to 2509.

6. The genome editing system of claim 1, wherein said Cas9 molecule is an *S. pyogenes* Cas9 molecule, and
(a) said genome editing system knocks out said HSV-2 RS1 gene, and said targeting domain consists of a nucleotide sequence that is identical to, or differs by no more than 3 nucleotides from, a nucleotide sequence selected from the nucleotide sequences set forth in SEQ ID NOS: 7098 to 9292;
(b) said genome editing system knocks out said HSV-1 RL2 gene, and said targeting domain consists of a nucleotide sequence that is identical to, or differs by no more than 3 nucleotides from, a nucleotide sequence selected from the nucleotide sequences set forth in SEQ ID NOS: 21324 to 22744;
(c) said genome editing system knocks out said HSV-2 RL2 gene, and said targeting domain consists of a nucleotide sequence that is identical to, or differs by no more than 3 nucleotides from, a nucleotide sequence selected from the nucleotide sequences set forth in SEQ ID NOS: 26613 to 28037;
(d) said genome editing system knocks out said HSV-1 LAT gene, and said targeting domain consists of a nucleotide sequence that is identical to, or differs by no more than 3 nucleotides from, a nucleotide sequence selected from the nucleotide sequences set forth in SEQ ID NOS: 31730 to 32746; or
(e) said genome editing system knocks out said HSV-2 LAT gene, and said targeting domain consists of a nucleotide sequence that is identical to, or differs by no more than 3 nucleotides from, a nucleotide sequence selected from the group consisting of: SEQ ID NOS: 35617 to 36926.

7. The genome editing system of claim 1, wherein said Cas9 molecule is an *S. aureus* Cas9 molecule, and
(a) said genome editing system knocks out said HSV-1 RS1 gene, and said targeting domain consists of a nucleotide sequence that is identical to, or differs by no more than 3 nucleotides from, a nucleotide sequence selected from the nucleotide sequences set forth in SEQ ID NOS: 2510 to 7073;
(b) said genome editing system knocks out said HSV-2 RS1 gene, and said targeting domain consists of a nucleotide sequence that is identical to, or differs by no more than 3 nucleotides from, a nucleotide sequence selected from the nucleotide sequences set forth in SEQ ID NOS: 9293 to 13614;
(c) said genome editing system knocks out said HSV-1 RL2 gene, and said targeting domain consists of a nucleotide sequence that is identical to, or differs by no more than 3 nucleotides from, a nucleotide sequence selected from the nucleotide sequences set forth in SEQ ID NOS: 22745 to 26601;
(d) said genome editing system knocks out said HSV-2 RL2 gene, and said targeting domain consists of a nucleotide sequence that is identical to, or differs by no more than 3 nucleotides from, a nucleotide sequence selected from the nucleotide sequences set forth in SEQ ID NOS: 28038 to 31720;
(e) said genome editing system knocks out said HSV-1 LAT gene, and said targeting domain consists of a nucleotide sequence that is identical to, or differs by no more than 3 nucleotides from, a nucleotide sequence selected from the nucleotide sequences set forth in SEQ ID NOS: 32747 to 35600; or
(f) said genome editing system knocks out said HSV-2 LAT gene, and said targeting domain consists of a nucleotide sequence that is identical to, or differs by no more than 3 nucleotides from, a nucleotide sequence selected from the nucleotide sequences set forth in SEQ ID NOS: 36927 to 40871.

8. The genome editing system of claim 7, wherein said targeting domain consists of the nucleotide sequence set forth in SEQ ID NO: 243, SEQ ID NO: 2515, SEQ ID NO: 2522, SEQ ID NO: 3362, SEQ ID NO: 3363, SEQ ID NO: 23489, SEQ ID NO: 23519, SEQ ID NO: 23527, SEQ ID NO: 23531, SEQ ID NO: 23535, SEQ ID NO: 23569, SEQ ID NO: 23571, SEQ ID NO: 23580, SEQ ID NO: 23583, or SEQ ID NO: 23587.

9. The genome editing system of claim 1, wherein said Cas9 molecule is an *S. pyogenes* Cas9 molecule, and
   (a) said genome editing system knocks down said HSV-1 RS1 gene, and said targeting domain consists of a nucleotide sequence that is identical to, or differs by no more than 3 nucleotides from, a nucleotide sequence selected from the group consisting of: nucleotide sequences set forth in SEQ ID NOS: 13637 to 14794;
   (b) said genome editing system knocks down said HSV-2 RS1 gene, and said targeting domain consists of a nucleotide sequence that is identical to, or differs by no more than 3 nucleotides from, a nucleotide sequence selected from the nucleotide sequences set forth in SEQ ID NOS: 17753 to 18784;
   (c) said genome editing system knocks down said HSV-1 RL2 gene, and said targeting domain consists of a nucleotide sequence that is identical to, or differs by no more than 3 nucleotides from, a nucleotide sequence selected from the nucleotide sequences set forth in SEQ ID NOS: 40886 to 42078;
   (d) said genome editing system knocks down said HSV-2 RL2 gene, and said targeting domain consists of a nucleotide sequence that is identical to, or differs by no more than 3 nucleotides from, a nucleotide sequence selected from the nucleotide sequences set forth in SEQ ID NOS: 49498 to 50652;
   (e) said genome editing system knocks down said HSV-1 LAT gene, and said targeting domain consists of a nucleotide sequence that is identical to, or differs by no more than 3 nucleotides from, a nucleotide sequence selected from the nucleotide sequences set forth in SEQ ID NOS: 45340 to 46479; or
   (f) said genome editing system knocks down said HSV-2 LAT gene, and said targeting domain consists of a nucleotide sequence that is identical to, or differs by no more than 3 nucleotides from, a nucleotide sequence selected from the nucleotide sequences set forth in SEQ ID NOS: 53858 to 55056.

10. The genome editing system of claim 1, wherein said Cas9 molecule is an *S. aureus* Cas9 molecule, and
   (a) said genome editing system knocks down said HSV-1 RS1 gene, and said targeting domain consists of a nucleotide sequence that is identical to, or differs by no more than 3 nucleotides from, a nucleotide sequence selected from the nucleotide sequences set forth in SEQ ID NOS: 14795 to 17741;
   (b) said genome editing system knocks down said HSV-2 RS1 gene, and said targeting domain consists of a nucleotide sequence that is identical to, or differs by no more than 3 nucleotides from, a nucleotide sequence selected from the nucleotide sequences set forth in SEQ ID NOS: 18785 to 21311;
   (c) said genome editing system knocks down said HSV-1 RL2 gene, and said targeting domain consists of a nucleotide sequence that is identical to, or differs by no more than 3 nucleotides from, a nucleotide sequence selected from the nucleotide sequences set forth in SEQ ID NOS: 42079 to 45315;
   (d) said genome editing system knocks down said HSV-2 RL2 gene, and said targeting domain consists of a nucleotide sequence that is identical to, or differs by no more than 3 nucleotides from, a nucleotide sequence selected from the nucleotide sequences set forth in SEQ ID NOS: 50653 to 53824;
   (e) said genome editing system knocks down said HSV-1 LAT gene, and said targeting domain consists of a nucleotide sequence that is identical to, or differs by no more than 3 nucleotides from, a nucleotide sequence selected from the nucleotide sequences set forth in SEQ ID NOS: 46480 to 49479; or
   (f) said genome editing system knocks down said HSV-2 LAT gene, and said targeting domain consists of a nucleotide sequence that is identical to, or differs by no more than 3 nucleotides from, a nucleotide sequence selected from the nucleotide sequences set forth in SEQ ID NOS: 55057 to 58731.

11. The genome editing system of claim 6, wherein said *S. pyogenes* Cas9 molecule recognizes a Protospacer Adjacent Motif (PAM) of NGG.

12. The genome editing system of claim 9, wherein said *S. pyogenes* Cas9 molecule recognizes a PAM of NGG.

13. The genome editing system of claim 7, wherein said *S. aureus* Cas9 molecule recognizes a PAM of NNGRRT (SEQ ID NO: 204) or NNGRRV (SEQ ID NO: 205).

14. The genome editing system of claim 10, wherein said *S. aureus* Cas9 molecule recognizes a PAM of NNGRRT (SEQ ID NO: 204) or NNGRRV (SEQ ID NO: 205).

15. The genome editing system of claim 1, wherein said Cas9 molecule is selected from the group consisting of an enzymatically active Cas9 (eaCas9) molecule, an enzymatically inactive Cas9 (eiCas9) molecule, and an eiCas9 fusion protein.

16. The genome editing system of claim 1, wherein said Cas9 molecule comprises a wild-type Cas9 molecule, a mutant Cas9 molecule, or a combination thereof.

17. The genome editing system of claim 16, wherein said mutant Cas9 molecule comprises a mutation selected from the group consisting of D10, E762, D986, H840, N854, N863, and N580.

18. The genome editing system of claim 1, wherein said Cas9 molecule is an *S. aureus* Cas9 molecule or an *S. pyogenes* Cas9 molecule.

19. The genome editing system of claim 1, wherein said gRNA is a modular gRNA molecule or a chimeric gRNA molecule.

20. The genome editing system of claim 1, wherein said targeting domain has a length of 16, 17, 18, 19, 20, 21, 22, 23, 24, 25, or 26 nucleotides.

21. The genome editing system of claim 1, wherein said gRNA molecule comprises from 5' to 3':
   a targeting domain;
   a first complementarity domain;
   a linking domain;
   a second complementarity domain;
   a proximal domain; and
   a tail domain.

22. The genome editing system of claim 21, wherein said linking domain is no more than 25 nucleotides in length.

23. The genome editing system of claim 21, wherein said proximal and tail domain, taken together, are at least 20, at least 25, at least 30, or at least 40 nucleotides in length.

24. The genome editing system of claim 1, comprising a second gRNA molecule.

25. The genome editing system of claim 24, wherein said second gRNA molecule comprises a second targeting domain that is complementary with a target sequence of a HSV viral gene selected from the group consisting of a RS1 gene, a RL2 gene, and a LAT gene.

26. A cell comprising the genome editing system of claim 1.

\* \* \* \* \*